(12) United States Patent
Gazdzinski

(10) Patent No.: US 8,068,897 B1
(45) Date of Patent: Nov. 29, 2011

(54) ENDOSCOPIC SMART PROBE AND METHOD

(76) Inventor: Robert F. Gazdzinski, San Diego, CA (US)

( * ) Notice: Subject to any disclaimer, the term of this patent is extended or adjusted under 35 U.S.C. 154(b) by 11 days.

(21) Appl. No.: 12/381,513

(22) Filed: Mar. 11, 2009

Related U.S. Application Data

(63) Continuation-in-part of application No. 09/817,842, filed on Mar. 26, 2001, which is a continuation-in-part of application No. 09/259,194, filed on Mar. 1, 1999, now abandoned.

(51) Int. Cl.
*A61B 6/00* (2006.01)

(52) U.S. Cl. ........ 600/476; 600/109; 600/128; 600/423; 600/424; 600/425; 600/426; 606/130

(58) Field of Classification Search .......... 600/109, 600/128, 423, 424, 425, 426, 476; 606/130
See application file for complete search history.

(56) References Cited

U.S. PATENT DOCUMENTS

| | | | |
|---|---|---|---|
| 3,901,220 A | 8/1975 | Koyasu et al. | |
| 4,041,461 A | 8/1977 | Kratz et al. | |
| 4,271,842 A * | 6/1981 | Specht et al. | 600/443 |
| 4,278,077 A | 7/1981 | Mizumoto | |
| 4,455,574 A | 6/1984 | Hashimoto et al. | |
| 4,605,844 A | 8/1986 | Haggan | |
| 4,692,604 A | 9/1987 | Billings | |
| 4,773,045 A | 9/1988 | Ogawa | |
| 4,795,898 A | 1/1989 | Bernstein et al. | |
| 4,802,757 A | 2/1989 | Pleitner et al. | |
| 4,816,654 A | 3/1989 | Anderl et al. | |
| 4,819,065 A | 4/1989 | Eino | |
| 4,833,538 A | 5/1989 | Hieda | |
| 4,851,914 A | 7/1989 | Pfanhouser et al. | |
| 4,862,407 A | 8/1989 | Fette et al. | |
| 4,925,274 A | 5/1990 | James et al. | |
| 4,963,793 A | 10/1990 | DePauli | |
| 4,973,848 A | 11/1990 | Kolobanov et al. | |

(Continued)

FOREIGN PATENT DOCUMENTS

| | | |
|---|---|---|
| DE | 34 40 177 A1 | 5/1986 |
| JP | 2-82889 | 3/1990 |
| WO | WO-0058752 | 10/2000 |

OTHER PUBLICATIONS

Chung, (Spring 1998), "Even Smarter Smart Materials", University of Buffalo, UB Research, vol. 8, No. 1.

(Continued)

*Primary Examiner* — Tse Chen
*Assistant Examiner* — Baisakhi Roy
(74) *Attorney, Agent, or Firm* — Gazdzinski & Associates, PC

(57) ABSTRACT

An improved endoscopic device which is introduced into the intestinal tract of a living organism and which operates autonomously therein, adapted to obtain and store or transmit one or more types of data such as visual image data, laser autofluorescence data, or ultrasonic waveform data. In another aspect of the invention, an improved endoscopic device useful for implanting the aforementioned endoscopic smart probe is disclosed. In another aspect of the invention, apparatus for delivering agents including nanostructures, radionuclides, medication, and ligands is disclosed. In another aspect of the invention, apparatus for obtaining a biopsy of intestinal tissue is disclosed. In another aspect of the invention, apparatus for detecting the presence of one or more molecular species within the intestine is disclosed. Methods for inspecting and/or treating the interior regions of the intestinal tract using the aforementioned apparatus are also disclosed.

42 Claims, 66 Drawing Sheets

U.S. PATENT DOCUMENTS

| | | | |
|---|---|---|---|
| 4,981,138 A | 1/1991 | Deckelbaum et al. | |
| 4,985,758 A | 1/1991 | Hashimoto | |
| 5,001,556 A | 3/1991 | Nakamura et al. | |
| 5,065,246 A | 11/1991 | Takemoto et al. | |
| 5,077,612 A | 12/1991 | Megrgardt et al. | |
| 5,100,381 A | 3/1992 | Burns | |
| 5,146,228 A | 9/1992 | Irani et al. | |
| 5,166,787 A | 11/1992 | Irion | |
| 5,173,949 A | 12/1992 | Peregrim et al. | |
| 5,205,171 A | 4/1993 | O'Brien et al. | |
| 5,231,990 A | 8/1993 | Gauglitz | |
| 5,267,033 A | 11/1993 | Hoshino | |
| 5,279,607 A | 1/1994 | Schentag et al. | |
| 5,293,329 A | 3/1994 | Wishart et al. | |
| 5,316,636 A | 5/1994 | Bunshah et al. | |
| 5,350,569 A | 9/1994 | Coppa | |
| 5,367,187 A | 11/1994 | Yuen | |
| 5,395,366 A | 3/1995 | D'Andrea et al. | |
| 5,395,496 A | 3/1995 | Tsantrizos et al. | |
| 5,491,097 A | 2/1996 | Ribi et al. | |
| 5,494,558 A | 2/1996 | Bunshah et al. | |
| 5,510,098 A | 4/1996 | Chow | |
| 5,534,921 A | 7/1996 | Sawanobori | |
| 5,547,748 A | 8/1996 | Ruoff et al. | |
| 5,563,655 A | 10/1996 | Lathrop | |
| 5,568,503 A | 10/1996 | Omori | |
| 5,604,531 A | 2/1997 | Iddan et al. | |
| 5,625,743 A | 4/1997 | Fiocca | |
| 5,640,705 A | 6/1997 | Koruga | |
| 5,671,015 A | 9/1997 | Yagi et al. | |
| 5,671,247 A | 9/1997 | Souissi et al. | |
| 5,697,885 A | 12/1997 | Konomura et al. | |
| 5,712,605 A | 1/1998 | Flory et al. | |
| 5,712,684 A | 1/1998 | Inoue et al. | |
| 5,745,427 A | 4/1998 | Freyman et al. | |
| 5,754,422 A | 5/1998 | Lowles et al. | |
| 5,797,898 A | 8/1998 | Santini et al. | |
| 5,808,967 A | 9/1998 | Yu et al. | |
| 5,819,736 A | 10/1998 | Avny et al. | |
| 5,821,226 A | 10/1998 | Tang et al. | |
| 5,821,235 A | 10/1998 | Henning et al. | |
| 5,827,190 A | 10/1998 | Palcic et al. | |
| 5,874,316 A | 2/1999 | Cornell et al. | |
| 5,882,300 A | 3/1999 | Malinouskas et al. | |
| 5,896,037 A | 4/1999 | Kudla et al. | |
| 5,902,583 A | 5/1999 | Buchsbaum et al. | |
| 5,903,321 A | 5/1999 | Tung et al. | |
| 5,905,220 A | 5/1999 | Lee et al. | |
| 5,907,339 A | 5/1999 | Evans et al. | |
| 5,916,642 A | 6/1999 | Chang | |
| 5,943,171 A | 8/1999 | Budd et al. | |
| 5,951,832 A | 9/1999 | Tanaka et al. | |
| 5,963,132 A | 10/1999 | Yoakum | |
| 5,965,267 A | 10/1999 | Nolan et al. | |
| 5,984,780 A | 11/1999 | Takemoto et al. | |
| 5,984,875 A | 11/1999 | Brune | |
| 6,012,017 A | 1/2000 | Van Bemmel et al. | |
| 6,016,449 A | 1/2000 | Fischell et al. | |
| 6,032,253 A | 2/2000 | Cashman et al. | |
| 6,065,027 A | 5/2000 | Cashman et al. | |
| 6,073,962 A | 6/2000 | Wu et al. | |
| 6,081,821 A | 6/2000 | Hopkinson et al. | |
| 6,090,363 A | 7/2000 | Green et al. | |
| 6,092,784 A | 7/2000 | Kalfsbeck | |
| 6,123,861 A | 9/2000 | Santini et al. | |
| 6,128,220 A | 10/2000 | Banyai et al. | |
| 6,131,386 A | 10/2000 | Trumble | |
| 6,154,321 A | 11/2000 | Melville et al. | |
| 6,159,502 A | 12/2000 | Russell-Jones et al. | |
| 6,165,440 A | 12/2000 | Esenaliev | |
| 6,171,451 B1 | 1/2001 | Miley et al. | |
| 6,222,677 B1 | 4/2001 | Budd et al. | |
| 6,223,274 B1 | 4/2001 | Catthoor et al. | |
| 6,226,738 B1 | 5/2001 | Dowling | |
| 6,240,312 B1 | 5/2001 | Alfano et al. | |
| 6,293,911 B1 | 9/2001 | Imaizumi et al. | |
| 6,324,418 B1 | 11/2001 | Crowley et al. | |
| 6,329,920 B1 | 12/2001 | Morrison et al. | |
| D457,236 S | 5/2002 | Meron et al. | |
| D457,621 S | 5/2002 | Meron et al. | |
| D457,948 S | 5/2002 | Meron et al. | |
| 6,388,702 B1 | 5/2002 | Konomura et al. | |
| 6,394,602 B1 | 5/2002 | Morrison et al. | |
| 6,409,674 B1 | 6/2002 | Brockway et al. | |
| 6,428,469 B1 | 8/2002 | Iddan et al. | |
| D464,425 S | 10/2002 | Meron et al. | |
| D469,864 S | 2/2003 | Meron et al. | |
| 6,525,648 B1 | 2/2003 | Kubler et al. | |
| 6,558,324 B1 * | 5/2003 | Von Behren et al. | 600/440 |
| 6,573,936 B2 | 6/2003 | Morris et al. | |
| 6,580,456 B1 | 6/2003 | Jacobs | |
| 6,584,348 B2 | 6/2003 | Glukhovsky | |
| 6,593,845 B1 | 7/2003 | Friedman et al. | |
| 6,607,301 B1 | 8/2003 | Glukhovsky et al. | |
| 6,628,336 B2 | 9/2003 | Hamamura | |
| 6,632,171 B2 | 10/2003 | Iddan et al. | |
| 6,636,566 B1 | 10/2003 | Roberts et al. | |
| 6,636,748 B2 | 10/2003 | Monroe | |
| 6,642,956 B1 | 11/2003 | Safai | |
| 6,709,387 B1 | 3/2004 | Glukhovsky et al. | |
| 6,712,276 B1 | 3/2004 | Abali et al. | |
| 6,714,249 B2 | 3/2004 | May et al. | |
| D492,403 S | 6/2004 | Iddan et al. | |
| 6,764,440 B2 | 7/2004 | Iddan et al. | |
| 6,771,981 B1 | 8/2004 | Zalewski et al. | |
| 6,806,808 B1 | 10/2004 | Watters et al. | |
| 6,823,459 B1 | 11/2004 | Horikoshi et al. | |
| 6,836,377 B1 | 12/2004 | Kislev et al. | |
| 6,847,490 B1 | 1/2005 | Nordstrom et al. | |
| 6,884,213 B2 | 4/2005 | Raz et al. | |
| 6,904,308 B2 | 6/2005 | Frisch et al. | |
| 6,934,093 B2 | 8/2005 | Kislev et al. | |
| 6,934,573 B1 | 8/2005 | Glukhovsky et al. | |
| 6,936,003 B2 | 8/2005 | Iddan | |
| D510,139 S | 9/2005 | Gilad et al. | |
| 6,939,290 B2 | 9/2005 | Iddan | |
| 6,944,316 B2 | 9/2005 | Glukhovsky et al. | |
| 6,950,690 B1 | 9/2005 | Meron et al. | |
| 6,951,536 B2 * | 10/2005 | Yokoi et al. | 600/128 |
| 6,958,034 B2 | 10/2005 | Iddan et al. | |
| D512,150 S | 11/2005 | Iddan et al. | |
| 6,984,205 B2 | 1/2006 | Gazdzinski | |
| 6,986,738 B2 | 1/2006 | Glukhovsky et al. | |
| 7,009,634 B2 | 3/2006 | Iddan et al. | |
| 7,017,822 B2 | 3/2006 | Aisenbrey | |
| 7,022,067 B2 | 4/2006 | Glukhovsky et al. | |
| 7,058,397 B2 | 6/2006 | Ritter | |
| 7,354,397 B2 * | 4/2008 | Fujita et al. | 600/109 |
| 7,515,953 B2 * | 4/2009 | Madar et al. | 600/476 |
| 2001/0017649 A1 | 8/2001 | Yaron | |
| 2002/0032435 A1 | 3/2002 | Levin | |
| 2002/0109774 A1 | 8/2002 | Meron et al. | |
| 2003/0016293 A1 | 1/2003 | Hamamura | |
| 2003/0058345 A1 | 3/2003 | Morris et al. | |
| 2003/0058354 A1 | 3/2003 | Parulski et al. | |
| 2003/0095193 A1 | 5/2003 | May et al. | |
| 2003/0174208 A1 | 9/2003 | Glukhovsky et al. | |
| 2004/0092825 A1 | 5/2004 | Madar et al. | |
| 2004/0199061 A1 | 10/2004 | Glukhovsky | |
| 2005/0024198 A1 | 2/2005 | Ward | |

OTHER PUBLICATIONS

Chung, D.D.L., et al., (Mar. 1998), "Carbon Fiber Polymer-Matrix Structural Composite as a Semiconductor", Part of the SPIE Conference on Sensory Phenomena and Measurement Instrumentation for Smart Structures and Materials, San Diego, California, SPIE Vo. 3330, pp. 401 to 409.

(Undated) "Carbon Fiber Polymer-Matrix Composite as Semiconductor", The Research Foundation of State University of New York, Technology Transfer Services, University of Buffalo, Non Confidential Description, R-5482, consisting of one page.

Wang, Shoukai, et al., (1999), "Apparent Negative Electrical Resistance in Carbon Fiber Composites", Composites, Part B. vol. 30, pp. 579-590.

Yang, Xiaoyu, (Fall 1999), "Carbon Nanotubes: Synthesis, Applications, and Some New Aspects", Thin Films and Nanosynthesis Laboratory, Department of Mechanical and Aerospace Engineering, SUNY at Buffalo, consisting of 32 pages.

PulsON, (May 2000), "Time Modulated Ultra-Wideband for Wireless Applications", 2000Time-Domain Corporation, Time Domain, Rev. 2, (13 pgs.).

Information sheets on Rapid Reader Portable RAPIDViewing Software for the Given Diagnostic System, Given Imaging, (01/02), (2 pages), (www.givenimaging.com).

Information sheets on Rapid 2 Application Software Diagnostic Tools for Effective Patient Management for the Given Diagnostic System, Given Imaging, (© 2001-2002), (2 pages), (www.givenimaging.com).

Information sheets on Rapid Booster System Increased Productivity for the Given Diagnostic System, Given Imaging, (© 2001-2003), (2 pages), (www.givenimaging.com).

* cited by examiner

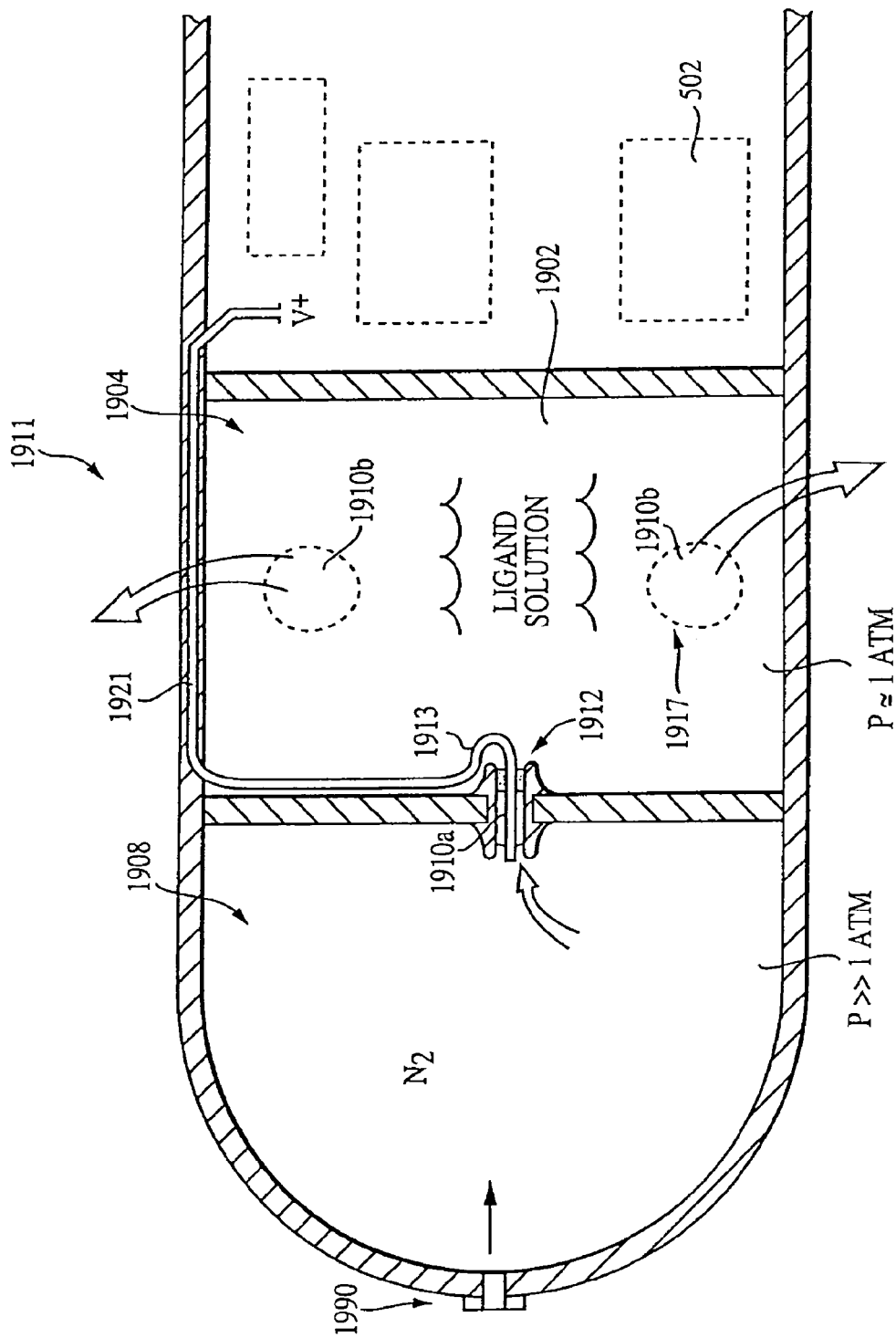

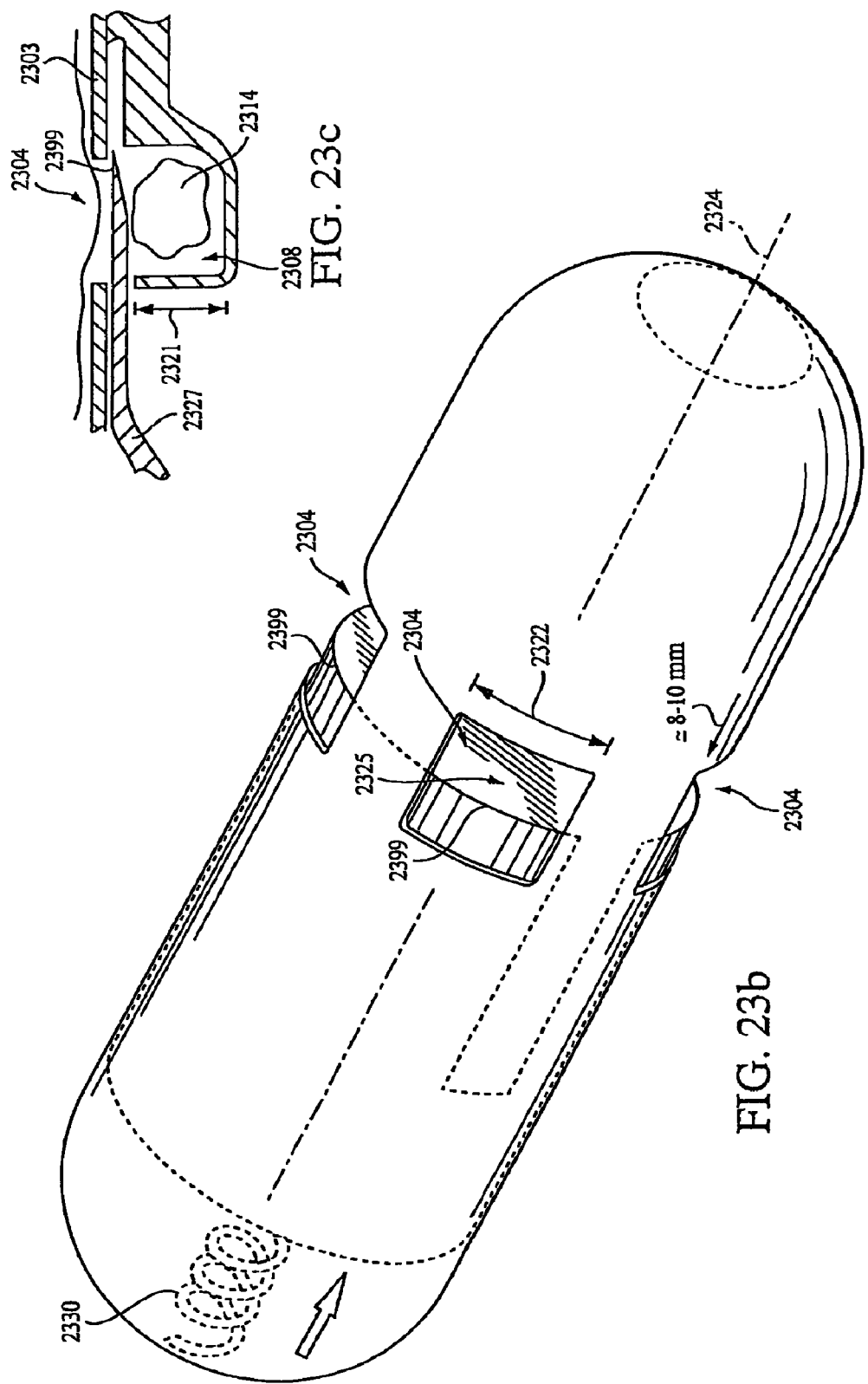

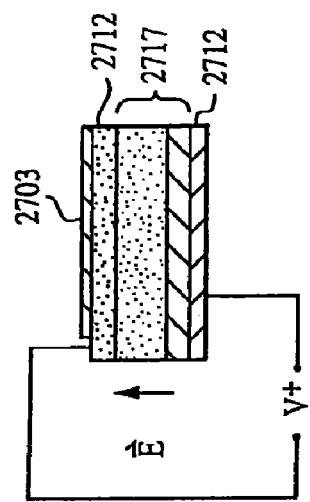
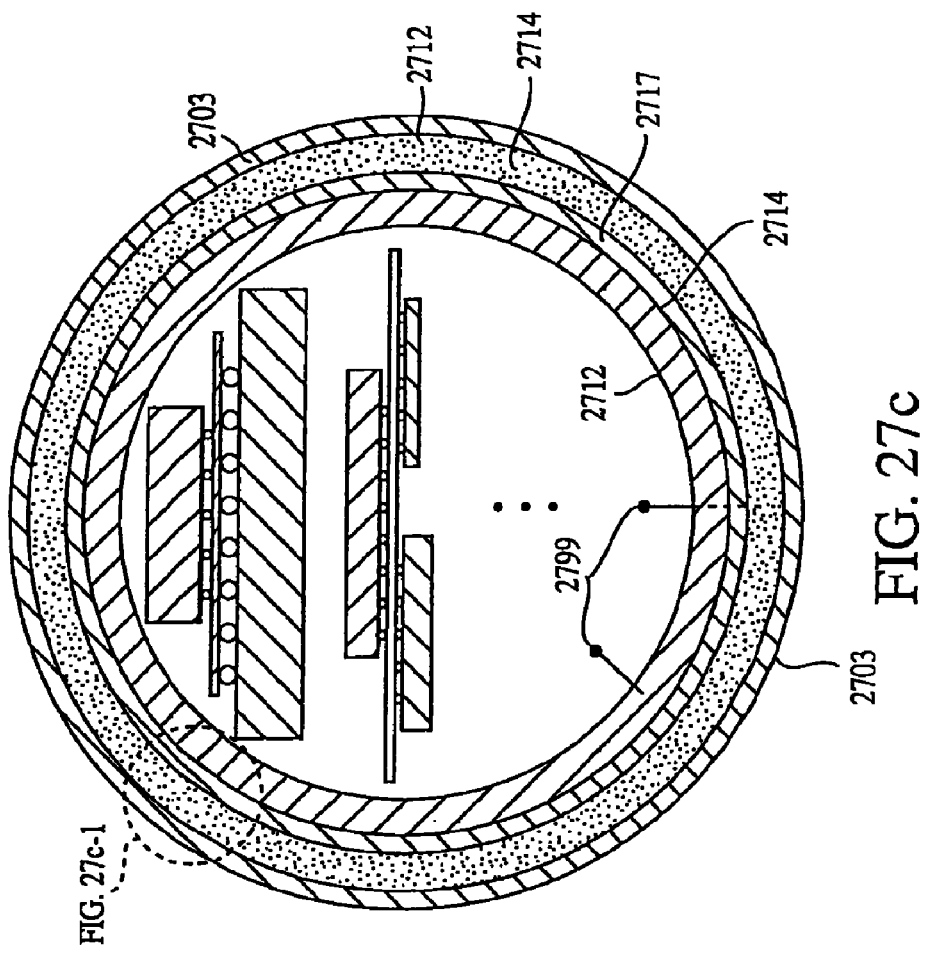
FIG. 27c-1
FIG. 27c

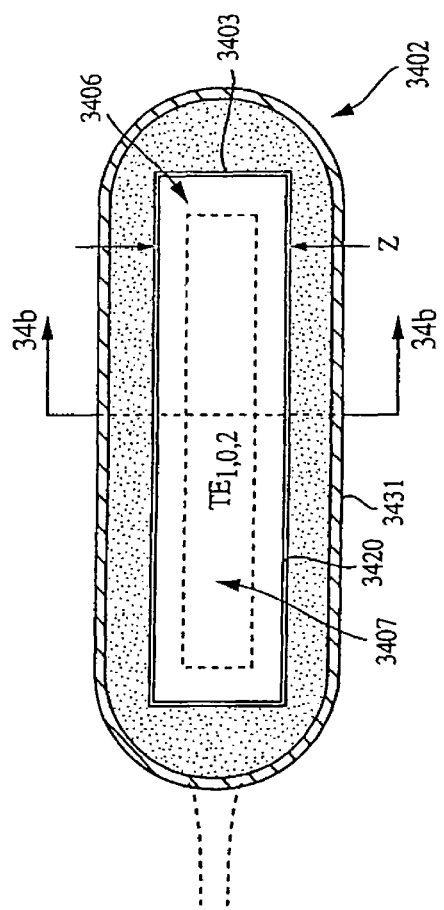
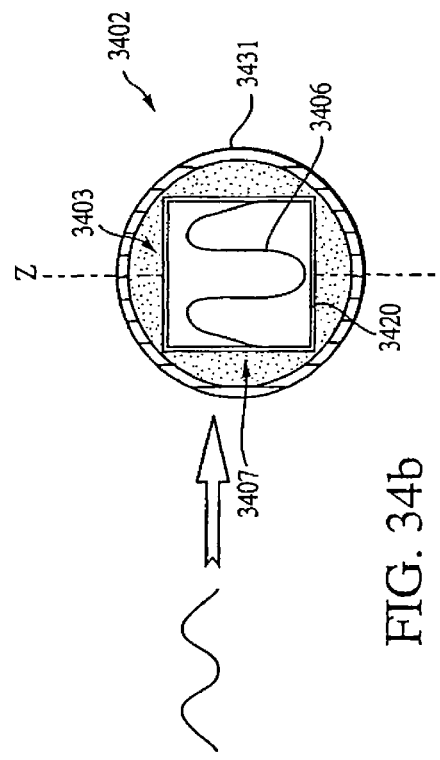
FIG. 34a
FIG. 34b

SOP = START OF PACKET FIELD
EOP = END OF PACKET FIELD
TS = TIME STAMP DATA
EC = ERROR CORRECTION DATA

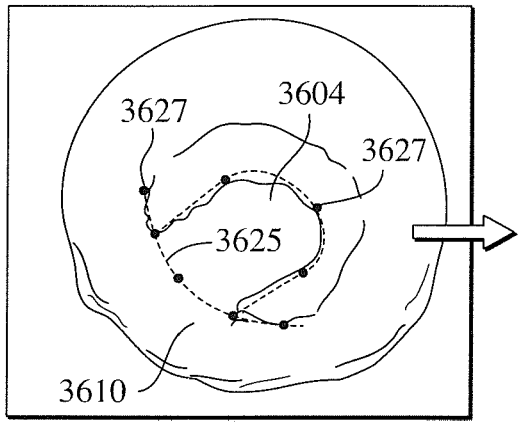
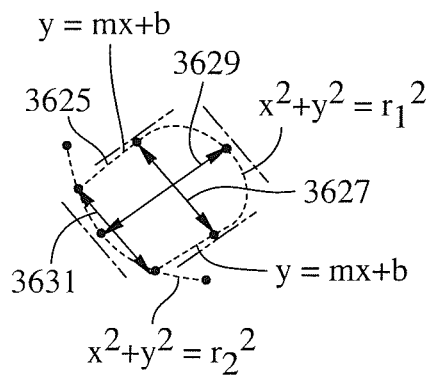
FIG. 36D    FIG. 36E
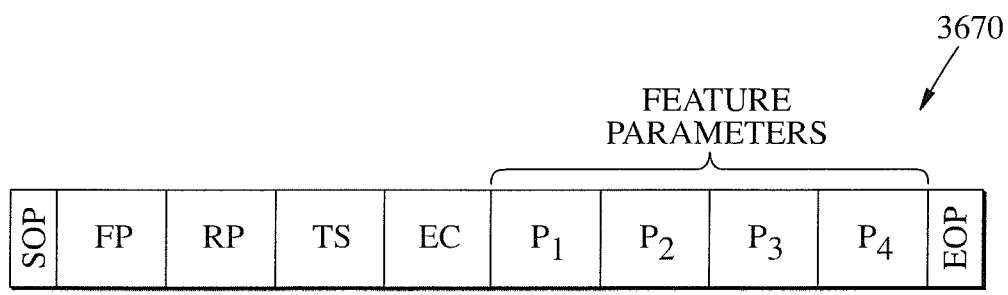
SOP = START OF PACKET
EOP = END OF PACKET
TS = TIME STAMP
EC = ERROR CORRECTION
FP = FORWARD POINTER
RP = REVERSE POINTER
$P_1$-$P_3$ = FEATURE PARAMETER VALUES
$P_4$ = OPTIONAL PAYLOAD DATA
FIG. 36F

ENDOSCOPIC SMART PROBE AND METHOD

This application is a continuation-in-part of prior application Ser. No. 09/817,842 entitled "Endoscopic Smart Probe and Method" filed Mar. 26, 2001, which is a continuation-in-part of Ser. No. 09/259,194 filed Mar. 1, 1999 now abandoned, both of which are incorporated by reference herein in their entirety.

BACKGROUND OF THE INVENTION

1. Field of the Invention

The present invention relates to the field of medical instrumentation, specifically to the use of smart technology within miniature remote devices for the inspection, diagnosis, and treatment of internal organs of living organisms.

2. Description of Related Technology

Endoscopic and colonoscopic techniques are commonly used to inspect the accessible upper and lower portions, respectively, of the human gastrointestinal tract. A traditional endoscopic inspection of a human being (an example of which is the "EGD") requires the patient to be partially or completely sedated while a long, thin, tubular probe is introduced into the esophagus, routed through the stomach, and ultimately into the upper portion of the small intestine (duodenum). This tubular probe typically contains a self-illuminating fiber optic cable and viewing device to allow visual inspection of tissue in the vicinity of the probe tip. See, for example, U.S. Pat. No. 3,901,220, "Endoscopes" issued Aug. 26, 1975. However, due to the tortuous path, fragility, small diameter, and length of the digestive tract, prior art endoscopic inspection such as the aforementioned EGD is limited to only the stomach and upper portions of the small intestine. See FIG. 1.

Similarly, traditional colonoscopic examination utilizes a thin, tubular fiber optic probe inserted into the large intestine (colon) via the rectum. Even the most penetrating colonoscopic inspections are limited to the colon and the terminal portion of the small intestine (ileum), due again primarily to the tortuosity and fragility of the large intestine and ileum. While a substantial number of diseases and conditions afflict the stomach, duodenum, colon, and ileum, several others may occur within the remaining, inaccessible portions of the gastrointestinal tract including the jejunum of the small intestine.

Both endoscopic and colonoscopic inspections further run a small but significant risk of physical damage to the patient, such as perforation of the duodenum or ileum, especially where disease has progressed to an advanced stage and the surrounding tissue has weakened or degenerated.

Alternatively, non-invasive diagnostic techniques such as X-ray inspection (e.g., so-called "upper-GI" and "lower-GI" series), which involves introducing barium or other contrast agents into the patient, are useful in identifying gross abnormalities, but require careful interpretation and are susceptible to misdiagnosis, shielding effects, and a plethora of other potential pitfalls. Furthermore, such techniques expose the patient to significant doses of ionizing X-ray radiation which ultimately may be deleterious to the patient's health.

The somewhat related technique of X-ray computed axial tomography (CAT) scanning provides information about the general condition of an individual's intestinal tract and internal organs, yet does not possess the necessary resolution to facilitate diagnosis of many types of conditions. It also suffers from the drawback of exposing the patient to substantial quantities of X-ray radiation. CAT scans of the GI tract also may require the use of ingested and/or intravenous contrast agents, the latter notably having a small but non-zero incidence of patient mortality. Furthermore, certain patients may not be given such contrast agents due to allergies or other pre-existing medical conditions, thereby substantially reducing the efficacy of the CAT scan as a diagnostic technique for these patients.

Magnetic resonance imaging (MRI) techniques, well known in the medical diagnostic arts, have certain benefits as compared to the aforementioned CAT scan, yet also suffer from limitations relating to resolution and interpretation of the resulting images, and in certain instances the required use of "contrast" agents. More recently, enhanced MRI techniques are being used to aid in the diagnosis and treatment of Crohn's disease, yet even these enhanced techniques suffer from limitations relating to resolution, especially when the disease has not progressed to more advanced stages.

Another related and well-known medical diagnostic technology is that of autofluorescence endoscopy. Simply stated, autofluorescence endoscopy uses a light source having specific characteristics (typically a coherent source such as a laser) to illuminate a portion of tissue under examination; the incident light excites electrons within the atoms of the tissue which ultimately produce a quantum transition therein resulting in an emission of electromagnetic radiation (fluorescence) from the tissue at one or more wavelengths. Additionally, so-called "remitted" energy, which is incident or excitation energy reflected or scattered from the tissue under analysis, is also produced. The fundamental principle behind the autofluorescence technique is that diseased or cancerous tissue has a different autofluorescence (and remitted light) spectrum than that associated with healthy tissue of similar composition; see FIG. 2. Generally speaking, diseased tissue autofluoresces to a lesser degree at a given wavelength under the same incident excitation radiation than healthy tissue. See, for example, U.S. Pat. No. 4,981,138, "Endoscopic Fiberoptic Fluorescence Spectrometer" issued Jan. 1, 1991. Unfortunately, however, the applicability of autofluorescence techniques has traditionally been limited to external areas of the body, or those accessible by endoscopic probe, thereby making this technique ineffective for diagnosing diseases of the central portion (jejunum) of the small intestine. See also U.S. Pat. No. 5,827,190, "Endoscope Having an Integrated CCD Sensor".

In summary, endoscopic inspection is arguably the most efficient and effective prior art method of diagnosing conditions of the intestinal tract, especially those of a more chronic and insidious nature. However, due to its limited reach, endoscopic inspection is not an option for diagnosing or treating the central portions of the digestive tract, specifically the central region of the small intestine.

Delivery of Pharmaceutical or Other Agents

Oral administration is perhaps the most desirable approach for delivering an antigen or pharmaceutically active agent to a living subject. This approach, however, suffers from the significant disability relating to the generally poor uptake of antigens or pharmaceutically active agents by the intestinal tract. Some compounds are not suited for oral administration due to their poor penetration into the blood stream of the subject. Additionally, some orally administered agents may be destroyed through exposure to various substances present in the gastrointestinal system, such as proteolytic enzymes. The digestive process involves the physical and chemical breakdown of ingested food, followed by selective absorption of digested molecules in the intestine. Protease, lipases and other hydrolases secreted into the intestine effect the chemical breakdown of proteins, carbohydrates and other larger molecules present in food, and may also effect the operation or properties of administered agents.

So-called "controlled release" systems for delivery of agents have been developed to counter some of the foregoing problems with oral administration. Such systems are typically designed to administer drugs in specific areas of the body, such as the small intestine where absorption is comparatively good. In the intestinal tract it is critical that the agent not be carried beyond the site of delivery, or otherwise eliminated before it can exert pass into the bloodstream or exert the desired topical effect. In many cases, if a delivery vehicle can be made to couple itself to the lining of the appropriate viscus, its associated agent will be delivered to the targeted tissue, generally as a function of proximity and duration of the contact. Such functional relationship is especially true of radioisotopes.

Another current method of targeting drugs in the gastrointestinal tract involves the uncomfortable, time-consuming and often expensive method of intubation, in which a long, flexible tube containing the drug for delivery is literally snaked into the intestine of the subject.

Most pharmaceuticals or drugs are specific, in that they are recognized by key molecules which are involved in the disease. These drugs are then able to act directly on their relevant targets. For other diseases, such as cancer and inflammatory diseases, drug molecules are much less specific, and considerable often undesirable side effects are seen with these drugs. Hence, if these agents could be delivered to a specific location within the intestine, such diseases could potentially be treated more effectively with reduced side effects.

For tumorous tissue, it has been demonstrated that particles coated with a surfactant show prolonged circulation time after intravenous administration, and selectively accumulate in tumors because of comparatively high tumor vasculature leakage. These circulating surfactant-coated particles avoid rapid clearance by reticuloendothelial system. This technique of delivery to tumors is commonly referred to as "passive".

Conversely, so-called "active" delivery is based on attachment of circulating particles to antibodies directed against antigens associated with the tumor vasculature. These antibodies (and other molecules, including short peptide sequences) can be used for targeting anti-cancer drugs in living subjects having tumorous tissue.

Receptors and Ligands

The interaction between a drug molecule and its receptor is often complex, and relates to the chemical mechanisms of drug action. Drug molecules attach (frequently in a reversible manner) to their receptors, not at a single site or by a single type of interaction, but rather in a variety of chemical modes with a number of complementary sites on the receptor molecule. Interactions that can be involved include relatively strong forces such as covalent bonding (comparatively rare), hydrogen bonding, or ion-ion interactions, and/or much weaker forces such as ion-dipole interactions, dipole-dipole interactions, charge-transfer complexation, van der Waals interactions, and hydrophobic bonding. The weaker attractive forces are often of most significance in drug-receptor interactions. Although individually weak, in the aggregate they provide a strong attachment of the drug to the receptor.

Most human immune system cells are white blood cells, of which there are many types. Lymphocytes are one type of white blood cell, and two major classes of lymphocytes are T cells and B cells. T cells are immune system cells that help to destroy infected cells, and coordinate the overall immune response. As is well known, the T cell includes a molecule on its surface known as the T-cell receptor. This receptor interacts with, inter alia, molecules called MHC (major histocompatibility complex). MHC molecules are disposed on the surfaces of many other cells of the body, and help the T cell to recognize antigen fragments present in its environment. B cells are best known for making antibodies which bind to an antigen, and marks the antigen for destruction by other immune system cells. In auto-immune dysfunction, the healthy, viable cells of the subject (as opposed to invading antigens) are marked for destruction. Hence, if receptor sites or antibody markers can be properly manipulated through the introduction of specially designed molecules (such as via the probe of the present invention), the defective auto-immune response may be at least partially blocked.

The gastrointestinal tract is lined with a single layer of epithelial cells (the mucosa, or epithelium). In the intestine, this layer protects a highly convoluted surface of projections into the lumen of the small intestine, and crypts, which penetrate into the underlying connective tissue. The epithelium is a particularly attractive site for certain types of therapy (e.g., gene therapy) because of its large mass of cells and its relative ease of access via the intestinal lumen. The lumenal surface of the epithelium interfaces with the external milieu, whereas its basolateral surface interfaces with the internal milieu. Hence, the epithelium may receive nucleic acids applied externally (via the lumen) and to direct the protein or peptide products to, inter alia, the luminal surface (such as for correcting a defect of digestion or absorption) or to the basolateral surface for secretion into the circulatory system (so as to act systemically).

The surface area of the intestinal epithelium is greatly increased by the presence of long, projections known as villi. Villi are microscopic, hairlike, thin-walled structures that contain many small blood vessels. There are large numbers of villi per square inch of intestine and, as a result, the total surface area of the inner wall of the small intestine is increased several hundred times. The physiological function of the villi is to facilitate absorption of dietary components that have hydrophilic and lipophilic properties that do not favor passive diffusion processes. Villi serve the same purpose in the case of negatively charged (drug) molecules: The large surface area created by the villi permits a large total absorption of hydrophilic molecules that have a poor diffusion tendency.

Additionally, the intestine has substantial length. This means there is a very large mass of tissue available for gene transfer. Moreover, the longitudinal character offers a high degree of precision with respect to the dosing of an introduced gene. The present invention provides a method for the in vivo targeting of the intestinal epithelium for the introduction of nucleic acids.

It has been known for some time that a number of specific uptake mechanisms exist in the intestinal tract for the intake of molecules. Thus, there are specific uptake mechanisms for a variety of different molecules. Most of these uptake mechanisms depend upon the presence of a specific protein or enzyme situated in the mucosal lamina which binds to the molecule and transports it into the cells lining and lamina. In certain cases, however, a specific binding protein is released into the intestine, which binds to its ligand in the lumen of the intestine. For example, during iron uptake in the intestine transferring is released from the stomach, binds to iron and is in turn bound by a receptor on the duodenal mucosa. The receptor-iron-iron complex is then taken up by receptor mediated endocytosis.

Despite the foregoing techniques, no existing prior art approach presently provides the ability to deliver pharmaceuticals, ligands, or other therapy agents directly to the central regions of the small intestine, without surgical intervention.

Tissue Ablation

Anatomical organs, such as the intestine, can develop a variety of abnormal conditions. It is known to treat such abnormal organ conditions in more severe cases by removal of the affected portion of the intestine. However, removal of even a portion of the intestine requires invasive surgery and general anesthesia, as well as a long recovery period. Other deleterious side effects (such as stomata) generally accompany such surgery, thus making such procedures highly undesirable from the perspective of the patient.

Alternatively, tissue may be ablated by heating the tissue (thermal ablation), freezing the tissue (cryogenic ablation), mechanically scraping or cutting of the tissue, or otherwise applying energy or manipulation of the tissue. The terms "ablating" and "ablation" as used herein broadly refer to the destruction, removal, or alteration, of tissue or the function of tissue, such as through cauterization, coagulation, scalloping, necrosing, removal, or the like. Ablation is most frequently accomplished by introducing an ablating member to an area or volume in proximity to the damaged tissue. Thermal ablation devices utilize a variety of ablation techniques including laser (i.e., coherent electromagnetic) energy, RF energy such a millimeter waves, radiation such as alpha and beta particles or gamma rays, an electrically resistive coil, or any other method of delivering energy.

Lasers are one of the most common devices used for surgical ablation. Lasers are inherently focused to a small area, However, laser energy (as well as other thermal and cryogenic devices) must be carefully applied and controlled to ensure that the abnormal tissue is ablated without damaging other normal tissue or organs in proximity to the target tissue.

Typically, large laser radiation sources, such as a Nd:YAG laser or a $CO_2$ laser, have been coupled to a mobile hand-held device ("laser scalpel") by means of fiber optic cabling. Thus, by correctly orientating the scalpel, the light generated by the laser generator is applied to the desired area. The use of such large lasers, however, suffers from several deficiencies. One such deficiency is size of the laser energy source, and the requirement that it be physically positioned within a fairly short distance from the scalpel so as to minimize problems with the fiber optic coupling. Additionally, such lasers inherently inefficient in comparison to semiconductor laser diodes.

Accordingly, most ablation techniques relating to intestinal tissue use endoscopes or other such devices to (i) inspect the condition of the tissue, and (ii) control the application of energy to the damaged tissue. However, as with other endoscopic techniques, ablation of the intestine is limited to those areas reasonably within reach of the endoscope. In cases where ablation of the central portion of the small intestine is required, the prior art provides no suitable approach short of invasive surgery.

Radiation Therapy

Typical prior art ionizing radiation treatment (such as for cancer or other malignant lesions) utilizes gamma or X-ray radiation to induce molecular-level damage within the cancerous or malignant tissue cell nuclei to ablate and effectively kill such cells and/or thwart their further reproduction. Existing radiation delivery systems include an external gamma/X-ray radiation source, or in certain cases, use of a radioisotope introduced by injection into the tissue or introduced intravenously, or other vehicle which is swallowed by or introduced endoscopically into the patient. However, these methods generally have the substantial drawback of indiscriminately irradiating mass amounts of undiseased tissue adjacent to the malignant cells. For example, the deposition profile of highly penetrating forms of radiation such as gamma or X-ray radiation (both forms of electromagnetic radiation with comparatively high frequencies, and hence energies) can not in many cases be accurately controlled within the human body; hence, there is significant collateral damage resulting from such external treatments to tissue and organs immediately in front of and behind the malignancy in the radiation line-of-sight. Hence, the use of gamma and/or X-ray radiation generally contributes significantly to whole body dose to the subject. Furthermore, gamma (and to a lesser degree X-ray) radiation is not easily collimated or laterally focused due to its highly penetrating nature, relating largely to its high energy photons. Such radiation exhibits a significant "tenth" thickness in most materials, even dense materials such as lead.

For a myriad of reasons including the increase likelihood of adhesions or perotineal cavity infection, it is also impractical and highly undesirable to surgically perforate the abdomen wall (via lapriscopy or other such techniques) in order to gain closer access to the intestine for radiation treatment. Esophogeal and rectal endoscopes of the type well known in the arts are useful in the localized inspection, biopsy, and treatment of accessible areas of the intestine, but again suffer from the inability to reach the central portions (majority) of the small intestine. Based on the foregoing, an improved method and apparatus for accurate, localized irradiation of the small intestine, including the interior regions thereof, is needed.

A more recent approach has been to use "targeted" delivery of radioisotopes to tumor sites or other areas of the intestine. See for example, U.S. Pat. No. 5,902,583 entitled "Genetic Induction of Receptors for Targeted Radiotherapy" issued May 11, 1999, wherein radio-labeled ligand localization comprising transducing the tumor with a gene encoding a membrane expressed protein unique to the tumor is described. Monoclonal antibodies directed to "tumor-associated" antigens on cancer cells, and radioactively labeled peptides able to bind to receptor positive tumor cells are also available. However, an improved method of administration and localized delivery of such radio-labeled ligands, especially to the epithelium of the intestine, is needed.

Ultrasound Imaging

Ultrasound imaging systems are commonplace in the prior art. During operation of these systems, ultrasonic signals, typically on the order of 250 kHz to 20 MHz, are transmitted into a subject's anatomy where they are absorbed, dispersed, refracted and reflected. The reflected ultrasound energy is received at a plurality of transducer elements which convert the reflected ultrasound energy back into electronic echo signals via the piezoelectric properties of the transducer. These received echo signals undergo a process known as beamforming; this process correlates the ultrasound signals into spatially coherent "beams." Subsequently the processed signals are further analyzed to extract echo and Doppler shift information, and ultimately obtain an image of the subject's targeted anatomy (e.g., tissue, organs, vessels). Such images are represented in any number of common formats, including the so-called "B-mode." A B-mode image is an image in which the brightness or luminosity of component pixels is adjusted in proportion to a corresponding echo signal strength or other measured parameter. The B-mode image represents a two dimensional cross-section of the subject's target area tissue through a transducer's scanning plane. The typical ultrasound B-mode image is formed by scanning the subject's target tissue in a predetermined pattern (e.g., linear, raster, conic, or sector scan) of the patient's target area by the transducer probe. The individual images produced by ultrasound imaging systems include discrete frames. Each frame has a limited field of view due to a relatively narrow region traversed by the transmitted ultrasound energy. As the transducer probe is manipulated along the patient's body surface, each previous image is replaced on the viewing display by a new image defined by the current position, and thus field of view, of the transducer probe. Interposed tissue (i.e., that between the organ of interest and the transducer(s)) also adds noise and "clutter" to both the transmitted and reflected signals, however, thereby reducing the accuracy of the system, and reducing the minimum spatial resolution of which the system is capable.

Inspection and Diagnosis

Another disability associated with prior art "capsule" based inspection systems such as the M2A device manufactured by Given Imaging relates to the practicalities of viewing the image data derived therefrom. Specifically, several hours worth of data (non-compressed) are typically generated by the device during its traversal of the human intestinal tract. Reviewing this data on a minute-by-minute basis can be very time consuming and cost-inefficient for a physician or health care provider, since likely only a very small portion of the data is of any significance in a diagnosis. In many cases, disease (e.g., polyps, etc.) is quite localized in nature; hence, the physician must necessarily analyze several hours worth of data for potentially only a few minutes of worthwhile information. This disability makes the diagnosis and treatment process more lengthy than needed, and thereby introduces significant cost inefficiencies which may actually act as a barrier to adoption or use of the technology in the first place. This is especially true since, in most cases, a highly skilled and qualified physician or expert is required to analyze the data produced by the probe in order to make a diagnosis, thereby resulting in either (i) excessive fees for performing the diagnosis as compared to other prior art treatment options; or (ii) the physician or health care provider absorbing the additional cost of performing the diagnosis as compared to the other available techniques. On a "dollars per hour" basis, prior art devices such as the M2A capsule are very cost inefficient for the physician and health care provider, and are generally avoided despite their desirable technological features.

Another problem associated with the requirement under the prior art to view all of the visual data obtained from the probe relates to fatigue of the viewer (physician). Specifically, it is known that the quality of review will degrade as a function of viewing time, since the viewer invariably becomes tired or fatigued after extended durations of viewing. This is particularly true of the viewer's eyes and higher cognitive functions. Continuous viewing of several hours of intestinal visual data, which comparatively speaking has little in the way of variation or change, can significantly reduce the physician's acuity and mental/visual faculties. Ideally, the physician could review the data in shorter segments; however, this approach does not address the foregoing issues regarding time efficiency, since the physician must still view all of the data, whether in segments or as one uninterrupted segment.

Additionally, there is a significant potential drawback associated with viewing multiple segments of data for one patient at different times, namely the reduction in correlation of the data from different segments by the viewing physician. Specifically, if the physician views for example four 60-minute segments of a patient's data on four different days, their chance of correlating artifacts or data of interest present in one segment (such as the presence of diseased tissue, polyps, etc.) to that of another segment, which may be viewed as much as four days later in the present example, is potentially reduced. Even when taking notes, the physician may forget conscious or subconscious information gleaned from reviewing an earlier segment when viewing a subsequent segment several days later. Furthermore, the physician may have to refresh their memory by running back all or a portion of the earlier segment(s). The physician may also, when viewing data from multiple patients over the course of a given week, confuse data associated with one patient with that for another. This effect is even present to a lesser degree when viewing the data in contiguous (i.e., uninterrupted) fashion. Hence, there is in effect a "synergy of correlation" associated with viewing all of the data for one patient at the same time (or in close sequence).

Yet a further problem associated with the prior art capsule diagnosis techniques relates to the potential for legal liability associated with the diagnosis. Specifically, under a medical malpractice theory, physicians and health care providers may expose themselves to potential liability under various laws if their review of the data generated by the capsule fails to detect a condition or disease which would normally be detectable by such means. Hence, if the physician or other diagnostic professional "skips over" part of the data in an attempt to reduce the length of time spent performing the diagnosis (and hence the effective cost), they are in effect significantly increasing the risk that they will be sued for medical malpractice. When coupled with the aforementioned cost disincentives, the caregiver is faced with the choice of (a) reducing their cost efficiency (and hence profit) while increasing their risk for a significant malpractice legal action, or (b) continuing to use the prior art technologies which generally do not suffer from either of these disabilities to anywhere near the same degree.

Based on the foregoing, it would be highly desirable to provide an apparatus and method by which treatment could be rendered remotely to various portions of the intestinal tract. More specifically, it would be highly desirable to provide an apparatus and method for, inter alia, (i) visual, autofluorescent, ultrasonic, or other types of inspection; (ii) delivery of medication, pharmaceuticals, radioisotopes, direct radiation; (iii) biopsy; (iv) physical expansion of constricted or scar tissues; (v) detection of the presence of one or more molecules present in vivo; and (vi) selective tissue ablation, in all portions of the interior of the digestive tract including the small intestine without invasive surgery or other extraordinary and potentially deleterious means.

Furthermore, such improved apparatus and methods would address the barriers to more widespread adoption of the technology within the medical community, including the high relative cost per evaluation, and the significantly increased risk for medical malpractice liability.

SUMMARY OF THE INVENTION

The present invention satisfies the aforementioned needs by providing an improved endoscopic device and method of diagnosing and treating patients utilizing the same.

In a first aspect of the invention, an endoscopic "smart probe" is disclosed which operates autonomously of external devices and is sized and shaped such that it may be introduced into the esophagus and ultimately small intestine of the patient undergoing examination/treatment. The probe traverses the patient's intestinal tract by virtue of normal peristaltic contractions occurring therein. In a first embodiment, the probe utilizes a miniature sensor such as a charge-coupled device (CCD) camera and a fiber optic/diode illumination system for inspection of the intestine wall. The CCD camera operation is supported by, inter alia, a "flash" analog-to-digital converter (ADC), microcontroller, and an inductive (or capacitive) data transfer sub-circuit which facilitates real-time transfer of the acquired image data out of the probe to an external monitoring and control device (MCD) in order to provide real-time data analysis and to minimize probe memory requirements and size. The MCD incorporates a signal processor, microprocessor, video driver and display, and storage device. Inductive coupling is utilized as a source of power to the probe to permit operation of the CCD, ADC, and microcontroller, as well as other functions such as illumination. The probe is completely sealed so as to be protected against damage by gastric acids or other potentially damaging substances residing within the patient.

In a second embodiment, the smart probe of the present invention further includes a miniature package digital signal processor (DSP), and random access memory (RAM) with associated memory controller in addition to the CCD array, ADC, and other components. The DSP provides data formatting and compression functions within the probe to permit storage of discrete amounts of image data within RAM during probe operation without the need to transfer data out of the probe. Accordingly, the probe can operate autonomously of the MCD for greater periods of time, thereby providing the operator/physician with additional flexibility. Alternatively, the probe can transfer data out at a faster rate in compressed format. A flash memory of the DSP may also modified by way of program data transmitted to the probe via the data transfer sub-circuit.

In another embodiment, a miniature NiMH or comparable battery is used to power the device during its progression through the patient either in conjunction with or in lieu of the aforementioned inductive power transfer circuit.

In yet another embodiment, the probe includes a fully integrated "system on a chip" (SoC) application specific integrated circuit (ASIC) incorporating, inter alia, a digital processor core, embedded program and data random access memories, radio frequency (RF) transceiver circuitry (such as a "Bluetooth™" 2.4 GHz transceiver or TM-UWB PPM device), modulator, ADC, and analog interface circuitry. The processor core comprises, inter alia, an extensible RISC processor which is user configurable with respect to a set of predetermined extension instructions specifically adapted to various processing tasks associated with various embodiments of the probe, such as (visual) image processing, autofluorescense imaging and analysis, ultrasonic signal processing, and the like. Such user-customizable, optimized extensible processor cores advantageously have a reduced gate count require less silicon, and consume less power than comparable non-optimized cores. Accordingly, the manufacturer or designer may select the appropriate optimized core configuration and instruction set applicable to the anticipated use of the probe, thereby reducing the required space needed within the probe to accommodate the ASIC, and the power consumed thereby. Additionally, the core (and in fact the entire SoC device) optionally includes one or more processor "sleep" modes which allow portions of the core and/or peripherals to be shut down during periods of non-operation in order to further conserve power within the device and reduce heat generation.

In yet another embodiment, the imaging array comprises an infrared (IR) imaging sensor array adapted to receive thermal energy (infrared-band electromagnetic radiation) radiated by the intestine wall tissue.

In a second aspect of the invention, an endoscopic smart probe is disclosed which is useful for autofluorescence analysis of the intestinal tract of a patient. In one embodiment, the smart probe incorporates a miniature semiconductor (diode) laser tuned to emit coherent light energy in the desired autofluorescence band. A complementary CCD array is used to detect the fluorescent energy radiated by the surrounding intestinal tissue during or after excitation by the laser energy. The charge accumulated on the CCD cells is then amplified and converted to a digital format for further processing and analysis as previously described with respect to the first aspect of the invention. In another embodiment, both visual and autofluorescence imaging capability are included within a single smart probe.

In yet another embodiment, the laser diode and associated circuitry and power supply are adapted to ablate intestinal tissue through direct irradiation with coherent electromagnetic energy.

In a third aspect of the invention, an improved endoscopic device useful for implanting the aforementioned endoscopic smart probe is disclosed. The device utilizes a probe housing which retains the smart probe during insertion of the device tip into the patient, yet which also allows remote expulsion of the probe from the device into the patient when desired by the operator. In one embodiment, the probe is expelled by air or fluidic pressure transmitted down the length of the device; a rupturable closure or diaphragm is used to protect the probe during insertion.

In a fourth aspect of the invention, a method for inspecting and/or treating the interior regions of the intestinal tract using the aforementioned smart probe is disclosed. The probe is introduced endoscopically as described above (or orally), and monitored via the data transfer circuit previously described, thereby providing real-time visual and/or autofluorescense imaging of the interior surfaces of the intestinal as the probe traverses the intestinal tract. Alternatively, the probe may be deployed within the patient, activated to obtain data for one or more periods, and then analyzed after expulsion from the patient.

In a fifth aspect of the invention, an improved apparatus and method for delivery of radionuclides to diseased tissue within the intestinal tract of a living subject are disclosed. In one exemplary embodiment, the apparatus comprises the foregoing "smart" probe which has been further adapted to carry and expose a radioactive source at a prescribed location within the intestine. The source can comprise a gamma, beta, alpha, and/or even neutron emitting material which is shielded by a retractable shield. The retraction of the shield is controlled via the on-probe processor or microcontroller, or alternatively via an externally generated signal.

In a second embodiment, a plurality of ligands "tagged" with radionuclides are carried within a repository or container within the probe until the desired location within the intestinal tract is reached. Under either internal or external control, the probe deploys the ligands such that the ligands are deposited on the intestine wall structures such as, for example, the villi of the small intestine. Receptor sites on the tumor cell membrane or other affected locations within the intestinal wall, which are specifically targeted by the ligands, receive the tagged ligands, which then proceed to ionize tumor cell material via emitted beta, alpha, gamma, or neutron radiation until decay or evacuation of the radionuclide.

In a third embodiment, the probe is adapted to contain a plurality of nanostructures (e.g., $C_{60}$ fullerenes, also known as "Buckyballs") which each include one or more "captured" atoms or molecules of a desired radionuclide within the cavity of the nanostructure. The nanostructures are implanted into the interior wall (such as the villi) of the subject's intestine in the localized region of the diseased tissue or tumor and absorbed at least partially thereby either by passive diffusion or other mechanisms. In one variant, the radionuclide held within the fullerene is chosen to have a very short half-life so as to mitigate unwanted exposure to non-diseased tissue after absorption of the fullerenes into the intestine wall.

In a sixth aspect of the invention, an improved apparatus and method for delivering chemical or biological agents (such as ligands, medication, microspheres, contrast agents, or even liquid radionuclides) is disclosed. The apparatus generally comprises an endoscopic smart probe having at least one reservoirs containing at least one chemical or biological agent, the agent being selectively releasable from the reservoir(s). In one exemplary embodiment, the apparatus comprises a smart probe configured with an etched substrate element having one or more reservoirs with permeable or controlled release coverings (caps). The release of the medication occurs through (i) the predetermined disintegration or dissolution of the caps; (ii) permeation or diffusion through the caps; and/or (iii) controlled dissolution of the cap material, such as through the application of an electrical current.

In a second exemplary embodiment, one or more molecules of the chemical/biological agent are disposed within the cavities of nanostructures, the nanostructures being carried within a repository in or on the probe. The nanostructures are released at a desired location and subsequently absorbed into or diffused through the tissue wall, thereby ultimately delivering the molecules of medication directly to the desired location(s).

In seventh aspect of the invention, an improved method of medication or ligand delivery within a living subject via nanostructure structures is disclosed. The method generally comprises providing at least one molecule within a nanostructure structure; disposing said nanostructure structure (and molecule) within an autonomous probe; disposing said probe in vivo, such as in the intestinal tract of the subject, and depositing the nanostructure structure at a desired location in vivo. In one exemplary embodiment, the molecule is a ligand targeted for specific receptor sites on a tumorous entity within the subject's small intestine, and the nanostructure comprises a Carbon-60 "fullerene" structure. Upon deposition of the fullerene(s) in the region of the tumor cells, the ligand is received by the targeted receptor, the fullerene "cage" effectively intact and acting to protect the ligand from other potentially degrading or interfering processes.

In another exemplary embodiment, one or more specially selected polymerized molecules are disposed within the cavity of the nanostructure structure such that the polymerized molecule(s) is/are captured therein. The polymerized molecule(s) may comprise, for example, a grouping of ligands, or a ligand with a co-associated "retainer" molecule. Upon introduction of the structure in vivo, the polymerized molecule(s) are depolymerized or otherwise, thereby allowing selected components of the molecule(s) to be extracted or released from the nanostructure. These released components are then diffused, received by complementary receptors, or otherwise absorbed by the targeted tissue in the subject. Alternatively, a ligand is disposed externally to the fullerene cage, thereby allowing bonding to a receptor site with the fully polymerized molecule intact. In one variant, the polymerized ligand and associated fullerene/retainer molecule is sufficiently unstable that the ligand is "torn" from the fullerene/retainer, thereby allowing the ligand to remain disposed on the receptor.

In yet another exemplary embodiment, "nanotubes" are formed which contain one or more molecules for delivery to the subject. In one variant, the nanotubes contain ligands targeted to one or more receptors on a tumor. The nanotubes are disposed within solution in a reservoir of the smart probe such that they may be selectively released at a desired location, such as at the site of the tumor within the subject's intestine. Upon exposure to acids in intestinal tract (after release from the probe), the nanotubes preferentially degrade at their tapered ends and release their internal molecules (e.g., targeted ligands). Alternatively, the active portion of the ligand is disposed in a free end of the nanotube, such that the ligand may be readily received by the targeted receptor on the tumor cells. In yet another variant, the nanotubes are disposed in an array, ligand-side out, such that the ligands may be readily extracted from the nanotubes upon reception by the targeted receptors.

In an eighth aspect of the invention, an improved apparatus and method for obtaining a biopsy of the intestinal wall of the subject are disclosed. In one exemplary embodiment, the apparatus includes at least one selectively controlled aperture and associated reservoir disposed in the outer region of the probe. Upon the probe reaching the desired location within the subject's intestine, the aperture is selectively opened, thereby exposing the reservoir beneath. Intestinal tissue protruding through the aperture due to, inter alia, surface tension, is excised by closing the aperture shutter, the excised tissue being retained within the reservoir until the probe is expelled from the subject, at which point the excised biopsy may be examined using any number of well known techniques. In another embodiment, one or more selectively controllable "scoops" disposed on the surface of the probe are provided which, when activated, collect tissue cells as the probe traverses the intestine.

In a ninth aspect of the invention, an improved apparatus and method for treating constrictions, obstructions (or adhesions occurring between the interior surfaces of the intestine wall) of the intestinal tract are disclosed. In one exemplary embodiment, the apparatus comprises the smart probe of the invention having a reduced radius and being equipped with an inflatable element which expands the effective radius of the probe in at least a portion of its cross-section, thereby simultaneously expanding the surrounding intestinal tissue. In one variant, the probe includes a pressurized gas reservoir (e.g., "trailer") which acts as a source of potential energy for the inflatable element upon activation, thereby minimizing the electrical power requirements of the device.

In another embodiment, the trailer acts as a reservoir for the probe for dispensing chemical or biological agents, microspheres, fullerenes, nanotubes, or the like, as previously described.

In yet another embodiment of the apparatus, the probe comprises a micro-solenoid assembly with a cam-like structure which, based on the application of electrical current through the solenoid, permits a portion of the probe to expand (and subsequently contract) under command of the probe's microcontroller or other external signal.

In a first embodiment, the method of treating generally comprises first disposing the probe within the intestine of the subject proximate the constriction; and causing the probe to expand in radius or otherwise deform its shape so as to expand at least a portion of the constriction. In one exemplary variant of the method, the probe is tracked using conventional X-ray techniques such that its proximity to the constriction can be accurately determined. When properly positioned, the probe is expanded within the constriction as required to at least partially relax the constriction. In another variant, the probe location is tracked via a radio frequency, ultrasonic, or other tracking signal emitted from the probe. In yet another variant, a piezoelectric transducer element disposed on the probe (described below) is used to acoustically determine the proximity of the probe to the constriction/obstruction. In yet another variant, the CCD or MOS imaging array is used to optically (visually) determine the proximity of the probe to the constriction/obstruction.

In a second embodiment, the method comprises disposing the probe within the intestine of the subject proximate the constriction; and causing the probe to release one or more chemical substances or electrical charge so as to induce expansion or contraction of at least a portion of the constriction.

In a tenth aspect of the invention, an improved smart probe having a "smart" housing and electronics configuration is disclosed. Portions of the housing are fabricated from a multi-layer laminated semiconducting/conducting carbon fiber polymer matrix which integrates the functionality of one or more components within the housing itself, thereby obviating the need for separate, discrete components which consume additional space within the probe. In one embodiment, a semiconductor laser is formed within the housing itself, the semiconductive region of the device having bandgap energy in the range of approximately 0.1-2 eV, and being used to generate the desired wavelength of light for autofluorescense or infrared analysis of the tissue within the subject's intestine.

In another embodiment, at least a portion of the smart housing is used as "battery" for the storage of electrical energy used by the probe when deployed in vivo. The housing is constructed in two or more polarized fiber/matrix layers which form a capacitive element capable of storing electrical charge.

In yet another embodiment, the housing includes one or more piezoelectric transducers adapted to sense pressure variations on the outer surface of the housing, such as would result from peristaltic contractions of the subject's intestine. The transducer(s) produce an electrical signal related to the pressure applied thereto, the signal being converted to a digital representation for analysis either on-probe by the digital processor (if so equipped), or off-probe.

In an eleventh aspect of the invention, an improved apparatus and method for obtaining acoustic images using an autonomous endoscopic smart probe are described. In one embodiment, the apparatus comprises a smart probe having an piezoelectric transducer (e.g., "ceramic") adapted to transmit and receive ultrasonic acoustic waves. Processing of the acoustic signals may be performed "on probe" using optimized algorithms within the probe's digital signal processor, or alternatively raw data is streamed from the probe to a sensor disposed external to the subject using a wireless communications link, and subsequently analyzed "off probe".

In a twelfth aspect of the invention, an improved apparatus and method for detecting the presence of certain substances or antigens is disclosed. In one embodiment, the apparatus comprises a sensing array disposed at or near the surface of the probe. The sensing array is exposed to the tissue of the intestine wall, allowing the sensing array to detect the presence of certain substances. In one variant, the sensor comprises a plurality of molecular receptor sites which are configured to receive only one target molecule (or class of molecules). The sensing array is selectively exposed at the desired location within the intestinal tract, and then subsequently covered to avoid further contamination of the array during the remaining length of the intestine. After expulsion, the sensor array is examined to determine the presence of any of the target molecule within the area of array exposure within the intestine.

In another embodiment, electrical conductivity (or alternatively resistivity) is measured across a membrane or other device; the presence of target molecules (analytes) is reflected in changes in the conductivity due to, inter alia, ion diffusion. In yet another embodiment, the detection of the target molecules is performed using a bioelectronic sensor comprising a thin, electrically conductive surfactant polymeric layer to which members, (e.g., receptors) of specific binding pairs are bound.

In yet another embodiment, electrical conductivity (or resistivity) is measured across at least one discontinuous "bridge" of receptor molecules disposed between inorganic conductor terminals. When the bridge is completed via the reception of the target molecule(s), the electrical conductivity increases (or conversely, the resistance decreases) due to outer shell electron transfer across the target molecule(s) and receptor(s). The conductivity increase (or resistance decrease) is detected by conductivity circuitry within the probe. In one sub-variant, a plurality of parallel bridge circuits are provided, and coincidence logic is used to help avoid detection of "false positives". The sensitivity of the device to detecting the target molecule(s) is also increased. The organic receptor molecules may also be bound directly to certain inorganic materials of the probe or sensing array, thereby enhancing the conductivity of the receptor/conductor junction.

In another aspect of the invention, the aforementioned smart probe ("primary" probe) is used to deploy one or more special function secondary probes within the subject's intestinal tract, the special function probes being adapted to perform a variety of therapeutic or analytical functions such as irradiation of a portion of the subject's intestine, expansion of the intestinal wall, timed release of ligands or other pharmaceuticals, etc. In one exemplary embodiment, the primary smart probe includes a "trailer" probe which is selectively separable from the primary probe by the operator or upon the occurrence of a predetermined condition or set of conditions. The trailer probe is further equipped to subsequently expand and/or "wedge" itself within the intestine, such that it remains effectively stationary for a period of time while the primary probe continues down the intestinal tract via peristalsis. The therapy agent (such as, for example, a radionuclide source) is disposed within the trailer, thereby allowing the extended application of the therapeutic action to the desired intestinal tissue. Upon command from the operator and/or the occurrence of a predetermined event, the trailer probe alters its shape/configuration (e.g., deflates), thereby allowing it to subsequently proceed down the intestinal tract via peristalsis. In one variant, the trailer probe comprises a microchip pharmaceutical delivery device adapted for controlled release of pharmaceuticals or other agents to a localized region of the intestine for an extended period.

In a fourteenth aspect of the invention, improved apparatus and methods for enhancing the efficiency of diagnosis of the intestinal tract of the subject, as well as for on-probe/off-probe processing, are disclosed.

BRIEF DESCRIPTION OF THE DRAWINGS

FIG. 13a is a cross-sectional view of a first embodiment of an improved endoscopic delivery device capable of implanting the smart probe of the present invention within the intestinal tract of a patient.

FIG. 13b is a elevated plan view of the closure of the delivery device of FIG. 13a.

FIGS. 18c and 18d are partial perspective views of one embodiment of the track and ball assembly of the smart probe of FIG. 18a.

FIG. 19a is a partial cross-section of one exemplary embodiment of the smart probe of the invention, incorporating a fluid (e.g., ligand solution) reservoir an pressurized gas chamber therein.

FIGS. 23a-23d are various views of one exemplary embodiment of the smart probe of the invention, configured for tissue biopsy within the intestinal tract.

FIG. 27c is a cross-sectional view of the probe of FIG. 27a, illustrating the relationship of various components therein.

FIG. 31d is a block diagram of the electronic functions associated with the 2-D array of the probe of FIG. 31a.

FIGS. 34a-34b are side and front cross-sectional views, respectively, of one exemplary embodiment of the smart probe of the invention including microwave ablation target with resonant cavity.

FIG. 36d is a graphical representation of the intestinal polyp of FIG. 36a, illustrating the feature identification and curve-fitting methodology of the invention.

FIG. 36e is a graphical representation of the parametric identification process used to characterize features such as the polyp of FIG. 36d.

FIG. 36f is a graphical representation of an exemplary feature packet protocol used with the system of FIG. 35.

DETAILED DESCRIPTION OF THE INVENTION

Figure 1:
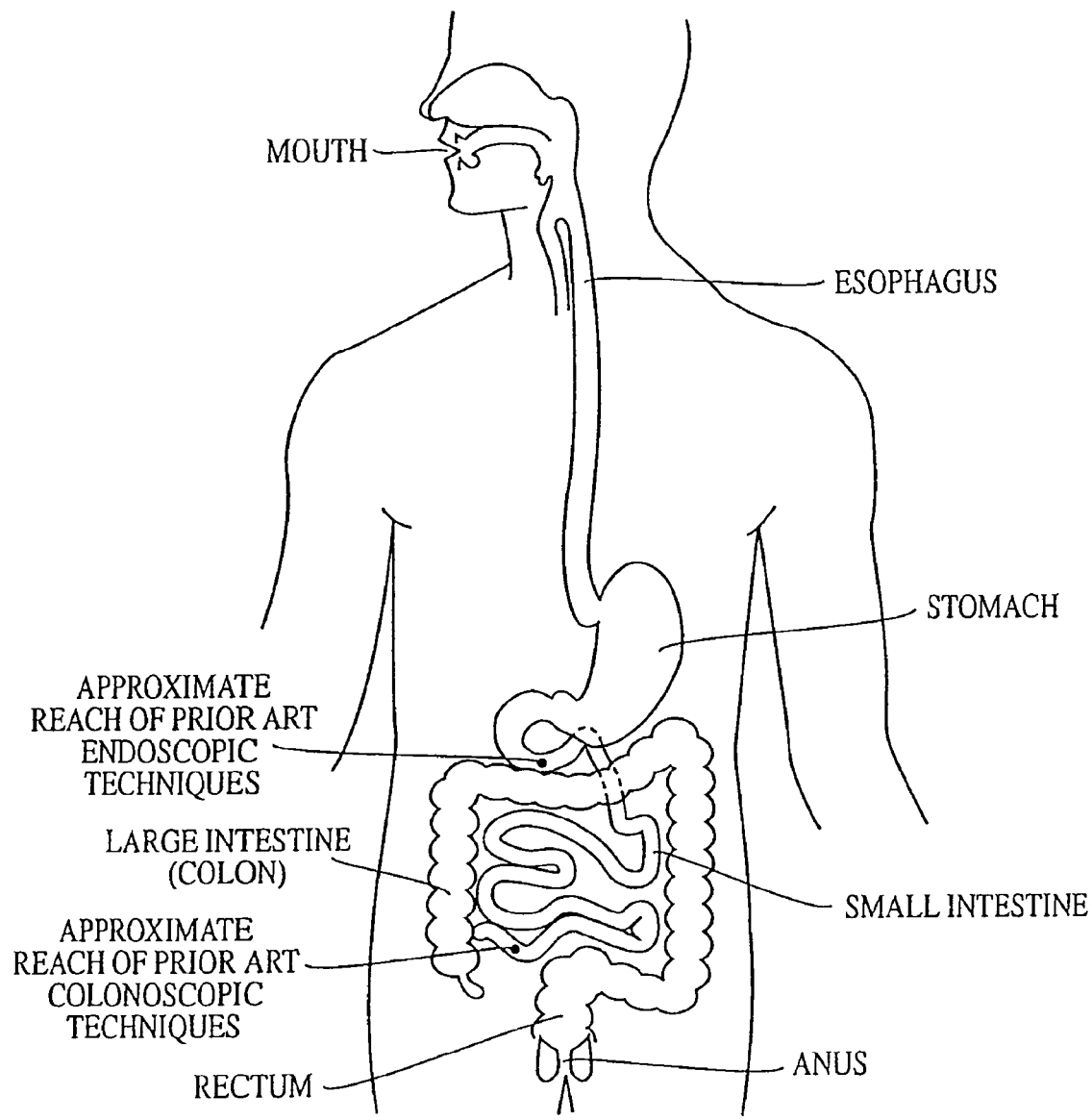
FIG. 1 is a representation of the human digestive tract, illustrating the locations and typical extent of prior art endoscopic and colonoscopic inspection techniques.

Reference is now made to the drawings wherein like numerals refer to like parts throughout.

As used herein, the term "autonomously" shall mean independent of direct physical or tactile control by an operator or external device. As will be described in greater detail below, the smart probe of the present invention is designed to be initially introduced into the patient after which time the probe operates autonomously; i.e., only utilizing electrical, inductive, magnetic, or radio frequency signals to enable or perform certain desired functions, with no direct external physical contact or connections. This is to be distinguished from prior art endoscopic inspection or treatment devices, which always maintain some physical or tactile link (such a tube, electrical wire, or fiber optic bundle) with the operator, and hence which do not operate autonomously while in the patient.

The term "ionizing radiation" as used herein refers to any form of radiation, whether particulate or wave-like in nature, which has sufficient energy to remove an electron or other particle from an atom or molecule, thus producing an ion and a free electron or other particle. Examples of ionizing radiation include, but are not limited to, gamma rays, X-rays, protons, positrons, electrons, and alpha particles.

The term "polymer" and "polymerization" shall mean any molecule which forms one or more structures or linkages (which may be repeating) such that a larger, composite molecule is produced. Similarly, the term "depolymerization" shall mean any process whereby the foregoing structures or linkages are dissolved or broken.

The term "fullerene" as used herein shall mean not only C60 (i.e., the common buckminster-fullerene) but also the higher molecular weight fullerenes (e.g., C70, C84 ... C240) and also their derivatives, regardless of shape.

The term "nanostructure" shall mean the aforementioned fullerenes, as well as nanotubes and any other discrete nanometer-scale carbon structure having a plurality of atoms.

The term "agent" shall mean any antigen or compound, pharmaceutical or otherwise, introduced in vivo to produce at least one desired result.

The term "ligand" as used herein shall mean any atom, radical, ion, or molecule in a complex (polyatomic) group which is bound to a central atom.

The term "receptor" shall mean any protein or other molecule which receives or binds to one or more specific types of target molecules or atoms.

The term "imaging" or "imaging sensor" or "imaging array" shall mean any device adapted to receive energy of a certain type including, without limitation, electromagnetic energy or particulate radiation.

As used herein, the term "numerical aperture" shall mean a measure of the capture angle of EMR, including the maximum angle of EMR rays that will be reflected down the transfer medium (e.g., fiber) by total reflection. Numerical aperture (NA) is given by the following relationship:

$$NA = \sin\theta = SQRT(n_1^2 - n_2^2)$$

Where:
$n_1$ = refractive index of core
$n_2$ = refractive index of clad

Figure 3:
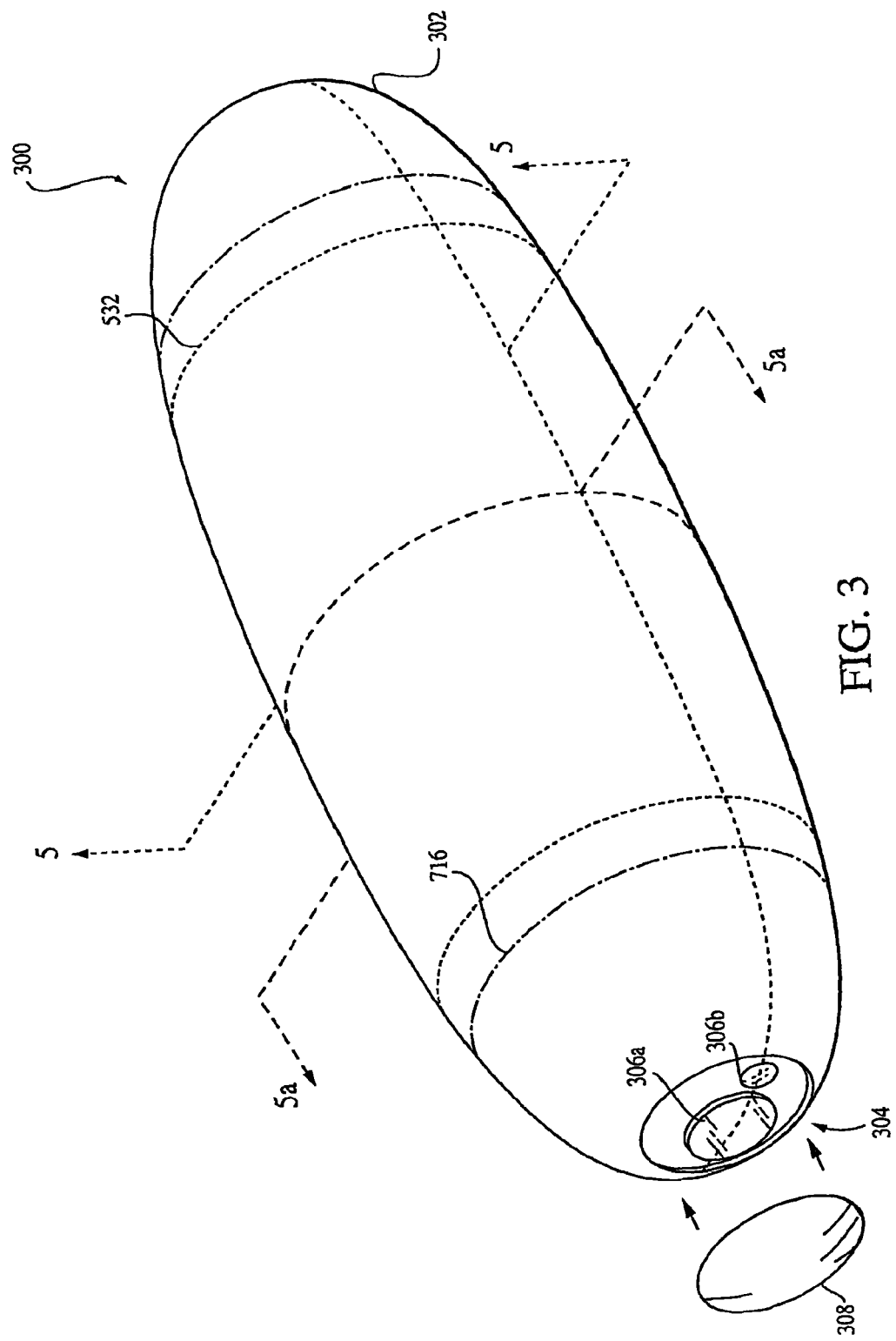
FIG. 3 is a perspective view of a first embodiment of the smart probe of the present invention.

FIG. 3 is a perspective view of a first embodiment of the smart probe of the present invention. The probe 300 comprises an outer housing 302 having a generally ellipsoid shape and an inner cavity 303 (not shown), a lens aperture 304 positioned in one end of the housing 302, and lenses 306a, 306b mounted in alignment with the aperture 304 within a lens retaining board 305. An optional lens cover 308 covers the lenses 306a, 306b and seals the aperture 304. A plurality of other components (including, inter alia, a CCD or other imaging array, microcontroller, clock, parallel/serial drivers, and sample and hold circuitry, not shown) are disposed within the aforementioned cavity 303 or otherwise within the outer housing 302 itself. These other components are described in greater detail below with reference to FIGS. 6-7. A generally ellipsoid shape is used for the outer housing 302 of the present embodiment to facilitate passage of the probe 300 through the intestinal tract of the patient, and to assist in maintaining the proper orientation of the probe during use; e.g., such that the lenses 306 are oriented to have sufficient perspective and focal length to adequately view portions of the interior of the patient's intestine. Optionally, the rear portion of the probe 300 may be flared, or other contours or devices utilized to assist in orientation within the intestine. While the present embodiment utilizes a generally ellipsoid shape for the outer housing 302, it will be recognized that other shapes and configurations for the outer housing (and lens aperture 304) may be used in accordance with the present invention. For example, substantially cylindrical or "bullet-shaped" outer housings could be used. Alternatively, an outer housing having a non-symmetric lateral cross-section (i.e., that taken in a plane to which the longitudinal axis of the housing 302 is normal) could be employed. Many other suitable shapes exist.

Furthermore, it will be recognized that the probe 300 may operate in both a "forward looking" and "rearward looking" orientation within the patient. Specifically, the probe may be disposed within the intestine such that the aperture 304 (and associated CCD array) is oriented in the direction of probe advance, or alternatively rearward. As described in more detail below, it is further contemplated by the present invention that the probe may be equipped with both forward and rearward looking CCD arrays.

The outer housing 302 is sized in the present embodiment to have a diameter (at its widest point, measured across its circumference) on the order of 12 mm (roughly 0.5 in.) in order to allow unencumbered passage through the intestinal tract and even the ileocecal valve. However, it will be appreciated that other sizes of probe, both smaller and larger, may be used depending on a variety of factors including the size of, and any peculiarities associated with, a given patient's intestines, as well as the instrumentation/components desired to be carried by the probe 300.

The outer housing 302 is in the present embodiment constructed of a mechanically rigid and stable polymer such as ethylene tetrafluoroethylene (Tefzel®) which is also resistant to chemical exposure and other environmental influences, and which is also non-toxic to the patient. Tefzel® also has the desirable property of being able to be fabricated with a smooth (i.e., low coefficient of friction) surface which further facilitates passage of the probe 300 through the intestinal tract, although this property is not essential. It can be appreciated, however, that other materials (such as certain metals, resins, composites, or even organic materials) may be used to form all or part of the outer housing 302. For example, the housing need not be a discrete component, but rather may be an encapsulant such as that used on integrated circuit devices.

Figure 5:
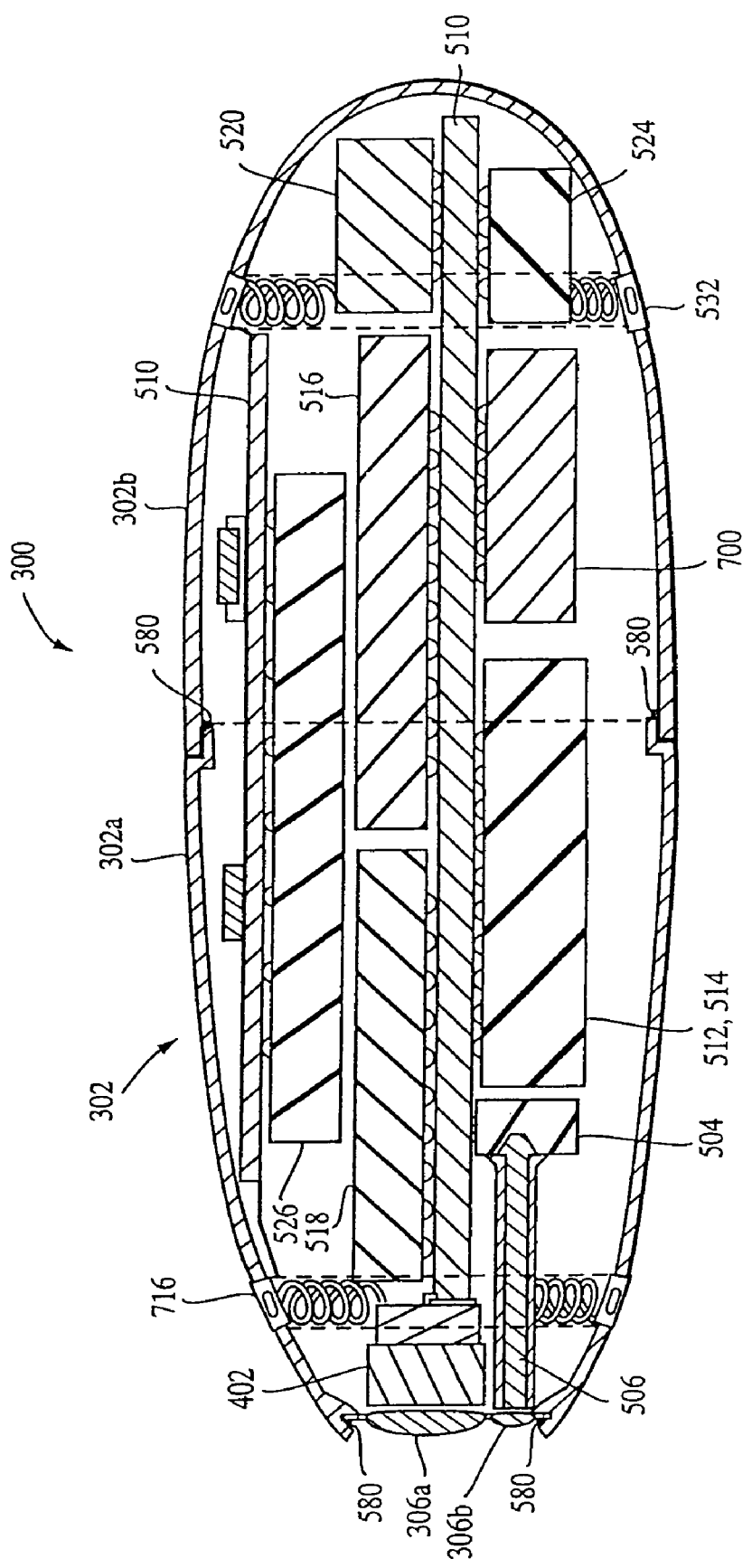
FIG. 5 is a cross-sectional view of the smart probe of FIG. 3 taken along line 5-5, showing the internal arrangement of components therein.

The housing 302 is made of minimal wall thickness so as to have adequate rigidity yet permit the maximum size cavity therein. In the present embodiment, a wall thickness of 0.5 mm (roughly 0.020 in.) is selected, although other values may be used. The outer housing of the probe of FIG. 3 is split circumferentially at the mid-section to facilitate component insertion and removal. The halves of the housing 302a, 302b are fit tightly together so as to minimize the possibility of fluid leaking into the cavity 303. A sealing agent 580 (and/or a sealing ring or gasket) is used to further prevent fluid leakage. Note also that such sealing is applied around the interface of the lens board 305 and the outer housing 302, as shown in FIG. 5.

Figure 8:
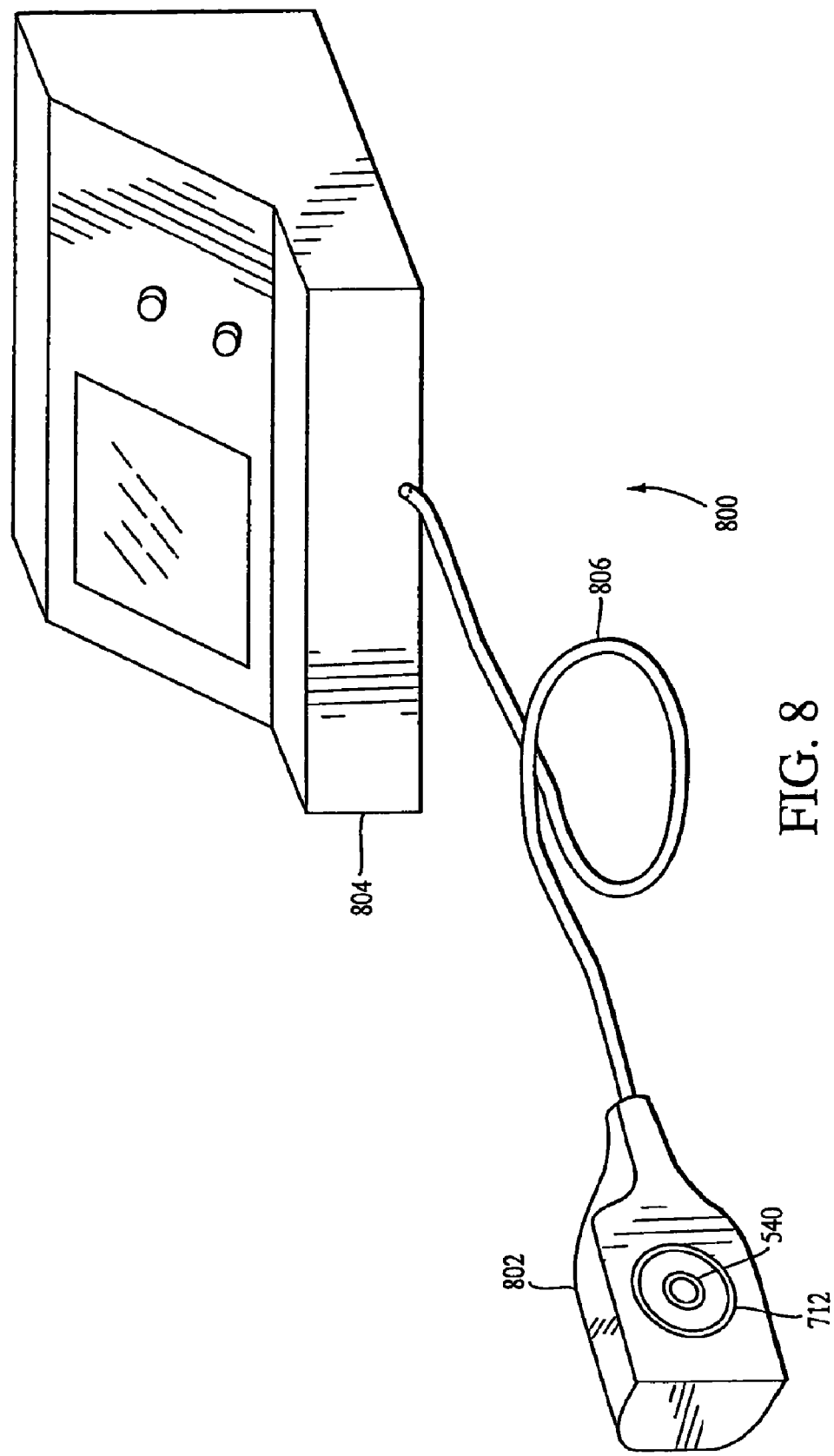
FIG. 8 is a perspective view of one embodiment of the MCD and its associated remote unit according to the present invention.

One or more data transfer terminals 532 and power transfer terminals 716 are embedded at or near the surface of the probe housing 302 to facilitate data and power transfer, respectively, between the probe 300 and the MCD 800 (FIG. 8). In the present embodiment, the terminals 532, 716 are ring-shaped so as to permit data/power transfer in any rotational orientation of the probe 300 around its longitudinal axis; however, it will be recognized that other terminal shapes and configurations may be used.

The lens cover 308 shown in FIG. 3 is designed to protect the lenses 306a, 306b, 306c from becoming occluded by substances present in the intestine of the patient during probe travel. Ideally, the patient will be restricted from eating or ingesting any substance for a suitable period prior to probe use so as to minimize any such occlusions; however, the lens cover 308 further assists in maintaining the lenses clear prior to use. The lens cover 308 of the present embodiment is a thin membrane (on the order of a few thousandths of an inch thick) and is comprised of a substantially clear gelatin-like substance comparable to that commonly used to contain and deliver pharmaceutical products (such as so-called "gel caps" which are well known in the pharmaceutical arts) or equivalent thereof. The design and composition of the lens gel substance is, in the present embodiment, controlled so as to provide a timed dissolution within the patient. For example, if it is estimated that the intestinal motility of the patient is X cm/hr, and the region of the intestine desired to be inspected using the probe 300 is Y cm from the point of introduction of the probe, then the lens cover 308 can be chosen to dissolve in roughly Y/X hr or less (allowing for some margin of error). The lens cover 308 of the present embodiment is shaped to conform roughly with the outer surface of the lens(es) 306 and with the profile of the outer housing 302 such that the cover 308 is maintained within the housing aperture 304, and provides minimal optical distortion, until it dissolves. Note also that a substantially clear material is chosen to permit the passage of some light through the cover 308 before its dissolution, although lens covers with other optical properties (such as selective wavelength filtration) may be used.

It should be noted that while the present embodiment makes use of a lens cover 308, the use of such cover may not be necessary in certain applications, and therefore need not be present. Furthermore, while the present embodiment describes a lens cover which is chemically dissolvable, other types of lens covers may be employed with the present invention. For example, a mechanical shutter arrangement could be used to selectively cover/uncover the lenses 306. Alternatively, a lens cover which dissolves or otherwise alters its properties when exposed to an electrical current or coherent electromagnetic radiation may be employed. A permanent (i.e., non-dissolving) lens cover having desirable optical properties could also be used.

Figure 4:
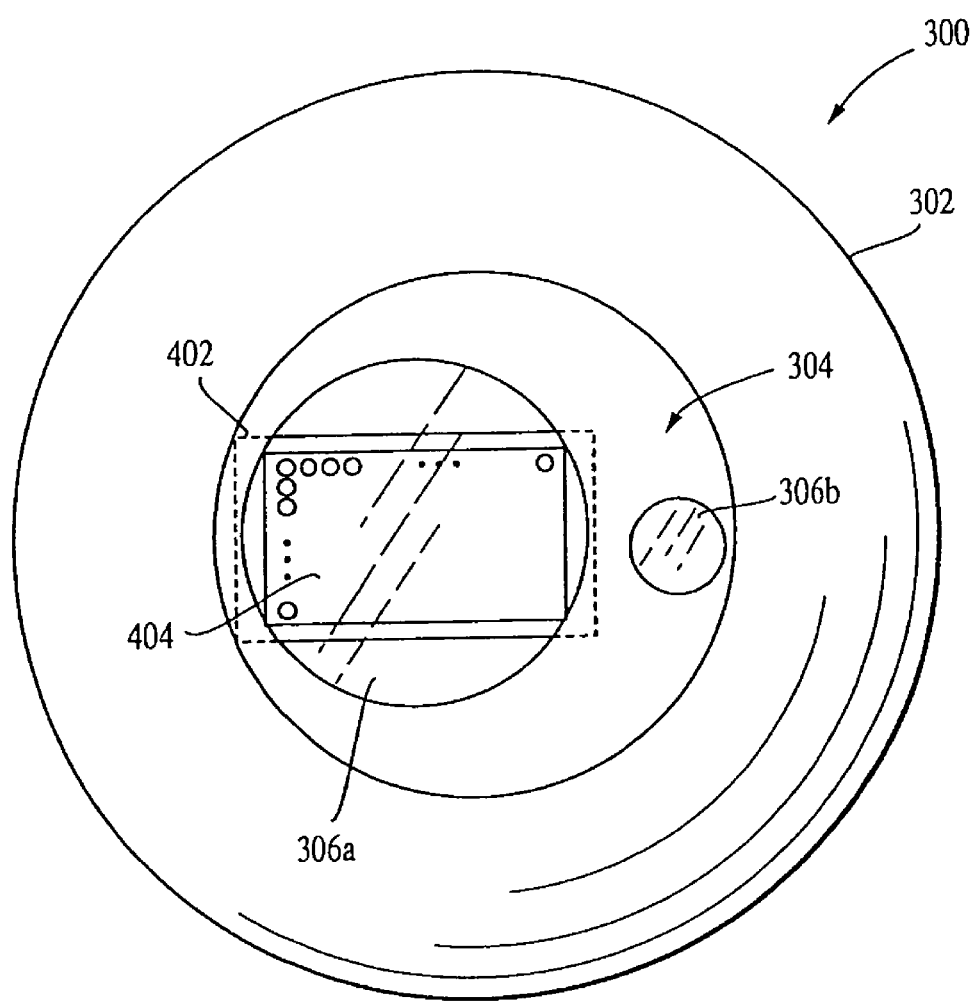
FIG. 4 is a front view of the smart probe of FIG. 3 illustrating the arrangement of the lenses and the CCD array.

Referring now to FIG. 4, a front view of the smart probe 300 of FIG. 3 is shown, illustrating the relationship of the housing aperture 304, lenses 306, the CCD array 402, and the lens cover 308. Specifically, the aperture 304 is sized and shaped to permit light of varying wavelengths to impinge upon the active region 404 of the CCD array 402, and to accommodate the optical light lens 306b which is positioned laterally to the main lens 306a in this embodiment. The aforementioned lens cover 308 generally conforms to the outer surface of each of the lenses 306a, 306b, thereby acting as a protective cover for each before dissolution. As will be described in greater detail herein, the optical lens 306b acts to transfer and distribute broad spectrum visible light generated within the probe 300 to intestinal tissue in proximity to the lenses. Remitted or reflected visible is passed through the main lens 306a (which is chosen to be effectively transparent to a broad range of wavelengths in the spectral regions of interest) to the CCD array 402. The main lens 306 is, in the embodiment of FIGS. 3 and 4, a substantially convex lens designed to gather and more narrowly focus energy originating from various positions outside the probe 300 onto the CCD array 402. The optical lens 306b is, conversely, designed to radiate and distribute light incident on its inner surfaces (via the associated fiber optic bundle, described below) more broadly within the intestine.

The CCD array 402 of the present embodiment is a multi-pixel semi-conductive device having anti-blooming protection, and being sensitive to various wavelengths of electromagnetic radiation. A Texas Instruments Model TC210 192× 165 pixel CCD image sensor is chosen for use in the present embodiment, based on its performance attributes, spectral responsivity, and size (i.e., the package outline is roughly 5 mm by 3 mm), although myriad other devices (CCD or otherwise) could be used with equal success. The operation of the CCD array 402 is described in greater detail below.

Figure 5A:
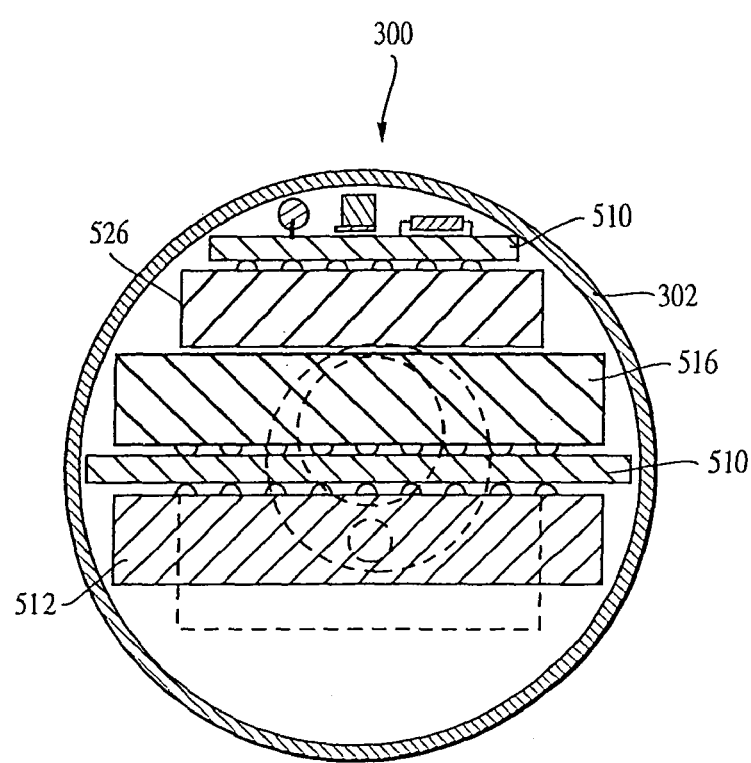
FIG. 5a is a cross-sectional view of the smart probe of FIG. 3 taken along line 5a-5a, further showing the internal arrangement of components therein

Referring now to FIGS. 5 and 5a, cross-sections of the probe 300 of FIGS. 3 and 4 are illustrated. The probe outer housing 302 generally contains a number of different components in its internal cavity 303 including the aforementioned lenses 306 and CCD array 402, as well as a light emitting diode (LED) 504, a single mode fiber optic bundle 506, and one or more inductive data transfer terminals 532. A number of discrete or integrated semiconductor components are also present within the probe 300, including a "flash" analog-to-digital converter ADC 512, sample and hold circuit 514, parallel and serial drivers 516, 518, microcontroller (or microprocessor) 520, clock driver 524, and a data interface circuit 526 as described in greater detail below. The LED 504 is located roughly co-linearly with the central axis of its lens 306b with the fiber optic bundle 508 disposed there between as shown in FIG. 5. The LED 504, its fiber optic bundle 508, and its lens 306b are optically coupled so as to transmit light energy to the lens in an efficient manner. The A/D converter 512, drivers 516, 518, microcontroller 520, and other electronic components are disposed within the cavity 303 on one or more miniature printed circuit board assemblies (PCBAs) 510 in a space-efficient manner, with the semiconductor components being disposed and electrically connected on either side of the assemblies 510. The semiconductor packages are chosen so as to fit within the housing, as discussed in more detail herein. One or more inductive data transfer terminals 532 generally in the form of circumferential rings are disposed within the outer housing at or near the surface thereof as previously described in order to provide for data transfer between the probe 300 and the remote unit 802 of the MCD data processing and analysis equipment 800 external to the patient (see discussion of FIG. 8 below). Additionally, one or more inductive power transfer terminals 716 are positioned on the outer portion of the housing to facilitate inductive power transfer between the MCD and the probe 300. Inductive power transfer is chosen in the present embodiment so as to obviate the need for a chemical battery or other potentially hazardous power source within the probe 300, although a battery may be used. Alternatively, in another embodiment, a radio frequency (RF) oscillator and supporting circuitry (not shown) is disposed within the housing 302 on the PCBA 510 to receive radio frequency energy generated externally to the patient and convert this energy to direct current power within the probe 300.

So as to fit within the limited volume of the cavity 303, each of the aforementioned components 504, 510, 512, 514, 516, 518, 520, 524, 526 is chosen to have the minimum physical profile. While several discrete component functions are depicted in the functional block diagram of the probe data acquisition and transfer circuitry 600 (described below with reference to FIG. 6), in actuality many of these functions can be integrated and performed by a lesser number of devices so as to economize on space. For example, a Texas Instruments MSP430x MSP ultra low power microcontroller (such as in the "DW package") incorporating internal memory, clock, and ADC may be used in the present embodiment. Application specific integrated circuits (ASICs), FPGAs, or other custom ICs having a high degree of integration may also be used for such purposes, as described in greater detail below with respect to FIG. 16. Such integration is desirable in the present invention, and is presently well within the capability of those skilled in the semiconductor design and fabrication arts. Alternatively, a larger number of discrete components (as shown in FIG. 5) may be used. For example, a Texas Instruments TLV2543C flash ADC with a 20 pin "DB" package (roughly 8 mm×7.5 mm×2 mm) may be used as the ADC 512 of the present embodiment. This package more than adequately fits within the aforementioned 12 mm outer housing 302 (assuming a 0.5 mm housing wall width), while preserving space for the other components. Preferably, a BGA (ball grid array) package is utilized to eliminate leads along the edge of the package(s) and further economize on space. It will be appreciated, however, that a wide variety of integration schemes, packages, profiles, and lead (pin) structures may be used in the present invention in order to simultaneously fit all of the desired components within the aforementioned outer housing 302.

The circuit board assemblies 510 of the present embodiment are preferably multi-layer boards having a plurality of circuit traces, vias, and contact pads disposed therein to facilitate electrical interconnection of the various terminals of the integrated circuits (ICs) and any discrete electrical components (such as the LED 504, resistors, capacitors, or transistors). The design and fabrication of such circuit boards is well known in the electrical arts. Electrical interconnection between the multiple PCBAs 510 of FIG. 5 is accomplished via miniature flexible electrical tracing (not shown). Note that in the present embodiment, the PCBAs 510 are disposed in a generally longitudinal fashion (i.e., parallel to the longitudinal axis of the probe housing 302); however, other orientations, such as transverse to the longitudinal axis, could be used.

The LED 504 used in the embodiment of FIGS. 3-5 is a standard, low voltage light-emitting diode having a spectral emission characteristic centered in the visible wavelengths. In the present embodiment, a "white light" LED of the type well known in the electrical arts is preferred, although other types, power ratings, and spectral outputs are possible. This LED 504 is used as an optical illumination source for the CCD array 402 previously described. Specifically, light generated by the LED is passed via its fiber optic bundle 508 to the optical lens 306c and radiated out of the probe 300 into the region immediately surrounding the CCD array 402. The fiber optic bundle is, in this embodiment, a single mode optical fiber of the type well known in the optical transmission arts. Light reflected by the interior surfaces of the patient's intestine is gathered by the main lens 306a and focused on the CCD array 402, including the visual sub-array 402b, where it generates charge within the individual CCD array cells. The voltage and power rating of the LED 504 is chosen to be compatible with the desired light intensity, power supply circuit capacity, and system voltage available within the probe. In the present embodiment, a milliwatt LED is used having a voltage rating on the order of 2-5 Vdc, although other may be used.

Figure 6:
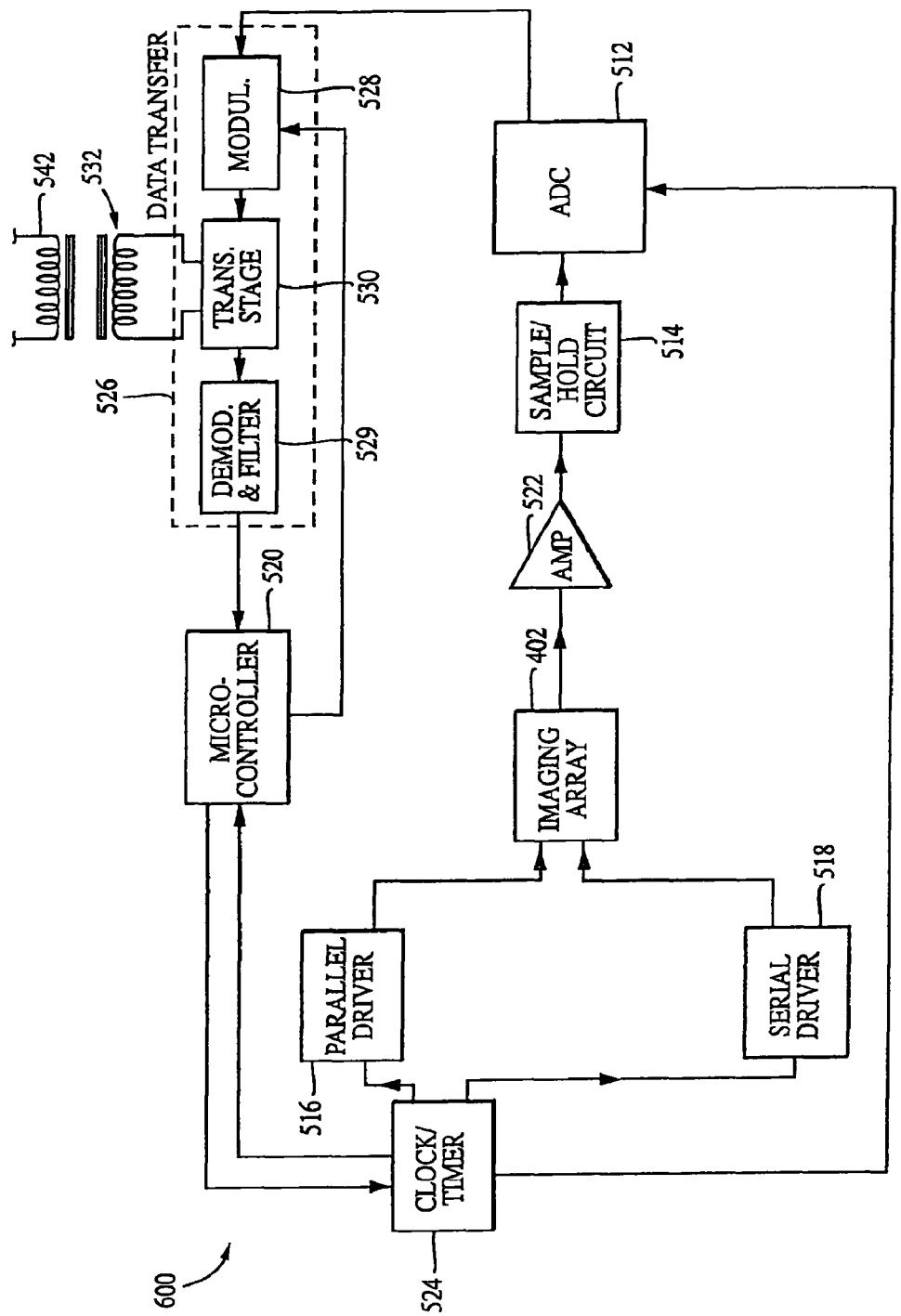
FIG. 6 is a block diagram of one preferred embodiment of the data acquisition, processing, storage, and transfer circuitry of the smart probe of FIG. 3.

Referring now to FIG. 6, one embodiment of the data acquisition, processing, and transfer circuit 600 of the smart probe of FIGS. 3-5 is disclosed. As previously described, the circuit 600 of the present embodiment comprises a number of components including, inter alia, a CCD array 402, parallel and serial drivers 516, 518, sample and hold circuit (SHC) 514, system clock 524, microcontroller 520, amplifier 522, ADC 512, and data transfer sub-circuit 526. Other electronic elements (such as capacitors, resistors, transistors, and diodes; not shown) are also used to facilitate operation of the circuit 600; the use of such components is well known in the relevant arts and accordingly will not be discussed further herein. Furthermore, it will be noted that such electronic elements are ideally integrated with one or more of the aforementioned components 512, 514, 516, 518, 520, 522, 524, 526 in order to minimize space consumed within the probe outer housing 302.

As shown in FIG. 6, the CCD array is driven by the parallel and serial drivers 516, 518 based on a user-defined clock signal output from the clock/timer 524 and controlled by the microcontroller 520. Analog signals output from the CCD array are amplified by amplifier 522 and passed to SHC 514. Analog signals output from the SHC 514 are rapidly converted by the ADC 512 into digital signals, the latter being input to the data transfer sub-circuit 526. A "flash" ADC (i.e., one with a sampling rate on the order of microseconds or less) is used to permit streaming of video data at video rates, typically 7-20 MHz. A 10 or 12-bit resolution ADC may be used, for example, to accommodate the dynamic range of the CCD. The required ADC resolution can generally be determined by the following relationship:

$$N \geq (DR/6.02)$$

Where:
N=Number of data bits
DR=Dynamic Range of CCD in db

Figure 9:
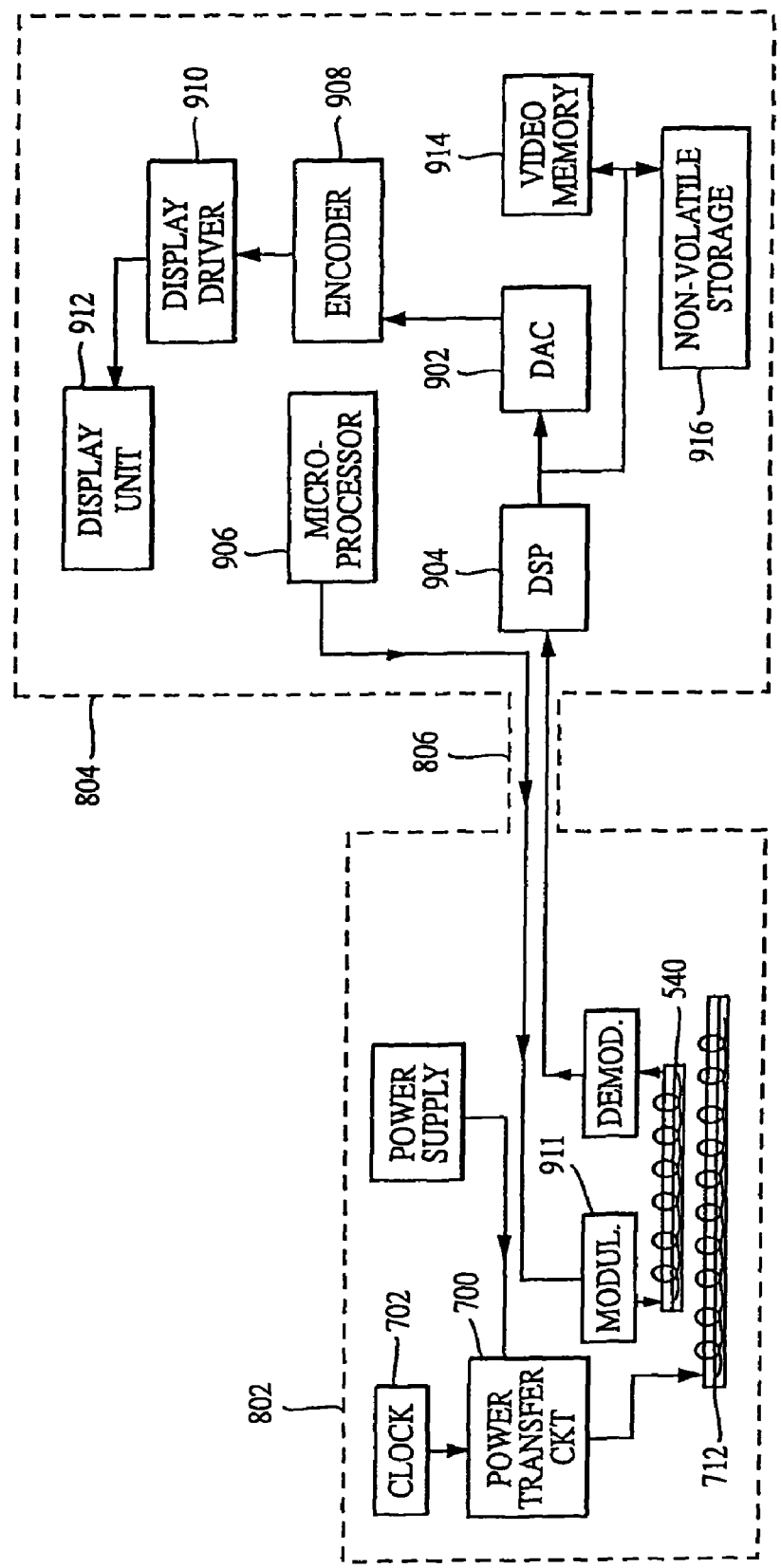
FIG. 9 is a block diagram illustrating the data processing and power transfer components of the MCD and its associated remote unit.

The data transfer sub-circuit 526 comprises a modulator 528, demodulator/filter 529, transistor stage 530, and data transfer terminal 532. The construction and operation of such inductive data terminals is well known in the electronic arts, and is described in, inter alia, U.S. Pat. No. 4,692,604 "Flexible Inductor" issued Sep. 8, 1987, which is incorporated herein by reference in its entirety. Note that in the present embodiment, the "flexible" inductor of the '604 patent is configured so as to form a circumferential ring within the probe outer housing, as shown in FIG. 3. A high frequency (MHz) clock signal is supplied by the clock 524 to the modulator 528 so as to generate an ac carrier. The data signal output from the ADC 512 is used by the modulator 528 to modulate the aforementioned ac carrier, thereby producing an amplitude modulated ac waveform on the coil of the data terminal 532 by way of the transistor stage 530. The output of the probe data terminal 532 is a magnetic flux which varies according to the amplitude modulated ac signal carried on the terminal coil. The coil 542 of the MCD remote unit data terminal 540 is inductively coupled to the probe data terminal coil via the magnetic flux; accordingly, an amplitude modulated, alternating current signal of the same phase and frequency is generated in the remote unit coil 542. This signal is then demodulated using, for example, a diode and filter capacitor as described in U.S. Pat. No. 4,605,844, "Computerized Transaction Card With Inductive Data Transfer", issued Aug. 12, 1986, which is also incorporated by reference herein in its entirety. The resulting demodulated data signal, a replica of the data signal supplied by the output of the ADC 512, is input to the front-end processing (e.g., DAC or DSP) of the MCD, as described with reference to FIGS. 8 and 9 below. It will be further recognized that the design of the data transfer sub-circuit 526 must consider the video data rates previously described (typically 7-20 MHz).

The demodulator/filter 529 performs two functions: (i) demodulating the control and data signals sent by the MCD microprocessor during probe startup and operation; and (ii) isolation and filtering of any errant power transfer signal which couples to the inductive coil(s) of the data transfer terminal 532.

Figure 7:
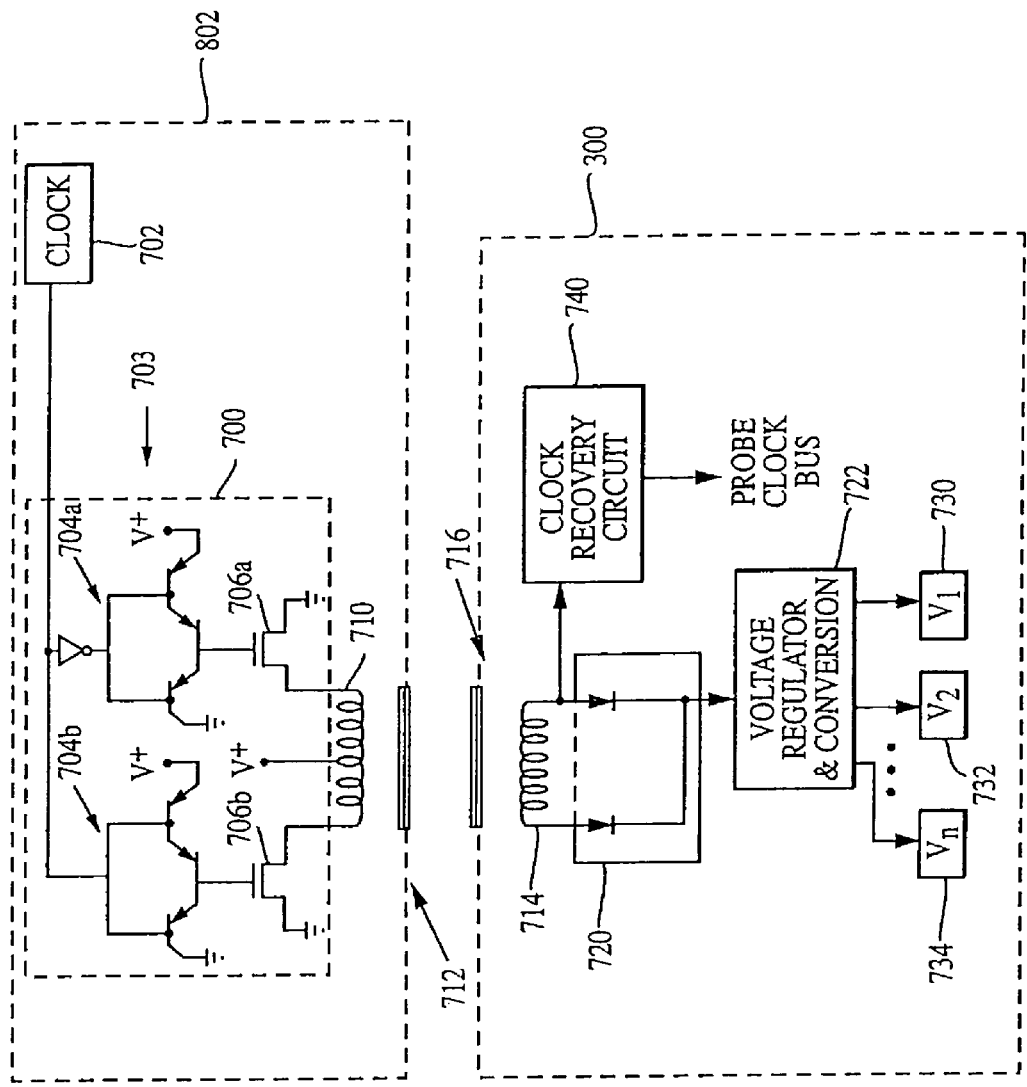
FIG. 7 is a block diagram of one preferred embodiment of an inductive power transfer circuit used in the smart probe of FIG. 3.

Referring now to FIG. 7, one embodiment of the inductive power transfer circuit 700 used in the smart probe of FIGS. 3-6 and MCD remote unit 802 is described. Similar to the inductive data transfer sub-circuit 526 illustrated in FIG. 6, the power transfer circuit 700 utilizes a clocking signal generated by the clock 702 in the MCD remote unit 802 to supply a parallel transistor stage 703 including two pairs of transistors 704a, 704b and associated MOSFETs 706a, 706b. One pair of transistors 704a is supplied via an signal inverter 708 so as to invert the phase (i.e., shift by 180 degrees) of the signal with respect to the non-inverted signal supplied to transistors 704b. An alternating current waveform (of a different frequency than that imposed upon the data transfer terminal(s) 532) is accordingly generated within the coil 710 of power transfer terminal 712, which is inductively coupled to the coil 714 of the power transfer terminal(s) 716 in the probe 300. A diode (rectifier) stage 720 including filter capacitor (not shown) is used to convert the induced ac signal in the probe coil 714 to direct current. A voltage regulator and conversion circuit 722 is used to regulate and adjust the voltage of the converted dc power prior to supply to the other components 402, 504, 512, 514, 516, 518, 520, 522, 524, and 526 within the probe 300 via the various voltage busses 730, 732, 734. The construction and operation of voltage regulating and conversion circuits is well known in the electrical arts, and will not be discussed further herein. U.S. Pat. No. 4,605, 844, previously cited herein, describes the construction and operation of inductive power transfer circuits such as that utilized herein in greater detail.

Similarly, it will be noted that the method of clocking signal recovery described in the above-referenced patent may be utilized in the present invention to obviate the clock 524 of FIG. 6. Specifically, the ac waveform transferred from the MCD remote unit 802 can be used to generate a clock signal prior to rectification by the diode stage 720 using a clock recovery circuit 740. This clock signal may then be used to drive those components requiring a clock signal, such as the CCD array 402, ADC 512, etc.

It will be further recognized that while the present embodiment utilizes inductive data and power transfer, other methods of such transfer are possible. See, for example, the capacitive data transfer apparatus described in U.S. Pat. No. 4,816, 654, "Improved Security System for a Portable Data Carrier", issued Mar. 28, 1989, which is incorporated herein by reference in its entirety.

Referring now to FIG. 8, the monitoring and control device (MCD) 800 of the present invention includes, in a first embodiment, a remote unit 802 which can be placed in close proximity to the patient's abdomen in the region of the intestine where the probe 300 is located to permit inductive data and power coupling thereto. The remote unit 802 includes, inter alia, one or more inductive data terminals 540, and one or more inductive power transfer terminals 712 These terminals 540, 712 are located within the unit so as to provide adequate separation during operation, yet still permit simultaneous contact with the probe 300 while in the patient. The operation of these terminals is described in greater detail above with respect to FIGS. 6 and 7. As shown in FIG. 8, a circular "ring" configuration is used for the terminals 540, 712 in the present embodiment so as to minimize the effects of different azimuthal orientations of the remote unit 802 with respect to the probe 300, although it will be appreciated that other configurations (such as pins, rods, strips, etc. may conceivably be used). As the probe 300 slowly moves within the intestine, the remote unit 802 is moved accordingly by the operator so as to maintain contact therewith. Since the inductive coupling between the data and power transfer terminals 540, 712 of the remote unit and terminals 532, 716 of the probe is substantially affected by the distance between the respective terminals, as well as the interposed material (tissue, fluids, etc.), the remote unit 802 must be periodically moved while the probe 300 is in use.

The remote unit is connected to the MCD main unit 804 via a standard data transmission cable 806 of the type well known in the electrical arts. As further illustrated in FIG. 9, the MCD main unit 804 of the present embodiment includes, inter alia, a "flash" digital to analog converter (DAC) 902, digital signal processor (DSP) 904, microprocessor 906, encoder 908, video display driver 910, display unit 912, video memory 914, and non-volatile storage device 916. Image data transmitted from the probe 300 is passed to the main unit 804 from the remote unit 802, de-compressed if required by the DSP 904, converted to an analog format by the DAC 902, coded by the video encoder 908, and displayed on the display unit 912. These displayed visual or autofluorescence images constitute one form of diagnostic aid according to the present invention, although it will be recognized that other such aids (such as ultrasound images) may be produced. Images may be stored in the storage device 916 for a variety of functions (such as later retrieval or enhancement) if desired, as is well known in the electronic arts. The microprocessor 906 acts to control the operation of the MCD 804 as well as the probe 300 via data signals transmitted to the probe during startup and operation. Specifically, the microprocessor 906 of the MCD generates and passes control data to the microcontroller 520 of the probe via a modulator circuit 911 and the inductive data terminals 532, 540 on startup to initiate microcontroller control of the probe. The probe microcontroller 520, which is connected to and receives input from the clock 524 (or alternatively, the clock recovery circuit 740 associated with the power transfer circuitry), switches power to the remaining (non-powered) probe components such as the SHC 514 and ADC 512 and generates the necessary signals to the various probe components (based on its internal programming) so as to initiate operation of the LED 504, collection of image data via the CCD array 402, and subsequent processing/transfer of the collected data.

The remote unit 802 of the MCD 800 is, in a second embodiment, a band which is fitted around the abdomen of the patient (not shown). This band includes a plurality of individual data and power transfer terminals each of which are capable of transferring data and power inductively between the MCD and the probe 300. The terminals are physically arranged in an interleaved fashion (alternating data and power transfer terminals) so as to provide a high density of terminals yet minimize any interference between terminals. The data terminals are electrically arranged so as to allow the MCD to select and display data received from one or more of the data terminals (channels). This multi-terminal approach is used to allow the probe to maintain contact with the MCD remote unit with minimal or no movement of the remote unit. As the coupling between one set of data terminals is increased with respect to the other terminals, the signal quality for that channel increases accordingly. In one embodiment, the digital data received from the data terminals is input to a high frequency multiplexer. The multiplexer generates a single multiplexed output (based on the multiple data channel inputs) which is input to a DSP. The DSP samples and analyzes the data on the single multiplexed channel for each input channel using an internal algorithm to evaluate the strength and quality of signal on that input channel. The microprocessor selects the most viable channels at any given time based on the output of the signal sampling algorithm running on the DSP, and utilizes the selected input channel as the data source for the DAC and video driver.

Conversely, all of the multiple power transfer terminals in the remote unit of the second embodiment are driven synchronously and simultaneously by the MCD so as to permit inductive coupling with the probe at all times, thereby minimizing power "drop outs".

Figure 10A:
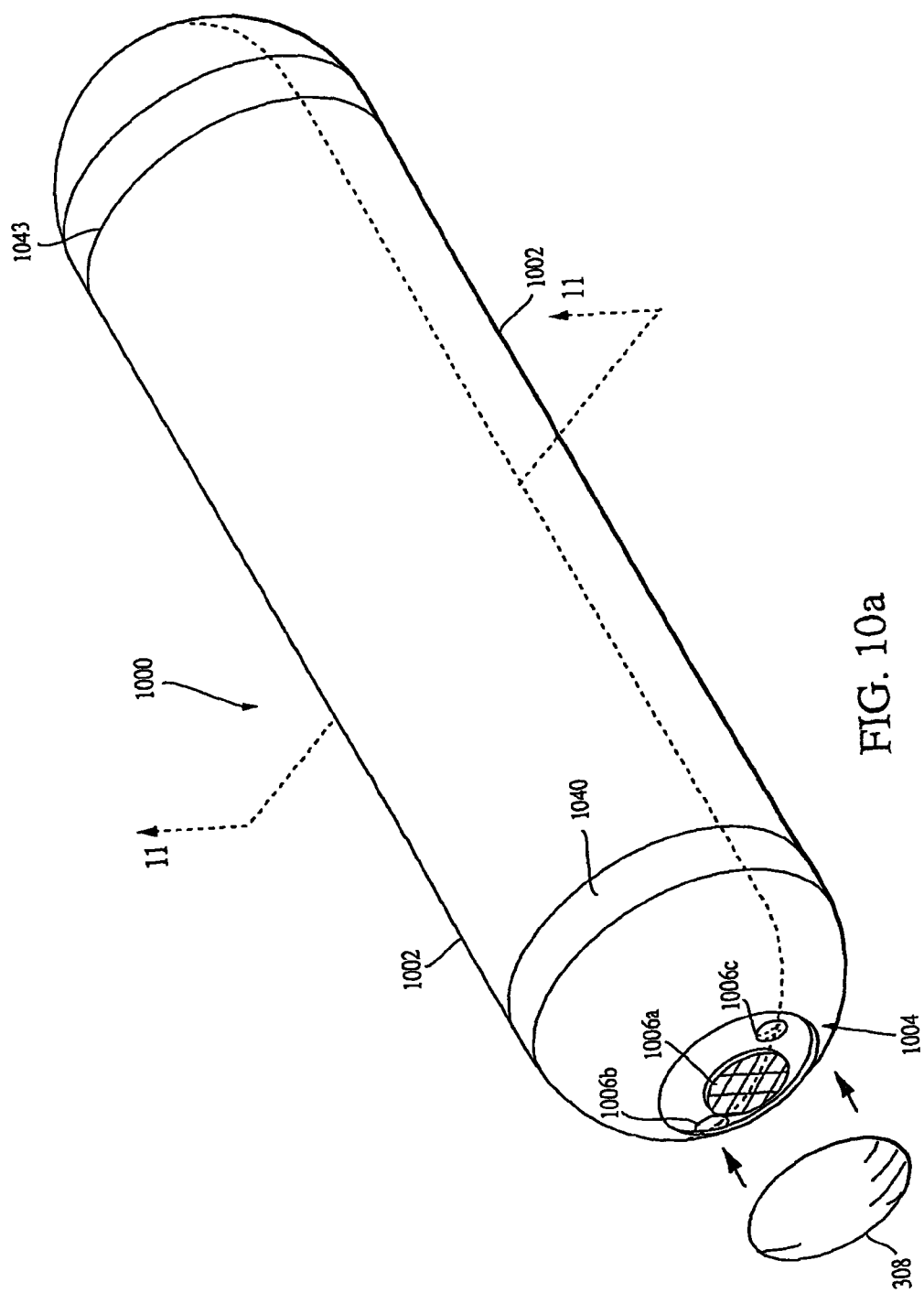
FIGS. 10a and 10b are perspective and front views, respectively, of a second embodiment of the smart probe of the present invention.

FIG. 10*a* is a perspective view of a second embodiment of the smart probe of the present invention. The probe 1000 of FIG. 10*a* comprises an outer housing 1002 having a generally cylindrical shape with rounded ends ("capsule"), an inner cavity 1003 (not shown), and a lens aperture 1004 positioned in one end of the housing 1002. Three lenses 1006*a*, 1006*b*, 1006*c* are mounted in alignment with the aperture 1004, and optionally protected by a lens cover. The third lens 1006*c* of the present embodiment is used to distribute laser (coherent) light energy generated by a laser diode which is described in greater detail below. The CCD array 1010 includes two sub-arrays 1010*a*, 1010*b* (FIG. 10*b*) for the collection of visible ambient and light emitted by autofluorescence, respectively. The probe 1000 further includes a digital signal processor (DSP) and memory (not shown) which facilitate processing and storage of the data collected by the CCD sensor and control of the probe, as described below. Data transfer terminals 1040 and power transfer terminals 1043 are embedded at or near the surface of the housing 1002, as in previous embodiments.

Figure 10B:
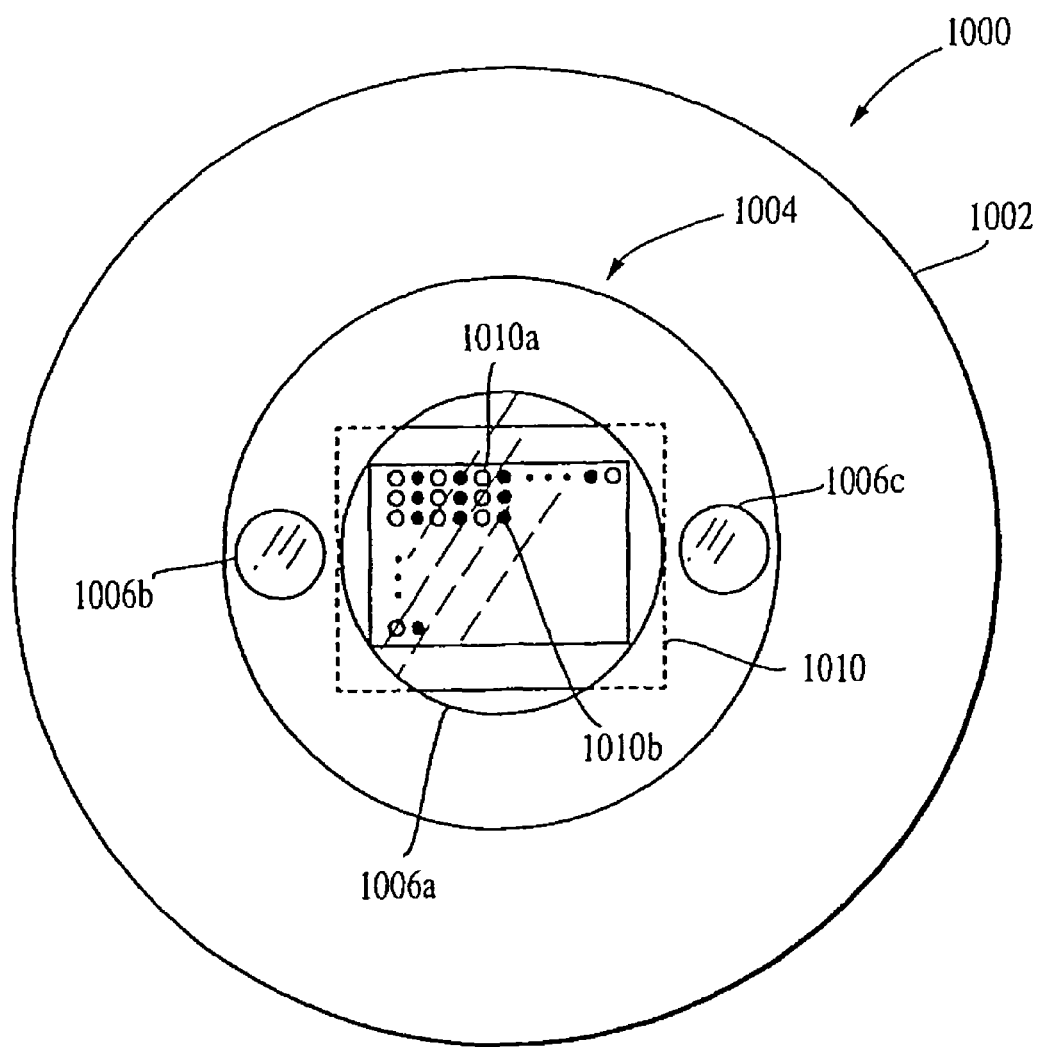

Referring now to FIG. 10*b*, a front view of the smart probe 1000 of FIG. 10*a* is shown, illustrating the relationship of the housing aperture 1004, lenses 1006, the CCD array 1010, and the lens cover 1008. Specifically, the aperture 1004 is sized and shaped to accommodate the CCD array 1010 and associated main lens 1006*a*, laser energy lens 1006*b*, and the optical light lens 1006*c*. The laser and optical lenses 1006*b*, 1006*c* are positioned laterally to the main lens 1006*a* in this embodiment. The aforementioned optional lens cover 1008 conforms to the outer surface of each of the lenses 1006*a*, 1006*b*, 1006*c*. Both remitted visible light and emissions resulting from the autofluorescence of the surrounding tissue are passed through the main lens 1006*a* (which is chosen to be effectively transparent to a broad range of wavelengths in the spectral regions of interest) to the CCD array 1010. The main lens 1006*a* is, in the embodiment of FIGS. 10*a* and 10*b*, a substantially convex lens designed to gather and more narrowly focus energy originating from various positions outside the probe 1000 onto the CCD array 1010. The laser lens 1006*b* and optical lens 1006*c* are, conversely, designed to radiate and distribute light incident on their inner surfaces (via their associated fiber optic bundles) more broadly within the intestine.

The CCD array 1010 of the present utilizes an interleaved design whereby individual charge collecting cells having sensitivity to broad spectrum visible light are spatially mixed with cells having sensitivity within a range of wavelengths ideally centered on the autofluorescence peak associated with biological tissue within the interior of the patient's intestine (530 nm in the present embodiment). Hence, two separate CCD sub-arrays are formed (each having approximately half of the total number of cells in the array 1010); (i) a "visible" light sub-array 1010*a*, and (ii) an "autofluorescence" sub-array 1010*b*. As shown in FIG. 10*b*, the pixels of the two sub-arrays 1010*a*, 1010*b* are physically interleaved such that alternation between the pixels of each sub-array occurs in the row dimension only. Therefore, when reading voltage data out of the array 1010 on a row-by-row basis, data from successive cells will be associated with alternating sub-arrays. When data is serially read out of the array 1010 of FIG. 10*b* in the column direction, an entire column is associated with the same sub-array. This arrangement is used to permit the data acquisition circuitry (described further below with respect to FIG. 12) to readily parse data from the two sub-arrays 1010*a*, 1010*b* and store it at different locations within the device memory 1026. It will be recognized that other types of interleaving of the array 1010 may be used in conjunction with the present invention, however. For example, alternation of pixels on a column basis may be used. Alternatively, pixels could be alternated on both a row and column basis. Furthermore, interleaving of the pixels need not be used; rather, a single multifunction CCD array, or a system of two or more discrete CCD arrays arranged in some other spatial relationship (such as side-by-side, or over-under) could be used, either with a single lens 1006*a* as shown in FIG. 10*b*, or separate, dedicated lenses.

Figure 11:
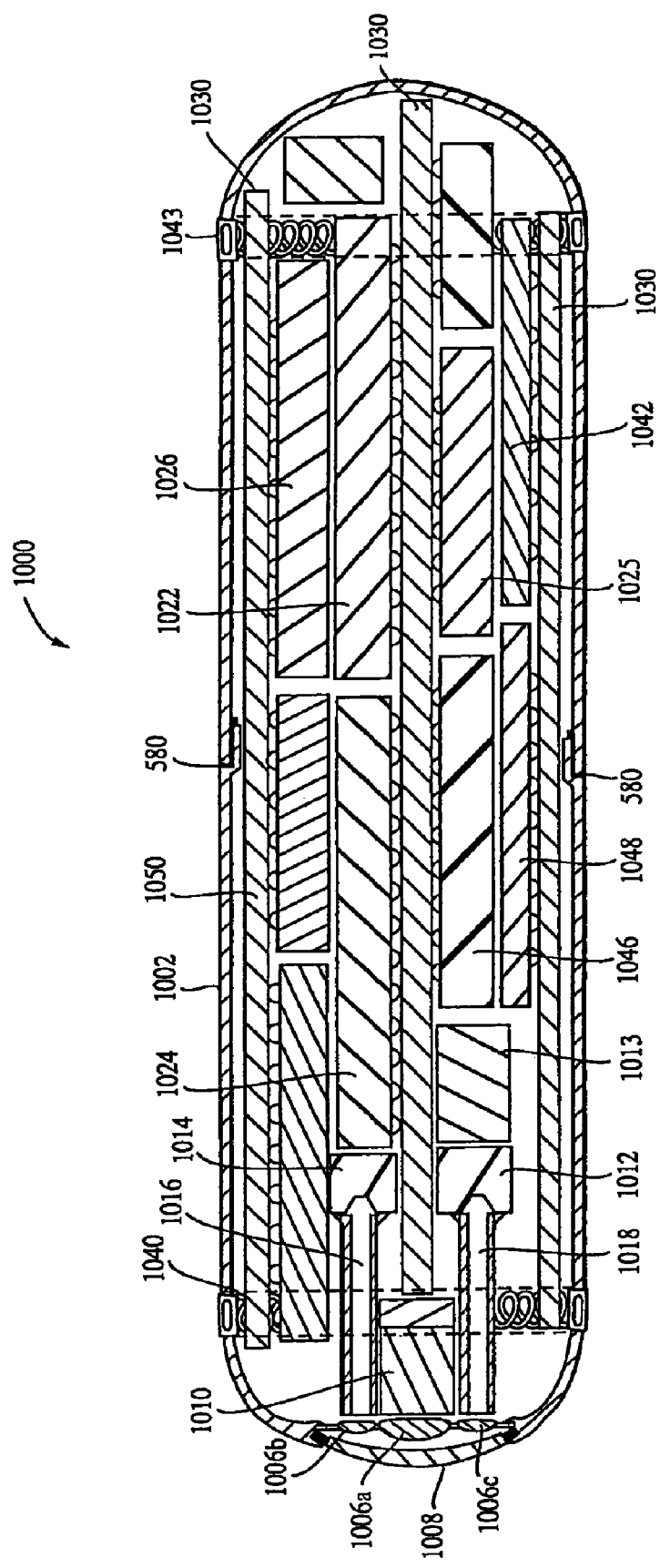
FIG. 11 is a cross-sectional view of the smart probe of FIG. 10a, taken along line 11-11.

Referring now to FIG. 11, a cross-section of the probe 1000 of FIGS. 10*a* and 10*b* is illustrated. The probe outer housing 1002 generally contains a number of different components in its internal cavity 1003 including the aforementioned lenses 1006*a*, 1006*b*, 1006*c* and CCD array 1010, as well as a semiconductor laser 1012, light emitting diode (LED) 1014, two respective single mode fiber optic bundles 1016, 1018, and one or more data transfer terminals 1020. A number of discrete or integrated semiconductor components are also present within the probe 1000, including, inter alia, an analog-to-digital converter (ADC) 1022, a digital processor 1024, microcontroller 1025, digital memory 1026 with integral memory controller, as described in greater detail below. The semiconductor laser 1012 and LED 1014 are located approximately co-linearly with the central axis of their respective lenses 1006*b*, 1006*c*, with the fiber optic bundles 1016, 1018 disposed there between as shown in FIG. 11. The laser and LED 1012, 1014, their respective bundles 1016, 1018, and respective lenses 1006*b*, 1006*c* are optically coupled so as to transmit light energy to the lenses in an efficient manner. The ADC 1022, signal processor 1024, memory 1026, and other electronic components are disposed within the cavity 1003 on one or more miniature printed circuit board assemblies (PCBAs) 1030 in a space-efficient manner, with the semiconductor components being disposed and electrically connected on either side of the assemblies 1030. One or more data transfer terminals 1040 in the form of circumferential rings are located within the outer housing at or near the surface thereof in order to provide for data transfer between the probe 1000 and the MCD remote unit (not shown). Additionally, a power transfer circuit 1042 with transfer terminals 1043 similar to that described with respect to the embodiment of FIGS. 3-7 is disposed within the housing 1002 on a PCBA 1030 to receive and demodulate inductive modulated energy generated externally to the patient by the MCD remote unit. Optionally, in yet another embodiment, a NiMH or comparable miniature battery (not shown) and supporting circuitry may be included within the outer housing 1002 as a power source in lieu of the aforementioned inductive power circuit 1042.

Figure 16:
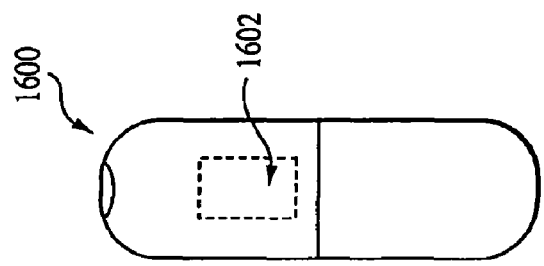
FIG. 16 is a side plan view of one exemplary embodiment of the smart probe of the present invention, illustrating relative location of the SoC device.

As previously discussed with respect to the embodiment of FIGS. 3-7, the package profiles of the components used within the present embodiment are chosen so as to permit all of the above-described components to be fit within the outer housing. This becomes particularly critical with respect to the embodiment of FIGS. 10*a*, 10*b*, and 11, since there are substantially more components contained within the outer housing 802. The size of each component package must be weighed against the necessity of the component and the overall available space within the probe housing 1002. For example, when choosing a DSP package, the necessary MIPS, degree of integration of other functions within the DSP (such as, DMA, internal memory, etc.) are balanced with the available space within the housing. Similarly, the memory storage capacity is balanced with the physical package size in order to optimize all parameters. Also, as previously discussed, the use of highly integrated multifunction devices such as that of FIG. 16 is desirable in order to reduce the size of the probe 1000. For example, embedded memory (i.e., that integrated within the DSP or other component package) may be employed as the capability of such devices increases. Furthermore, the placement of the individual components at various locations on the PCBAs 1030 (as well as the placement of the PCBAs themselves) is optimized for space.

In light of the foregoing, it will be appreciated that the size and shape of the probe outer housing 1002 can be adjusted to accommodate internal components of varying sizes, consistent with the requirement that the housing be sized and shaped to permit passage through the desired portion of the patient's intestinal tract. Typically, the ileocecal valve at the juncture of the small and large intestines will constrain the maximum diameter of the probe housing. The probe housing 1002 of the embodiment of FIGS. 10-11 is larger (roughly 40 mm in length, and 15 mm in diameter) than that of the embodiment of FIGS. 3-5 (roughly 30 mm in length, and 12 mm in diameter), although it will be recognized that other sizes and shapes may be used.

Figure 2:
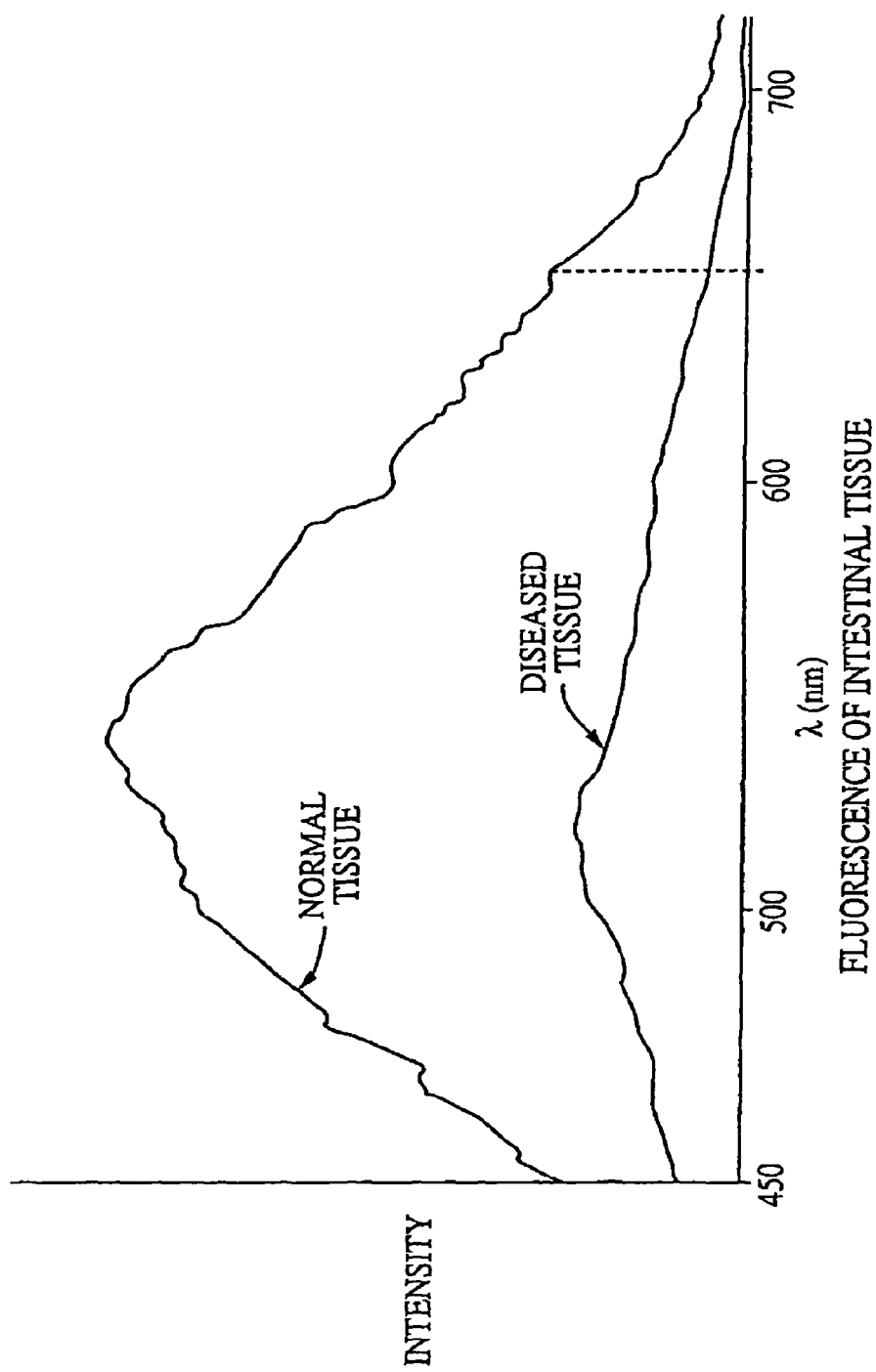
FIG. 2 is a typical autofluorescence spectrum of intestinal tissue illustrating the difference in response for normal and diseased tissue based on exposure to light at a is wavelength in the range of 450 to 700 nm.

The laser 1012 of the smart probe 1000 is now described. A semiconductor (diode) laser is used in the embodiment of FIGS. 10-11 to generate laser energy in the desired wavelength band. In the present embodiment, a center wavelength of 530 nm (corresponding to green light) is used, although it will be recognized that other wavelengths may be chosen based on the response of certain types of tissue and the needs of a specific application. As shown in FIG. 2, the ratio of measured fluorescent intensity for diseased tissue to that of normal tissue is minimized (and both the absolute intensity and intensity difference maximized) at roughly 530 nm, thereby effectively increasing the resolution and signal-to-noise ratio of the system without additional processing. A micro-package diode laser is utilized based on availability and cost, output power, size, and power consumption considerations, although other lasers may be used. A laser driver circuit 1013 (such as a model NS102 manufactured by NVG Corporation) is used in conjunction with the aforementioned laser diode in order to control the operation and output of the diode. Note that the size of the laser diode and driver circuit (on the order of a few millimeters in all dimensions) allows conservation of space within the probe outer housing 1002. The laser 1012 may be configured to operate in either pulsed or CW (continuous wave) modes, or both, depending on the needs of the operator. Switching between modes of operation is accomplished via the microcontroller 1025, as is well known in the art.

In yet another embodiment, the aforementioned laser diode 1012 and associated circuitry and power supply are adapted to ablate intestinal tissue through direct irradiation with coherent electromagnetic energy. Due to the increased power output requirements of ablation, the laser diode is adapted to radiate increased power as compared to the autofluorescence laser diode previously described herein. The semiconductor laser of the present may generate for example, between 0.05 W and 1.0 W of continuous wave (cw) laser power at a wavelength of between 800 nm and 900 nm, although other wavelengths may be substituted. The laser may consist of a single semiconductor laser element, an array of semiconductor lasers, several individual semiconductor lasers or a combination thereof. The coherent light energy generated by the semiconductor laser(s) is transmitted into the single mode optical fiber (bundle). The fiber may contain a single fiber or several optical fibers to accommodate the increased light intensity. In the preferred embodiment, a single laser diode generating 0.15 W cw of 800 nm laser energy out of a 150 micron diameter, 0.25 Numerical Aperture (NA) optical fiber, although other configurations may be used.

An exemplary semiconductor laser diode 1012 comprises a GaAs substrate upon which an N-doped AlGaAs cladding layer is deposited, as is well known in the semiconductor arts. Upon this structure, a single quantum well of GaAs is formed as a thin layer between the layers of AlGaAs, the index of infraction varying as the layer proceeds from the cladding layer to the quantum well. A semiconductor laser diode, as the one previously described, will produce an output in the portion of the quantum well region when a sufficient voltage difference is maintained between the N- and P contact layers. Other types of devices may also be substituted, consistent with the space and electrical power constraints of the particular probe configuration with which the laser diode is used.

Note that the supply of such power (i.e., 0.15 W=0.15 J/s) for the semiconductor diode ablation laser is derived either from on-probe sources; e.g., battery, structural capacitor (described below), or inductive/RF power coupling (previously described), and/or through use of a "trailer" probe as described subsequently herein with respect to FIG. 34. As will be readily appreciated, the trailer probe may be used to store additional energy for use by the laser in vivo, including for example additional battery cells or structural capacitance.

Figure 12:
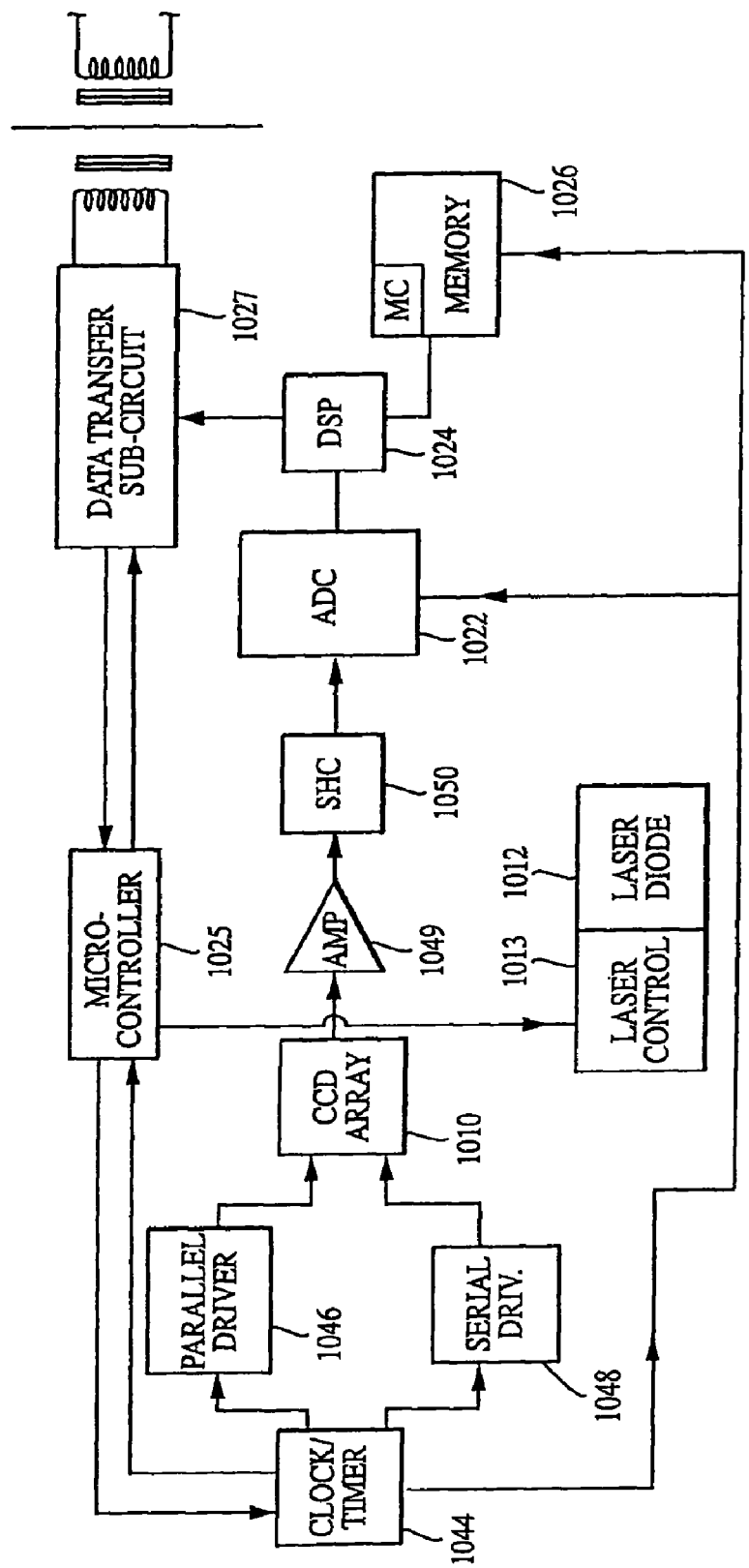
FIG. 12 is a block diagram of one preferred embodiment of the data acquisition, processing, storage, and transfer circuitry of the smart probe of FIG. 10.

Referring now to FIG. 12, one embodiment of the data acquisition, storage, and transfer circuit 1200 of the present invention is described. As shown in FIG. 12, the circuit 1200 comprises generally a combined CCD array 1010, analog-to-digital converter (ADC) 1022, digital signal processor (DSP) 1029, microcontroller 1025, random access memory (RAM) with integral memory controller 1026, and a data transfer sub-circuit 1027. Other components include a system clock/timer 1044, parallel/serial drivers 1046, 1048, sample and hold circuit 1050, data compression algorithm (running on the DSP), and data transfer terminal(s) 1040. The function and operation of these components are described in greater detail below.

As previously described, the CCD array 1010 or other device is used to gather light energy of varying wavelengths, and produces a voltage output which is proportional to the intensity of the incident light. Note that during laser operation, the cells of the CCD may be drained if required to prevent damage. The analog output of the CCD array is fed to the ADC 1022, which converts the analog signal to a digital representation. The ADC of the present embodiment has at least two analog input channels which are multiplexed to permit the conversion of analog voltage data generated by either of the CCD sub-arrays 1010a, 1010b to a digital format. The digital output of the ADC is fed to the DSP 1024 which performs a variety of control and signal processing functions including demultiplexing of the multiplexed ADC signals, and signal compression for storage in the memory 1026. The DSP takes the digital data received from the ADC, demultiplexes and formats it, and optionally compresses it for storage within the memory using any number of data compression techniques such as pulse code modulation (PCM) or delta pulse code modulation (DPCM), which are well known in the signal processing arts. Data compression is performed within the DSP using an algorithm adapted for such purpose which is stored within the program or flash memory of the DSP 1024 or, alternatively, within the off-chip memory 1026. It will be appreciated that while a DSP having a program memory is used in the present application, other types of processors may be substituted based on the chosen data acquisition and transfer properties. A discretely packaged DSP such as a Texas Instruments TMS320C2xx series processor (roughly 14 mm×14 mm×2 mm in the "PN" PQFP package) can be used in the present embodiment, although as previously discussed, it is desirable to integrate as many probe functions into one IC as possible in order to economize on space within the probe outer housing. Note that if data compression is not used, the need for a DSP is obviated, since other functions may be performed by the microcontroller 1025. The DSP 1024 interfaces with the memory controller within the memory 1026 which controls the accessing and storage of data therein. The probe memory 1026 of the present embodiment is a standard 3.3.V logic static random access memory (SRAM), although other types of memory (such as DRAM, SDRAM, double-data rate (DDR) SDRAM, "flash", or SLDRAM) may be used. 3.3.V SRAM is preferred based on its comparatively low power consumption and static data storage properties. The memory 1026 is chosen to have adequate storage capacity for compressed (or non-compressed) data output from the DSP 1024 during imaging. The memory 1026, depending on the operating mode of the probe (e.g., streaming data externally via the data transfer sub-circuit, or storing internally), must be able to store a sufficient amount of data so as to permit (i) any buffering of the data necessitated by the data transfer sub-circuit 1026, and (ii) storage of at least one frame (and preferably more) obtained by the CCD array 1010. In the present embodiment, a sub-array of 31,680 pixels is used (192 pixels per line, 165 lines per sub-array); hence, a memory storage capacity corresponding to binary representations of at least this number of pixels is used. The memory storage capacity needed is further determined by the type and efficiency of compression utilized, if any. Compression is used not only to minimize the size and increase the capacity of the memory 1026 within the probe, but also to minimize the bandwidth necessary to transmit data via the data interface sub-circuit 1027.

It will be recognized that while the foregoing descriptions of the smart probe of the present invention are cast in terms of embodiments having laser and/or broad spectrum visual light sources, a CCD array, inductive power and data transfer, and signal processing and/or data storage capability, any number of different combinations of these features (or even other features) may be used consistent with the present invention. For example, a probe having a laser diode, CCD array, capacitive data transfer, and battery power supply is contemplated. Alternatively, other embodiments of the smart probe could include a device for obtaining a microsample (biopsy) of intestinal tissue, or for delivering a dose of a drug, chemical, or even ionizing radiation to, inter alia, otherwise inaccessible portions of the intestine of the patient. A large number of alternate configurations are possible, all being within the scope of the present invention. Some of these alternate configurations are described in greater detail herein with respect to FIGS. 16-35c.

Endoscopic Delivery Device

Figure 13:
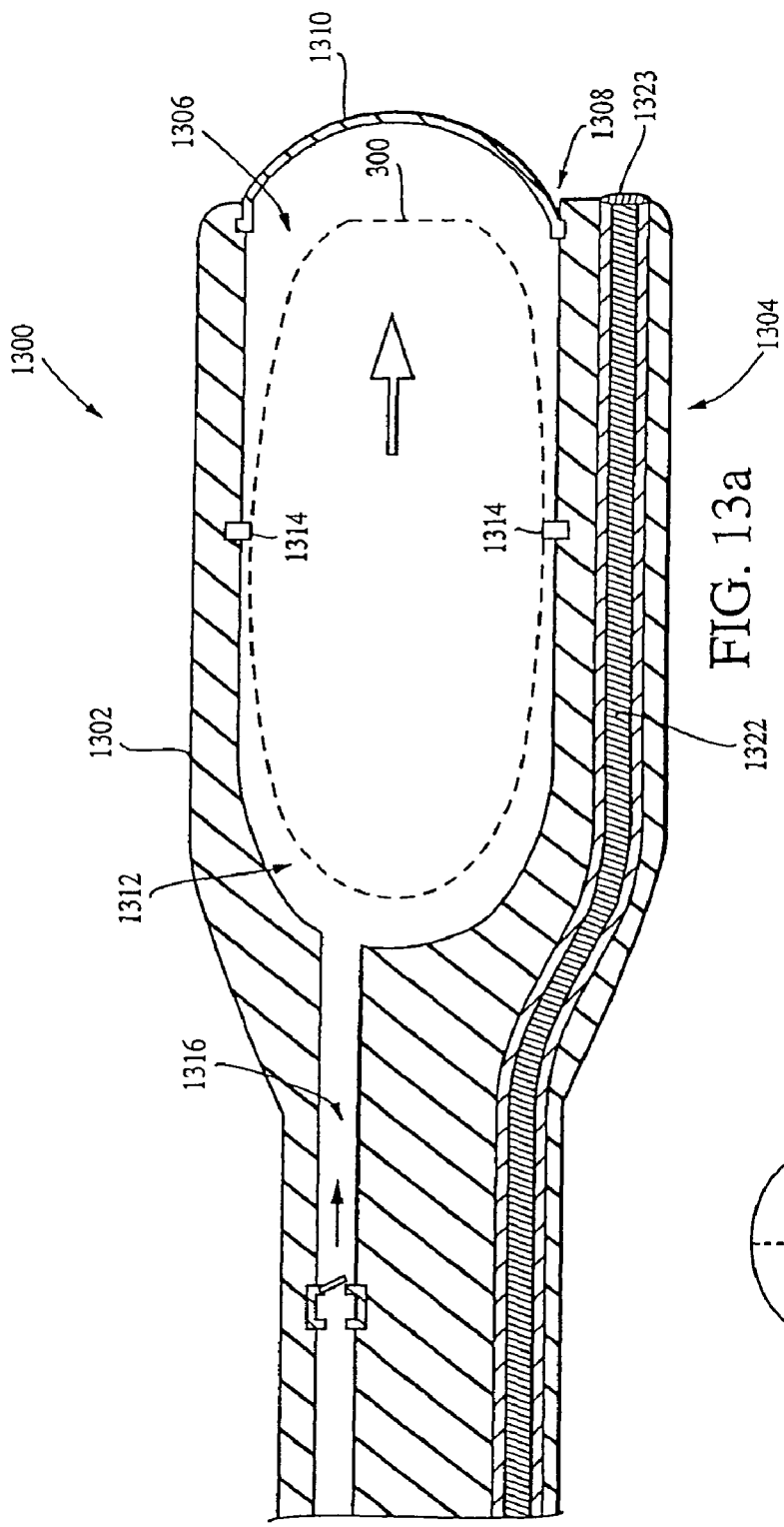

Referring now to FIG. 13a, a first embodiment of the endoscopic delivery device of the present invention is disclosed. Specifically, the device 1300 of FIG. 13a includes a housing 1302 located at its distal end 1304, the housing having an internal cavity 1306 sized to receive the smart probe 300 of FIG. 3 (or alternatively, other embodiments). The housing 1302 and distal end of the device 1304 are sized so as to permit passage through the esophagus and stomach of a patient. The cavity 1306 is open at the distal end of the device, such that the smart probe 300 may be inserted into the cavity via an aperture 1308. A closure or diaphragm 1310 is mounted over the aperture 1308 as shown in FIG. 13*a*. The closure 1310 is, in the present embodiment, a substantially hemispherical membrane which is scored or perforated in one or more areas of its surface so as to be substantially weakened in these areas (see FIG. 13*b*). In one embodiment, the closure is scored radically as shown in FIG. 13. One or more tubes 1316 running down the length of the delivery device 1300 terminate in the cavity 1306 in the region 1312 behind the probe 300 (when inserted in the housing 1302). A pliable, ring-shaped seal 1314 is fitted to the interior of the housing near the aperture 1308, the seal having an inner diameter of its sealing surface approximating that of the probe outer housing 302. The seal 1314 is sized so as to permit easy movement of the probe 300 through the seal, yet also maintain adequate sealing against the gross leakage of fluid (or gas) past the seal. A non-toxic fluid or gas (such as water, or air) is applied via the tube(s) 1316 during implantation of the smart probe in order to expel the probe from the housing 1302 and cavity 1306. Collectively, this arrangement comprises the release mechanism.

As the portion of the cavity 1306 behind the probe and seal 1314 is pressurized by the fluid/gas, the probe 300 is displaced forward within the cavity so as to contact the closure 1310. The scores 1320 in the closure 1310 will eventually yield under the force exerted by the probe, thereby rupturing the closure and allowing the expulsion of the probe from the cavity. It will be recognized that the yield stress of the closure scores 1320 is preferably set such that an extremely low fluid/gas pressure is required to rupture the closure, thereby causing the probe 300 to move slowly out of the housing 1302 and preventing any potential trauma to the interior region of the patient's intestine from the expulsion transient. Additionally, the rate of pressure increase within the cavity 1306 can readily be controlled by the operator using any number of available means such as a hand pump, low volumetric flow rate mechanical pump, or the like.

While the present embodiment describes a mechanically ruptured closure and associated fluid system for expelling the probe, it can be appreciated that a number of different ways of rupturing or dissolving the closure may be employed. For example, minute electrical filaments could be used to melt portions of the closure prior to probe expulsion. Alternatively, the closure could be dissolved or weakened by the presence of one or more chemical agents, or even light energy. It will be further recognized that the closure is optional and may not even be used in certain applications, especially if a lens cover 308 is used on the probe 300.

In the embodiment of FIG. 13*a*, a narrow fiber optic bundle 1322 and lens 1323 is routed around the periphery of the probe and within the housing 1302 of the endoscopic delivery device 1300 in order to assist the operator in locating and implanting the smart probe 300. Light gathered by the bundle 1322 and lens 1323 is transmitted to a video display unit or other means of viewing (not shown). It will be recognized, however, that other means of viewing the probe 300 during delivery (both direct and indirect) may be used. For example, the probe/delivery device location could be viewed using ultrasonic, magnetic resonance, or X-ray imaging.

Figure 14:
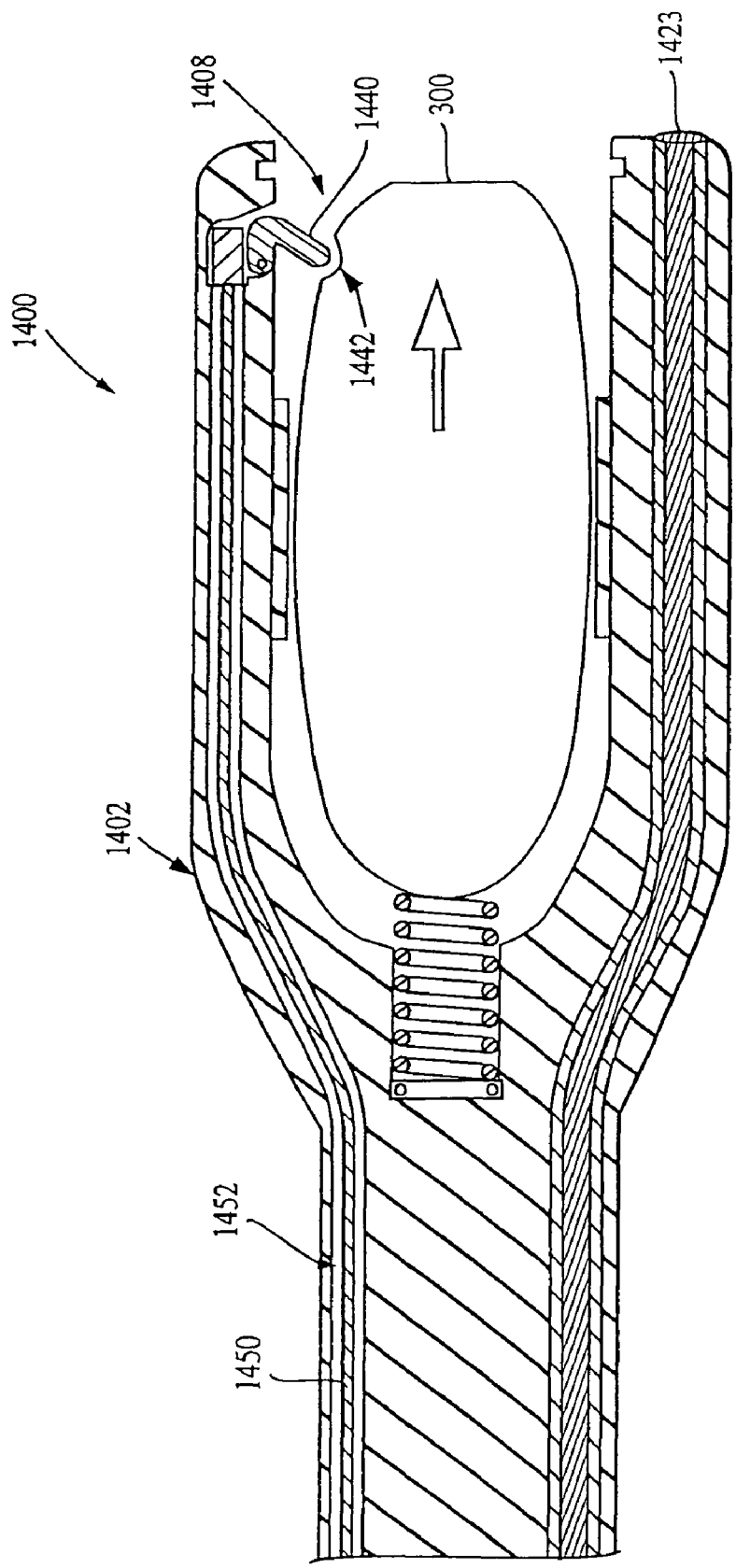
FIG. 14 is a cross-sectional view of second embodiment of an improved endoscopic delivery device capable of implanting the smart probe of the present invention within the intestinal tract of a patient.

A second embodiment of the improved endoscopic delivery device according to the present invention is shown in FIG. 14. In this embodiment 1401, the smart probe is biased by a spring or other means (such as an elastic member) toward the aperture 1408 in the housing such that the probe is urge from the cavity 1406 and housing 1402, as shown in FIG. 13*b*. A retaining detent or latch 1440 is positioned at or near the aperture 1408 and engages a recess 1442 in the outer housing 302 of the probe 300 such that when the probe is inserted into the cavity and latched, the spring 1446 (or other biasing means) biases the probe 300 against the latch 1440. The latch is, in the present embodiment, actuated by a miniature cord or cable 1450 disposed within a channel 1452 running longitudinally up the side of the delivery device 1401, although it will be recognized that a myriad of different release mechanisms may be used. Alternatively, an outer closure (not shown) may be used in place of the latch 1440 to retain the probe 300 within the housing against the biasing force until the closure is sufficiently weakened by electrical energy, light energy, or the presence of a chemical agent.

Method of Providing Diagnosis and Treatment

Figure 15:
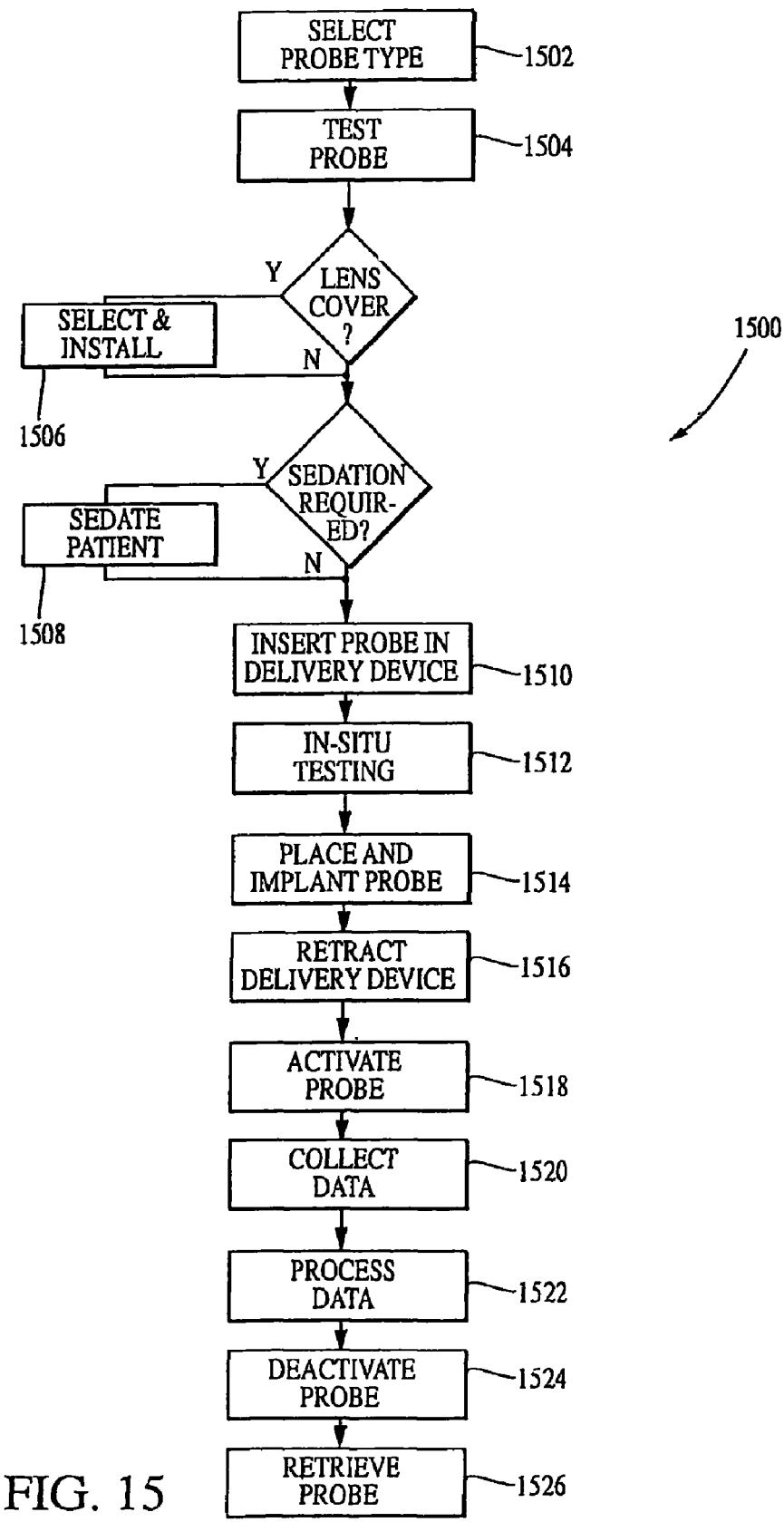
FIG. 15 is flow diagram illustrating one embodiment of the method of diagnosing and/or treating the intestinal tract of a patient using the smart probe of the present invention.

Referring now to FIG. 15, a method of providing diagnosis and treatment of a patient using the apparatus of the present invention is disclosed.

It will be recognized that while the following method recites a series of steps in a given order, this order may be permuted where appropriate such that the steps recited herein may be performed in alternate sequences. Additionally, certain steps (including, for example, the installation of the lens cover) may be completely omitted, or other steps added. The following description is meant only to be illustrative of the method of the present invention.

It will be further recognized that while not recited as a specific step in the embodiment of the method described below, patient intestinal preparation prior to introduction of the smart probe is essential to the proper operation of the probe while in the patient. Such intestinal preparations exist in a myriad of different varieties and are well understood by those of ordinary skill in the medical arts, and accordingly shall not be discussed further herein.

Additionally, while the following description of the method of the present invention is cast in terms of delivery via an endoscopic delivery device, it will be appreciated that other methods or forms of delivery device may be used, and that the method is not limited to one form of delivery. For example, the probe may be sized such that it can be swallowed by the patient. Ultimately, as the probe is passed through the stomach into the small intestine after swallowing, it will be oriented based on its shape (substantially ellipsoid or cylindrical in the preferred embodiments) so as to facilitate data gathering.

In the first step 1502 of the instant method 1500, the type/configuration of probe to be used is determined based on the parameters of the patient and the information desired, and a testing protocol selected. For example, if only a visual inspection of a portion of the intestinal wall of a patient is desired, then a probe of the type described with reference to FIGS. 3-7 above is selected. Such a probe can arguably have a smaller profile (due to its simpler construction as compared to the probe of FIGS. 10-11), and therefore may be better suited in applications where intestinal strictures may exist.

The probe is then tested outside of the patient to verify proper operation in step 1504. Such testing may include, inter alia, testing of the operability of the CCD array, laser diode and DSP (if so equipped), LED, data transfer circuit, and inductive power circuit. It will be recognized that a number of different test protocols may be used depending on, inter alia, the specific configuration of the probe.

Next, the proper lens cover is chosen for use with the probe and installed if desired in step 1506. As previously discussed, the lens cap is in one embodiment comprised of a material which dissolves in the presence of one or more gastric substances (or due to other conditions such as exposure to coherent light energy). Information regarding the motility of the patient's intestinal tract, and the location of the region of prospective examination/treatment, may also be used in making the selection of the proper lens cover if appropriate. In the embodiment of FIGS. 3-5, the lens cap may simply be installed to fit within the recess around the lens 306, as described above.

In step 1508, the patient is optionally sedated using any number of techniques which allow the probe to be inserted (via the aforementioned endoscopic delivery device) into the esophagus of the patient. Sedation techniques are commonly used in endoscopic examination and are well known in the medical arts, and accordingly are not described further herein.

Next, in step 1510, the smart probe 300 is introduced into the patient. In one embodiment of the present method, the probe is inserted using the specially adapted fiber optic endoscopic delivery device previously described. It will be recognized, however, that other methods of delivering and placing the probe can feasibly be used with equal success.

In the next step 1512 of the present method, the smart probe is tested in-situ while still retained within the housing of the delivery device 1300 to ensure proper data and/or power transfer between the external monitoring and control device (MCD) 800 and the probe. The probe 300 is first powered up using the inductive (or RF) signal applied from the MCD remote unit 802 via the power transfer circuit 700. Then, the CCD and probe circuitry and LED circuitry is activated to generate ambient light and an image using the CCD array 402. This image data is then transferred to the MCD via the data transfer circuit 600 to verify proper operation of the CCD and associated components. Optionally, the functionality of the laser 1012, 1013 and the autofluorescence CCD sub-array 402b (if so equipped) can be verified as well. Note that if the lens cover 308 is utilized, the image transferred will be blurry and out of focus due to the optical characteristics of the lens cover. However, the operation of the CCD and laser can be suitably verified even with the lens cover in place.

After proper operation of the probe 300 is verified, the probe is positioned and implanted within the patient in step 1514. Ideally, the probe 300 is implanted in the ileum region of the patient's small intestine; however, other locations may be used. Implantation preferably occurs using the aforementioned fluid/gas pressurization technique which expels the smart probe 300 from the endoscopic device housing 1302.

Next, the endoscopic delivery device 1300 is retracted from the patient in step 1516. The smart probe 300 is then activated and tracked (or, alternatively, tracked and subsequently activated when the desired probe position is achieved, or maintained in an activated state continuously) in step 1518. Tracking can occur in a number of ways including, inter alia, via direct feedback (i.e., by maintaining continuous data transfer between the probe and the MCD remote unit), or by using an ultrasound imaging system.

Next, in step 1520, visual or autofluorescence image data is streamed out of the probe and/or stored, based on memory limitations, within the memory of the probe if so equipped. Note that if a lens cover 308 is utilized on the probe 300, the lens cover must be dissolved prior acquiring image data. Furthermore, if a probe having the aforementioned laser module 1012, 1013 is used, and laser-excited autofluorescence data is desired, the laser diode will need to be activated for a period of time beginning prior to the acquisition of autofluorescence image data by the autofluorescence sub-array 402b.

In step 1520, data streamed from the probe 300 is processed and analyzed in the MCD 800. Note that this step may be performed at a later time; i.e., the image data can be stored within the storage device 916 of the MCD or other external storage device for later analysis.

When all data acquisition is complete, the probe is deactivated (such as by simply by powering it down) in step 1522. Lastly, in step 1524, the probe 300 is retrieved from the patient via normal excretory function. Any remaining data stored in memory 1026 at that point may be retrieved using the MCD 800 and data transfer circuit 600 previously described, and subsequently analyzed.

Figure 16A:
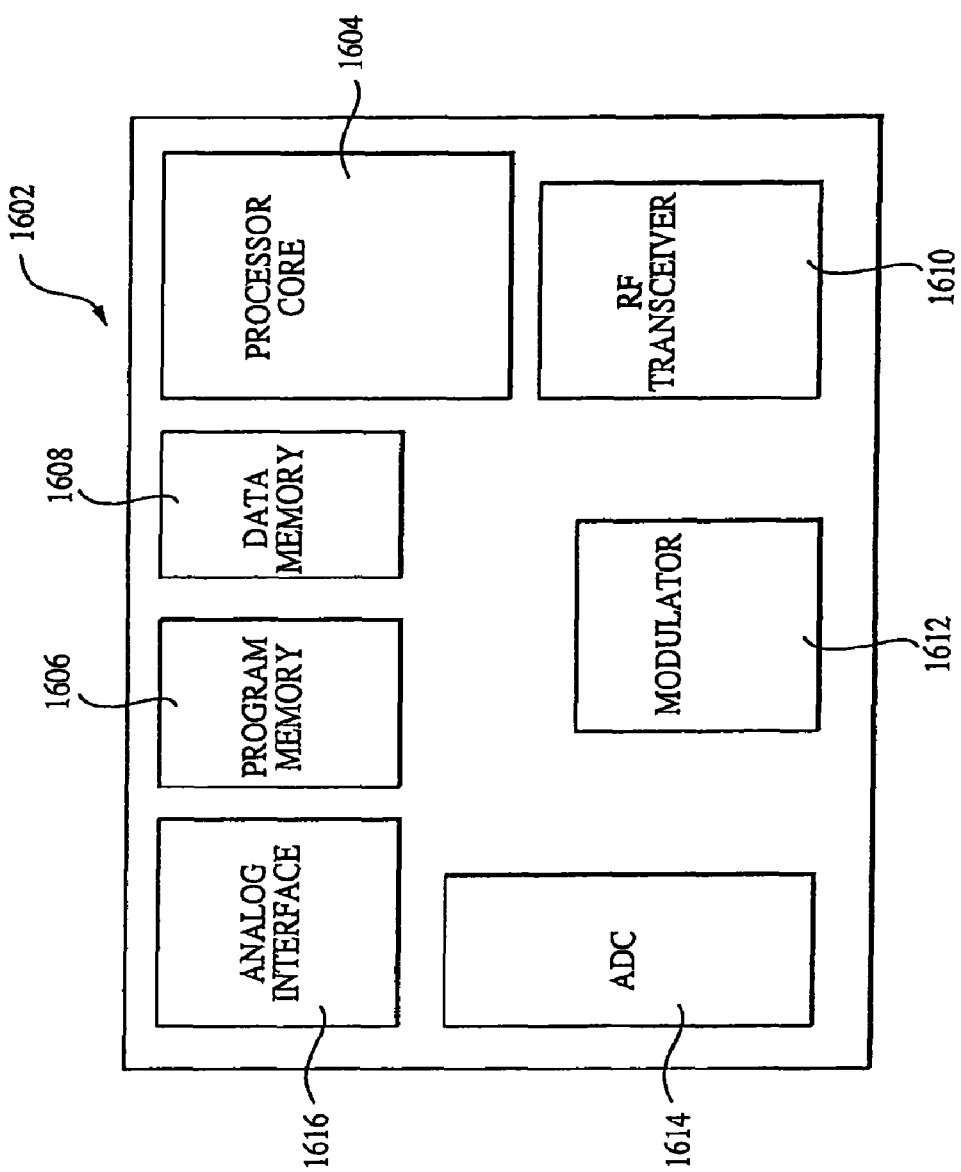
FIG. 16a is a block diagram illustrating the various functional components of the SoC device of FIG. 16.

Referring now to FIGS. 16 and 16a, another embodiment of the endoscopic apparatus of the invention is described. As illustrated in FIG. 16, the probe 1600 includes a fully integrated low-voltage "system on a chip" (SoC) application specific integrated circuit (ASIC) 1602 of the type generally known in the semiconductor fabrication arts. The SoC ASIC 1602 (FIG. 16a) incorporates, inter alia, a digital processor core 1604, embedded program and data random access memories 1606, 1608, radio frequency (RF) transceiver circuitry 1610, modulator 1612, analog-to-digital converter (ADC) 1614, and analog interface circuitry 1616. The digital processor core of the illustrated embodiment comprises an extensible reduced instruction set computer (RISC) which is advantageously selected to be user-configurable with respect to one or more sets of predetermined extension instructions. It will be recognized, however, that a variety of core architectures and features may be used, however, depending on the particular purpose, including Harvard architecture (separate program and data busses), very long instruction word (VLIW), multiple multiply-accumulate stages (e.g., dual MAC), etc.

The set(s) of instructions of the RISC core of the embodiment of FIG. 16a is/are specifically adapted to efficiently perform various processing computations (such as multiply-accumulate (MAC) operations) and tasks associated with the different various embodiments of the probe described herein. For example, with respect to (visual) or autofluorescense image processing, the operation and speed of filtering and/or compression algorithms of the type well known in the art may be enhanced through use of an optimized instruction set specifically adapted to those algorithms. Similarly, ultrasonic signal processing may be enhanced through selection of an instruction set adapted to perform, inter alia, fast Fourier transforms (FFTs) and associated "butterfly" calculations, time frequency distribution calculations (e.g., spectrograms) and associated windowing functions, or discrete wavelet transforms (such as the well known Haar wavelet transform). On-probe/off-probe communications may further be enhanced through improved execution of cyclic redundancy code (CRC) calculations for use in error detection.

Such user-customized and optimized extensible processor cores advantageously have a reduced gate count requiring less silicon than comparable non-optimized cores or multi-purpose (e.g., "CISC") processor designs, since the selection of a highly optimized instruction set substantially eliminates non-essential functionality during processor design synthesis and fabrication. With lower gate count, static and switching power losses are reduced, thereby providing the further benefits of reduced power consumption and lower rates of heat generation. Accordingly, with the present invention, the manufacturer or designer may advantageously select the appropriate optimized core configuration and instruction set applicable to the anticipated use of the endoscopic probe, thereby reducing the required space needed within the probe to accommodate the ASIC to the absolute minimum consistent with the extant or subsequently developed semiconductor fabrication process employed, and the power consumed and heat generated thereby.

Additionally, the core 1604 (and in fact the entire SoC device 1600) optionally includes one or more processor "sleep" modes of the type well known in the digital processor arts, which allow portions of the core and/or peripherals to be shut down during periods of non-operation in order to further conserve power within the device and reduce heat generation. For example, the pipeline and memory can be selectively shut down to significantly reduce power consumption when these components are not required (e.g., the probe is dormant before activation in vivo). It will further be appreciated that the aforementioned sleep modes may be preprogrammed; e.g., upon the occurrence of (or lack of) a certain event, such as the passing of a predetermined number of processor clock cycles, falling below a certain battery voltage level, detection of certain antigens via the antigen sensor array (FIG. 32), etc. Alternatively, the sleep modes may be actively invoked such as by the user based on operational parameters, such as when the shutdown of the probe for a period of time is desirable in order to conserve power for later activation.

The processor core 1604 of the embodiment of FIG. 16 comprises an extensible RISC processor of the design provided by ARC International plc of Elstree, Herts, UK, although other configurations may be used. The construction of optimized, extended instructions and instruction sets is well known in the processor design arts, and is described, for example, in U.S. Pat. No. 6,032,253 entitled "Data Processor with Multiple Compare Extension Instruction" issued Feb. 29, 2000, and U.S. Pat. No. 6,065,027 entitled "Data Processor with Up Pointer Walk Trie Traversal Instruction Set Extension" issued May 16, 2000, both or which are incorporated herein by reference in their entirety.

The SoC device 1600 (including core) design is generated using VHSIC Hardware Description language (VHDL) in conjunction with design and synthesis tools of the type well known in the art. An International Business Machines (IBM) "Blue Logic™" 0.11 micron Cu-11 ASIC process is used to fabricate the device of the illustrated embodiment, although other semiconductor fabrications processes including for example 0.35 micron or 0.18 micron may be substituted, depending on the degree of integration required. The IBM process further affords ultra-low power consumption by the device (1.5 V supply, which reduces power consumption by more than 50% over comparable 3.3 V devices). It will be recognized, however, that such higher voltage processes and devices may be substituted consistent with the integration and power requirements of the probe.

Furthermore, combinations of discrete components or collections thereof may also be used consistent with the invention. For example, the SiW1502 Radio Modem IC manufactured by Silicon Wave Corporation of San Diego, Calif., is a low-power consumption device with integrated RF logic and Bluetooth protocol stack adapted for Bluetooth applications. The chip is a fully integrated 2.4 GHz radio transceiver with a GFSK modem contained on a single chip. The SiW1502 chip is offered as a stand alone IC or, may be obtained with the Silicon Wave Odyssey SiW1601 Link Controller IC. The SiW1502 form factor is 7.0×7.0×1.0 mm package which is readily disposed within the interior volume of the probe described herein.

The RF transceiver 1610 and modulator device 1612 used in the embodiment of the SoC 1600 of FIG. 16a is adapted to generally comply with the well known "Bluetooth™" wireless interface standard, or alternatively, other so-called "3G" (third generation) communications technologies. The Bluetooth wireless technology allows users to make wireless and instant connections between various communication devices, such as mobile devices (e.g., cellular telephones, PDAs, notebook computers, remote monitoring stations, and the like) and desktop computers or other fixed devices. Since Bluetooth uses radio frequency transmission, transfer of data is in real-time. The Bluetooth topology supports both point-to-point and point-to-multipoint connections. Multiple 'slave' devices can be set to communicate with a 'master' device. In this fashion, the endoscopic probe of the present invention, when outfitted with a Bluetooth wireless suite, may communicate directly with other Bluetooth compliant mobile or fixed devices including the subject's cellular telephone, PDA, notebook computer, or desktop computer. Alternatively, a number of different subjects undergoing endoscopic analysis using the smart probe may be monitored in real time at a centralized location. For example, video data for multiple different patients within the ward of a hospital undergoing endoscopic analysis using the smart probe may be simultaneously monitored using a single "master" device adapted to receive and store/display the streamed data received from the various patients. A variety of other configurations are also possible.

Bluetooth-compliant devices, inter alia, operate in the 2.4 GHz ISM band. The ISM band is dedicated to unlicensed users, including medical facilities, thereby advantageously allowing for unrestricted spectral access. Maximum radiated power levels from the transceiver 1610 of FIG. 16a are in the mW range, thereby having no significant deleterious effect on the physiology of the subject due to radiated electromagnetic energy, especially given the comparatively transient nature of the transmissions from the transceiver, and the movement of the probe within the intestine. As is well known in the wireless telecommunications art, radiated power from the antenna assembly (not shown) of the transceiver 1610 may also be controlled and adjusted based on relative proximity of the transceiver 1610 (and probe), and/or the relative proximity and location of one or more other probe transceivers, thereby further reducing electromagnetic whole body dose to the subject.

The modulator 1612 uses one or more variants of frequency shift keying, such as Gaussian Frequency Shift Keying (GFSK) or Gaussian Minimum Shift keying (GMSK) of the type well known in the art to modulate data onto the carrier(s), although other types of modulation (such as phase modulation or amplitude modulation) may be used.

Spectral access of the device is accomplished via frequency divided multiple access (FDMA), although other types of access such as frequency hopping spread spectrum (FHSS), direct sequence spread spectrum (DSSS, including code division multiple access) using a pseudo-noise spreading code, or even time division multiple access may be used depending on the needs of the user. For example, devices complying with IEEE Std. 802.11 may be substituted in the probe for the Bluetooth transceiver/modulator arrangement previously described if desired. Literally any wireless interface capable of accommodating the bandwidth requirements of the system may be used.

Figure 16B:
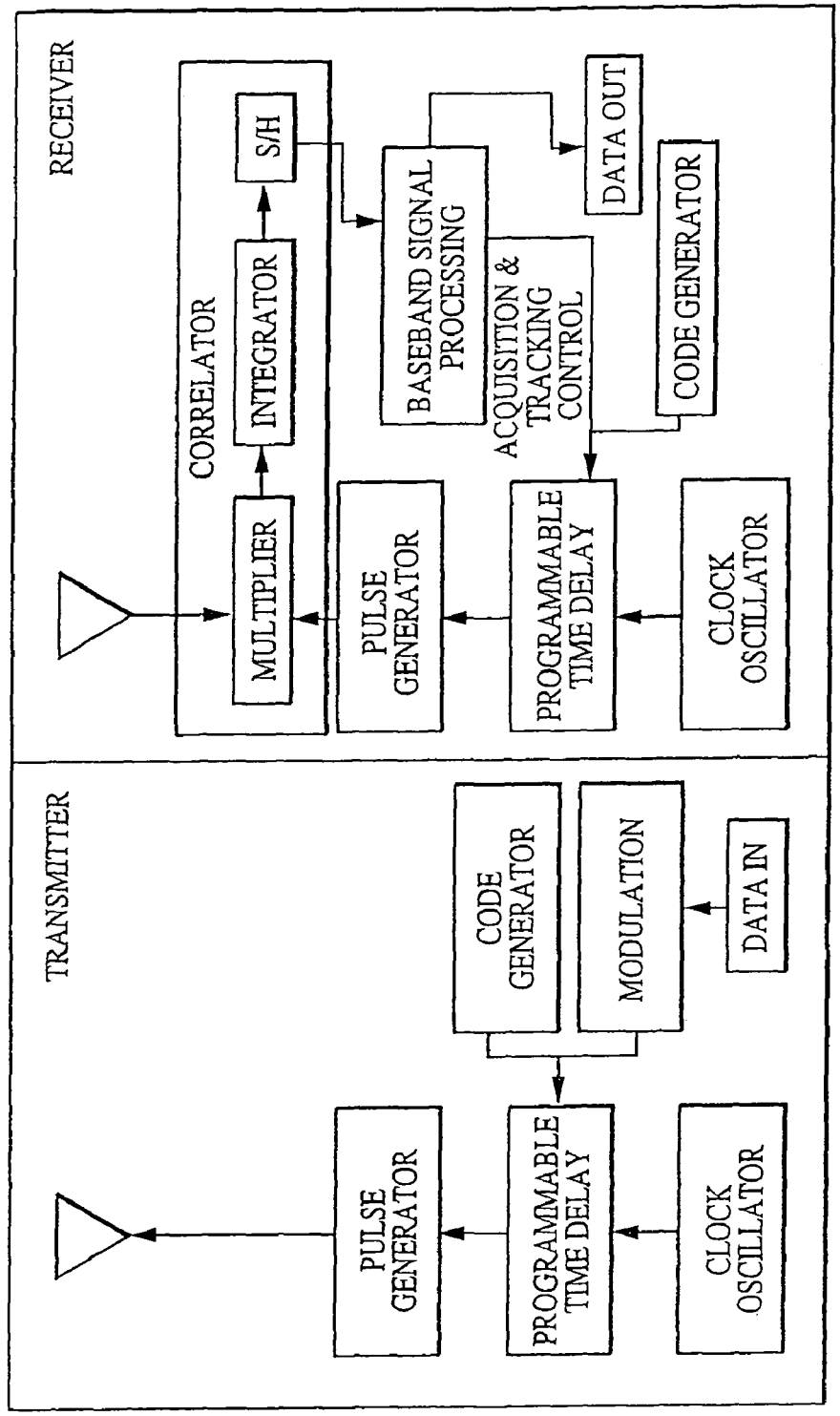
FIG. 16b is a block diagram illustrating the various functional components of another embodiment of the SoC device of the invention incorporating a TM-UWB transceiver.

In yet another embodiment of the invention, the probe utilizes a time-modulated ultra wide-band (TM-UWB) protocol for communication with one or devices external to the subject while the probe is in vivo. Specifically, the probe is fitted with an SoC device similar to that described previously herein with respect to FIG. 16; however, the SoC device of the present embodiment utilizes pulse-position modulation (PPM), wherein short duration "Gaussian" pulses (nanosecond duration) of radio-frequency energy are transmitted at random or pseudo-random intervals and frequencies to convey coded information. Information is coded (modulated) onto the short duration carrier pulses by, inter alia, time-domain shifting of the pulse. For example, a pulse encodes a bit by being temporal shifting of the pulse with respect to a reference, such that a "late" pulse encodes a "0", while an early pulse encodes a "1". This scheme is somewhat akin to the well known frequency shift keying (FSK), wherein two (or more) side-band frequencies are utilized to encode data; e.g., 67 kHz down-shift=0; 67 kHz up-shift=1. TM-UWB devices have the advantage of ready penetration of various mediums, as well as ultra-low power consumption and low spectral density, thereby reducing probe power requirements and potential interference with other device, respectively. In one exemplary variant, the TM-UWB device of the invention comprises a half duplex, 2.0 GHz with variable data rate in excess of 1 Mbps with no forward error correction (FEC). The Gaussian monopulse is of the form:

$$V(t)=(t/\tau)e^{-(t/\tau)2}$$

Where $\tau$ is a time decay constant related to the Gaussian monopulse duration, and center frequency $f_c=k/\tau$. The monopulse's bandwidth and center frequency are therefore directly related to the monopulse's temporal width or duration. This approach also shifts the transmission time of each monopulse over a significant time interval in accordance with a pseudo-nose (pn) "hopping" code of the type well known in the art, thereby advantageously distributing spectral density to make the spread. This approach is roughly comparable to frequency hopping spread spectrum (FHSS) except in the time domain. FIG. 16b illustrates one embodiment of the TM-UWB transceiver used in conjunction with the invention, although it will be appreciated that other configurations may be substituted. Exemplary devices incorporating TM-UWB components including the timer, correlator, and digital baseband signal processor and controller units (not shown) are available from IBM Corporation (silicon germanium-based) in the form of a chip set, although it will be recognized that an integrated single device is optimal for the invention. Additional detail on the implementation of TM-UWB systems is found in, e.g., "*Time Modulated Ultra-Wideband for Wireless Applications*"; Time-Domain Corporation, 2000, which is incorporated herein by reference in its entirety.

Figure 17:
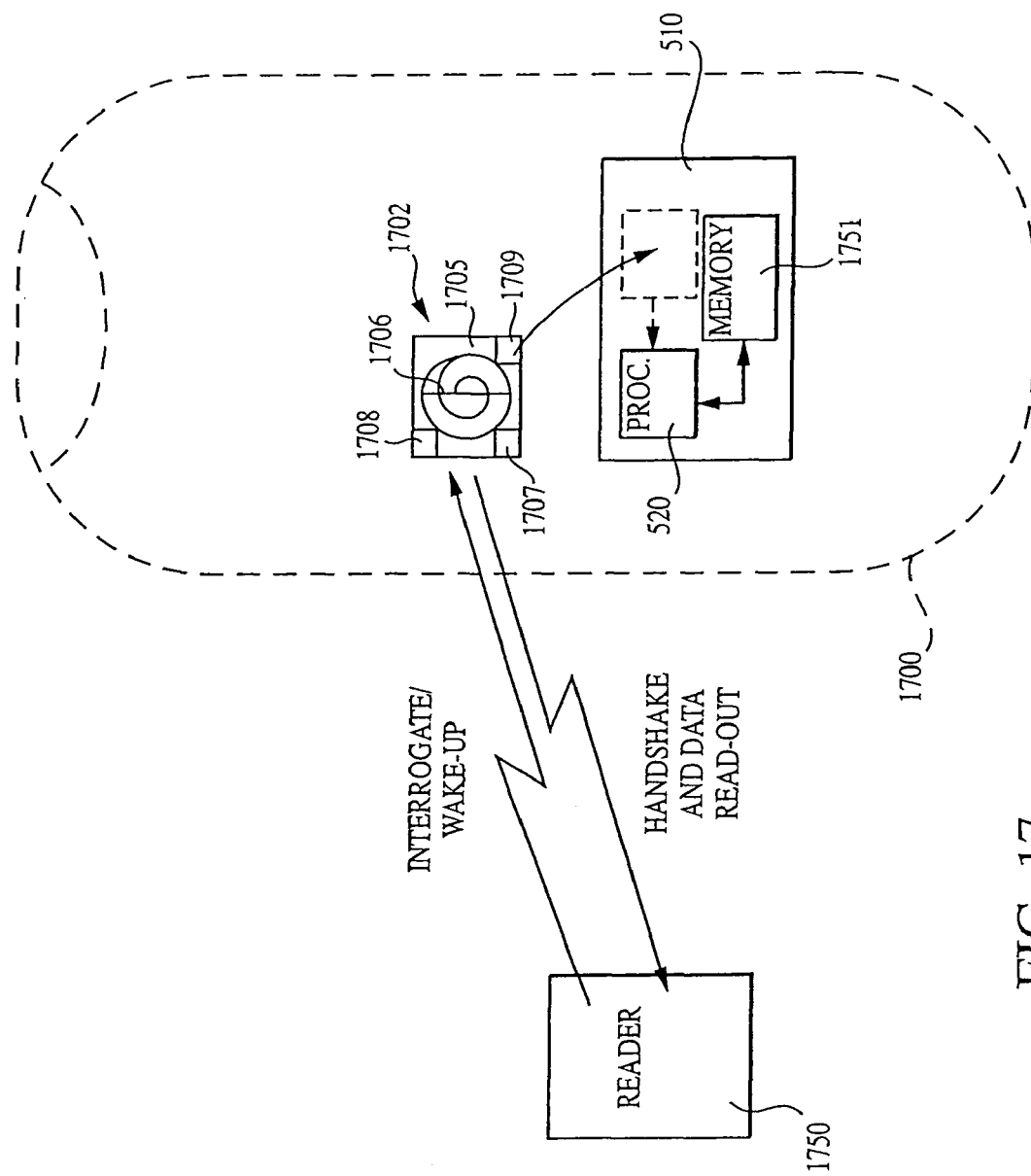
FIG. 17 is a functional block diagram illustrating the operation of the SoC device of FIGS. 16-16a, including interaction with a remote tag reader.

Referring now to FIG. 17, another embodiment of the invention is described having a radio frequency identification (RFID) tag 1702 installed within or made part of the autonomous smart probe 1700 to provide a variety of functions, including (i) retention of subject- or context-specific data; (ii) capsule inventory and security after manufacture; (iii) selective interrogation of probes; and (iv) writing or reading data to or from multiple probes simultaneously. Each of these aspects are described in greater detail below.

RFID tags are well known in the communications art. The main advantages of an RFID sensor and tag system over other forms of ID tagging include (a) the orientation of the tag with respect to the sensor is not critical for a correct read of the tag information; (b) communication can occur within comparatively harsh operating environments including those present in the intestinal tract of a living subject; and (c) the communication range between the sensor and tag can be significant (up to several hundred meters) even when the RF frequencies used are within the power limitations of Federal Communications Commission (FCC) rules concerning unlicensed transmitters. Accordingly, RFID technology is useful for several applications, especially those relating to security and asset management.

The process of "reading" and communicating with an RFID tag such as that used in the probe 1700 of FIG. 17 comprises bringing a RFID tag within proximity to an RFID sensor ("reader") 1750 which emanates a radio frequency wake-up field having a limited range. The RFID tag 1702 detects the presence of the wakeup field of the sensor 1750, and subsequently various forms or protocols of handshake occur between the tag 1702 and the sensor 1750 in order to exchange data. All of this communication between the tag and the sensor is performed using RF carriers of one or more prescribed frequencies. As is well known in the art, so-called "low-frequency" systems operate in the kHz to low-MHz range (unlicensed). Low frequency systems are generally low cost and complexity and have comparatively limited range, but are attractive since the low frequency energy tends to suffer low losses from materials like metal, polymers, tissue, and the like. High-frequency systems operate in the low-MHz to GHz range (often licensed). High-frequency systems in general have greater range, but are more directional. Additionally, the performance of these high frequency tags may be adversely affected by electromagnetic radiation or proximate metallic objects.

Additionally, RFID tags are generally categorized as being "active" (i.e., carry an associated power source for operation of the on-tag integrated circuit, and are capable of spontaneous transmission after reader interrogation), or "passive" which utilizes incident RF energy (from the reader, for example) to generate electrical energy for use by the IC, and transmission. Passive tags are highly energy efficient, and require only a small amount of electrical power to function.

In the present application, due to the premium on space within the probe 1700, a small antenna and package form factor (less than about 10 mm across) is required. Based on the foregoing considerations, the present embodiment of the invention utilizes a high frequency (e.g., 15 GHz nominal) miniature passive tag having a miniature monopole antenna 1706 of the type well known in the art, although it will be recognized that active tag architectures, lower or higher frequency systems, and alternate antenna configurations (such as "FIG. 8" loop, etc.) may be used depending on the particular application. A nominal frequency of 15 GHz is used as the carrier for the system, 10 mm corresponding to about one-half wavelength at that frequency.

The RFID tag 1702 of the present invention further includes an integrated circuit (IC) device 1705 including a transceiver section 1707 and processing logic 1709, as well as an integrated random access memory (RAM) device 1708 of the type commonly available with such devices adapted to store a plurality of data bytes such as data correlating to an individual subject, date of administration of treatment, social security number, and the like. The memory device 1708 may also comprise, without limitation, PROMS, EPROMS, EEPROMs, UVEPROMS, SRAMs, DRAMs, SDRAMS and ferroelectric memory devices. As illustrated in FIG. 17, the memory 1708 of the present embodiment is effectively independent of the on-probe memory 1751 (e.g. DSP "flash" or discrete memory previously described herein with respect to FIG. 10). In this capacity, the construction of the probe 1700 is simplified, and less complex or even "off the shelf" RFID devices meeting the physical space limitations may be used with little or no adaptation.

It will be recognized, however, that if data communication between the RFID memory 1708 and other memory devices or signal processing disposed on-probe or off-probe is desirable (such as described with respect to the alternate embodiment(s) below), such communication may be affected via techniques well known in the electronic arts. The present invention further contemplates, in an alternate embodiment, the integration of the RFID "tag" components including memory into a single silicon or semiconducting die, such as in the form of the aforementioned ASIC. Such embodiment has the advantage, inter alia, of further conserving on space within the probe.

In yet another embodiment, the RFID tag is distributed on one or more surfaces of the probe. See for example the "Bistatix™" RFID devices manufactured by Motorola Corporation, which utilize a very thin and low cost substrate employing printed circuit technology. Hence, by employing the Bistatix technology within the RFID tag of the present invention, the RFID tag may be disposed on any surface within the probe, such as the interior of the housing, on an unused section of PCBA, etc.

In operation, the tag "reader" 1750 of FIG. 17 interrogates the probe 1700 and RFID device 1702 at its designated frequency, causing the tag to "wake" and initiate communications protocols disposed within the tag memory 1702. Once such protocols are established, the reader transmits preformatted data representative of the parameters desired to be loaded into the RFID memory device 1708. For, example, prior to a given subject swallowing or having the probe introduced endoscopically, the tag memory 1708 is encoded with the subject's name, SSN, and date of administration via signals received from the reader 1750 via the antenna 1706 and transceiver section 1707 and processing logic 1709.

In yet another embodiment, the tag 1702 is coupled to the microcontroller IC 520 (FIG. 5) of the probe, thereby allowing the tag to "wake up" the probe indirectly (instead of using the aforementioned transceiver 1610 of the embodiment of FIG. 16, or alternatively an inductive/capacitive signal). In this fashion, the probe may be completely powered down until it is awaken by the tag 1702, thereby providing significant power savings prior to in vivo operation. Such power savings are even greater than those provided by the processor "sleep mode" previously described with respect to FIG. 16, in that when using the RFID tag 1702 wake up feature, the digital processor core 1604 of the ASIC may be completely shut down, including clock generator, pipeline, and (static) memory. Such complete shut down is possible since the passive tag generates a small amount of electrical power, on the order of a few mW, sufficient to re-initiate processor (and probe) operation on the battery or other power source providing electrical power after wake-up. It will be recognized, however, that the transceiver 1610 may alternatively be constructed to generate the required electrical power upon "interrogation" by a complementary RF transmitter.

The RFID tag 1702 of the embodiment of FIG. 17 has further utility for conducting inventory of "smart" probes after manufacture. Since each probe carries it's own tag, each capable of uniquely identifying itself (whether by unique frequency assignment, or data encoded on the tag memory 1708 and transmitted to the reader), rapid reading of a plurality of tags disposed in close proximity to one another is possible. For example, since the probes may be a valuable and easily pilferable commodity, regular inventory can be rapidly accomplished using the aforementioned RFID technology.

In yet another application, the foregoing unique identification capability of the tag 1702 coupled with the range of the high-frequency antenna system allows for the selective interrogation of the tag so as to load information, retrieve data, or initiate probe functions (such as wake up) while in proximity to other similar devices. For example, it is contemplated that the smart probe 1700 of the invention will be used in, inter alia, hospitals or other care facilities where a number of subjects undergoing various types of treatment are present. Such treatment likely includes several patients for which the smart probe 1700 has been administered. Rather than having to individually interrogate each tag by physically disposing it local to a communications device or reader 1750, the caregiver may selectively interrogate any tag within range of a central reader (not shown) to upload information (such as name, SSN, etc.), and/or induce wake-up of the tag and its associated probe, and the collection of data, or alternatively conduct of other types of operations such as the delivery of medication, radioisotope therapy, tissue biopsy, or any other number of probe-related tasks as described in detail herein. Such central reader may further be programmed to automatically initiate and monitor such activities, such as through a software routine running on a processor disposed within the central reader. Many other control schemes are possible (e.g., upon the occurrence of predetermined events, the passage of time, a signal generated by a miniature accelerometer disposed within the probe adapted to sense motion of the subject indicating that they are awake/ambulatory, etc.), and may be used in place of or in combination with the techniques previously described. The construction of such miniature accelerometers is well known in the electronics arts; see, for example, U.S. Pat. No. 5,205,171 entitled "Miniature Silicon Accelerometer and Method" issued Apr. 27, 1993, and incorporated by reference in its entirety herein.

In another embodiment, the tag reader 1750 is placed within the home or on the person of the subject receiving treatment (in a portable configuration, such as a hand-held reader unit provided to the subject prior to treatment). The reader 1750 is linked to a central control or monitoring facility via any available communications channel having sufficient bandwidth including analog ("copper") telephone, wireless telephone or other wireless service, optical network, inter- or intra-network, local or wide area network, satellite communications link, etc., as is well known in the art. Accordingly, the central facility can initiate probe wakeup or other functions remotely within the subject's home by prompting the reader 1750 to interrogate the RFID device 1702. The reader can further be programmed to repeatedly transmit the wake-up interrogation signal until confirmation of tag wake-up, thereby assuring that subject monitoring, data collection, or other desired functions are accomplished, regardless of the subject's physical location at time of first transmission by the central facility. Eventually, the subject (and tag 1702) will pass proximate to the reader 1750 such that wake-up is accomplished. Accordingly, the reader 1750 can even be configured as a portable personal device, such device being carried on the subject's person during the monitoring period.

It will be appreciated that many different variations and combinations of the foregoing radio frequency communications apparatus and methods may be employed consistent with the invention; such different variations and combinations being too numerous to describe herein. All such variations and combinations, however, are easily recognized and within the possession of those of ordinary skill.

Radiation Therapy Apparatus and Method

Figure 18D:
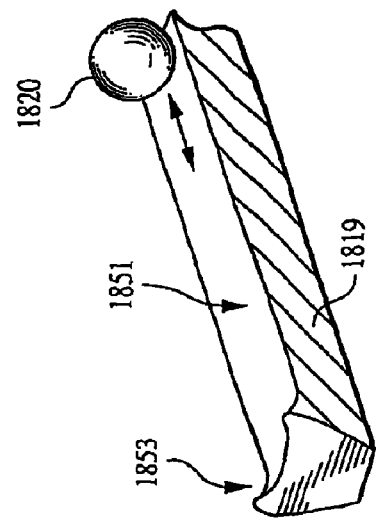
Figure 18A:
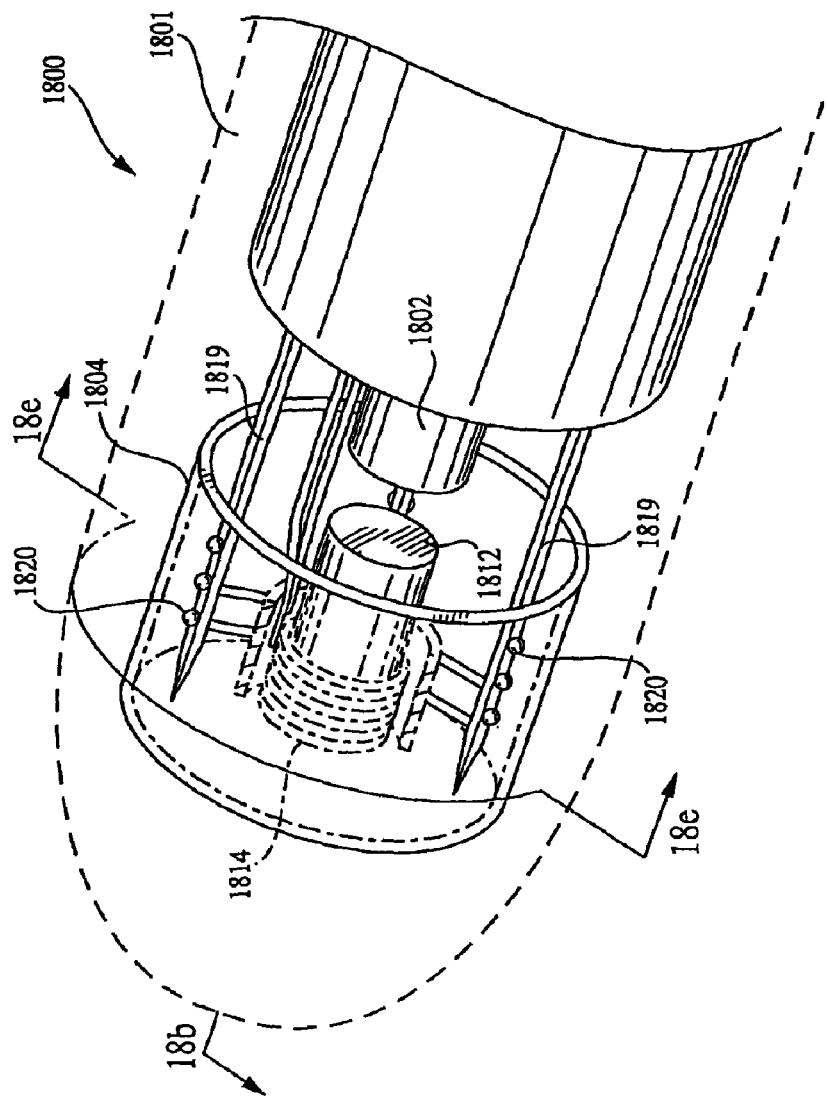
FIG. 18a is a partial perspective view of one exemplary embodiment of the smart probe of the invention equipped with ionizing radiation source and shield element(s).
Figure 18B:
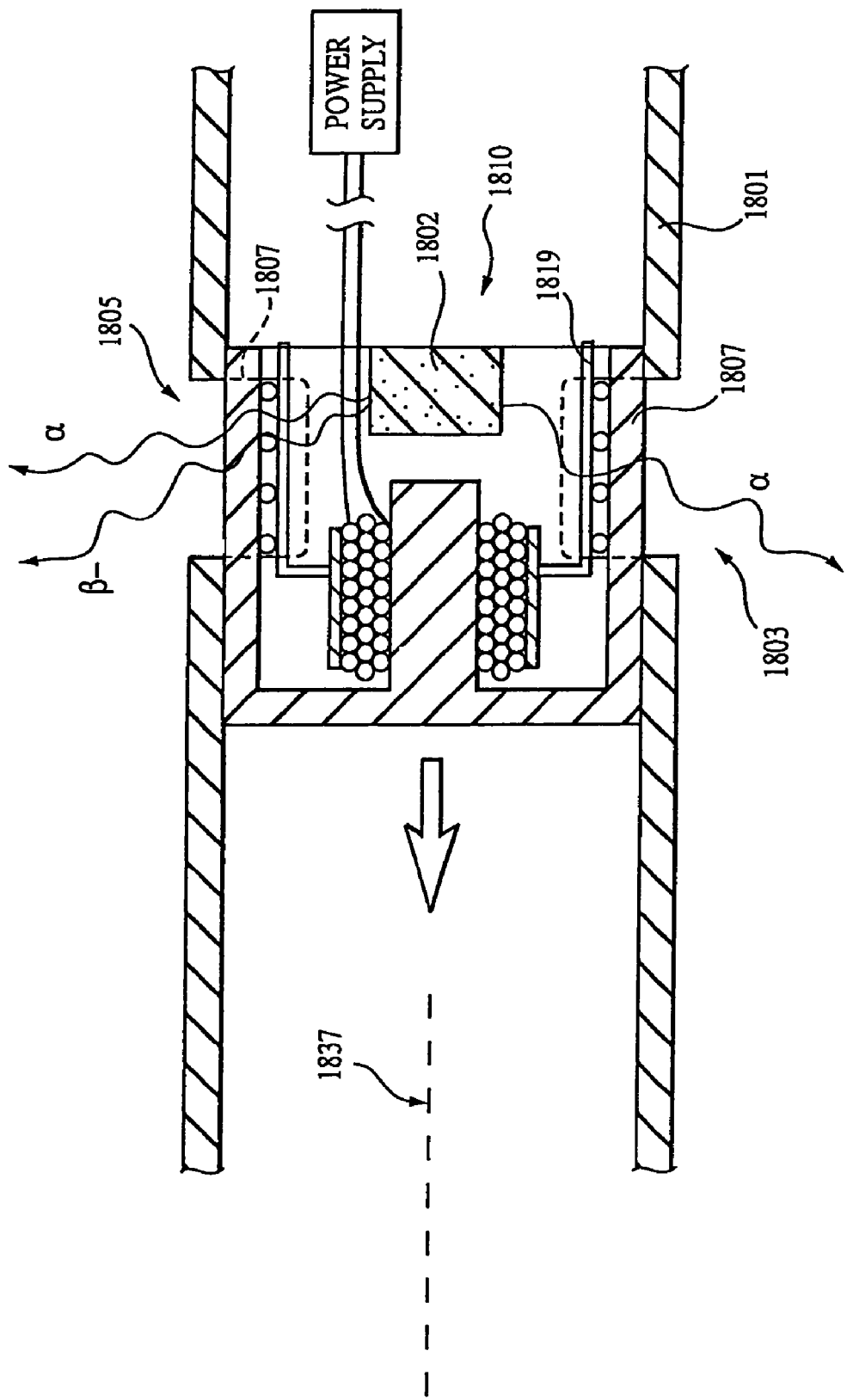
FIG. 18b is a partial cross-sectional view of the probe of FIG. 18a taken along line 18b-18b illustrating the internal components thereof.

Referring now to FIGS. 18*a* through 18*h*, an improved apparatus and method for delivery of radionuclides to tissue within the intestinal tract of a living subject are disclosed. In one exemplary embodiment shown in FIGS. 18*a-e*, the apparatus 1800 comprises, for example, a "smart" probe according to the invention as previously set forth herein which has been further adapted to carry and expose a radioactive source 1802 for emitting ionizing radiation at a prescribed location within the intestine. The source 1802 may comprise a gamma ray, beta particle, alpha particle, and/or even neutron emitting material, depending on the needs of the particular application as described in greater detail below. The source 1802 is shielded while carried in the probe by a retractable shield element 1804. The shield element 1804 of the present embodiment comprises a high-density metallic annular element fabricated disposed on a micro-ball track assembly 1806, the entire assembly being contained within the rear portion 1807 of the outer housing 1801 of the probe 1800. Complete containment of the shield element 1804, source 1802, and associated mechanisms within the probe 1800 provides a number of potential advantages, including (i) prevention of externally applied frictional forces or even portions of the epithelial tissue, from interfering with the retraction and restoration of the shield element 1804; (ii) prevention of gastric or intestinal fluids from entering the probe 1800; (iii) the ability to rotate the shield element(s) and/or source 1802 with respect to one another, thereby providing for selective collimation or "pointing" of the emitted quanta or subatomic particles in vivo. It will be recognized, however, that for alpha radiation sources (and potentially certain sources emitting low energy beta particles), the intervening portion of the outer housing 1803 of the probe 1800 will substantially mitigate any dose to the adjacent intestine wall. Accordingly, for such sources, the probe is optionally configured with selectively controlled "windows" 1805 or apertures formed in the outer housing 1801 allow alpha particles and other radiation unencumbered passage from the source 1802 to the target intestinal tissue, as illustrated in FIG. 18b. In one variant, the windows 1805 are covered by a series of complementary tabs (not shown) disposed on the periphery of the shield element 1804, coincident with the windows 1805. When in the restored position, the tabs cover the windows to mitigate the ingress of intestinal tissue, fluid, or other materials there through. When the shield element is retracted, the windows 1805 are uncovered.

Furthermore, it will be recognized that the thickness and composition of the outer housing 1801 in the region directly radial to the source 1802 may be adjusted, in conjunction with the source strength and radionuclide selected, to effectuate the desired spatial, temporal, and energy irradiation profiles. For example, if it is desired to expose the selected region of the intestine only to comparatively high energy beta particles from a source having multiple energy alpha and beta particle emissions, the thickness and/or constituent material of the outer housing may be selected such that effectively all alpha radiation, as well as low energy beta particles, are shielded by the relevant portion of the outer housing 1801. Accordingly, only the more energetic beta particles (and any gamma, neutrino, or other penetrating radiation emitted by the nuclide(s)) will exist in sufficient quantity outside the outer housing to effectuate the desired therapeutic exposure. The selection of materials to attenuate various constituent types and energies of radiation to achieve a desired spectral distribution is well known in the radiologic arts, and accordingly is not described further herein.

Figure 18C:
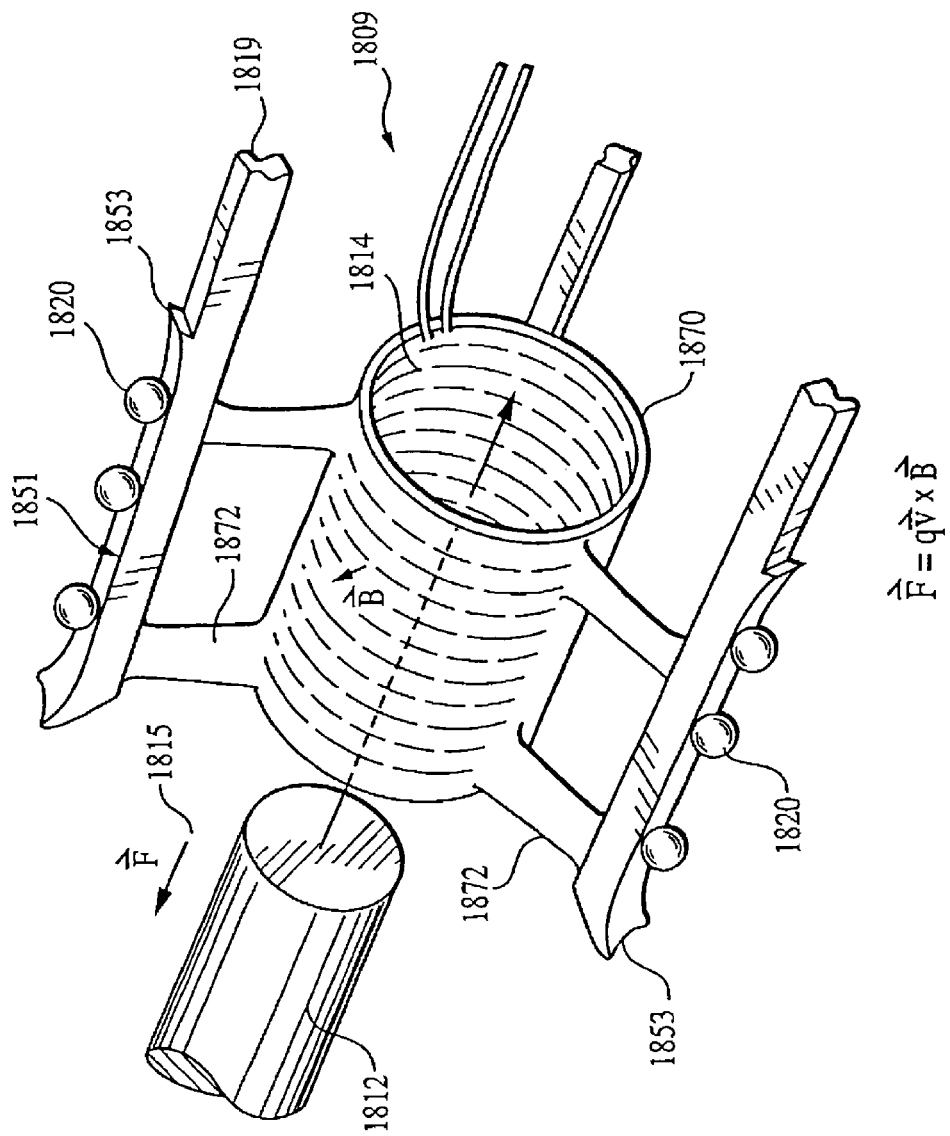
Figure 18E:
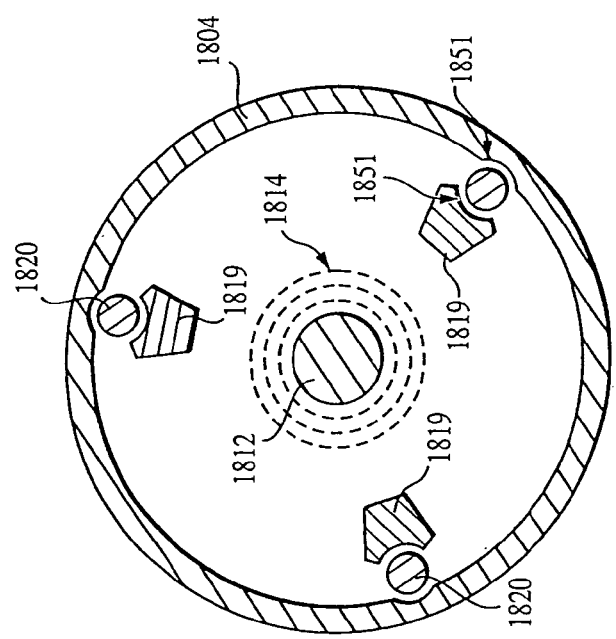
FIG. 18e is a partial cross-sectional view of the probe of FIG. 18a taken along line 18e-18e illustrating various components of the shield assembly.

As shown in FIGS. 18c and 18d, the shield element 1804 of the probe is disposed on the micro-ball track assembly 1806 such that the shield element may be dislocated or translated longitudinally along the axis 1837 of the probe when retracted. The micro-ball track assembly 1806 comprises three tracks 1819 with races 1851 and associated bearing balls 1820 which are mounted so as remain rigid and engage the shield element 1804 during all phases of retraction of the latter. The assembly 1806 optimally is an ultra low friction device, thereby allowing guidance and movement of the shield element 1804 with a minimum of electrical power consumption. It will be recognized, however, that other arrangements for guiding and supporting the shield element 1804 may be used consistent with the invention, the present embodiment being merely exemplary. The tracks 1819 are further equipped with a series of raised stop elements 1853 which are disposed at either end of the portion of the tracks for which travel of the bearings 1820 is desired; the stops act to limit the longitudinal translation of the bearings 1820 within the races 1851 such that the bearings do not roll out of their races into the volume of the probe during all orientations of the probe with respect to the local gravitational field and all positions of the shield element 1804 during use (i.e., fully retracted, partially retracted, or closed).

A shown in FIG. 18a, the retraction mechanism 1809 of the present embodiment comprises a miniature solenoid assembly 1810 of the type well understood in the electromagnetic arts. See for example, U.S. Pat. No. 5,907,339 entitled "Ink jet printhead having solenoids controlling ink flow" issued May 25, 1999, and U.S. Pat. No. 6,092,784 entitled "Coil assembly useful in solenoid valves" issued Jul. 25, 2000, both incorporated by reference herein, which describe the construction of miniature solenoid valves. The solenoid assembly 1810 of the present embodiment includes a substantially cylindrical ferromagnetic core element 1812 which is coupled mechanically to the primary shield element 1804, and polymer-insulated (dielectric) electrically conductive solenoid coil element 1814 which is disposed around at least a portion of the ferromagnetic core 1812. As is well known in the art, the application of an electrical current through the coil element 1814 generates a magnetic (B) field, which, upon interaction with the magnetic lines of flux generated by the ferromagnetic core element 1812, induces a generally longitudinal displacement force (F) 1815 as shown in FIG. 18c. As is well known in the electromagnetic arts, the force F generated by the solenoid is given generally by:

$$F = qV \times B$$

Where:
F=resultant force vector
q=charge
V=charge velocity vector
B=magnetic field vector
x=vector cross product A restoring spring 1817 having a preselected spring constant is disposed at the rear portion of the probe and in communication with the rear end 1818 of the shield element/core assembly to urge the shield 1804 and core 1812 back into position in the event of a loss of electrical power, thereby causing the probe 1800 to "fail safe" with respect to the radiation source 1802. This arrangement also has the benefit of obviating the need for electrical power to return the shield element 1804 to its nominal (i.e., non-retracted) position. However, the desire to protect against unwanted exposure in the event of a power or other type of device failure must be balanced against the comparatively energy consumption required to displace the shield 1804 and core 1812 against the restoring spring 1817 for any period of time. As is well known in the mechanical arts, the spring force applied generally obeys the following relationship:

$$F = kx$$

Where:
F=restorative force exerted by the spring
k=spring constant (F/displacement)
x=linear displacement.

According to this relationship, as the shield element is displaced further from it's normal position (little or no compression of the spring), the force necessary to overcome the restorative spring force increases generally linearly. Therefore, progressively increased current flow through the solenoid coil is required to displace the shield element further.

The solenoid coil 1814 of the illustrated embodiment is physically retained and suspended around the core 1812 by an annular support element 1870 which is attached to the individual tracks 1819 of the assembly 1806 via a plurality of respective support members 1872. The coils 1814 is fixed with adhesive to the interior walls of the annular support 1870 such that no interference between the core 1812 and the coils 1814 occurs when the shield element 1804, disposed on the ball bearings 1820 of the tracks 1819, slides along the axis 1837 of the probe under magnetically induced force.

Hence, if power consumption is especially critical (such as in the case of where probe power is supplied by an on-probe battery), other safeguard mechanisms may be substituted or used in concert. For example, the type and strength of source 1802 may be selected so as to mitigate whole body gamma dose, such as by choosing a nuclide having a low energy gamma and low gamma yield in relation to emitted particulate radiation such as alpha or beta. Similarly, the half-life of the nuclide may be selected such that is will rapidly decay to a "safe" level irrespective of probe operation. Other techniques may also be used, such by using a fail-safe mechanism which does not require significant electrical power consumption (e.g., pressurized gas or other pre-stored potential energy, as in the form of a compressed bias spring). Furthermore, interlock logic functions of the type well known in the art may be applied to retraction of the shield element 1804, such as for example (i) the passing of a minimum or maximum amount of time as measured by the processor clock (described below), or (ii) the probe being in certain desired orientation within the subject's intestine (such as may be determined by a liquid metal or other similar type of switch), or even other criteria.

The retraction and release of the shield element 1804 is controlled via the on-probe processor/microcontroller 520 as is well known in the electronic arts. Control via the processor/microcontroller may be structured in any number of ways, including those generated internally to the probe (such as having the microprocessor "count" using its internal clock signal generator for a prescribed period of time, and then automatically retracting the shield 1804 via the microcontroller 520,) or by receipt of an external inductive, capacitive, radio frequency, magnetic, or other initiating signal to a corresponding sensor within the probe, such as a 2.4 GHz radio frequency control signal received by the SoC transceiver element 1610 ("control event"). Alternatively, the probe shield 1804 may be controlled by way of other sensor devices mounted on the probe, such as the molecular sensor array 3202 described subsequently herein with respect to FIG. 32. For example, electrical conductance (or resistivity) readings obtained from the molecular sensor array 3202 may be used to trigger retraction of the shield element 1804, such as when it is desired to irradiate tissue only when in the presence of certain molecules within the intestine. It will be recognized that a plethora of other control schemes may be employed consistent with the invention, all such control schemes being within the possession of those of ordinary skill in the art when taken in concert with this disclosure.

The power supply circuitry of the probe may also optionally be adapted to generate high discharge rates of the power supply (and accordingly high currents through the solenoid coil) such as by using diode current limiting devices with high threshold currents of the type well known in the electrical arts, thereby allowing for the generation of sufficient magnetic field strength to overcome an increased restoring spring force, the increased spring restoring force provided additional safety margin for return of the shield element 1804 to its nominal (closed) position) upon completion of irradiation or power failure. The tradeoff in such circumstance is, however, the reduced longevity of the on-probe power supply. As will be appreciated, the structural capacitor described below with respect to FIG. 27 may also be utilized for this purpose.

Figure 18F:
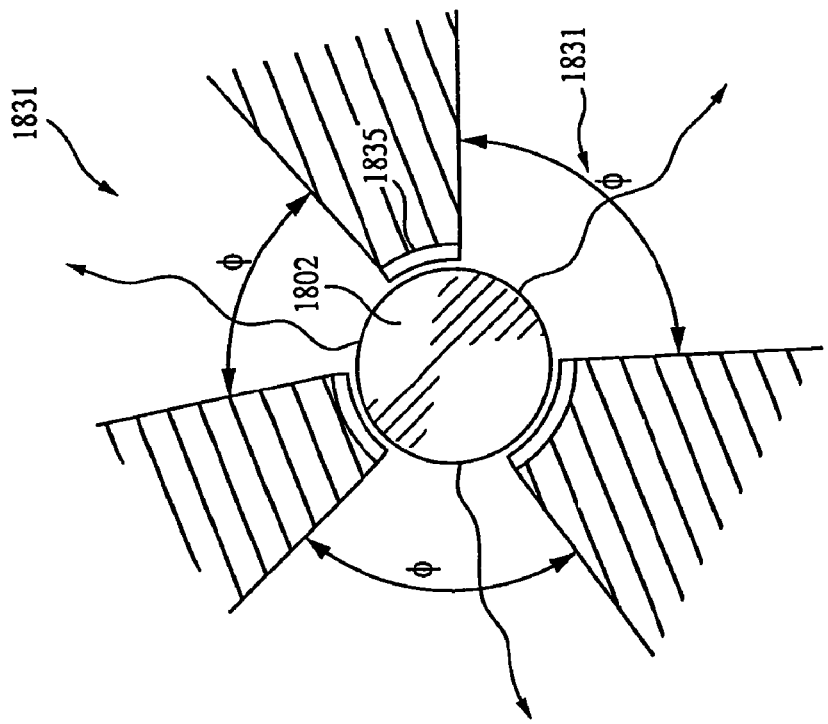
FIG. 18f is a front plan view of one embodiment of the radiation source and shield elements, illustrating the relative radiation emission patterns from the probe.
Figure 18G:
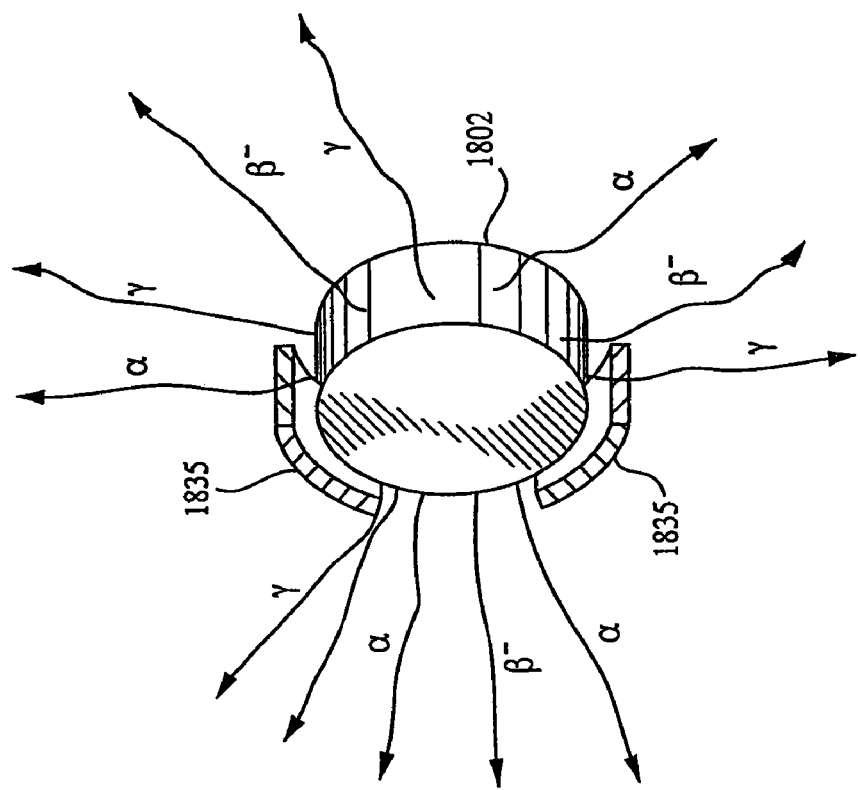
FIG. 18g is a perspective view of the radiation source and shield elements of FIG. 18f, illustrating the relative radiation emission patterns from the probe.
Figure 18H:
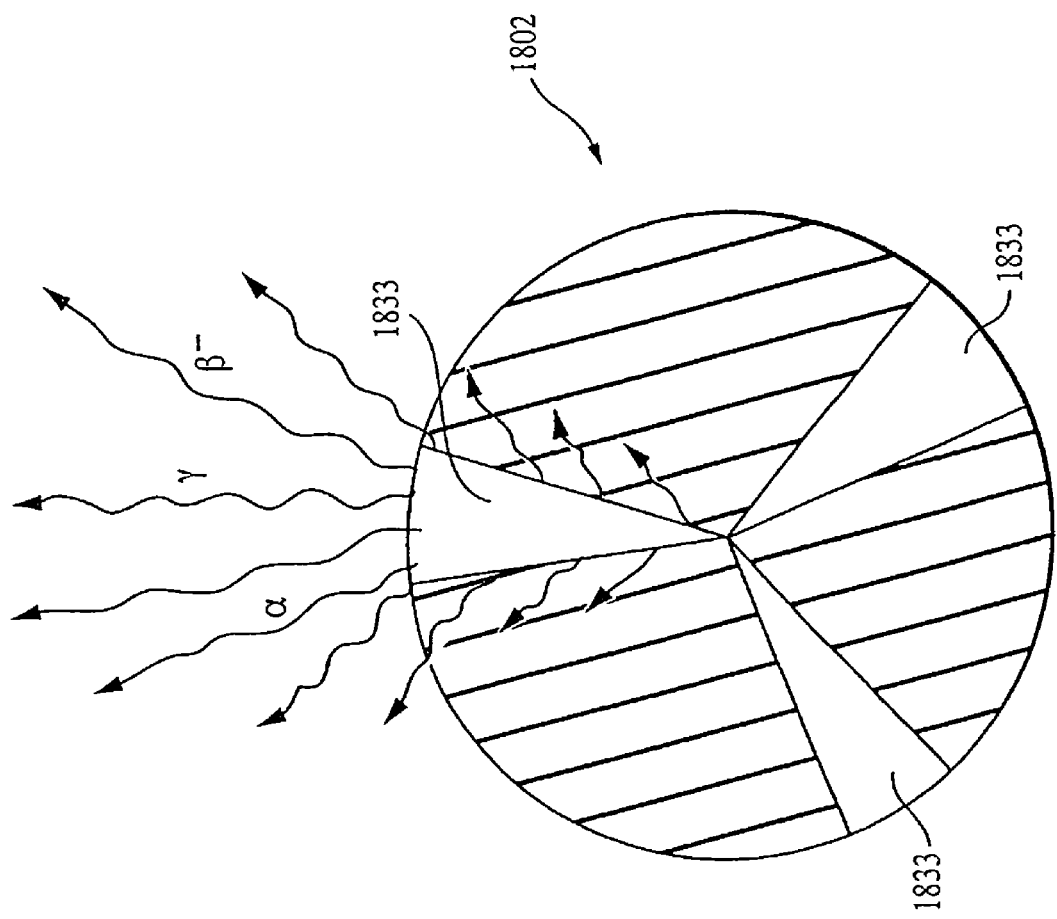
FIG. 18h is a plan view of another embodiment of the radiation source of the invention, illustrating the use of sectored radiation source elements therein.

As shown in FIG. 18f-18g, the radiation source 1802 may also be collimated in the circumferential dimension (e.g., around one or more portions of its circumference), so as to form discrete solid angles 1831 of radiation emission with respect to the source 1802. Such collimation may be accomplished using any number of techniques, including (i) a segregated source construction technique wherein the radioactive source regions 1833 are dispersed around the circumference of the source element 1802, as illustrated in FIG. 18h; (ii) a secondary shield element 1835 disposed around the source which blocks certain angles of emission, as illustrated in FIG. 18g; or (iii) by constructing the shield element 1804 such that when retracted, only certain portions of the circumference of the source 1802 are exposed. Furthermore, it will be appreciated that the relative angular position of the source 1802, secondary shield element 1835 (FIG. 18g), or primary shield element 1804, may be made alterable, such as through use of motor assembly housed within the probe (not shown) which rotates the source, secondary shield 1835, or primary shield 1802 around the axis 1837 of the probe, such that the operator may adjust the orientation of the uncollimated radiation beam to the desired relative orientation based on the position of the probe within the intestine. In this fashion, the operator may effectively steer the radiation beam with the probe in vivo if desired. The construction and operation of miniature motor assemblies (e.g., direct current commutated motors) such as those referred to herein are well known in the electromechanical arts, and accordingly will not be described further herein.

The physical and chemical properties of the radionuclide source 1802 are important criteria in its selection for radiotherapy according to the method described herein. Specifically, the type of radioactive emission (e.g., beta particle, alpha particle, gamma ray, etc.) must be considered with respect to the target tissue.

Alpha particles are essentially doubly-ionized Helium nucleii. They have a high kinetic energy (KE) transfer, and are effective in cell killing to a range of several cell diameters (up to approximately 100 microns). Due to their comparatively high mass and charge, alpha particles are completely attenuated by even a few mils of a low density shielding substance, and the likelihood of an alpha particle passing through a cell and not damaging a critical structure is roughly 4 to 10 times lower than for beta or gamma radiation. This relationship is often referred to as "quality factor". Generally speaking, a comparable level of tumor ablation (at least with respect to superficial regions of the tumor) can be achieved with lower alpha radiation doses as with higher doses. Another advantage of alpha emitters is their ability to create ionization in the absence of oxygen. This is an important advantage in the treatment of tumors that have areas of hypoxia.

One of the disadvantages of alpha emitters is their relatively limited selection. Astatine-211 has the disadvantage of requiring a cyclotron to produce it. This, coupled with its 7.2 hour half-life, makes its use somewhat impractical. Alternatively, Lead-212 has a 10.6 hour half-life and decays by beta emission to $^{212}$Bi. Bismuth-212 has a 1 hour half-life and decays by beta and alpha emission to stable $^{208}$Pb. Lead-212 is produced from Radium-224 which has a 3.6 day half-life.

Beta particles (essentially ejected electrons or positrons) are less effective at ionizing, and also have a significantly greater range in air than alpha particles. Not nearly as penetrating as gamma rays or X-rays, beta particle flux (dependent on energy) may be effectively attenuated with only a few mils of a high density substance, such as most metals.

Additionally, gamma-ray energies and abundances should also be considered when selecting a source 1802. In comparison to alpha and beta particles, gamma rays (even those at low energy) are highly penetrating, and accordingly add significantly to the whole-body radiation dose of the subject when used for radiation therapy.

Numerous beta emitters exist, offering a broad selection of particle energies and chemical properties. Many courses of therapy have utilized $^{131}$I, largely due to its ready availability at moderate cost, and relative familiarity $^{131}$I has a physical half-life of 8.04 days, maximum beta energy of 0.8 MeV, average beta energy of 0.2 MeV, and is considered a medium-range beta emitter (mean range between 200 μm to 1 mm in soft tissue) with a maximum range of about 1.5 mm. However, the gamma yield of $^{131}$I (0.36 MeV average) results in higher total body doses away from the tumor location, thereby contributing to subject toxicity.

Yttrium-90 ($^{90}$Y) may also be useful in certain applications because of its favorable characteristics, which include a 64 hour half-life and an intermediate beta energy (2.3 MeV).

Rhenium-186 has been used for radioimmunotherapy. The energy contribution from gamma rays of $^{186}$Re is 137 keV with only about 9% yield, which provides a lower dose to the whole-body than with $^{131}$I. X-rays produced by $^{186}$Re are low energy radiations (59-73 keV, about 9% yield), contributing only marginally to whole body dose.

It will be recognized that while the selection of radionuclide must be carefully considered, any number of different nuclides (including, for example, $1^{23}$I, $^{125}$I, $^{131}$I, $^{32}$P, $^{62}$Cu, $^{64}$Cu, $^{67}$Cu, $^{97}$Ru, $^{211}$At, $^{177}$Lu, $^{90}$Y, $^{186}$Re, $^{212}$Pb, $^{198}$Au and $^{212}$Bi) may be used alone or in combination as the source 1802 of the invention. Additionally, the "source" used in the probe may be paramagnetic or supramagnetic and/or facilitate diagnostic imaging procedures including gamma scintigraphy, single photon emission computerized tomography (SPECT), positron emission tomography (PET), nuclear magnetic resonance (NMR), or magnetic resonance imaging (MRI), such techniques being well known in the medical imaging arts. For example, the group consisting of elements 26-30 (Fe, Co, Ni, Cu, Zn), 33-34 (As, Se), 42-50 (Mo, Tc, Ru, Rh, Pd, Ag, Cd, In, Sn) and 75-85 (Re, Os, Ir, Pt, Au, Hg, Tl, Pb, Bi, Po, At).

Figure 19C:
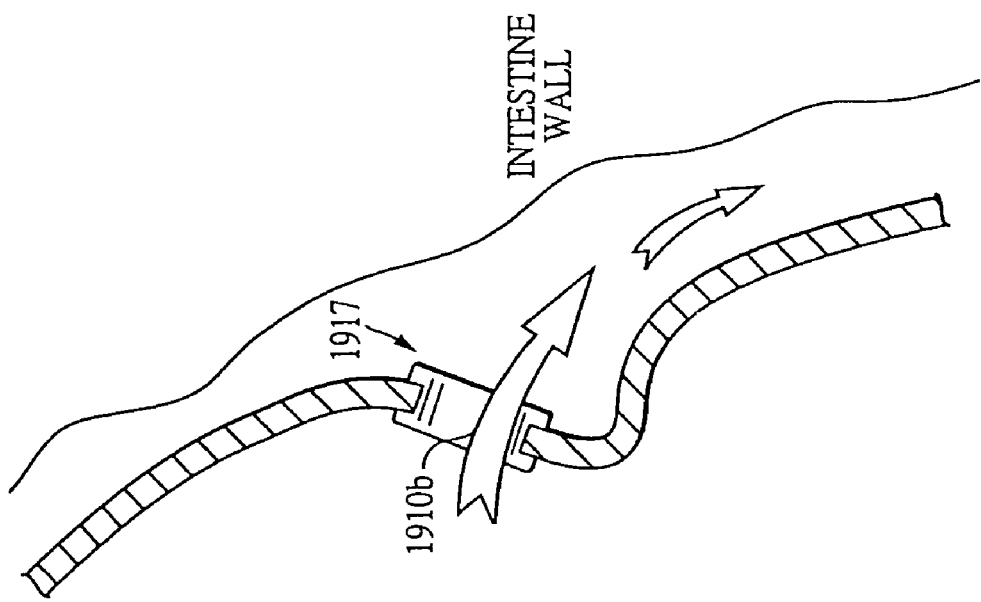
FIG. 19c is a partial cross-section of another embodiment of the probe aperture and seal of the invention, wherein the fluid ejection is generally oblique to the epithelium.
Figure 19B:
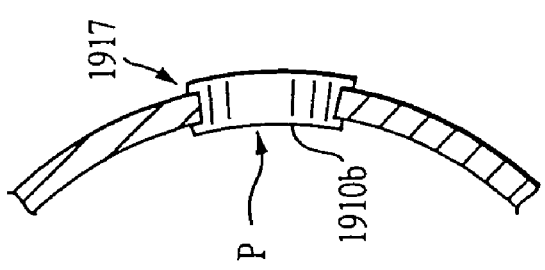
FIG. 19b is a partial cross-section of the probe of FIG. 19a, illustrating one of the apertures utilized therein and its associated dislocatable diaphragm element.

Referring now to FIGS. 19*a*-19*c*, a second embodiment of the radiotherapy apparatus is described. As part of this second embodiment, a plurality of ligands "tagged" with radionuclides 1902 are carried within a repository or container 1904 within the probe 1900 until the desired location within the intestinal tract is reached. The selection, production, and use of such exemplary tagged ligands is described in detail in various publicly available sources including, for example, U.S. Pat. No. 5,902,583 entitled "Genetic Induction of Receptors for Targeted Radiotherapy" issued May 11, 1999, which is incorporated herein by reference in its entirety.

Certain compositions may be used consistent with the invention to provide delivery of therapeutic compounds. The molecules are attached to a substance to be delivered thus enabling the substance to be delivered specifically to the intestine upon administration of the conjugate via the smart probe. In the intestine, these compositions bind to the intestinal surface resulting in delivery and/or long-term presence of the therapeutic compound at the intestinal lining. For example, the carboxy terminal (C tail) region of bile salt-activated lipase (BAL), or functional equivalents thereof, (C-tail peptides) may be used in this manner, as described in U.S. Pat. No. 5,821,226, entitled "BAL C-tail drug delivery molecules" to Tang, et al, issued Oct. 13, 1998, incorporated herein by reference in its entirety Receptor sites on the tumor cell membrane or other affected locations within the intestinal epithelium, which are specifically targeted by the ligands, receive the tagged ligands, the radiation emitted thereby proceeding to ionize tumor cell material via emitted beta, alpha, gamma, or neutron radiation until decay or evacuation of the radionuclide. Such approach further permits spatial localization of the radionuclide. Such localization may occur with certain receptor/ligand interactions, as described in greater detail below.

The container 1904 of the probe of FIG. 19*a* is constructed so as to retain a sufficient volume of the ligands 1902 in solution, and selectively release the ligand solution into the intestinal tract upon assertion of a command from the microcontroller 502 of the probe 1900, such command being initiated either internally from the digital processor 1604, or externally, via a communication channel established between an external device and the probe (e.g., a radio frequency, inductive, capacitive, or ultrasonic signal). The ligand solution in the present embodiment is expelled due to the back-pressure generated by a stored volume of compressed inert gas (e.g., $N_2$) disposed within a gas chamber 1908 in the cavity of the probe 1900. The gas chamber may be fabricated from any material of sufficient strength and dimension to both fit within the dimensional confines of the probe 1900 and withstand the required pressure (on the order of a few psi). The Tefzel outer housing is utilized in the present embodiment, due to its light weight, low cost, relative ease of molding, and strength. The gas chamber 1908 alternatively may be formed as a separate component.

The probe 1900 of the illustrated embodiment is somewhat increased in size over other embodiments described herein (i.e., approximately 15 mm in diameter, and roughly 50 mm long, providing an "empty" internal volume of roughly 8,500 mm$^3$ after accounting for housing wall thickness) in order to accommodate the volumes of pressurized gas and ligand solution in addition to the necessary communication, power, and control components. In that 1000 mm$^3$=1 cc, the volumetric delivery capacity of the probe 1900 is fairly limited; roughly on the order of 2 cc. However, it will further be recognized that the "trailer" configuration (i.e., use of two probe housings coupled via an umbilical) as described herein with respect to FIG. 34 may also be readily adapted to provide pressurized gas storage and/or ligand solution storage in the event that more on-probe capacity is required, or alternatively a smaller probe diameter is necessitated (such as for smaller subjects).

A system of sealed, rupturable polymeric diaphragms 1910*a*, 1910*b* are employed in the embodiment of FIG. 19*a* between (i) the gas chamber 1908 (if present) and the container 1904, and (ii) the container 1904 and the exterior of the probe 1900, such that upon controlled rupture of the first diaphragm 1910*a*, the comparatively high gas pressure resident in the container 1904 is applied to the ligand solution 1902 in the container 1904, which is ultimately expelled via the second diaphragm(s) 1910*b* to the exterior region 1911 of the probe 1900. The rate of pressurization of the container 1904 is controlled (limited) by the size of the diaphragm orifice 1912, which is purposely chosen to have a very small diameter (on the order of 2 mm). This feature advantageously mitigates the pressurization rate of the container 1904, thereby limiting the energy with which the outer diaphragm(s) 1910*b* and ligand solution are dislocated/ejected from the probe, thereby eliminating the opportunity for unintended trauma to the intestinal epithelium or other tissues.

In the illustrated embodiment, the interior diaphragm 1910 is selectively and controllably ruptured via the application of an electrical current to a conductive filament 1913 running through the diaphragm. The filament 1913 is provided current via a set of conductive traces 1921 formed within the housing of the probe 1900. The conductive filament 1913 is constructed from very fine gauge (e.g., 38 AWG) nichrome or similar wire which results in a weakening of the polymeric material of the diaphragm in the immediate region 1914 of the filament 1913 due to localized heating of the filament from the comparatively high electrical current induced by the low electrical resistance of the filament 1913 and the lack of any other resistive, inductive, or capacitive elements in the filament circuit. The diaphragm 1910a may also be scored or weakened in the selected regions such that rupture of the diaphragm is assured upon application of a minimal electrical current to the filament 1913. The filament 1913 may also be coated with a minute amount of chemically active substance which reacts with the diaphragm material or alternatively generates heat chemically (e.g., a non-toxic "igniter") to aid in rupturing the diaphragm 1910a.

In another variant, the inner diaphragm 1910a is obviated through the use of the aforementioned igniter material disposed around the filament 1913, the combination forming a pressure barrier upon manufacture which seals the small diameter of the aperture. When the igniter material is activated, the chemical reaction consumes the igniter material and evolves significant heat, thereby dissolving the pressure seal and allowing the pressurized inert gas to flow through the aperture.

Advantageously, the filament 1913 may also be combined with or embodied as the conductive-plane carbon fiber filaments present within the polymer matrix composite housing material of the embodiment of FIG. 27 (described below). Specifically, one or more carbon fibers present in the matrix may be used to conduct electrical current to and from the filament 1913 of the diaphragm, thereby obviating the need for separate metallic conductors or traces 1921.

The outer or second diaphragm(s) 1910b is constructed so as to dislocate immediately (i.e., under a predetermined differential pressure across the secondary diaphragm, $\Delta P$) from the retaining aperture 1917 upon the application of the gas chamber pressure to the ligand solution within the container 1904 as shown in FIG. 19b. The outer diaphragm(s) 1910b are constructed from a biologically inert material which may be soluble, such as the aforementioned "gel cap" material. If soluble, the diaphragm is of sufficient thickness and composition such that dissolution is prevented during the travel of the probe throughout the intestine, thereby preventing unwanted leakage of the ligand solution. After dislocation, the diaphragm(s) 1910b is/are dissolved by the subject's intestinal chemistry, or alternatively expelled. Note that until the inner diaphragm 1910a is ruptured, the ligand solution 1902 resides within the container 1904 at roughly atmospheric pressure, hence the differential pressure on the second, outer diaphragm 1910b is minimal.

Additionally, the aperture 1917 of the outer diaphragm(s) 1910b may be made somewhat recessed and oblique to the intestine wall as shown in FIG. 19c, thereby minimizing the chance of any localized trauma to the region of the intestine wall or epithelium immediately adjacent to the outer diaphragm(s) 1910b during rupture, and subsequent expulsion of the ligand solution 1902. This arrangement also tends to preclude the intestinal wall from obstructing the aperture(s) 1917, thereby necessitating a greater pressure to expel the ligand solution.

Inert gas is utilized in the present embodiment to avoid any potential toxicity to the subject due to the expulsion transient. Additionally, the pressure and volume of the gas chamber, and the cross-sectional area of the diaphragm(s) 1910a, 1910b, are optionally selected so as to eliminate any chance of rupture of the intestine wall at large due to inadvertent release or discharge of the gas chamber into the intestinal cavity (as opposed to via the diaphragms 1910a, 1910b as described above). Specifically, the cross-sectional area of the diaphragms 1910, relative volumes of the gas chamber 1908 and container 1904, and gas chamber pressure are selected such that the PV product of the pressurized gas will dislocate or rupture the diaphragms and expel at least a portion of the ligand solution into the intestinal volume, yet not pressurize the intestine to any significant degree. Calculations in support of such selection are well known in the mechanical arts, and accordingly not detailed herein. A pressurization port 1990 is also provided to permit charging of the chamber 1908 externally before administration.

Pressurized gas is chosen as the motive force of the present embodiment so as to reduce the complexity of, and electrical loading on, the probe while in vivo; specifically, the potential energy stored in the form of pressurized gas substantially obviates the need for other electrical and/or mechanical means to deploy or discharge the ligand (or other) payload. Additionally, the use of rupturable or dislocating diaphragms obviates the complexity (and space requirements) associated with valving or other types of regulation mechanism, although it is conceivable that such latter arrangements may be compatible with certain configurations of the present invention within the constraints of the available space.

Alternatively, in yet another variant, a minute amount of a gas generating compound (such as, for example, that described in U.S. Pat. No. 6,073,962 entitled "Gas Generant" issued Jun. 13, 2000, incorporated herein by reference in its entirety, or alternatively a complex of transition metals of an aminoalazol, carbodihydrazide, or sodium azide-based compounds) is disposed behind a non-rupturable diaphragm (not shown) or "bag" and separated from the ligand solution 1902. The gas generating compound is ignited via electrical current from the power supply of the probe (via a control signal generated by the microcontroller 502), thereby increasing the pressure on the outer diaphragm 1910b such that the latter is dislocated or ruptured. Toxicity to the subject may be avoided, inter alia, through sealing of the diaphragm/bag (even after inflation), and/or through careful selection of a non-toxic gas generant.

In an alternative embodiment, two non-toxic reactants capable of producing an exothermic or gas-evolving reaction having non-toxic byproducts are mixed, such as common acetic acid and sodium bicarbonate combined to produce carbon dioxide, according to the following reaction:

$$NaHCO_3 \ + \ H+ \ \longrightarrow \ Na+ \ + \ H_2O \ + \ CO_2$$
(soda)   (acid)            (sodium)   (water)   (gas)

The reactants are selectively mixed via rupture of a diaphragm similar to that previously described herein which is induced by an internally or externally generated command signal (such as that produced by the aforementioned microcontroller upon receipt of an RF command via the on-probe transceiver, or alternatively the occurrence of a predetermined event) to evolve gas within the fixed volume mixing chamber (not shown), which comprises the combined volume of the two reactant chambers. The heat and/or gases evolved by the exothermic reaction increase the pressure within the chamber, which is used to expel the ligand solution from the probe through distension of an elastomeric bladder disposed between the mixing chamber and the ligand container.

As yet another alternative, the microchip release methodology provided for in U.S. Pat. Nos. 5,797,898 entitled "Microchip Drug Delivery Devices" issued Aug. 25, 1998, and 6,123,861 entitled "Fabrication of Microchip Drug Delivery Devices" issued Sep. 26, 2000, both assigned to Massachusetts Institute of Technology, both incorporated by reference in their entirety herein, and described in detail below, may be used in conjunction with the smart probe of the present invention to effectuate release of the tagged ligands 1902. Specifically, in one embodiment, the etched substrate is disposed at or near the surface of the probe, such as by being embedded into the outer housing, and the contents of reservoirs of the substrate released at the desired point during probe travel within the intestine. As yet another alternative, the container 1904 and enclosed ligand solution 1904 may be directly pressured above atmospheric (or prevailing intestinal pressure, if different than atmospheric) using the inert gas previously described, or other comparable mechanism. As will be readily appreciated by those of ordinary skill, such methodology may also be coupled with the use of a single outer diaphragm 1910 as previously described, the aforementioned "microchip" release apparatus, or even a diffusion membrane which allows for selective diffusion of the tagged ligands through its thickness into the intestinal tract. Many configurations and combinations of the foregoing techniques, and in fact many others, may be used consistent with the present invention, all such configurations and combinations falling within the scope of the claims appended hereto.

Figure 20:
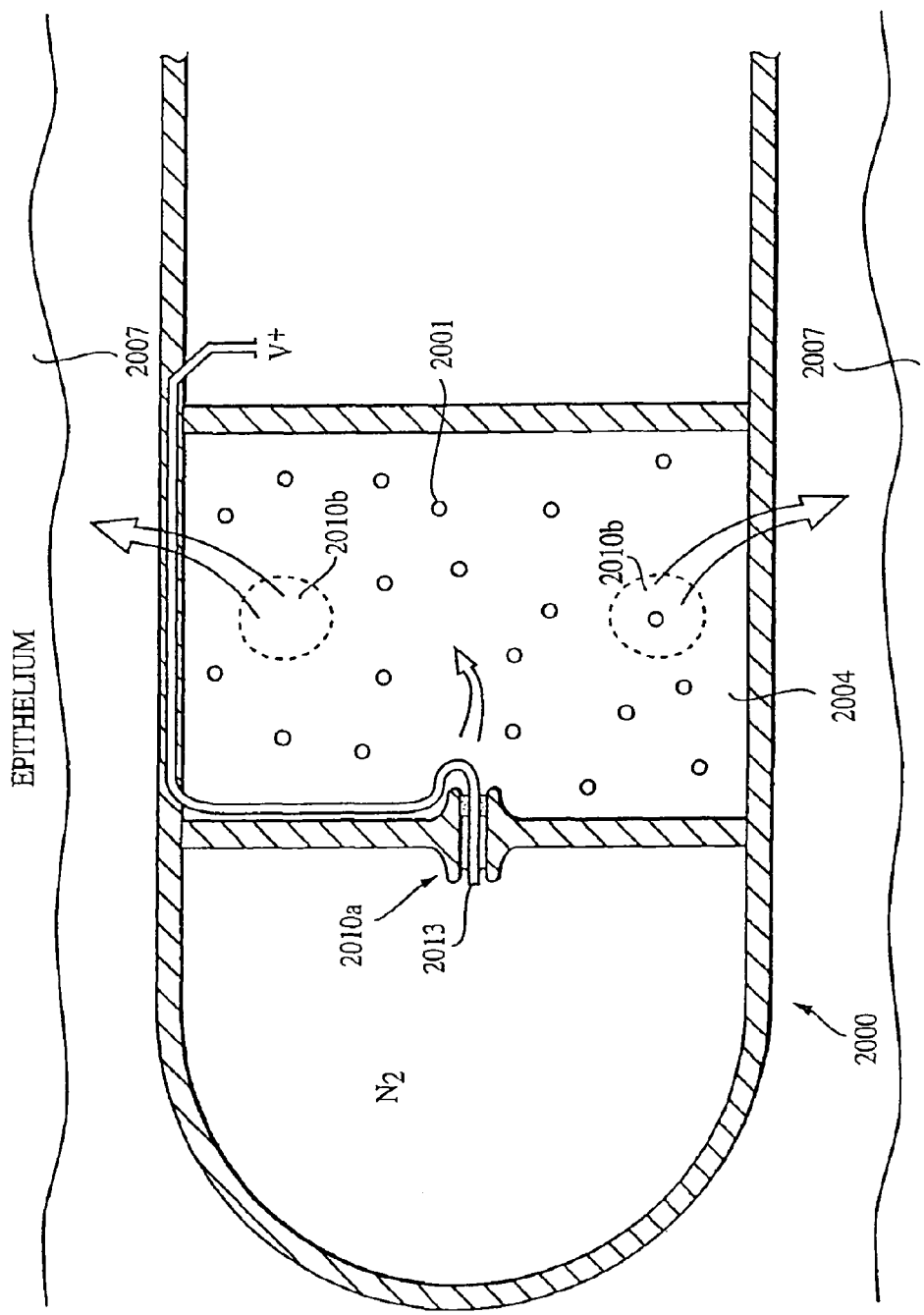
FIG. 20 is a partial cross-sectional view of the probe of FIG. 19a, illustrating the ejection of fluid from the probe while in vivo.

Referring now to FIG. 20, a third embodiment of the apparatus for providing radiation therapy to a living subject is disclosed. In the embodiment of FIG. 20, the probe 2000 is adapted to contain a plurality of nanostructures 2001 (e.g., C-60 fullerenes, aka "Bucky-balls", and annular graphite film structures, or "nanotubes") which each include one or more "captured" atoms or molecules of a desired radionuclide within the cavity of the nanostructure structure.

"Buckyballs", Nanotubes, and Other Nanostructures

Figure 20A:
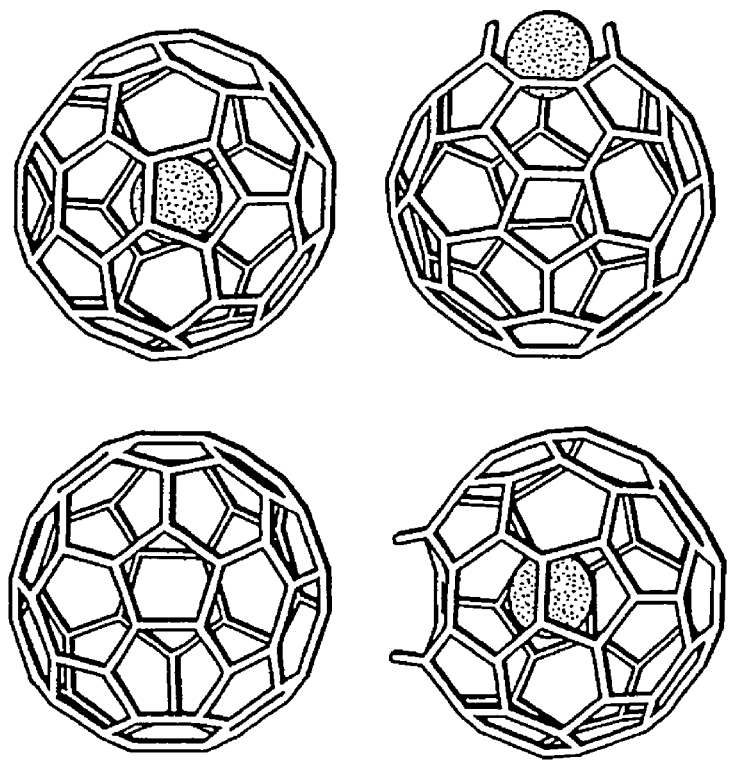
FIG. 20a is a graphical representation of a carbon-based fullerene structure with "caged" payload.

Besides graphite and diamond, carbon exists as C-60 in structures primarily composed of hexagons and heptagons whose edges are formed by the carbon-carbon bonds. The first and best known of these structures is the Buckminster-Fullerene C-60 "bucky-ball". The bucky-ball is composed of 20 hexagons and 12 heptagons arranged in the same way as the 'facets' on a soccer ball (i.e., truncated icosahedron). See FIG. 20a.

Each carbon atom in an all-carbon C-60 fullerene network is bonded to three other carbon atoms. The C-60 fullerene network forms a molecule with a cage-like structure and generally aromatic properties. All-carbon fullerene networks contain even numbers of carbon atoms generally ranging from 20 to 500 or more. Larger fullerenes are known as well, with many hundreds of carbon atoms bonded together in a fullerene network. Additionally, "nested" fullerenes (hyperfullerenes) may be prepared wherein one closed fullerene structure is contained within a second larger closed fullerene structure, these structures being contained in turn within a larger closed fullerene structure. While these hyperfullerene spheroidal carbon molecules are considered to be the most stable forms of fullerenes in terms of cohesive energy per carbon atom, other shapes are possible.

Another useful aspect of the carbon fullerene (e.g., C-60) is the ability to dispose one or more entities within the "cage" of the molecule, as shown in FIG. 20b. The truncated icosahedron structure produces a cavity or void within the fullerene, which, depending on the fullerene configuration, may act to contain or house and protect molecules contained therein. Such contained molecule may be captured within the fullerene until one or more carbon-carbon bonds are broken, thereby opening a "window" for the extraction or escape of the molecule. Numerous mechanisms for breaking carbon-carbon bonds within a fullerene are known to those of ordinary skill, and accordingly will not be described in detail herein.

The production of C-60 or other fullerene structures containing "captured" molecules or atoms (including radioactive species) is also well known. See for example, U.S. Pat. No. 5,350,569 entitled "Storage of Nuclear Materials by Encapsulation in Fullerenes" issued Sep. 27, 1994, and U.S. Pat. No. 5,640,705 entitled "Method of Containing Radiation Using Fullerene Molecules" 5,640,705 issued Jun. 17, 1997; U.S. Pat. No. 6,171,451 entitled "Method and apparatus for producing complex carbon molecules" issued Jan. 9, 2001; U.S. Pat. Nos. 5,510,098, 5,316,636, 5,494,558 and 5,395,496, which use various processes to vaporize carbon rods, producing carbon atoms that recombine into fullerenes; U.S. Pat. No. 5,951,832, "Ultrafine particle enclosing fullerene and production method thereof" issued Sep. 14, 1999, wherein atomic or crystalline species are driven into nanostructure structures using an energetic electron beam; and U.S. Pat. No. 5,965,267 entitled "Method for producing encapsulated nanoparticles and carbon nanotubes using catalytic disproportionation of carbon monoxide and the nanoencapsulates and nanotubes formed thereby" issued Oct. 12, 1999, which are incorporated by reference herein in their entirety.

Furthermore, the shape of all C-60 structures is not necessarily spherical. Football and cigar shaped structures have been reported, and very long capped tubes ("bucky tubes", or carbon nanotubes) have been produced. Nanotubes generally comprise a network of hexagonal graphite rolled up onto itself to form a hollow tube-like structure. These nanotubes have been made with diameters as small as roughly one (1) nanometer. The length-to-width aspect ratio of nanotubes can be made extremely high, with lengths on the order of a millimeter or more (1E06 nm) compared to diameters on the order of a few nm. Single-walled carbon nanotubes (SWNTs) are produced by any one of several methods, including (i) carbon arcing to vaporize a metal-impregnated carbon electrode; (ii) laser ablation of a heated target; and (iii) catalytic chemical vapor deposition (CCVD), the latter comprising a low temperature technique more suited for large scale production of nanotubes. See, for example, U.S. Pat. No. 5,916,642 entitled "Method Of encapsulating a material in a carbon nanotube" issued Jun. 29, 1999, incorporated herein by reference in its entirety.

Another deposition technique for either individual or multiple multi-walled carbon nanotubes is based on electron beam lithography. Carbon nanotubes are deposited from the solution phase onto a substrate (such as that of the aforementioned MIT microchip drug delivery device) through lithographically determined openings in an electron beam photoresist layer. The openings may be in size from a few microns upwards. See Yang, Xiaoyu, "*Carbon nanotubes: Synthesis, Applications, and some new aspects*", Thin Films and Nanosynthesis Laboratory, Department of Mechanical and Aerospace Engineering, SUNY at Buffalo, Fall 1999, incorporated herein by reference in its entirety.

It has further been found that selective dissolution of portions of the nanotube (i.e., the so-called "end caps") may be accomplished through exposure of the nanotubes to certain oxidizing substances such as acids. See, for example, U.S. Pat. No. 6,090,363, entitled "Method of opening and filling carbon nanotubes" issued Jul. 18, 2000, incorporated herein by reference. Selective dissolution techniques may be used to prepare nanotubes for filling after formation of the tubes, or conceivably be used to release molecules or atoms contained within the nanotube in vivo, either before or after release of the nanotubes by the probe into the intestine.

In an exemplary embodiment of FIG. 20, at least a portion of the nanostructures 2001 (in solution) are released from the container 2004 of the probe 2000 generally in contact with the interior wall (e.g., villi) of the subject's intestine in the localized region of the diseased tissue or tumor. Due to their small size (typically less than 200 nm), at least a portion of the nanostructures are drawn into the epithelium 2007 by passive diffusion across the epithelial cell membranes or other uptake mechanisms, or otherwise remain deposited among the villi or other structures of the epithelium, and thereby delivering the desired therapeutic dose to the target tissue.

In a second embodiment, one or more complexes comprising a radionuclide microparticle coupled to at least one carrier, the carrier being capable of enabling the complex to be transported to the desired tissue or system via the epithelium of the intestine. Complex formation and carrier coupling as used herein are set forth in detail in U.S. Pat. No. 6,159,502 entitled "Oral Delivery Systems for Microparticles" issued Dec. 12, 2000, and incorporated herein by reference. Natural mucosal binding proteins may be employed to target various protein molecules to the gastrointestinal mucosa and induce their uptake. These binding proteins may include, for example, any number of lectins, bacterial adhesions, or viral adhesions.

Figure 21:
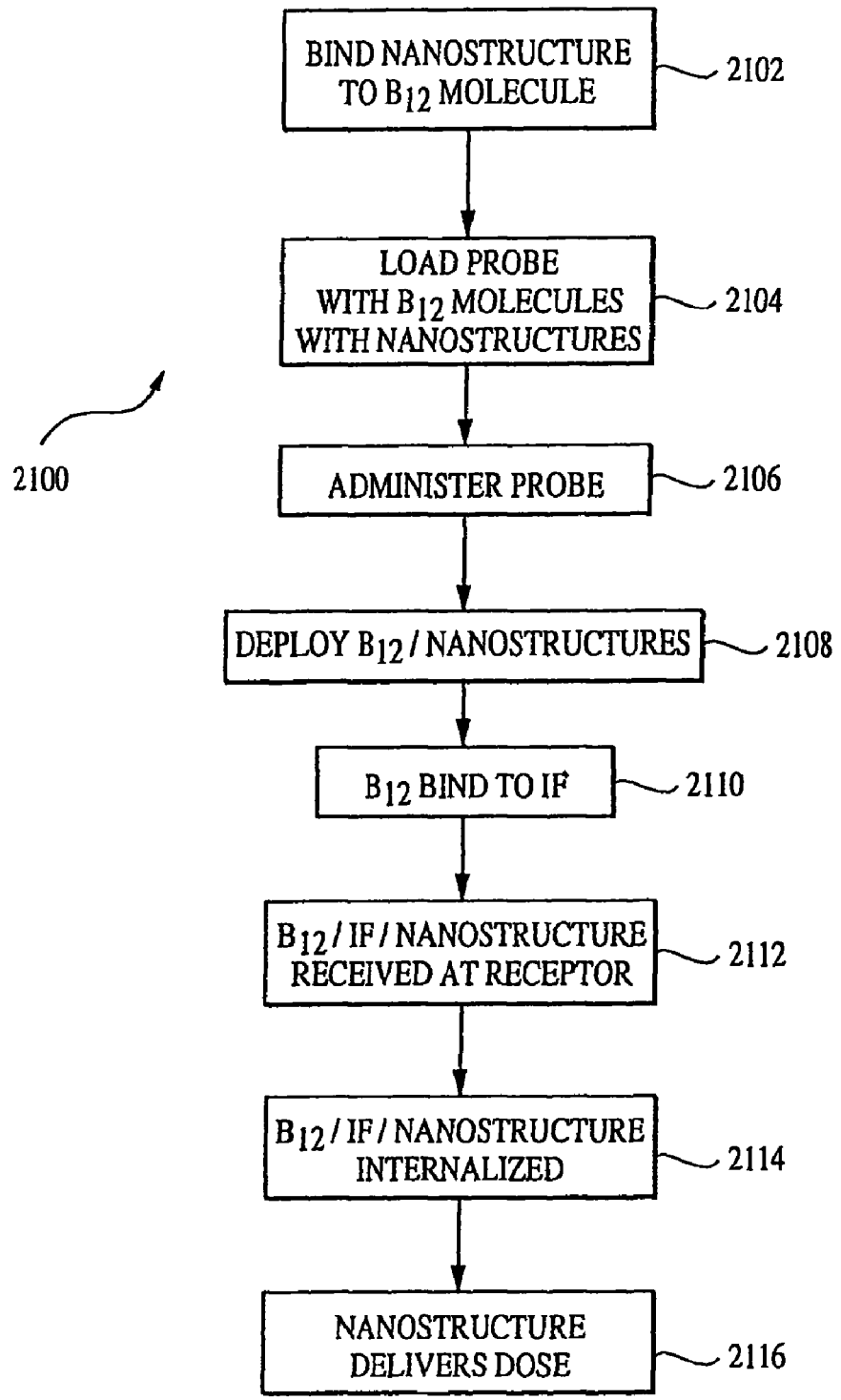
FIG. 21 is a logical flow diagram illustrating the general methodology of utilizing nanostructures to deliver radionuclide dose via the intestinal tract using the smart probe of the invention.
Figure 22:
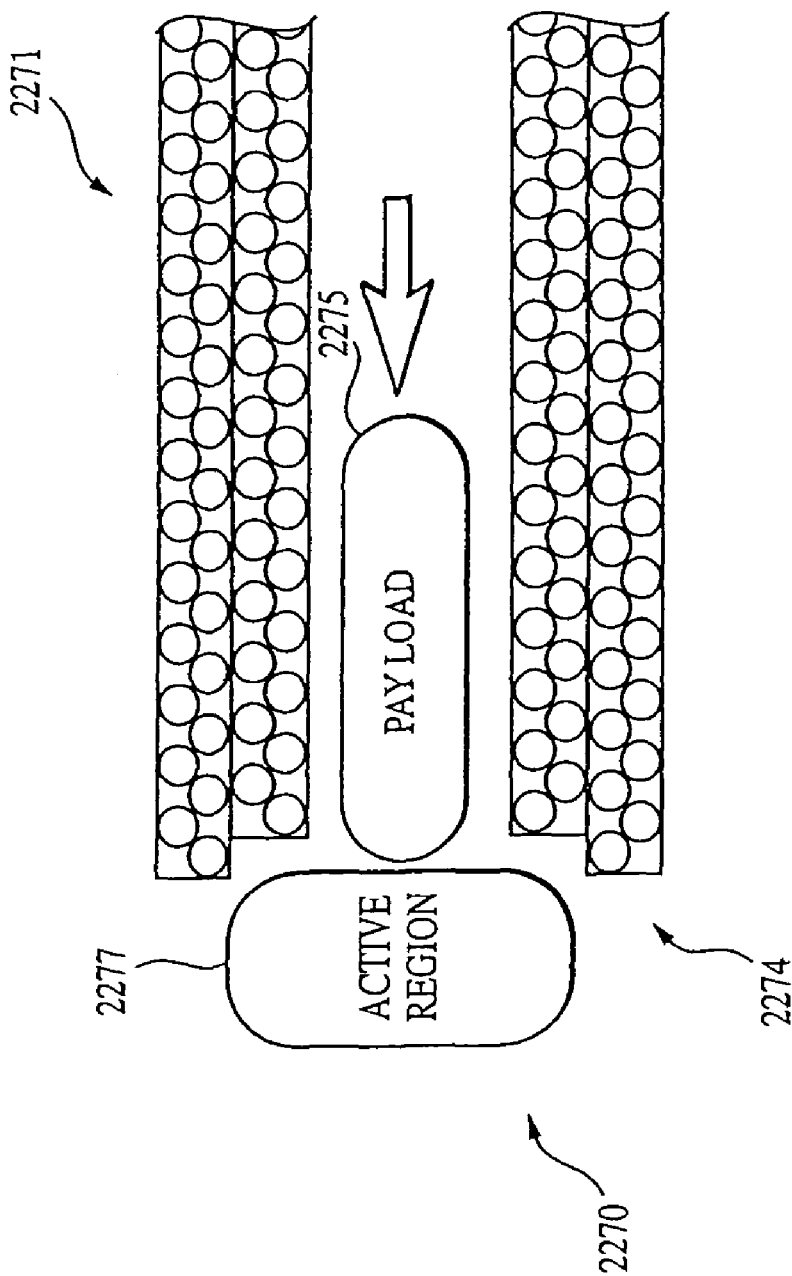
FIG. 22 is a cross-sectional diagram illustrating another embodiment of the invention, wherein a carbon nanotube is used in conjunction with an activated molecule and payload molecule for delivery of the payload to the intestinal tract.

In yet another embodiment of the invention, the pre-existing mechanism for the natural uptake of Vitamin B1/(e.g., $C_{63}H_{88}CoN_{14}O_{14}P; C_3H_6O; 20H_2O$) is used as the basis for an internalization methodology 2100. First, the nanostructure is bound to the B12 molecule (step 2102). The probe is then loaded with the B12 molecules (with nanostructures) per step 2104, and administered per step 2106. The probe deploys the B12/nanostructures in the small intestine (step 2108). During uptake, Vitamin $B_{12}$ initially binds to intrinsic factor (IF) in the small intestine per step 2110. The Vitamin $B_{12}$-IF complex then proceeds down at least a portion of the small intestine, and binds to an IF receptor (step 2112) located on the surface of the ileal epithelium. The entire Vitamin $B_{12}$-IF-receptor complex is then internalized by receptor-mediated endocytosis or similar mechanism (step 2114). Accordingly, by attaching the nanostructure (e.g., fullerene) 2040 to the B12 complex as illustrated in FIG. 21, the radioisotope 2050 present can "piggy back" to achieve internalization. Such methods of $B_{12}$ uptake are well known to those of ordinary skill in the art, and accordingly are not described further herein. In one variant of the present embodiment, the designated radionuclide held within the nanostructure cavity is chosen to have a comparatively short halflife so as to mitigate unwanted exposure to non-diseased tissue after internalization.

In yet another embodiment (not shown), Guanylyl cyclase C (GC-C) is used to receive the radionuclide. Guanylyl cyclase C (GC-C) is a transmembrane receptor molecule expressed primarily in the intestine. GC-C is expressed in the crypt and villus epithelium of the small and large intestine, consistent with normal electrolyte homeostasis.

It will be recognized that while the foregoing discussion is cast in terms of the preparation and delivery of radionuclides and their associated ionizing radiation to selected tissues within the body, such mechanisms may as appropriate be utilized with equal success for in vivo delivery of pharmaceuticals or other agents, including for example chemical compounds, intestinal lubricants, ligands, and gene therapy agents. As is well known, nucleic acids (e.g., DNA, RNA) can be introduced into the stem cells of the intestinal epithelium using any number of methods including transformation, transfection and transduction. For example, see U.S. Pat. No. 5,821,235 entitled "Gene therapy using the intestine" issued Oct. 13, 1998, incorporated by reference herein, which describes various gene therapies relating to the intestinal tract of a living subject. Where applicable, such gene therapies may be directly delivered by the probe of the present invention, when configured as described above.

The present invention may also be used to aid in suppressing auto-immune system reactions related to the gastrointestinal tract. Many diseases associated with the human gastrointestinal tract (such as Crohn's disease) result at least in part from an aberrant immune system response within the subject, the intervention of which may be accomplished through selected delivery of agents targeted for such reactions.

Additionally, it will be realized that mixing of reagents within the probe (or any "trailer" probe as subsequently discussed herein) may be accomplished in vivo by the aforementioned methods; e.g., by providing two or more chambers which communicate with one another and which are separated by a rupturable diaphragm or other controllable aperture; under control of the operator (and/or upon the occurrence of a predetermined event), the diaphragm is ruptured or other aperture opened, such as by stored gas pressure, and the reagents in the chambers mixed together. The reagents are subsequently released into the intestinal volume using methods described herein, or alternatively be retained within the probe (or trailer probe), such as in the case of an exothermic reaction where it is desired to produce heat within the intestinal tract, or produce inert or non-toxic gas within the probe to generate pressure for expulsion of ligands, or other functions.

In another exemplary embodiment of the invention (FIG. 22a), one or more specially selected "polymerized" molecules 2202 are disposed within the cavity 2204 of the nanostructure 2206 such that the polymerized molecule(s) is/are captured therein. The polymerized molecule(s) 2202 may comprise, for example, a grouping of ligands targeted for specific receptor molecules within the intestinal epithelium, or a ligand 2210 with a co-associated "retainer" molecule 2212 (FIG. 22b).

Upon introduction of the nanostructure(s) in vivo, the polymerized molecule(s) 2202 are depolymerized or otherwise separated from one another, thereby allowing selected components 2208 of the molecule(s) 2202 to be extracted or released from the nanostructure 2206 as illustrated in FIG. 22c. These released components 2208 are then diffused into, received by complementary receptors 2209, or otherwise absorbed by the targeted tissue in the subject. Alternatively, as illustrated in FIG. 22d, a ligand 2220 is disposed externally to the fullerene cage 2206, thereby allowing bonding to a receptor site 2209 with the fully polymerized molecule 2202 intact. In one variant, the ligand 2220 with retainer and fullerene attached is received at the receptor site 2209; the fullerene cage acting to protect the retainer molecule within until internalization of the latter. In another variant, the polymerized ligand and associated fullerene/retainer molecule is sufficiently mechanically unstable that the ligand/retainer is "torn" from the fullerene by scission or breaking of the carbon-carbon bonds of the fullerene, thereby allowing the ligand (and retainer) to remain disposed on the receptor.

In yet another exemplary embodiment of the invention, "nanotubes" are formed which contain one or more "payload" pharmaceutical or other molecules for delivery to the subject. As illustrated in FIG. 22e, the active portion 2277 of the ligand 2270 is disposed in a free end 2274 of the nanotube 2271, such that the ligand may be readily received by the targeted receptor on the tumor cells, the payload molecule 2275 being protected by the nanotube structure. In yet another variant, the nanotubes are disposed in an array, ligand-side out, such that the ligands may be readily extracted from the nanotubes upon reception by the targeted receptors.

As will be recognized by those of ordinary skill, numerous different combinations of nanostructure, retainer molecules, and ligands may be used consistent with the present invention in order to achieve the desired objectives of delivery of the agent to the desired cells of the subject via the intestinal tract thereof.

Apparatus and Method for Tissue Biopsy

Figure 23A:
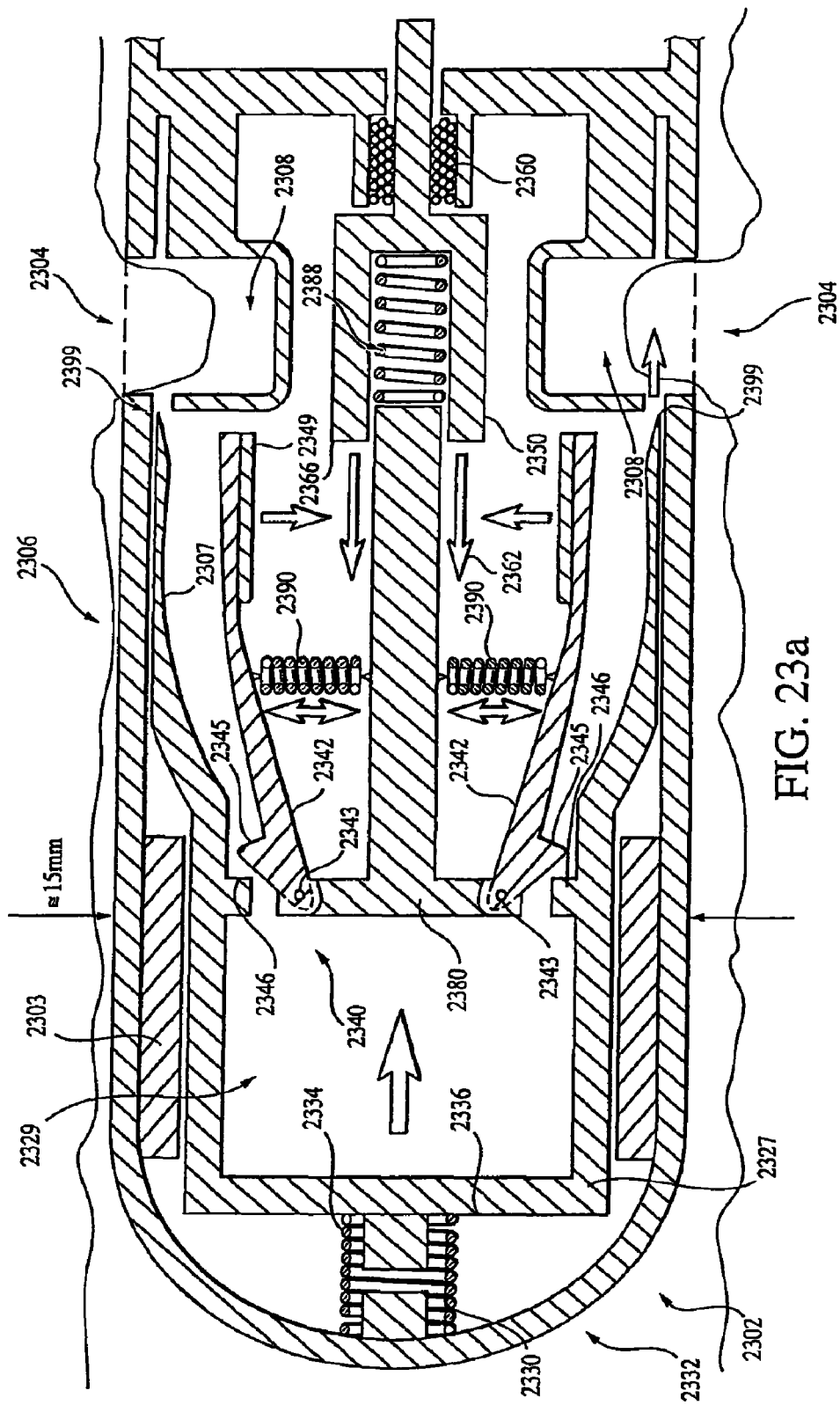
Figure 23D:
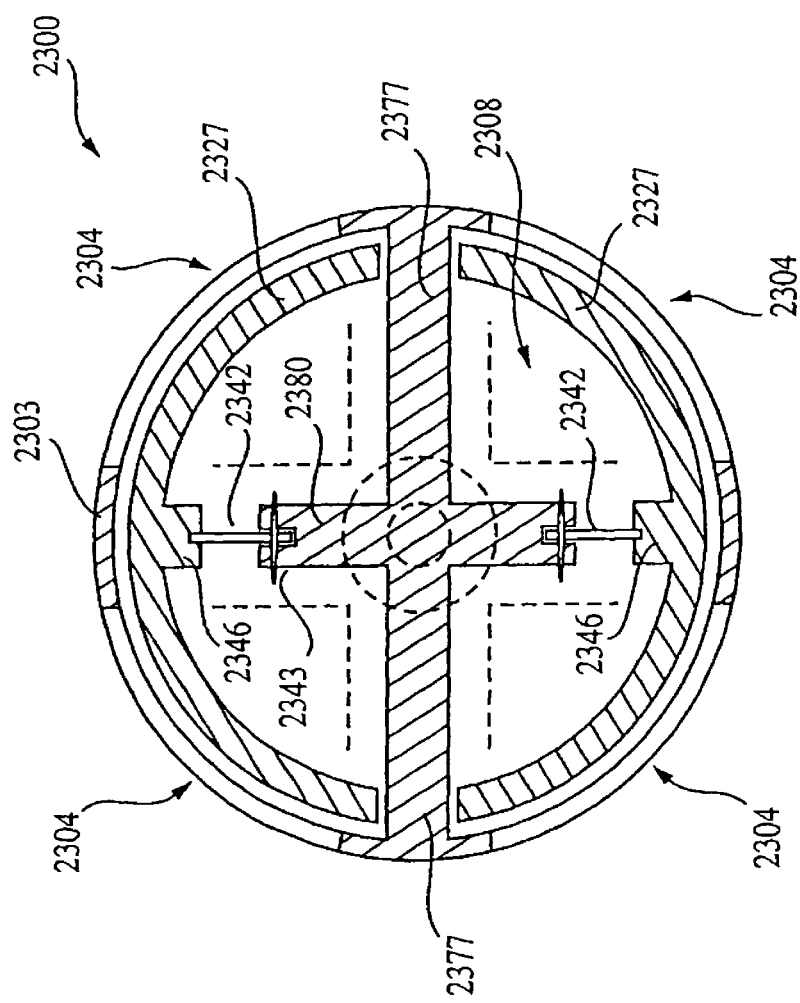

Referring now to FIGS. 23a-23d, an improved apparatus and method for obtaining a biopsy of the intestinal wall of the subject are described in detail. As shown in FIG. 23a, one exemplary embodiment of the apparatus comprises a smart probe 2302 of the type previously described herein, further including a sample mechanism having a plurality of selectively controlled apertures 2304, a shutter mechanism 2306 with respective shutters 2307, and associated reservoirs 2308 disposed generally in the outer region 2310 of the probe 2302. Upon the probe reaching the desired location within the subject's intestine, the shutters 2307 are selectively shut rapidly under spring force, thereby severing tissue present within the apertures and disposing the tissue into the reservoirs 2308. Intestinal tissue or epithelium protruding through the apertures due to, inter alia, surface tension and/or intestinal contractions, is excised by closing the aperture shutters as illustrated in FIG. 23b. The excised tissue 2314 is retained within the reservoirs 2308 until the probe 2302 is expelled from the subject, at which point the excised biopsy tissue may be examined using any number of well known analytical techniques.

Referring again to FIG. 23a, the shutter mechanism 2306 comprises a spring-loaded annular ram 2327 which is generally cylindrical in shape and which slides within a complementary bore 2329 formed within the housing 2303 of the probe 2302. The bore and ram are sized such to permit free longitudinal travel of the ram 2327 in the bore without cocking or pitching thereof. A return spring 2330 is disposed at the rear-most portion 2332 of the probe housing 2303, the forward end 2334 of the spring contacting the rear face 2336 of the ram 2327 and urging the latter forward (and shutters 2307 attached thereto) with sufficient force to sever the tissue protruding within the apertures 2304.

The shutter mechanism 2306 of the present embodiment further includes a selectively releasable retaining mechanism 2340. The retaining mechanism 2340 comprises generally a pair of articulated, retractable detents 2342 disposed relative to the ram 2327 such that when the ram is in its fully retracted position with the restoring spring 2330 nearly or fully compressed, the tabs 2345 of the detents 2342 engage the leading edges 2346 of the ram, such that the ram is retained in the retracted position. The pivot points 2343 of the detents are disposed, and the detents shaped, such that the detents will "lock" in position and retain the ram retracted with no force on the free ends 2349 of the detents. This is how the probe 2302 is configured upon administration within the subject. At least the free ends 2349 of the detents 2342 are metallic in construction (ferrous) such that they are attracted by a simple magnetic core 2350. The magnetic core 2350 comprises a substantially cylindrical ferromagnetic element with magnetic dipoles substantially aligned such that a polar magnetic (B) field is generated by the magnet 2350. A field coil 2360 is disposed in annular proximity to the core 2350 and electrically connected to a source of electrical potential (such as the probe battery, or external power supply coupled to the probe as previously described) and microcontroller 520 such that upon assertion of a command signal from the microcontroller (such as may be generated by receipt of an RF, inductive, capacitive, or ultrasonic control signal generated externally to the subject), the electrical potential difference induces current to flow within the field coil 2360, thereby generating a secondary magnetic field in proximity to the coil. As is well understood in the electromagnetic sciences, the interaction between this secondary magnetic field and that generated by the core 2350 results in a displacement force between the core 2350 and coil 2360. Since the field coil is fixed to the probe housing in the illustrated embodiment, the core 2350 is longitudinally displaced in a rearward direction 2362, thereby reducing the distance of the core to the free ends 2349 of the detents. As the aft end 2366 of the core 2350 closely approaches the free ends 2349, the magnetic coupling of the ferrous free ends and the magnet core increases, thereby generating an increased attractive force tending to draw the free ends 2349 to the magnetic core 2350. Due to the relative disparity in torque around the pivot points, the detents 2342 rotate around their respective pivots, thereby allowing the tabs 2345 to disengage the ram sufficiently that the latter is released and rapidly forced forward by the spring thereby "snapping shut." The shutters 2307 are each attached to the ram 2327 of the shutter mechanism 2306, and fashioned from metal or other non-brittle material capable of being sharpened to a tapered edge 2399. The leading edges 2399 of the shutters 2307 are, in the illustrated embodiment, tapered (sharpened) so as to cleanly sever the biopsy tissue upon repositioning of the shutters to their closed position by the ram/spring.

A bias spring 2388 is disposed between the central support and pivot assembly 2380, the latter being attached transversely via support elements 2377 to the interior walls of the probe housing 2303 as shown in FIG. 23c, thereby tending to bias the core 2350 forward from the fixed support 2380. This prevents inadvertent movement of the magnetic core (such as due to gravity) into proximity to the free ends 2349 thereby inadvertently triggering the shutter mechanism 2306. The bias spring size and constant is selected so as to just prevent translation of the core 2350, but not larger, thereby minimizing the electrical current required in the field coil 2360 to overcome the spring and translate the core assembly 2350 when desired.

Further bias springs 2390 are attached to the detents 2342 toward the free ends 2349 thereof. These springs 2390 have a low spring constant, thereby just tending to keep the detents 2342 biased outward, thereby ensuring continued engagement of the tabs 2345 to the leading edges of the ram retainer ring 2346.

The apertures 2304 of the illustrated embodiment are advantageously sized and shaped such that, at a maximum, only the desired amount of tissue will protrude into the reservoirs 2308 through their respective apertures, thereby limiting the amount of tissue that may be obtained in a single biopsy. Such limitation is desirable to preclude undesirable trauma to the intestinal wall, such as significant laceration or perforation. The elongated shape of the apertures 2304 (FIG. 23b) is further oriented such that the longer dimension 2322 of each aperture is perpendicular to the longitudinal axis 2324 of the probe 2302, and conformal to the outer circumference of the probe. In this fashion, the intestinal tissue strewn across each aperture when its respective shutter 2307 is retracted by the shutter mechanism 2306 "sags" or drapes within the apertures, especially in the central portions 2325 thereof. The depth 2321 of the reservoir is also selected so as to limit the penetration of the tissue into the probe, thereby further safeguarding the intestinal wall.

The foregoing biopsy mechanism arrangement has the advantage of storing potential energy for severance of the intestinal tissue in the form of the compressed spring, thereby obviating the need for significant electrical energy stores within the probe to operate the biopsy mechanism. It will be recognized, however, that other motive forces or sources of potential energy may be utilized consistent with the invention. For example, the ram 2327 may be motivated by the controlled release of compressed gas behind the ram, such gas being stored within a chamber in the probe (or a "trailer" probe). Many other such alternatives are available, all such alternatives being within the possession of those of ordinary skill in the mechanical arts.

In another embodiment (not shown), the normally closed shutters 2307 are selectively opened upon the probe reaching the desired location within the subject's intestine, thereby exposing the reservoirs 2308 to the environment external to the probe. An electromagnetic solenoid of the general type previously described herein with respect to the radiation shield retraction mechanism (FIG. 18) is used to overcome the restorative force of a spring 2330 during shutter retraction; upon collapse of the magnetic field of the solenoid (induced by a signal from the microcontroller or other control scheme which interrupts current flow to the solenoid field coil), the magnetic core 2350 and attached shutters 2307 translate forward along the longitudinal axis of the probe under spring force, thereby severing the intestinal tissue resident within the apertures 2304. While obviating the detents 2342, this approach requires significantly greater electrical power to overcome the restorative force of the severance spring 2330 during shutter retraction, and hold the shutter open until tissue enters the apertures.

In yet another embodiment (FIG. 24*a*), the probe 2400 includes one or more selectively controllable pop-up "scoops" 2402 which are disposed on or near the surface of the probe; when activated, the scoop(s) 2402 collect tissue cells as the probe traverses the intestine, and deposit the collected tissue within reservoirs 2403 disposed adjacent to the scoop inlets. The probe is then retrieved after secretion for biopsy tissue analysis.

Figure 24A:
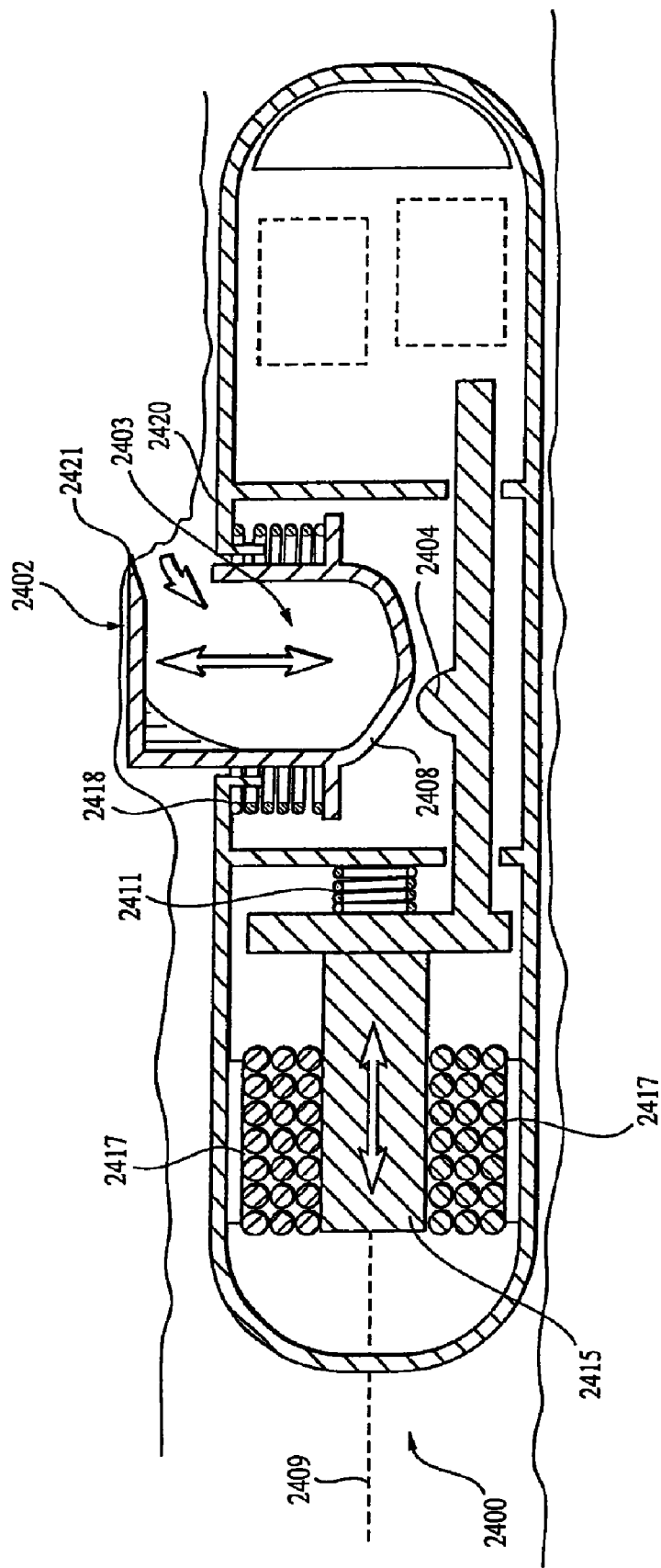
FIGS. 24a-24b are cross-sectional and perspective views, respectively, of another embodiment of the smart probe of the invention adapted for tissue biopsy.
Figure 24B:
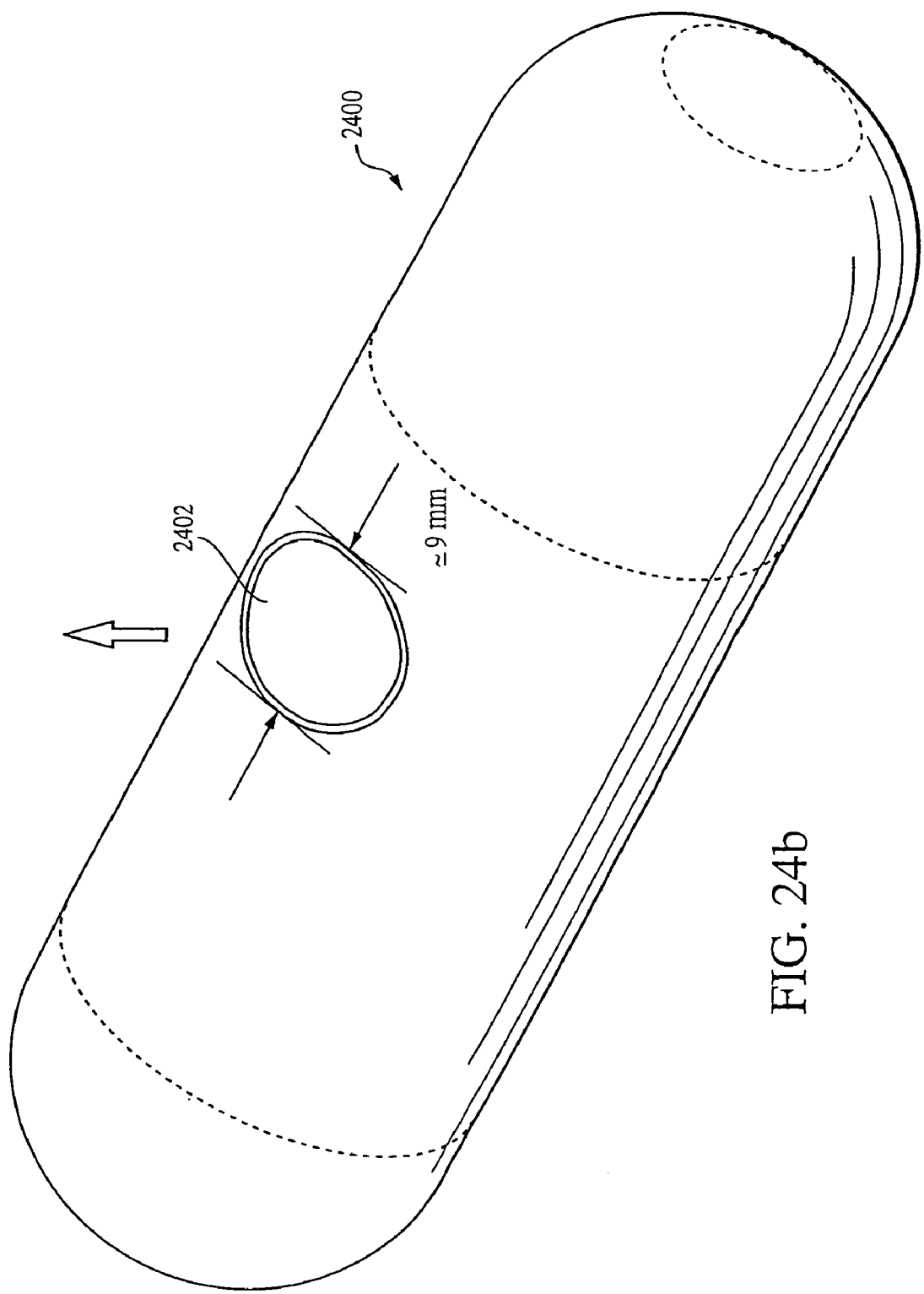

As illustrated in FIG. 24*a*, the scoop is mechanically coupled to an eccentric element 2404 which is disposed within the outer housing 2402 of the probe. The eccentric 2404 interacts with a cam surface 2408 formed on the lower surfaces of the scoop 2402 such that when the eccentric is translated along the longitudinal axis 2409 of the probe 2400, the scoop 2402 is extended (i.e., "pops up") above the surface of the outer housing 2402. Conversely, when the eccentric 2404 is translated in the opposite direction, the scoop is retracted to conform generally with the surface of the housing 2402, as illustrated in FIG. 24*b*. A restorative bias element (e.g., spring) 2411 is used to return the scoop 2402 to a nominal (retracted) position when the eccentric 2404 no longer bears on the cam surface 2408. Approaches other than a spring may be substituted with equal success, however.

The eccentric 2404 of the present embodiment is fabricated from a ferromagnetic material, and further includes a cylindrical end portion 2415 which is disposed substantially within a conductive coil element 2417. Electrical current applied to the coil element 2417 generates a magnetic (B) field local to the coil, thereby interacting with the magnetic field of the end portion 2415 to translate the eccentric, as previously described herein with respect to other aspects of the invention. A restoring spring 2418 is disposed against another portion 2419 of the eccentric 2404 as well as a bulkhead 2420 or other structure within the probe housing such that in the normal (non-energized) position of the eccentric 2404, the scoop is retracted as in FIG. 24*b*, due to the restoring force exerted by the spring. Hence, upon battery (or external power source) failure or degradation, the scoop 2402 fails shut, thereby allowing for unimpeded passage of the probe 2400 through the intestine of the subject.

Additionally, it is noted that the cam surface 2408 and eccentric 2404 may be configured such that a significant disparity in mechanical leverage exists between force applied at the leading edges 2421 of the scoops and the eccentric 2404. In this fashion, the eccentric 2404 may more readily overcome any normal or other forces on the scoops 2402 applied by the intestinal wall, etc. which would tend to resist scoop opening or closure. The cam surfaces and bottom of the scoop bucket 2403 are contoured to allow the scoop 2402 to be extended with minimal friction between the eccentric and the scoop. Accordingly, in conjunction with the aforementioned bias springs 2411, the scoops 2402 can be relied upon to both open and shut under the anticipated operating conditions.

The scoops 2402 of the present embodiment are shaped with generally rounded contours so as to mitigate the possibility of laceration or "catching" on the intestinal epithelium, as shown in FIG. 24*b*. It will be recognized, however, that under certain circumstances, it may be desirable to have the scoops 2402 shaped so as to increase the likelihood of such "catching", so as to ensure the capture of a sufficient biopsy sample. Accordingly, while the present embodiment shows a substantially cylindrical scoop 2402, the present invention contemplates scoops of a variety of different configurations.

The scoop 2402 of the present embodiment is also sized, and the maximum elevation above the outer surface of the probe selected, such that only incidental interaction between the scoop 2402 and the epithelium occurs, thereby mitigating the chances of the probe "sticking" in a given location within the intestine. Alternatively, however, the scoop(s) may be configured and used to intentionally "stick" the probe at a given location within the intestinal tract, thereby permitting more extended therapy to that region of tissue, such as in the case where extended radioisotope therapy is required. Specifically, the scoop(s) 2402 (or other projections without the capability to collect tissue biopsy, if desired) may be sized and positioned upon extension such that they are disposed a significant height above the surface of the probe, thereby contacting and slightly distending the intestine wall in the region immediately surrounding each scoop. This distension and friction on the probe scoops substantially slows and may even temporarily stop the movement of the probe within the intestine.

The embodiment of FIGS. 24*a-b* has the additional benefit of sampling repeatability; i.e., the scoop 2402 may be selectively raised and lowered repeatedly (assuming sufficient battery or other electrical power), thereby allowing for sampling of tissue at different portions of the intestine. In the embodiment of FIG. 24*a*, subsequent samples collected in the scoop bucket 2403 will be disposed generally in a layered fashion, irrespective of probe orientation. Such layers or strata are identifiable by those analyzing the biopsy sample after expulsion.

Note also that while the embodiment of FIGS. 24*a* and 24*b* illustrate a scoop 2402 which translates in generally a radial direction as measured from the longitudinal axis of the probe, other approaches may be employed, such as having the scoop 2402 substantially hinged at one end, such that it rotates around the hinge axis.

It will be recognized that in addition to the embodiments described in detail herein, many different mechanisms may be used to effectuate tissue sampling or biopsy within the intestine of the subject using an autonomous probe, such mechanisms being known to or readily fashioned by those of ordinary skill. Accordingly, the embodiments disclosed herein are considered merely exemplary in nature.

Apparatus and Method for Treating Constrictions

Figure 25A:
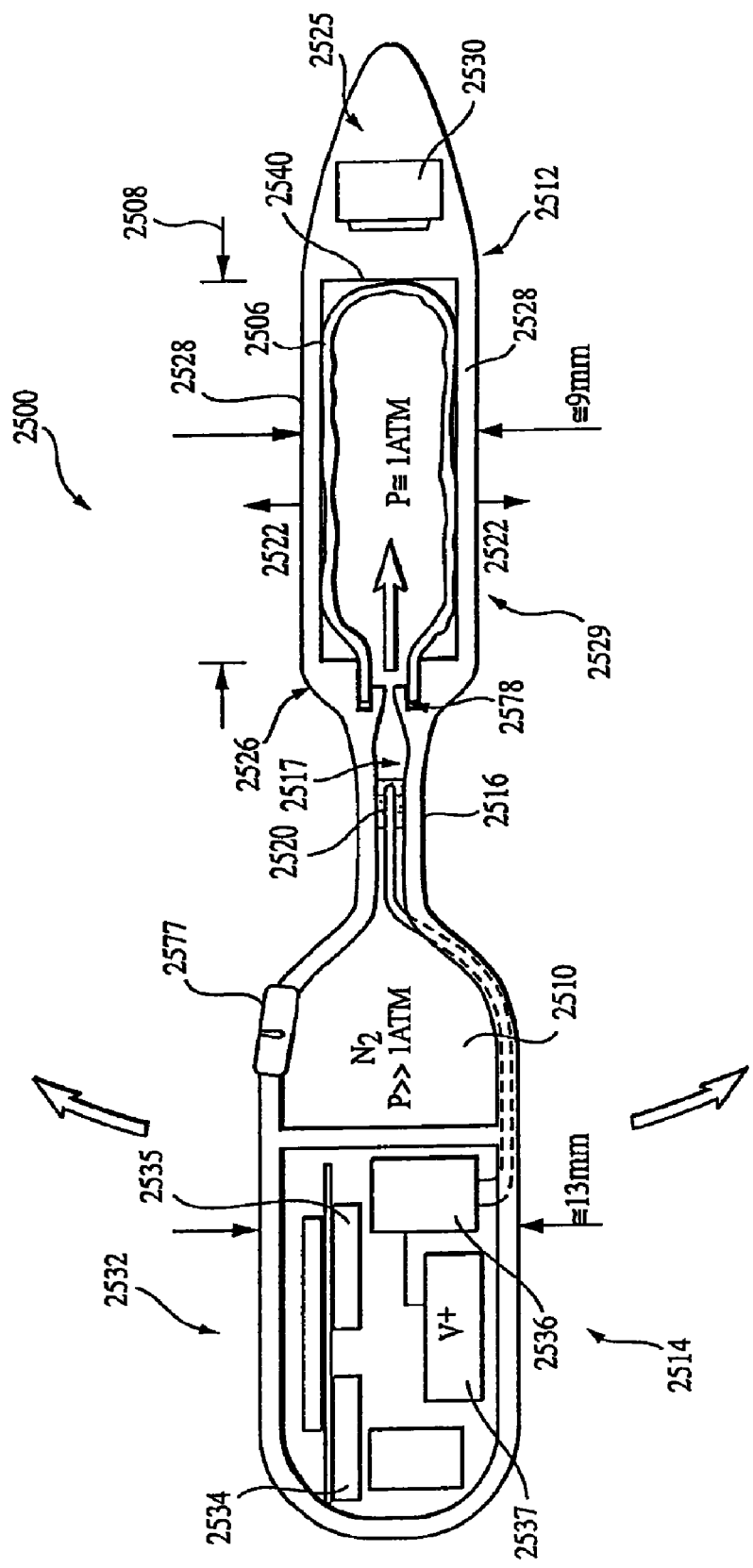
FIGS. 25a-25d are various views of yet another embodiment of the smart probe of the invention configured for in vivo expansion of the intestine.
Figure 25B:
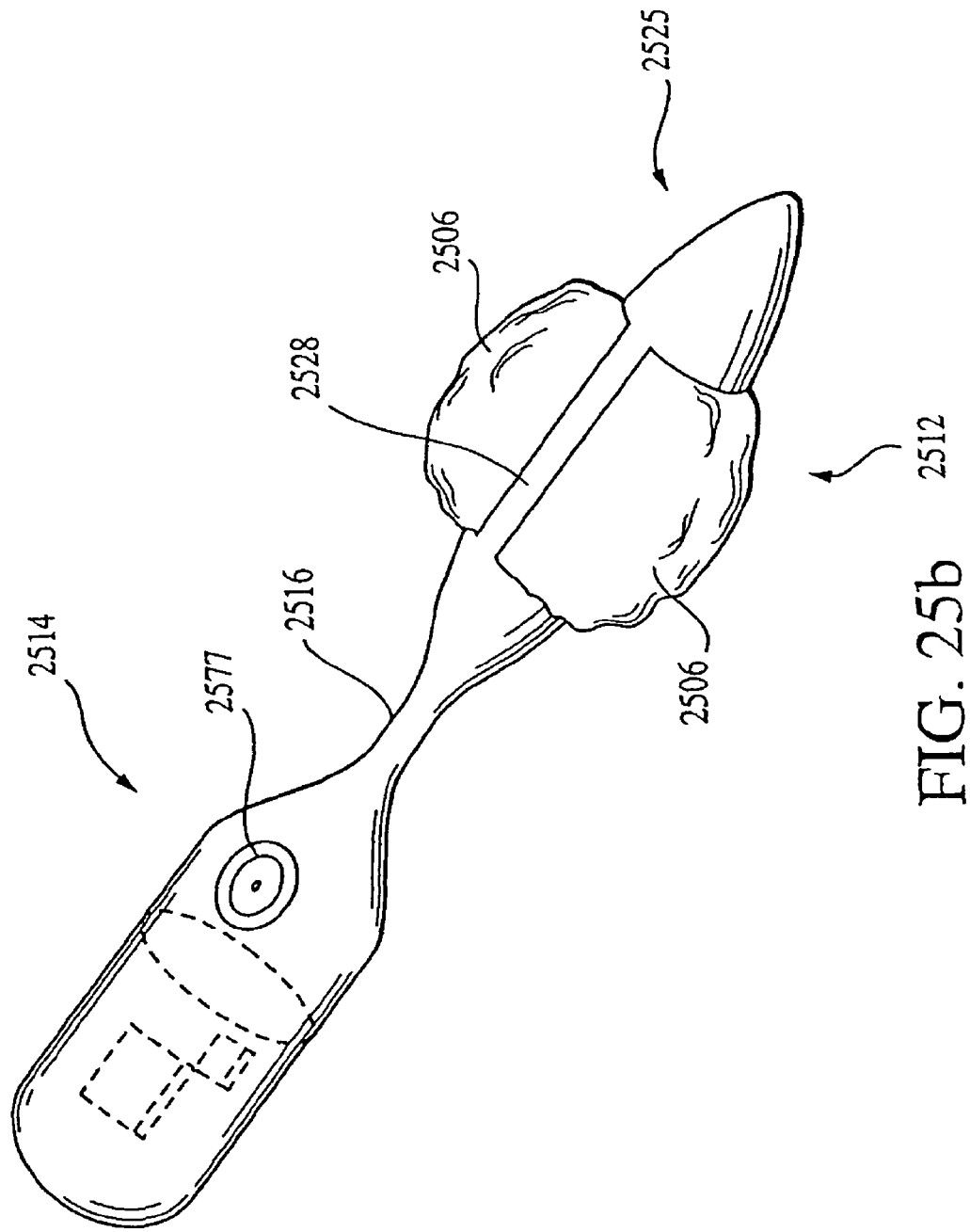

Referring now to FIG. 25a, an improved apparatus and method for treating constrictions, obstructions (or adhesions occurring between the interior surfaces of the intestine wall) of the intestinal tract are described in detail. In the exemplary embodiment of FIG. 25a, the apparatus 2500 comprises a two-part smart probe having a front section with reduced radius, and being equipped with a deformable element 2506 which expands the effective radius of the probe in at least a portion 2508 of its cross-section, thereby simultaneously expanding the surrounding intestinal tissue. The variant of FIG. 25a includes a pressurized gas reservoir 2510 in the form of a follow-on probe (or "trailer") which acts as a source of potential energy for the deformable element 2506 upon activation, thereby minimizing the electrical power requirements of the device. In the present embodiment, the deformable element 2506 comprises an elastomeric "bladder" akin to those used in well known arterial catheterization/angioplasty instruments, such as that described in U.S. Pat. No. 5,100,381 entitled "Angioplasty catheter" and issued Mar. 31, 1992, incorporated by reference herein. The probe 2500 comprises two major housing elements 2512, 2514 which are coupled by a flexible, annular coupler or umbilical 2516. The annular coupler is rigid enough to withstand pressurization by the gas reservoir 2510 of the trailer and preclude collapse of the annulus 2517 during bending, yet flexible enough to allow movement of the probe 2500 as a whole through the tortuous intestine. Myriad polymeric materials having sufficient flexibility and strength (including, for example polyethylene) may be used, although any material presenting the desired properties may be substituted.

The trailer housing element 2514 substantially comprises a pressurized gas reservoir 2510 containing a quantity of pressurized inert gas (such as $N_2$). The annular coupler 2516 includes an annulus 2517 and internal aperture 2518 with associated diaphragm 2520 disposed therein, such that prior to release of the pressurized gas, the pressure of the gas in the trailer 2514 is maintained substantially above atmospheric (or prevailing intestinal tract pressure) by the diaphragm 2520. The aperture 2518 communicates with the probe housing element 2512 such that upon rupture or dislocation of the diaphragm 2520, the gas volume of the trailer is permitted to expand into the deformable element 2506 such that the latter expands in a generally radial direction 2522 in response thereto (see FIGS. 25b and 25c). In the present embodiment, the deformable element 2506 comprises an elastomeric (e.g., natural or latex rubber) balloon adapted to contain the full pressure of the compressed gas stored in the trailer without bursting (at atmospheric pressure or alternatively the lowest pressure anticipated to be encountered within the intestine). The forward portion 2525 of the front housing element 2512 is rigidly attached to the rear portion 2526 thereof by two support members 2528, thereby forming a cavity 2529 there between. The cavity 2529 substantially contains the deformable element 2506 when the latter is in its non-inflated state. The rear housing element 2514 contains the electronics 2532 (e.g., RF transceiver 2534, controller 2535, power supply regulation circuit 2536, etc.) and power supply 2537. Alternatively, the forward portion 2525 may contain the probe battery/power supply 2530, electrical potential from which is communicated to the other electronics disposed within the rear portion of the rear housing element 2514 via two conductive traces (not shown) disposed on or within respective ones of the support members 2528, and the umbilical 2516.

Figure 25C:
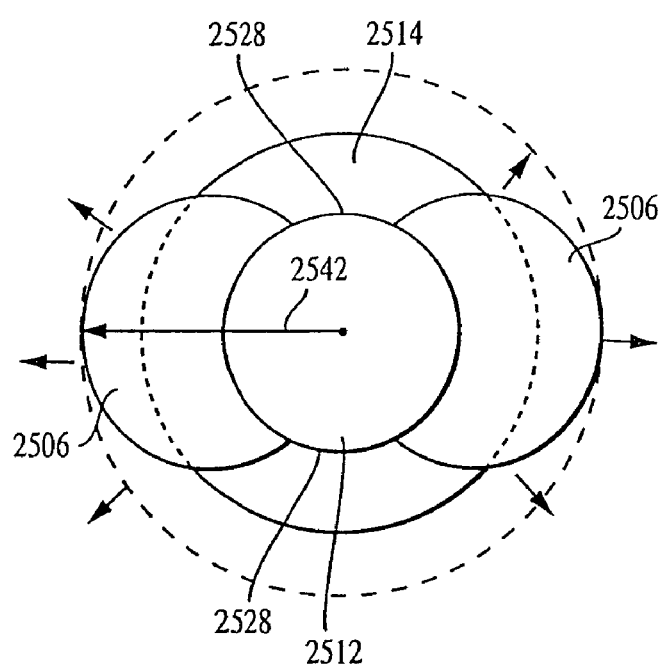

Upon pressurization, the deformable element (balloon) 2506 expands generally forward toward the front portion 2525 of the housing element 2512 until the rear bulkhead 2540 is encountered by the balloon 2506. At this point, the balloon expands more radically outward, increasing the effective radius 2542 of the front housing element 2512 significantly, as illustrated in FIG. 25c. Upon contacting the intestinal wall tissue, the balloon continues to expand radically at a slower rate (due to the restorative force applied thereto resulting from the elasticity of the intestinal tissue), thereby exerting force on the underlying constrictive element. At equilibration, the balloon 2506 is fully contacted with the distended intestinal wall, the pressure within the balloon and trailer gas chamber being equal. As is well known, the pressure-volume product PV for a gas remains constant at constant temperature (Boyle's Law). Hence:

$$P_1 V_1/T_1 = P_2 V_2/T_2$$

Where
$p_1$ = pressure at volume $V_1$
$p_2$ = pressure at volume $V_2$

Therefore, if the ratio of the volume of the expanded balloon 2506, gas chamber, and annular volume is five (5) times the volume of the gas chamber $V_1$, then the ratio of the pressures will be ⅕ or 20% (assuming constant temperature for both initial and final states). If the ultimate pressure needed to satisfactorily inflate the balloon 2506 is 5 psi, then the same gas chamber must be initially pressurized to roughly 25 psi. Total interior surface volume of an exemplary cylindrical chamber 2510 of length 20 mm and radius 6.5 mm (I.D.) is approximately 1.4 sq. in., thereby generating a total surface force of about 35 lb. on the chamber walls at 25 psi.

The foregoing calculation is merely exemplary, and the actual pressure required may vary based on changes in temperature, use of non-ideal gases and non-adiabatic processes, etc. Note that the elasticity and volume of the balloon, size and volumetric capacity of the trailer, and pressurization of the latter, are all readily calculated using well known mathematical modeling techniques, or alternatively may be empirically determined such as though trials using cadaver intestine. Furthermore, during expansion of the compressed gas into the balloon, the temperature (thermal energy content) of the gas will decrease slightly, thereby effectively "chilling" the balloon 2506, gas chamber, annulus 2516, and adjacent portions of the probe.

Pressurization of the gas chamber 2510 is accomplished in the illustrated embodiment using a pressurization port 2577 disposed on the side of the chamber 2510; the port contains a one-way bladder valve akin to that used in inflatable sports equipment, thereby allowing insertion of a small diameter (e.g., 1.0 mm) inflation probe or needle (not shown) for pressurization of the chamber. It will be recognized, however, that other approaches may be used.

In the simple case, design leak-off of the system (such as through utilization of a semi-permeable balloon membrane, or leak-by on the junction of the balloon and annular coupler) may subsequently be used to deflate the balloon 2506, although other methods such as selective rupture of a secondary diaphragm (not shown) under electrical current may be utilized to relieve pressure when desired.

However, despite the foregoing utility, certain intestinal constrictions may not respond to the therapy provided by the probe 2500. Use of the probe 2500 for treatment of complete obstructions of the intestine may be contra-indicated. In such circumstances, despite the reduced cross-sectional area of the probe 2500 (as compared to other embodiments described herein), the probe 2500 may become lodged against the obstruction or constriction. Surgical removal of the probe 2500 would then likely be required. However, such measures may be untenable for certain subjects (such as those not otherwise requiring invasive surgery); accordingly, a method of dislodging the probe under such conditions is needed.

Figure 25D:
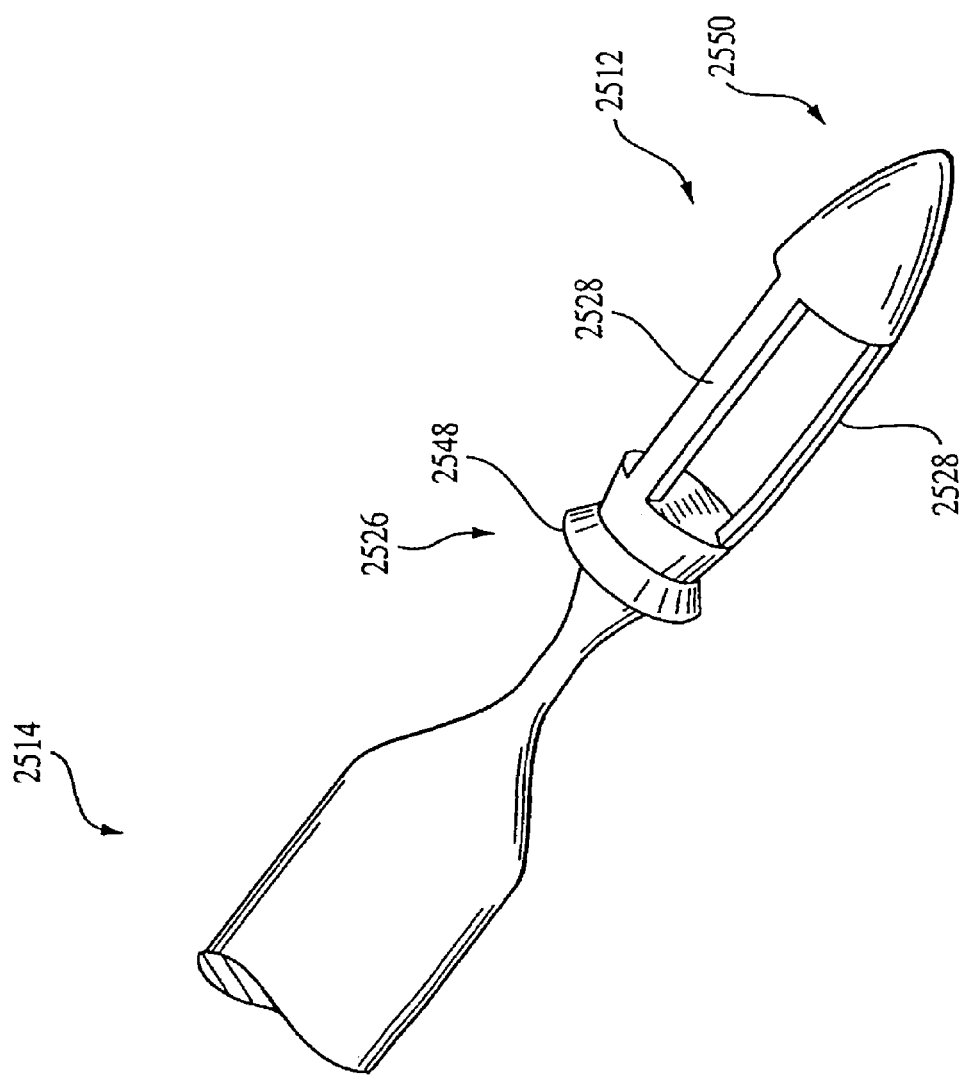

Accordingly, the probe 2500 of the invention may further be configured with a pressure sealing element (e.g., ridge or conic section) 2548 disposed on the rear portion 2526 of the front housing element 2512, shown in FIG. 25*d* with inflatable element 2506 removed. The sealing element 2548 acts to contact the inner surface of the intestinal wall, thereby forming at least a partial seal there between. To dislodge the probe, inert gas is administered to the intestinal tract via an endoscopic catheter or tube introduced via the esophagus of the subject such as by intubation (not shown); the inert gas fills the intestine, lightly pressurizing the same (the pressure being controlled so as to avoid any trauma or rupture thereof), and exerts a longitudinal force on the probe 2500 due to the differential pressure across the sealing element 2548. The frontal portion 2550 of the front housing element 2512 is further shaped in a tapered, elliptical semi-conic section ("bullet" configuration) such that penetration through the constriction is facilitated. The sealing device may further be equipped with a small fluid reservoir (not shown) containing a liquid lubricant, the latter being displaced from the reservoir and though passages in the frontal portion 2550 upon the application of differential pressure across the sealing element 2548, thereby reducing the coefficient of friction between the probe housing elements and the intestinal wall. The diameter of the rear (trailer) housing element 2514 is also made smaller than the diameter of the sealing element 2548, thereby allowing pressurized inert gas to flow readily around the periphery of the trailer.

As will be readily recognized, the aforementioned configuration affords several advantages, including (i) reduced cross-sectional area of both front and trailer probe housing elements 2512, 2514 as compared to a single probe so equipped; (ii) enhanced pressurized gas (potential energy) storage capacity for increased mechanical advantage against the constricted intestine, and (iii) provision of a sealing element useful for facilitating passage of the probe through constrictions.

It will be recognized, however, that a gas generant such as that previously described herein may be substituted for the pressurized nitrogen chamber of the embodiment of FIG. 25. Such gas generant may be contained within a specially constructed variant of the inflatable element 2506, the latter being adapted to withstand the heat generated by the gas generant during reaction. Since the gas generant consumes a smaller portion of space within the probe than the pressurized gas reservoir, the dimensions of the probe may be adjusted accordingly, or even contracted into a single housing element if desired.

In yet another embodiment of the apparatus for treating constrictions, the probe 2500 alternatively comprises a micro-solenoid assembly (not shown) with a cam-like structure such as that described previously herein with respect to FIG. 24 which, based on the application of electrical current through the coil of the solenoid, permits a portion of the probe to expand (and subsequently contract) under command of the probe's microcontroller or other external signal. Numerous electro-mechanical configurations for accomplishing such expansion and contraction of the probe are available and possessed by those of ordinary skill in the mechanical arts, and accordingly will not be described further herein.

Figure 26:
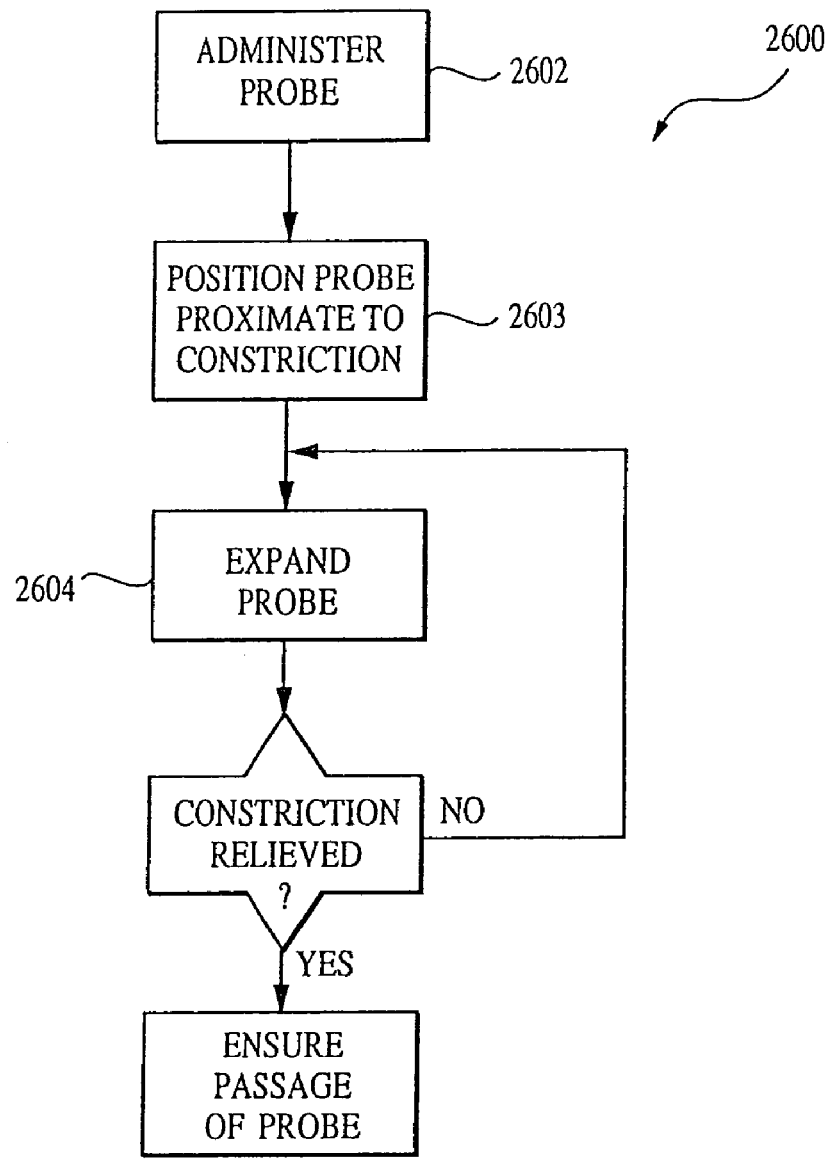
FIG. 26 is a logical flow diagram of one embodiment of the general methodology for relieving constrictions within the intestine utilizing the probe of FIGS. 25a-25d.

Referring now to FIG. 26, a method of treating constrictions within the intestinal tract of a living subject are disclosed. In one exemplary embodiment (illustrated in FIG. 26), the method of treating 2600 generally comprises first disposing the probe 2500 within the intestine of the subject proximate the constriction (step 2602 and 2603). This may be accomplished through direct oral administration of the probe 2500, or more preferably, through endoscopic insertion of the probe using an insertion/delivery device such as that described previously herein. Endoscopic delivery of the probe is preferred due to the asymmetries of the shape of the probe, and the need to orient the probe properly within the intestine (i.e., front housing element 2512 first into the intestine). The probe 2500 is next caused to expand in radius or otherwise deform its shape so as to expand at least a portion of the constriction, (step 2604) as previously described in detail. In one exemplary variant of the method 2600, the probe is tracked using conventional X-ray or ultrasonic techniques such that it's proximity to the constriction can be accurately determined. When properly positioned, the probe is expanded within the constriction as required to at least partially relax the constriction. In another variant, the probe 2500 is further outfitted with a radio frequency, ultrasonic, or other trackable signal emitting device, and the probe tracked via emitted radio frequency, ultrasonic, radiation, or other tracking signals. In yet another variant, a piezoelectric transducer element disposed on the probe (described below) is used in conjunction with on-probe or external signal processing apparatus to acoustically determine the proximity of the probe to the constriction/obstruction through "echo ranging" or alternatively ultrasonic imaging of the constriction. In yet another variant, the CCD or MOS visual or IR imaging array previously described is used to visually determine the proximity of the probe to the constriction/obstruction.

In a second embodiment, the method of treating intestinal constrictions according to the present invention comprises disposing the probe within the intestine of the subject proximate the constriction; and causing the probe to release one or more agents in the intestine so as to induce expansion or contraction of at least a portion of the constriction. For example, the present invention contemplates the delivery of pharmacological agents such as mesalamine (e.g., Asacol®) or amytriptaline (e.g., Elavil®) which may tend to induce relaxation of the intestine, although other even more aggressive agents may be substituted or used in concert with the foregoing.

Alternatively, the probe may be adapted to generate significant electrical potentials through use of a miniature capacitor or microelectronic toroidal core transformer of the type well known in the surface mount electronics arts, from energy stored in the improved graphite composite structural energy storage mechanism described subsequently herein, or alternatively via other on-probe storage devices or off-probe power sources. When applied to the intestinal wall, such potentials induce current flow therein, the latter resulting in stimulation of the intestinal muscle into a state of temporary contraction, as is well understood. Properly timed and positioned, such contraction around the centrally positioned probe can result in, inter alia, temporary relaxation of the intestinal constriction and/or passage of the probe.

As yet another alternative, the probe may be adapted to generate localized magnetic fields which, despite the current lack of credible evidence supporting their efficacy, may in certain contexts be proven to have therapeutic effect. Generation of such magnetic fields may be accomplished through the inclusion of a high-density ferromagnet or electromagnet within the probe, for example. Conductive coils disposed helically around the electromagnet carry electrical current (generated by the potential difference created by either on-probe sources, or off-probe power sources are electromagnetically or inductively coupled to the probe) which aligns the magnetic domains with the ferromagnetic material, and enhances the B-field strength in the vicinity of the probe. Alternatively, a "trailer" probe carrying a larger electromagnet may be utilized. The probe may then be purposely "stuck" within the intestine using the aforementioned outwardly projecting scoops or other component, thereby allowing for prolonged exposure of a selected region of tissue to the magnetic field generated by the probe.

"Smart" Probe Housing

Figure 27A:
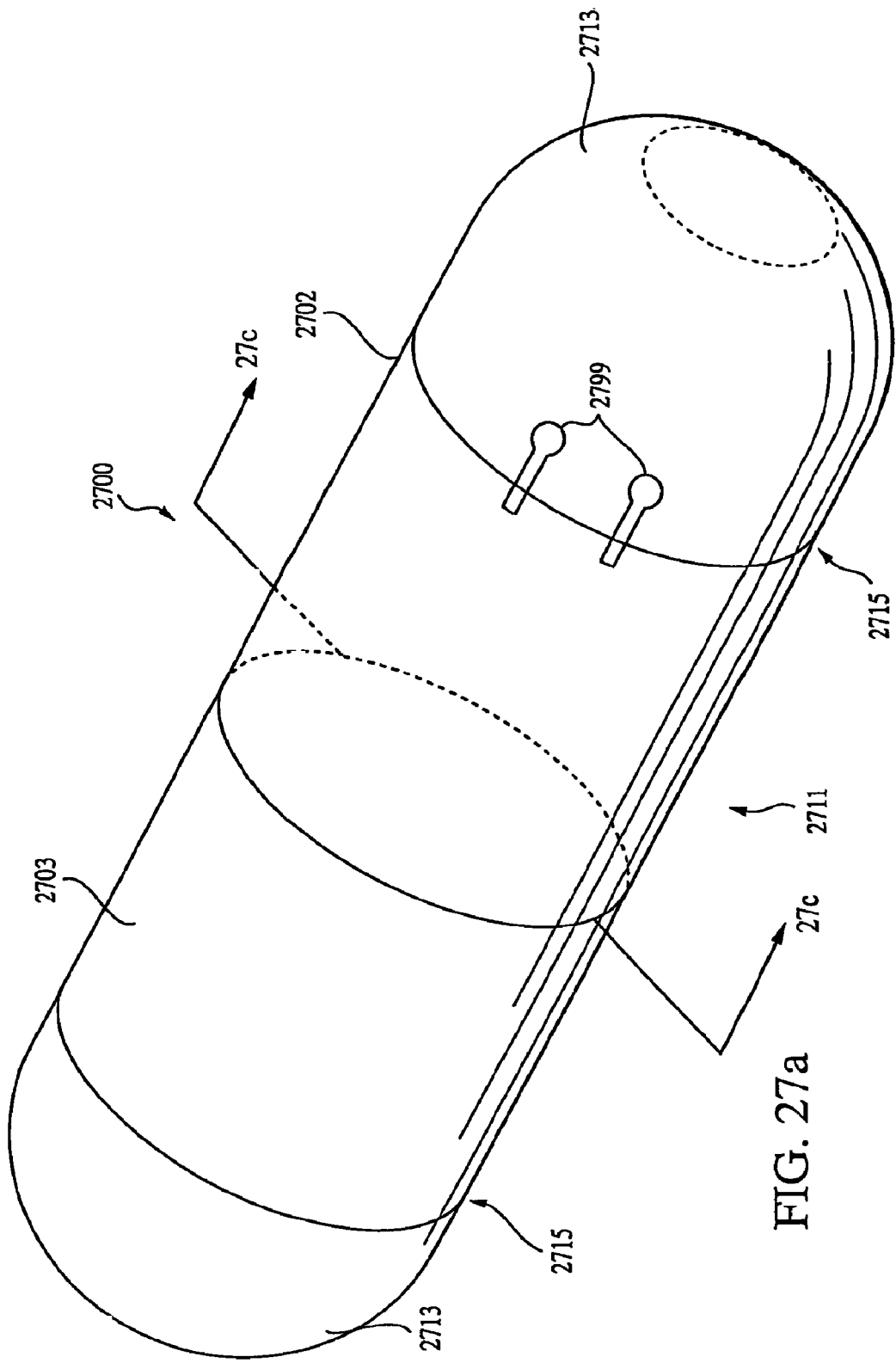
FIG. 27a is a perspective view of yet another embodiment of the smart probe of the invention, wherein the probe includes a structural electronics housing having an intrinsic capacitor energy storage device.
Figure 27B:
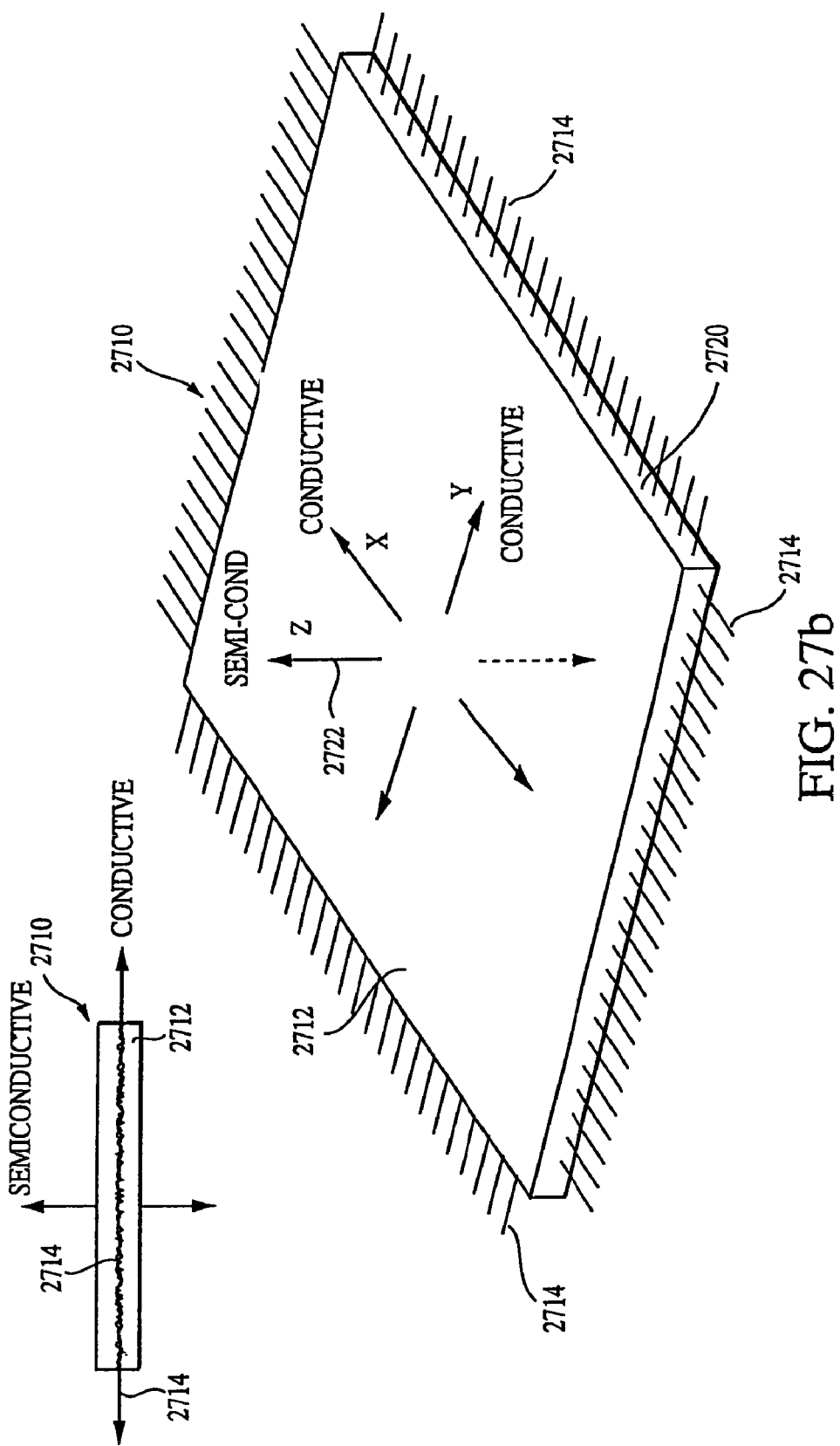
FIG. 27b is a composite view of a portion of the housing of the probe of FIG. 27a, illustrating the carbon composite matrix and the electrical properties thereof.

Referring now to FIGS. 27a-c, an improved autonomous probe having a "smart" housing and electronics configuration is disclosed. As used in the present context, the term "smart housing" refers generally to the science of structural electronics, largely pioneered by D. D. L. Chung, et al, of University of Buffalo, N.Y., although the invention is not limited to the methods developed by Dr. Chung or in fact any other specific technique. One of the salient benefits of such structural electronics is the significant savings in space provided by integrating otherwise discrete components or functionalities within a single device. Such benefit is particularly applicable in the context of the present invention, in that the size of the device which can successfully pass through the intestinal tract of a living subject is limited, and accordingly space it at a premium within such devices. Hence, the same probe incorporating structural electronics may be made smaller than its counterpart not so equipped, or alternatively more capacity and functionality can be included within a probe otherwise of the same size.

As illustrated in FIG. 27a, the probe 2700 comprises a structural electronic housing 2702 formed at least in part from multi-layer carbon fiber composite material which is encased in an insulating coating 2703. The carbon fiber composite material 2710 comprises a plurality of substantially concentric sheets 2712 of polymeric (e.g., epoxy resin) matrix in which a plurality of micro-diameter "electrically conductive" graphite carbon fibers 2714 have been selectively disposed (FIG. 27b) in a predetermined, non-colinear but generally planar orientation. The term "electrically conductive" is used with respect to the instant discussion to refer to any level of conductivity greater than that of a semiconductor, since in most cases, the graphite fibers are not nearly as electrically conductive as comparable traditional copper or alloy-based conductors.

In order to make the best possible of use of available space within the probe, and/or reduce the weight thereof via reduced battery requirements, the sheets 2712 of the housing 2702 are disposed centrally within the midsection 2711 of the housing 2702 such that two concentric cylinders are formed. It will be recognized that while the embodiment of FIG. 27a illustrates two concentric cylinders of matrix material which terminate at the juncture 2715 of the ellipsoid/hemispherical end portions 2713 of the housing 2702, the sheets 2712, with proper fabrication technique, may comprises a greater fraction of the housing element 2702, thereby affording greater energy storage capacity. The entire housing 2702 may conceivably be fabricated using the multi-sheet composite construction of the present invention; however, the cylindrical section disposed in the midsection of the probe 2700 of FIG. 27a is chosen for ease of construction, as well as ease of analysis.

As shown in FIG. 27c, the matrix sheets 2712 are separated by a high dielectric constant material (e.g., insulator) 2717 comprising a strontium titanate/Microlam® composite, having a dielectric constant of about 300. It will be recognized, however, that other dielectric materials such as impregnated kraft paper, ceramic, or any other one of a plethora of suitable insulating materials well known in the electrical arts, may be used, consistent with the power requirements of the probe as discussed below. The high dielectric constant of the strontium titanate/Microlam composite facilitates the storage of greater energy within the capacitor, as is desirable.

As is now known, such polymer matrices, when so formed, are electrically conductive in the plane 2720 of the sheets 2712, and also exhibit semiconductive properties in the transverse dimension 2722 (i.e., normal to the plane 2720 of the sheet 2712). See D. D. L. Chung and S. Wang, "Carbon Fiber Polymer-Matrix Composite as a Semiconductor"; 5th Annual International Symposium on Smart Structures and Materials, The International Society for Optical Engineering, San Diego, 1998. Although not verified, apparent negative electrical resistance in the transverse of similar composites was also observed. See also Shoukai Wang and D. D. L. Chung, "*Apparent Negative Electrical Resistance in Carbon Fiber Composites*," Composites, Part B, Vol. 30, 1999, p. 579-590. Furthermore, dependent on the temperature and pressure applied to the matrices during formation, the material and electrical properties of the resulting sheets 2712 may be substantially altered (Chung, et al.).

Accordingly, as the sheets 2712 are transverse semiconductors and co-planar conductors, the sheets with interposed dielectric act as a large parallel-plate capacitor (Chung; "*UB research*", University of Buffalo, Vol. 8, No. 1, Spring 1998) capable of storing quantities of electrical charge in a fashion akin to a conventional capacitor. Hence, the housing 2702 of the present embodiment of the invention acts as an energy storage device, thereby partially obviating (or even totally obviating in certain applications) the need for other on-probe energy storage.

As is well known in the electrical arts, the capacitance per unit length of infinite concentric conductive cylinders is given by the following relationship:

$$C/L = 2\pi \in / \ln(b/a)$$

Where:
C=capacitance
L=length
$\in$=permitivity of interposed dielectric ($\in_0 \times$ dielectric constant)
b=radius of outer conductive sheet
a=radius of inner conductive sheet The concentric cylinders of the present embodiment are by no means infinite, and hence there is error when applying the equation above to calculate the capacitance (and ultimately energy storage capacity) of the housing 2702. However, for purposes of illustration and simplicity, the concentric cylinders of the embodiment of FIG. 27a are considered infinite.

Based on a nominal outside sheet radius of 6.5 mm and an inside sheet radius of 5.75 mm (0.75 mm thickness of the composite strontium titanate/Microlam dielectric), and dielectric constant of 300, the capacitance obtained per unit length is roughly 0.136 E-06 Farad/meter. For a 25 mm long center section as in the exemplary embodiment, the capacitance is therefore roughly 3.4 nF or 0.0034 µF. The dielectric strength of Microlam is given to be greater than 700 V/mil, where one mil=0.0254 mm. Hence, for a 0.5 mm (6.5 mm-5.75 mm-0.25 mm strontium titanate) thick Microlam insulator sheet, the withstand voltage is on the order of 700 V/mil×1/0.0254 mil/mm×0.5 mm=13,780 V. Hence, a voltage of about 13,700 V can be readily sustained by the aforementioned insulator sheet without dielectric breakdown. The capacitor (specifically, the housing charging terminals) is placed across a charger (not shown) which generates this voltage prior to administration of the device in vivo, thereby charging the capacitor, at which point the probe may be removed from the charger. The probe charging terminals 2799 in the illustrated embodiment are disposed internal to the probe such that the probe must be disassembled in order to charge the housing capacitor; hence, an inherent patient safety feature is present, since the probe housing structural capacitor can not "short" and discharge across the subject's intestine or other tissue while in vivo, since (i) it is covered with a dielectric coating, and (ii) the terminals are contained entirely within the interior volume of the probe. It will be recognized, however, that other safety measures may be employed consistent with the invention.

The dielectric coating placed on the outer surface of the probe may be any commercially available polymer such as the aforementioned Tefzel or Teflon, although other materials may be used.

The charge Q stored in the structural capacitor is given by:

$$Q=CV$$

Therefore, for the capacitor of the present embodiment, the stored charge (at 13,700 V)=13,700 V×0.0034E-06 F=46.6 µC. Now assume a 50 ms, 100 µA (constant) current pulse drawn from the capacitor. This means a charge loss of ΔQ, where:

$$\Delta Q = I\Delta t = 100E{-}06 \times 50E{-}03 = 5.0 \ \mu C$$

The charge remaining after the pulse is 46.6 µC-5.0 µC=41.6 µC. The capacitor voltage is then $$V=Q/C=41.6 \ \mu C/0.0034E{-}06 F=12,235 \ V$$

If the current drawn from the capacitor is not constant, then $$V(t) = \frac{Q(t)}{C} = \frac{Q_0 - \int_0^t i(t)\,dt}{C}$$

$$= \frac{CV_0 - \int_0^t i(t)\,dt}{C}$$

$$= V_0 - \frac{1}{0}\int_0^t i(t)\,dt$$

where $V_0$ is the initial voltage on the capacitor. As is well known, the energy stored in a capacitor is given by:

$$E=CV^2/2$$

Hence, the maximum energy stored in the "structural" capacitor of the invention is roughly [3.4E-09×(13,700 V)$^2$]/2=0.319 Joules or 319 mJ, which can be discharged almost instantaneously if required. In terms of power, this relates to about 5 mW for about one minute, 0.5 mW for ten minutes, or 0.0866 mW for one hour. Accordingly, the structural capacitor of the invention can supply substantial power in support of probe operation, especially certain "high draw" transients such as ablation laser diode operation, micro-solenoid operation, and the like.

Comparatively, a typical miniature battery NiMH or Lithium battery of the type described previously herein, having a capacity of 10 mA-H at 3.0 V nominal, will produce power according to:

$$P=IV$$

Hence, when considering operation over a one-hour period (i.e., depletion of the battery's chemical enemy over one hour at a draw rate of 10 mA), the derived power equals 10E-03A× 3.0 V=3E-02 V-A=0.03 W or 0.03 J/s. Integrating over the one-hour time period (3600 seconds), the battery supplies a maximum of 0.03 J/s×3600 sec.=108 J of energy. However, such energy can only be drawn out of the battery at a comparatively slow rate based on, inter alia, internal resistance and thermal restrictions associated with the battery, and furthermore, the voltage characteristic at battery end-of-life (EOL) degrades, such that the battery is not practically usable for its entire stored energy (i.e., not all 108 J can be drawn from the battery by the probe, especially since the probe electronics will only operate down to a predetermined voltage level; roughly 1.0-2.7 V depending on the type of IC components used). Total power consumption of the probe device (based on DSP operation, CCD, ADC, and other related components/processing) is on the order of between 5-500 mw peak, depending on status (i.e., whether processor "sleep mode" is invoked, status of the white light/laser LEDs if so equipped, etc.)

It will be recognized that the structural capacitor of the invention may be enhanced for greater energy storage capacity through (i) increasing the size of the capacitor (i.e., effective length L, which correlates to increased "parallel" plate area; (ii) the use of a material with higher dielectric constant and/or higher dielectric strength; (iii) use of multiple layers of dielectric and additional plates (i.e., formation of a "double layer" capacitor; and/or (iv) the use of other on-probe capacitors. With respect to Item (iv), it will be recognized that a trailer probe as described below with respect to FIG. 34 may be configured as an additional "parallel plate" capacitor for this purpose.

Energy is transferred out of the structural capacitor using a plurality of conductive traces (not shown) disposed on the interior surfaces of the probe housing which are electrically connected to the terminals 2799 of the structural capacitor. The traces are deposited on the interior surface in sufficient thickness (on the order of 0.003 in) so as to endure the maximum transient (e.g., laser ablation) current without significant ohmic heating, yet maintain a small physical profile. Other attendant circuitry well known in the electronic arts (including for example a zener diode for maintaining a constant voltage across loads using the structural capacitor, load resistor, and transistor-based switch for transferring power supply from the battery, etc. to the structural capacitor) are disposed within the probe housing, such as on one of the miniature PCBAs 510 referenced herein, or alternatively in an application specific integrated circuit (ASIC) of the type previously described.

Figure 27D:
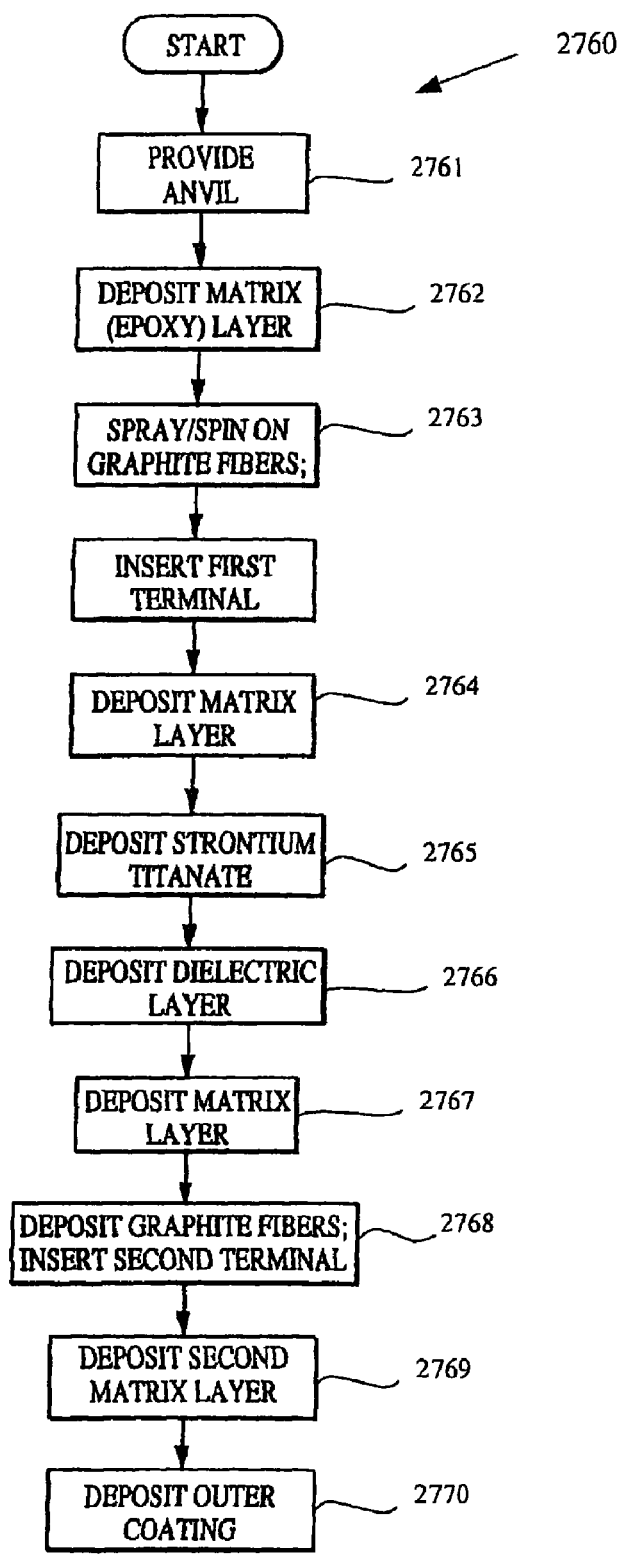
FIG. 27d is a logical flow diagram illustrating one embodiment of the methodology of manufacturing the structural probe housing of FIGS. 27a-c.

Referring now to FIG. 27*d*, one exemplary embodiment of the method of fabricating the structural capacitor of the invention is described. As shown in FIG. 27*d*, the method 2760 comprises first providing a form or anvil (e.g., cylindrical shape) over which the capacitor will be formed (step 2761). The first layer of matrix material (e.g., epoxy) for the inner sheet 2712 is then deposited on the anvil in step 2762. The carbon fibers are then spun or sprayed onto the first matrix layer in step 2763. The second layer of matrix material is then deposited over the carbon fiber layer in step 2764. Next, the strontium titanate layer is deposited on the second matrix layer per step 2765. The Microlam layer is then applied atop the strontium titanate to the desired thickness per step 2766. Subsequent layers of matrix, carbon fiber, and matrix are subsequently applied to the capacitor sequentially per steps 2767 through 2769. The two electrical terminals 2799 are also disposed in electrical contact with the carbon fibers of their respective sheet 2712 during deposition of the fibers per steps 2763 and 2768. Lastly, the outer insulative coating is applied to (e.g., sprayed onto) the finished capacitor after curing of the epoxy matrices per step 2770, thereby providing enhanced dielectric strength. Note that multiple matrix layers/sheets may be built up using the foregoing process; hence, three or more layer capacitors may be formed if desired. Additionally, the composite strontium titanate/Microlam dielectric layer(s) may be formed off of the anvil, and then deposited as a single layer atop the first sheet 2712. Other such variations are also possible.

Figure 28:
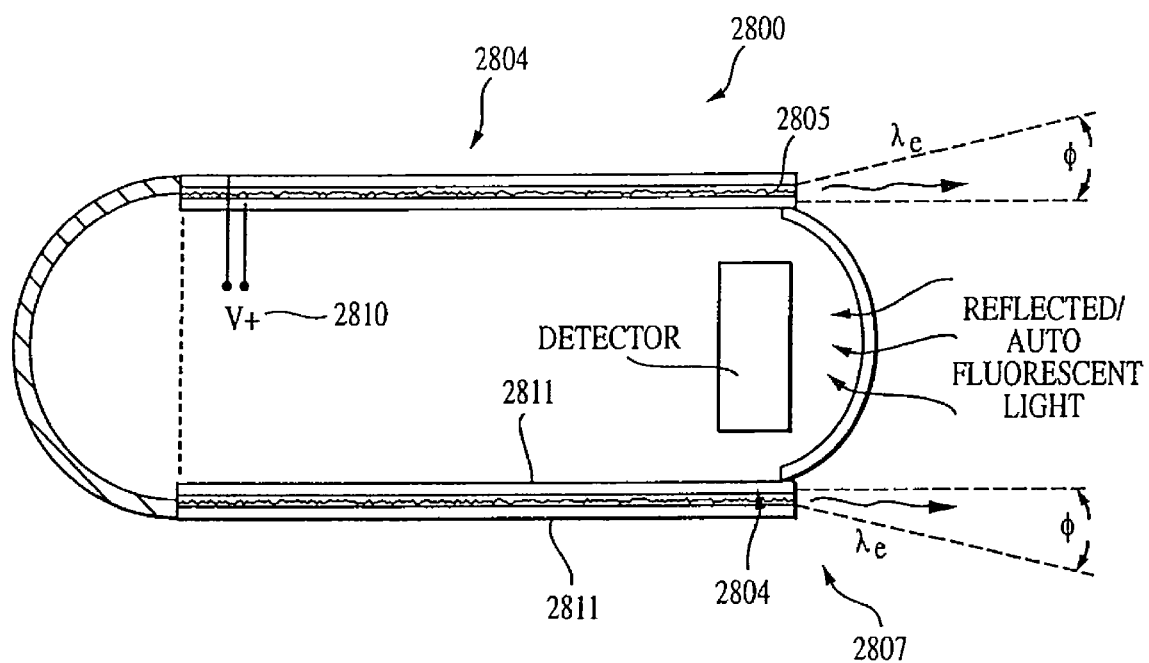
FIG. 28 is a cross-section of yet another embodiment of the smart probe of the invention employing structural semiconductive device(s) therein.

Referring now to FIG. 28, a second embodiment of the autonomous probe with "smart" housing is described. In this second embodiment, portions of the probe housing are fabricated from aforementioned multi-layer laminated semiconducting/conducting carbon fiber polymer matrix sheets 2712, the latter integrating the functionality of one or more otherwise discrete electronic or opto-electronic semiconductor components within the housing itself, thereby obviating the need for the separate components which consume much additional space within the probe.

As illustrated in FIG. 28, the probe 2800 comprises a carbon fiber composite matrix housing 2802 having at least one active semiconductive region 2804 formed therein. While the following discussion is cast in terms of an exemplary semiconductor device adapted to emit infrared radiation with band gap energy on the order of 0.01 eV to 0.1 eV (see D. D. L. Chung and S. Wang, previously cited herein), it will be recognized that semiconductor devices tuned to other band gap energy values may be fabricated and used consistent with the invention. For example, a device having bandgap energy in the range of approximately 1.7 eV and being used to generate the desired wavelength of light (roughly 700 nm) for autofluorescence analysis or ablation may be substituted or used in concert. Other band gap energies may be accommodated as well.

As is well known, semiconductive materials exhibit electron quantum energy bands and gaps there between (so-called "band gap") resulting from, inter alia, two standing quantum wave functions $\Psi(+)$ and $\Psi(-)$. The gap is the difference in energy between the lowest point of the conduction band (conduction band edge) and the highest point of the valence band (valence band edge). As illustrated in FIG. 27b, it has been found that a co-planar array of graphite carbon fibers embedded within a (doped) epoxy matrix exhibits semiconductive behavior in the direction normal to the plane of the fibers. Conductivity ranges broadly from roughly unity to 10 E-05 mho/cm, being largely a function of temperature applied to the matrix. As previously indicated, the pressure and temperature applied at time of composite formation also may affect the semiconductive properties (and even the conductive properties) of the matrix. The application of an electrical potential (V) across the thickness of the composite in the region 2804 induces electron transition across the band gap. Transition of excited electrons to a lower energy state generates the production of quanta having energy corresponding to the band gap (e.g., 0.01-0.1 eV), such quanta being radiated from the region 2804.

The conductive carbon fibers 2806 present in and adjacent to the semiconductive region 2804 are further utilized to conduct electrical current to the semiconductive region 2804 through the property of planar conductivity of composite matrices described previously. Specifically, regions of generally coplanar carbon fibers are etched or otherwise constructed within the housing polyer matrix so as to form conductive traces 2810 within the housing matrix itself, thereby obviating any other types of conductors and the additional space, cost, and labor associated therewith. Hence, the present invention advantageously employs graphite or other composite structures which act both as embedded electrical conductors and semiconductors.

As shown in FIG. 28, the present embodiment of the smart device 2800 includes a substantially cylindrical active semiconductive region 2804 disposed generally around the outer periphery 2807 of the probe 2800. The active region 2804 comprises a plurality of graphite, fiber-based layers which are laminated upon and in communication with one another so as to form a "sandwich" of materials, the junctions of the sandwich corresponding to p-n junctions within a traditional semiconductor. A central "optically" conductive layer 2805 disposed between the graphite composite layers 2811 is used as the medium for photon transport from the active region, thereby forming an effective annulus for photon emission from the front of the probe 2800. Population inversion within the medium may be selectively induced by the proper selection of the medium material and the application of the potential V+ 2810 across the junction(s), thereby resulting in stimulated emission of quanta of the desired energy.

Hence, the arrangement of FIG. 28 provides increased luminosity and photon dispersion within the intestine when activated (as compared to a "discrete" semiconductor device such as LED or semiconductor laser), since the entire circumference of the active region of the housing is stimulated to emit photons of the desired energy.

In the illustrated embodiment, polyacrylonitrile is used in the formation of the fibers. Specifically, the compound is heated to form the carbon fibers as is well known in the materials arts. This can comprises a multi-step heating process which involves elevation of temperature to between 400 degrees C. and 1300 degrees C. which forms aromatic carbon, although other processes may be used. Formation of the housing/structural components themselves may be accomplished by resin-transfer molding (RTM), pultrusion, manual or automated layup, or other techniques of the type well understood in the field.

Autonomous Pressure Sensing Apparatus and Method

Figure 30:
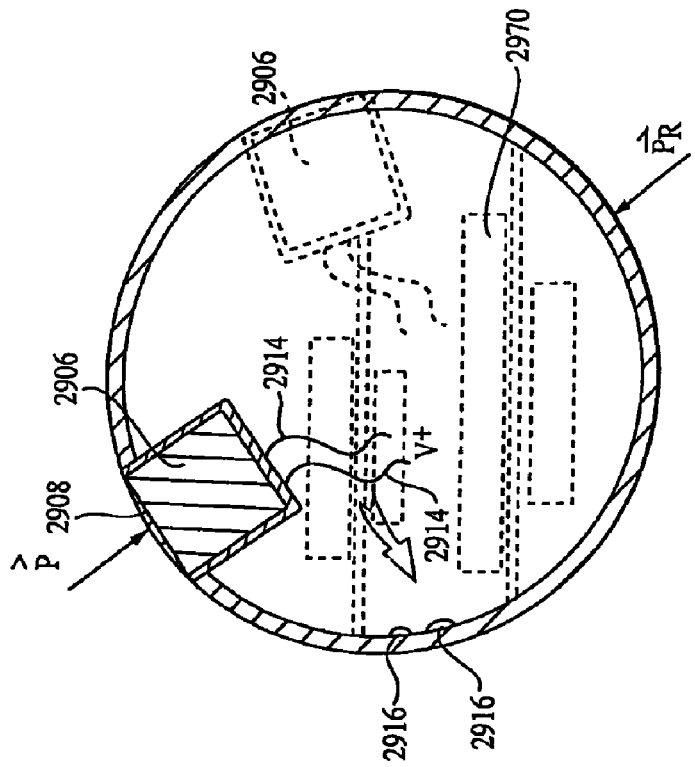
FIG. 30 is a cross-sectional view of the probe of FIG. 29, illustrating the various components therein.
Figure 29:
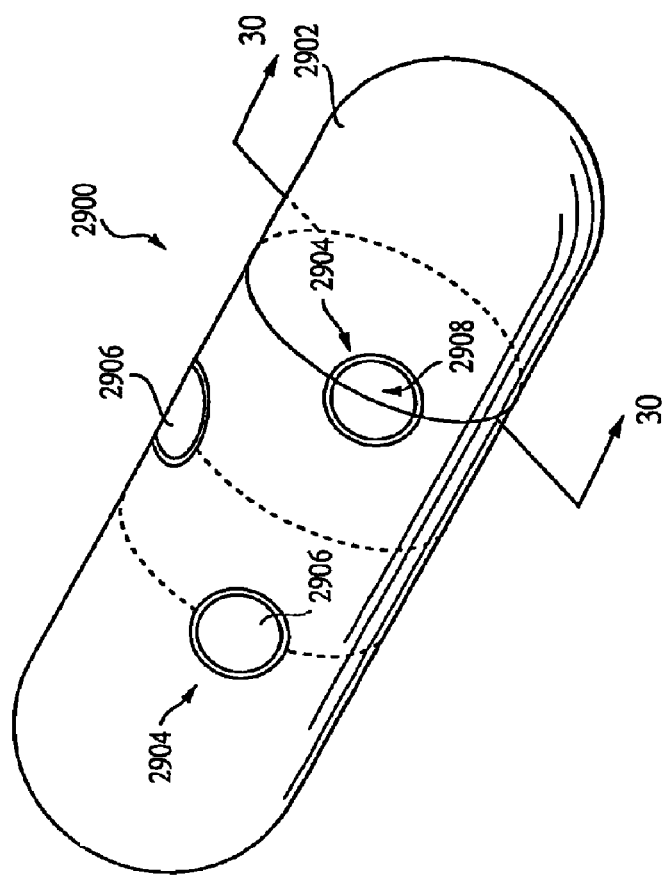
FIG. 29 is a perspective view of yet another embodiment of the smart probe of the invention, adapted for pressure measurement within the intestinal tract.

Referring now to FIGS. 29 and 30, yet another embodiment of the autonomous smart probe of the invention is described. In the instant embodiment, the probe 2900 includes a housing 2902 having one or more apertures 2904 formed therein, the apertures receiving respective ones of miniature piezoelectric transducer elements 2906 adapted to sense pressure variations on the outer surface of the housing 2902. The transducer elements 2906 have a small facial area 2908 (on the order of 15 mm$^2$) and depth so as to be readily accommodated within the probe housing. The active portion 2908 of the transducer elements 2906 each comprise a piezoelectric ceramic compound of the type commonly used in acoustic and pressure sensing devices, the manufacture and characteristics which are well understood by those of ordinary skill. The piezoelectric devices generate a small but measurable voltage across their output as a result of pressure applied to their face 2908, the output voltage being a function of, inter alia, the facial pressure applied.

The active faces 2908 of the transducer elements are disposed within the probe housing 2902 in a generally radial, offset fashion so as to obtain data from various different portions of the probe housing (thereby increasing the probability of a representative sample), although many other configurations may be used. The use of offset elements allows the outside diameter of the probe to be smaller as well, since each element may occupy almost the entire diameter of the interior of the probe housing 2902, as shown in FIG. 30. The transducer elements 2906 are further securely held within the housing apertures using, for example, an epoxy of other adhesive which also acts as a sealant against ingress of fluid past the transducer element/aperture edge interface. Since (i) the probe housing 2902 is rigid and non-collapsible, (ii) the transducer elements are tightly secured within the housing 2902, and (iii), the opposing outer surface of the probe housing is abutted against the opposing intestinal wall, thereby generating a reaction force PR, pressure applied to any given transducer element face 2908 will be generally reflected in the transducer element output voltage.

Figure 30A:
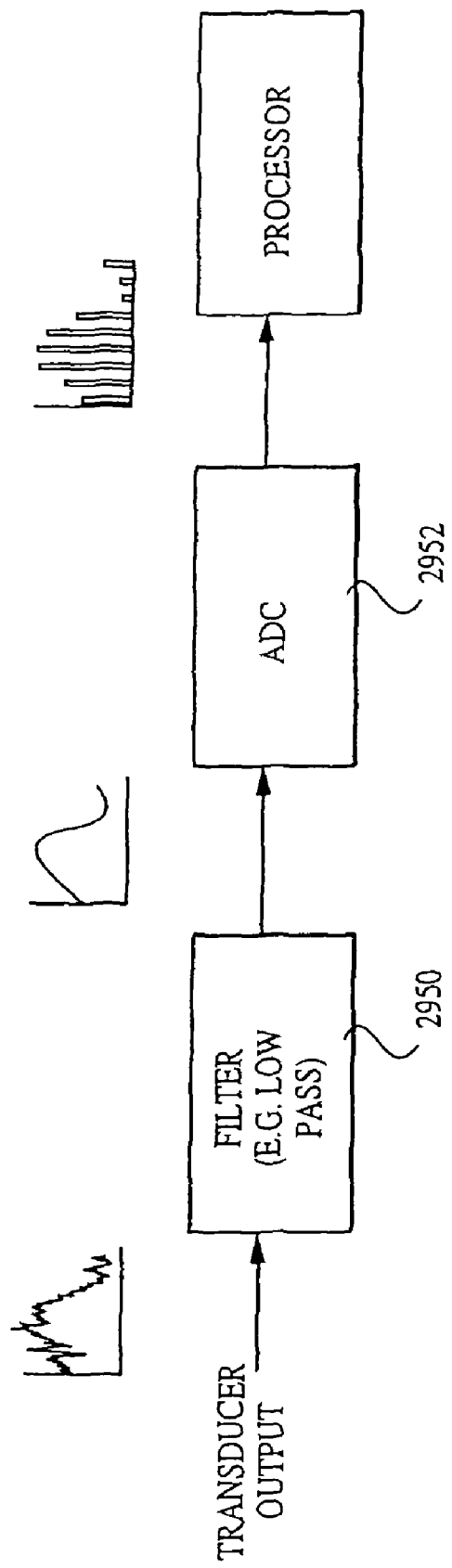
FIG. 30a is a functional block diagram illustrating the electronic processing of the pressure signal performed by the probe of FIG. 30.

The electrical terminals 2914 for each transducer element are routed to respective conductive traces 2916 formed on the interior surface of the housing 2902, thereby minimizing the volume used within the housing. In one embodiment, transducer element output voltage is filtered 2950 to remove noise and undesired out-of-band components (e.g., high frequency noise within the pressure waveform) and subsequently fed to an ADC 2952 of the type previously described herein to generate a binary digital representation of the filtered transducer output voltage waveform as a function of time (FIG. 30*a*).

The multiple transducer elements 2906 of the probe further provide increased level of statistical confidence in the results obtained from the different transducers. For example, if the standard deviation associated with pressure measurements obtained from the various transducer elements 2906 at a given time is large, the data (or portions thereof) may be suspect. Many other types of statistical analyses may be applied as well, such analyses being well known in the mathematic arts.

Figure 33:
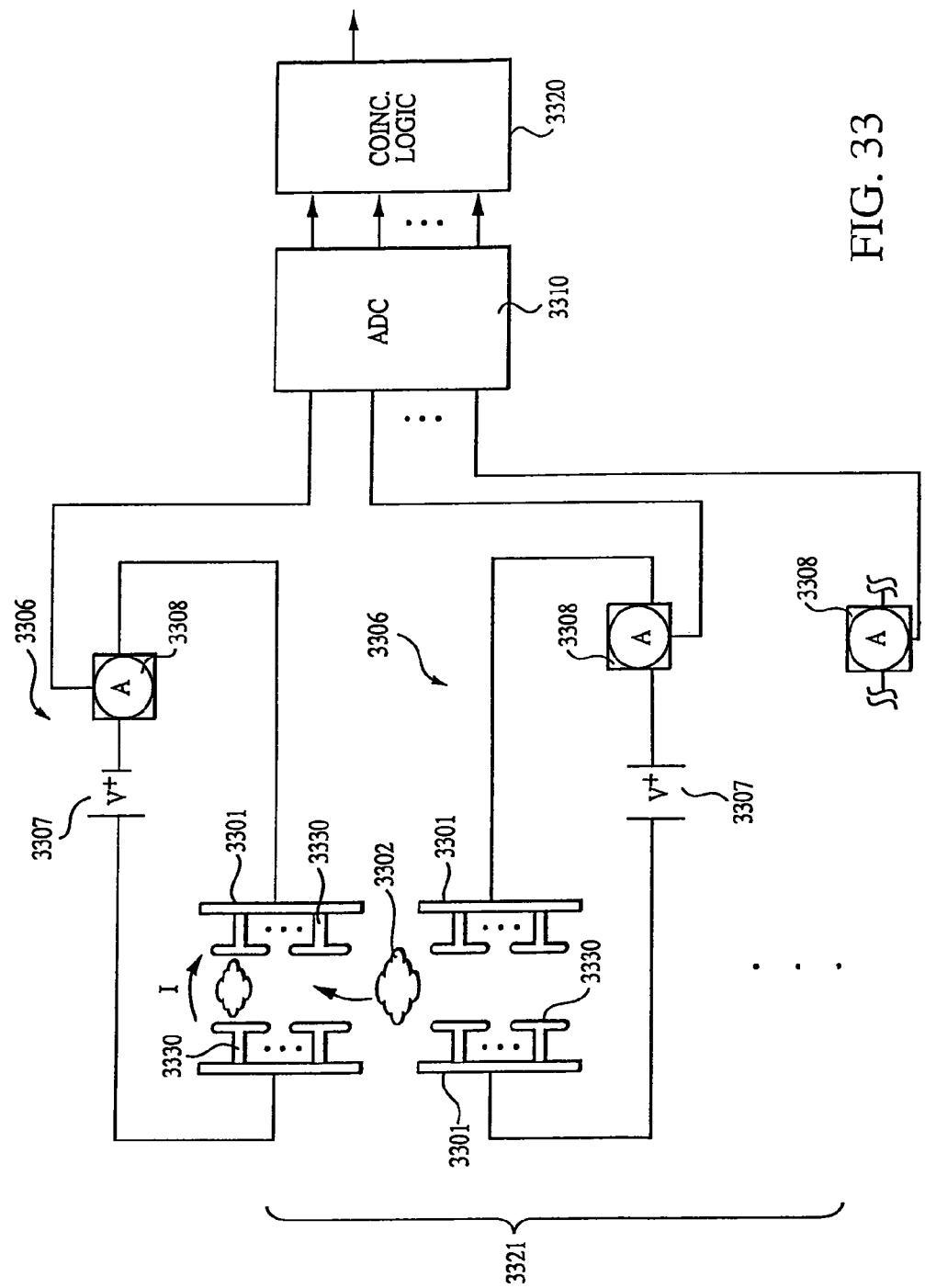
FIG. 33 is a partial schematic of one exemplary embodiment of the molecule detection circuit of the probe of FIG. 32.
Figure 33A:
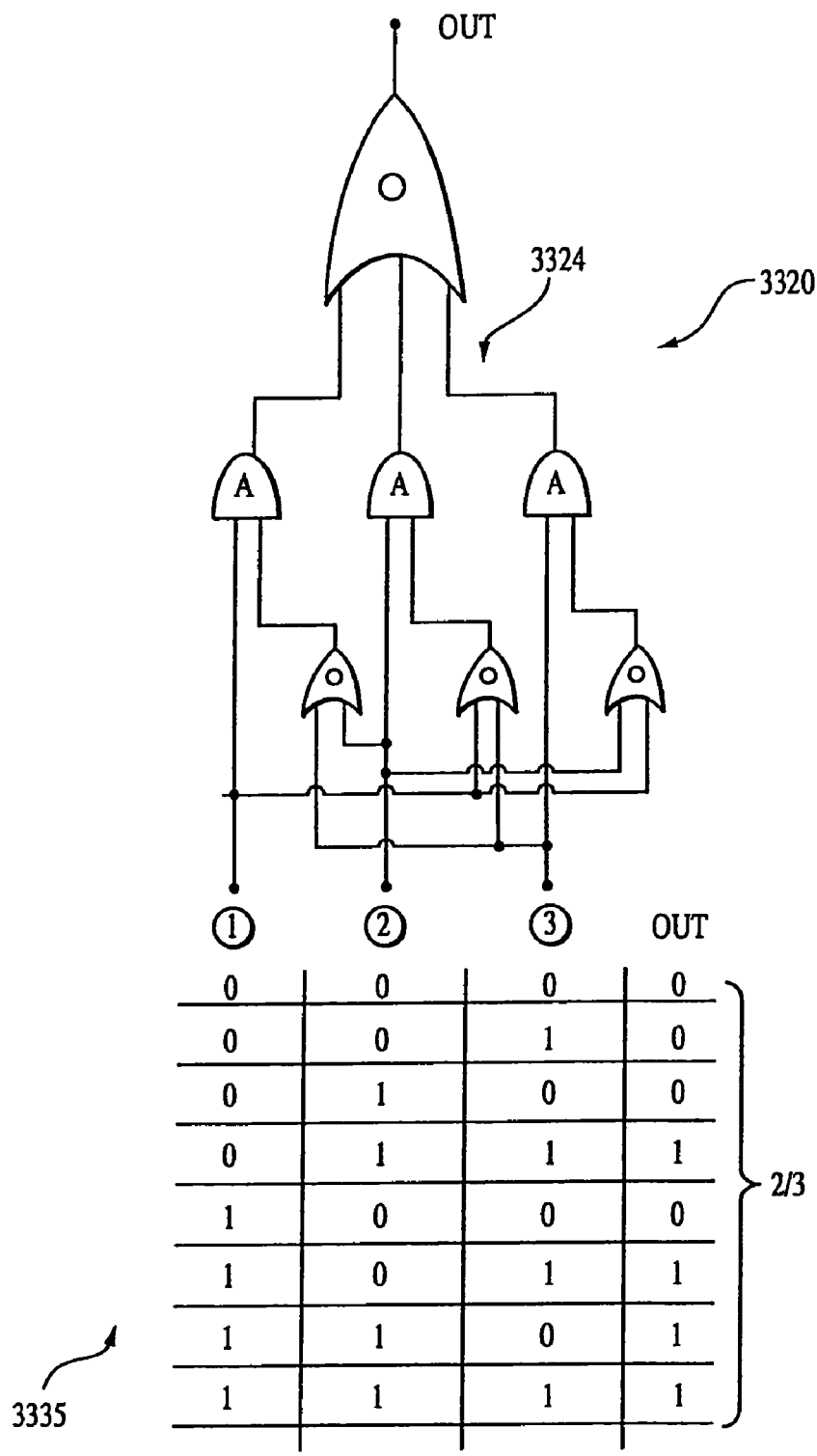
FIG. 33a is a schematic of exemplary gate logic used to implement the coincidence functionality of the probe of FIG. 32.

Furthermore, the use of multiple transducer elements 2906 permits the application of coincidence logic (such as that described herein with respect to FIG. 33*a*). Specifically, an output voltage threshold value is specified, the threshold voltage correlating to a given pressure applied to the transducer face such as would result from peristaltic contractions of the subject's intestine. The coincidence logic (not shown) will produce a "high" output signal only upon the selected transducer elements collectively meeting the designated coincidence requirement, such as ⅔ or ⅗. Hence, spurious pressure/voltage transients affecting one transducer element will mitigate the chance that a peristaltic contraction will be falsely indicated by the probe.

In the illustrated embodiment, the aforementioned filter circuit, ADC, coincidence logic, and any other related circuitry is disposed within an multi-function integrated circuit (IC) 2970 such as the ASIC as previously described herein, although other configurations may be used.

Ultrasonic Probe

Figure 31A:
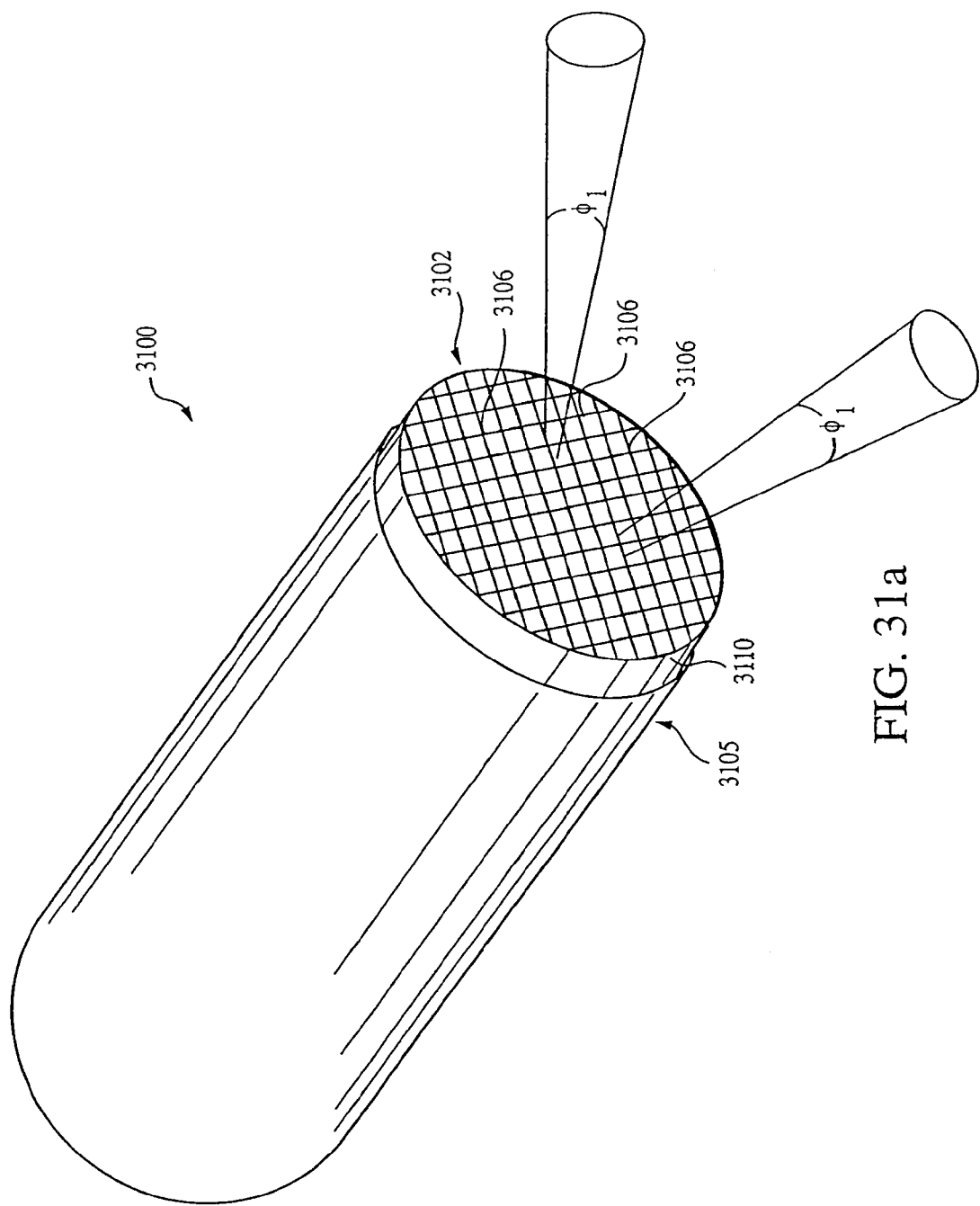
FIG. 31a is a perspective view of yet another embodiment of the probe of the invention, including 2-D phased ultrasonic transducer array and transmit/receive beams.
Figure 31B:
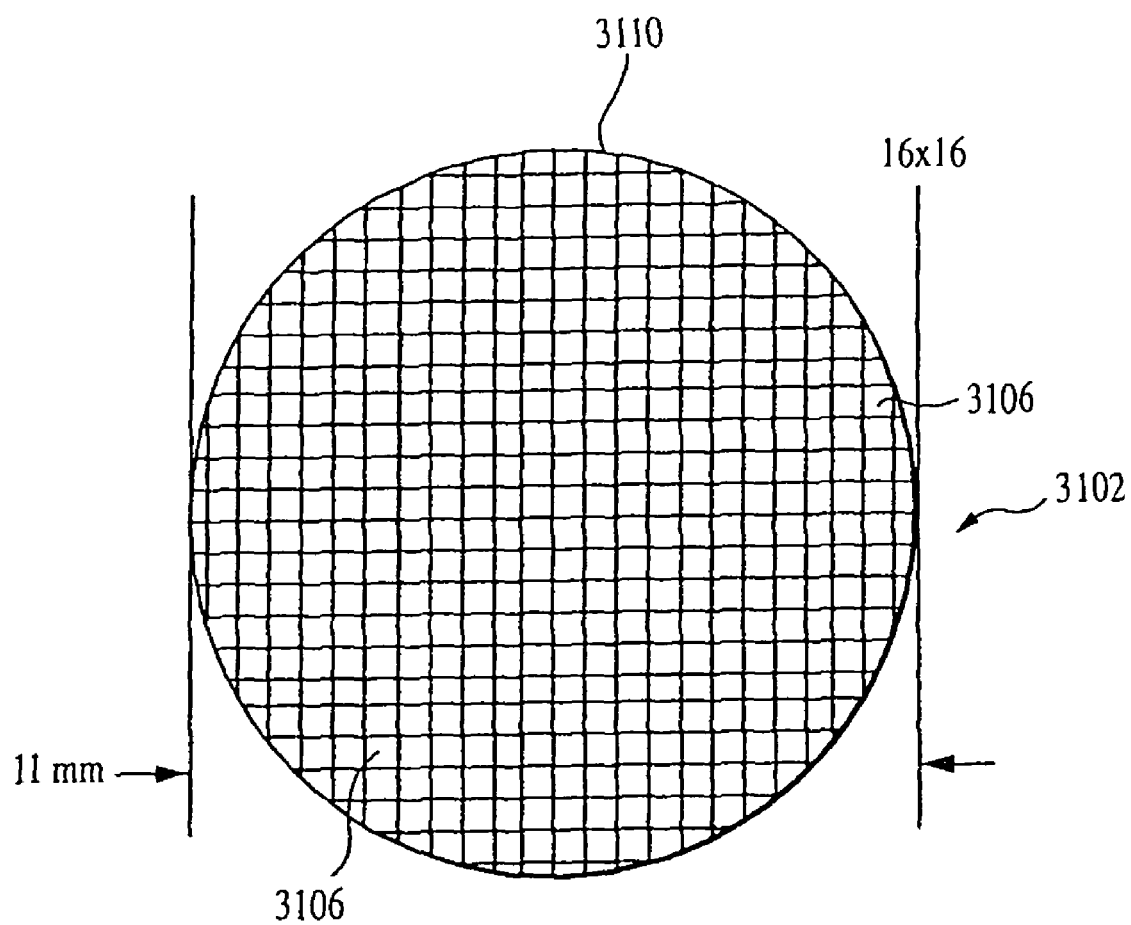
FIG. 31b is a front plan view of the transducer array of the probe of FIG. 31a, illustrating the relationship of the various transducer elements therein.

Referring now to FIGS. 31*a-g*, another embodiment of the autonomous smart probe of the present invention is disclosed. In this embodiment, the probe 3100 is adapted to obtain acoustic images and/or echo-location information via an installed acoustic narrowband phased transducer array. The smart probe 3100 includes a piezoelectric (e.g., "ceramic") transducer array 3102 disposed on the front end 3105 of the probe which is adapted to transmit and receive ultrasonic acoustic waves. The transducer array 3102 comprises a plurality of rows (m) and columns (n) to form an m×n array of ceramic elements 3106. The array 3102 of the present embodiment comprises a 16×16 array which, when overlayed onto the circular form factor, produces about 200 distinct transducer elements 3106 (FIG. 31*b*). The unique beamforming and electrical interconnection arrangement of the array permits simultaneous beamforming in two dimensions from a single aperture, as is described in detail in U.S. Pat. No. 5,808,967 entitled "Two-dimensional array transducer and beamformer" issued Sep. 15, 1998, and incorporated herein by reference in its entirety.

The array 3102 is generally cylindrical in shape (i.e., circular frontal cross-section) so as to facilitate travel through the intestinal tract of the subject, although other shapes (and numbers of transducer elements 3106) may be used. The array 3102 is further disposed at the front of the probe 3100 and mounted conformably therewith, such that the outer edge 3110 of the array conforms substantially with the housing 3104 of the probe in that region. This arrangement allows for the largest array diameter to be used with the probe, thereby increasing the number of elements 3106 in the array, the allowable aperture, and the spatial (and temporal) resolution thereof. The array dimensions are approximately 11 mm in diameter by 8 mm depth. The probe is fabricated using the multi-stage "slicing" methodology disclosed in U.S. Pat. No. 5,808,967, which has been adapted to the small dimensions involved by, inter alia, using a narrow aperture laser beam for cutting the ceramic "blanks". Alternatively, en extremely fine micro-edge saw blade of the type known in the microelectronic fabrication arts may be substituted. The use of such laser (or micro-edge saw) allows for extremely fine cuts (i.e., spacing) between the transducer elements 3106, typically on the order of 0.001-0.002 inch (roughly 0.02-0.04 mm).

Figure 31C:
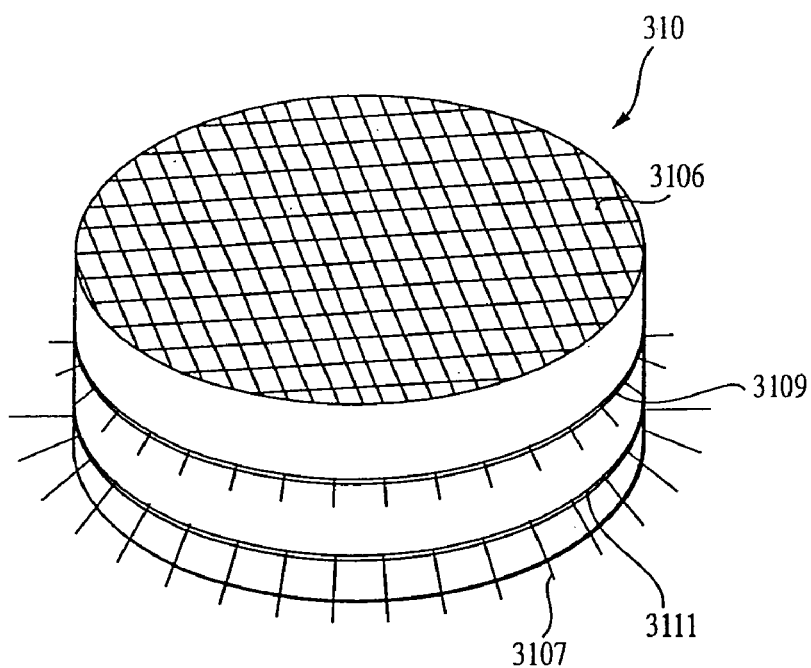
FIG. 31c is a side perspective view of the 2-D transducer array of FIGS. 31a-31b, illustrating the construction thereof.

The electrical leads of the X-axis flexible printed circuits (XFPC) 3109 and Y-axis FPCs (YFPC) 3111, which ultimately provide electrical connection to the various elements 3106 in the array 3102, are disposed such that the free ends of their electrical leads 3107 are disposed in essentially radial fashion around the periphery of the array 3102, as shown in FIG. 31*c*. The FPCs are fabricated from a suitable polymer (e.g., polyimide, aka Kapton®) using lithography techniques well known in the semiconductor and circuit fabrication arts, thereby allowing a very fine array of electrical leads which are adapted to connect signals to each of their respective elements 3106. The leads are, in one embodiment, conductively bonded (such as by direct frictional contact, solder, or other means) to corresponding ones of longitudinally-oriented graphite carbon fibers disposed within the polymer matrix of a "structural electronics" probe housing of the type previously described, into which the phased array 3102 is fitted. In another embodiment (not shown), the free ends of the FPC elements are conductively bonded to respective ones of (parallel) electrical traces formed on the inside surfaces of the front portion of the probe housing proximate to the array 3102. The traces are then routed to rear portions of the probe for electrical contact with the appropriate distal leads of the PCBAs previously described, or alternatively directly to the leads of the integrated or discrete electronic components in the probe housing. In yet another variant, conventional fine-wire (i.e., 38 AWG or smaller) conductors such as those manufactured by the Industrifill Corporation, are embedded in the thickness of the housing during molding or other formation process, the latter forming electrical insulation between the conductors, which are terminated to respective ones of the array electrical leads. It will be appreciated that yet other arrangements may be used as well.

The operating center frequency of the array and system is 500 kHz (narrowband), although other frequencies may be used. Based on a fluidic velocity of propagation of roughly 4300 fps, the wavelength of the resulting 500 kHz transmission is approximately 2.6 mm. In air (assuming the intestine to be evacuated), the propagation velocity is substantially reduced (about 1100 fps), and the wavelength afforded by the 500 kHz signal on the order of 0.7 mm. Hence, the ultrasonic apparatus of the invention may be adapted to operated in either fluidic or gaseous environments within the intestine, although due to evacuation procedures, it is anticipated that the gaseous (air) environment will predominate. Accordingly, acoustic transmission through air is used as the basis for the construction of the present embodiment.

Figure 31D:
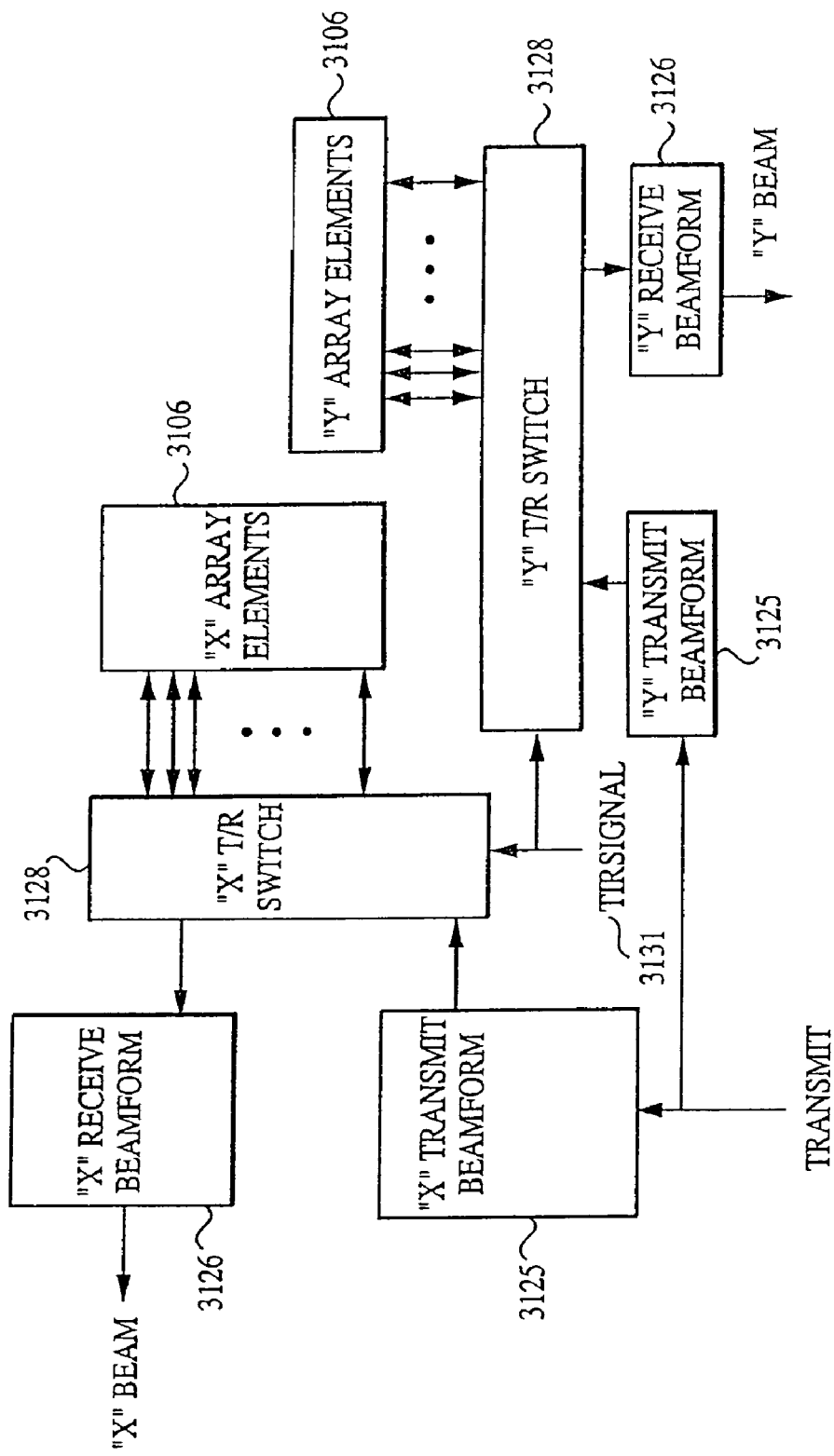

A block diagram of the preferred embodiment of the two-dimensional transducer array is shown in FIG. 31*d*. The individual Array elements 3106 are electrically interconnected along front-side columns and back-side rows. Array elements 3106 are interconnected to the associated beamformer 3125, 3126 through 2-axis transmit/receive (T/R) switches 3128. The transmit and receive 3125, 3126 beamformers may be either phase or time-delay beamforming networks of the type well known in the art.

The face width of each element is approximately one wavelength ($\lambda$), where $\lambda$ is the acoustic wavelength in air (0.67 mm) of the desired center frequency of 500 kHz. It will be recognized, however, that a larger or smaller number of transducer elements may be used (such as a 32×32 array at 0.5$\lambda$ yielding roughly 800 elements in circular form factor), consistent with the extant technology for fabricating the array. Note that to form beams with 4 degree beam width dispersion, an array diameter of approximately 16 wavelengths is required, consisting of a 16×16 element array of approximately 200 elements. The back side rows 3122 and front side columns 3120 of the array elements are electrically connected together along parallel lines of elements with thin acoustically transparent material, as shown in FIG. 31*c*. It will be recognized that while the rows and columns of the present embodiment are orthogonal, such need not be the case.

Each of the array X axis rows 3122 and Y axis columns 3120 are connected to a T/R switch 3128 which, as controlled by a T/R logic signal 3131, electrically connects the sets of X and Y lines to respective X and Y receive beamformers 3126 in the receive mode, and to X and Y transmit beamformers 3125 in the transmit mode. When receiving, the array lines are connected through the T/R switch to receive beamformers 3126 which receive the electrical signals from the transducer lines while providing a low electrical impedance path (relative to the electrical impedance of the line of transducer elements) to signal ground on each X and Y line. When transmitting, the array lines are connected through the T/R switch 3128 to the transmit beamformers. The transmit beamformers provide the electrical transmit drive signals from a low impedance electrical source (relative to the electrical impedance of the line of transducer elements 3106). This low electrical source/load impedance on each Y and Y line (i.e., low source impedance during transmit mode and low load impedance during receive mode) allows both simultaneous and independent access to each X row 106 and Y column 104 for the application of transmit electrical drive signals and the receipt of signals from each X row 3122 and Y column 3120.

Furthermore, the arrangement of the present invention allows parallel sets of X and Y axis line arrays can be simultaneously and independently formed. X-axis transmit and receive line arrays are formed by the parallel electrical connection along the back side rows, along with the low impedance signal ground on all of the front side Y-axis columns 3120.

During signal receipt, the electrical signal present on each X-axis row 3120 (with the front side low impedance path to signal ground) represents the sum of the received electrical signals of all elements in each row. Most conventional ultrasonic/acoustic receiver amplifiers provide a high impedance load to the receiving transducer. However, for the 2-dimensional array application of the present invention, an amplifier has been developed for use in the receiving beamformer which provides a low impedance load while receiving. This is accomplished by connecting each of the X and Y-axis lines to a virtual ground node (a point having the same potential level as ground but not directly connected to ground) on the receiving preamplifier within the receive beamformers. The signal current flowing into each virtual ground node is the sum of the signal currents from all the ceramic elements in the column or row. When receiving signals from a column, the column signal is independent of the row signals being simultaneously received due to the low impedance load presented by the virtual ground on all rows. Similarly, when receiving signals from row, because of the low impedance load presented by the virtual ground on all columns, this row signal is independent of the column signals being simultaneously received.

During receive operation, electrical signals received on the X rows are phase or time delayed and combined in the X row receiver beamformer to produce inclined receive acoustic beams in the Y direction. Simultaneously and independently, signals received on the Y columns and combined in the Y side beamformer produce inclined receive acoustic beams in the X direction. Thus, through superposition of the X and Y axis electrical and acoustic signals, 2-dimensional acoustic beam formation from a single planar array in both transmit and receive modes is achieved.

During signal transmission, transmit drive signals are applied through the T/R switch to the parallel X-axis back side electrical interconnection lines from a transmit amplifier which has a low output impedance relative to signal ground. While the X-axis drive signals are being applied to individual X-axis line arrays, the entire Y-axis 16 parallel line array face is maintained as a low impedance path to signal ground (via the signal path through the Y-axis T/R switch 3128*a* to the low impedance Y-axis drivers of the Y beamformer) to ensure that the X-axis drive signal is imposed solely across the X-axis rows, and does not couple to the Y-axis side of the array. Similarly, while the Y-axis drive signals are being applied to Y-axis line arrays, the entire X-axis array face is maintained as a low impedance path to signal ground to allow signals to be independently applied the Y-axis without coupling to the X-axis.

During signal transmission, phase or time-delayed signals applied to the X rows form inclined acoustic transmit beams in the Y direction (YZ plane). Simultaneously and independently, phase or time-delayed signals applied to the Y columns to produce inclined acoustic transmit beams in the X direction (XZ plane).

Thus, the low impedance associated with the transmit beamformer sources permits X- and Y-axis line transmit arrays to be formed simultaneously and independently by superposition of both X and Y axis transmit drive signals.

The foregoing independent and simultaneous X row and Y column electrical access during both transmit and receive modes via the X and Y signal lines allows the array to be used as a 2-dimensional array to simultaneously and independently form multiple inclined acoustic beam set in both the X-Z and Y-Z planes. The beamforming operation in each plane is the same as conventional 1-dimensional phased and/or time-delay arrays. Thus, the 2-dimensional beamforming operation is in general the equivalent of two overlaid 1-dimensional arrays, with one array rotated 90 degrees from the other Receive operation of the frontside (Y) columns with the backside rows 3122 all coupled to signal ground in the X-axis receive beamformer will first be considered. Each set of four X-axis electrical signals (in the 16×16 array) are connected to virtual ground nodes in the receiver preamplifier of the receive beamformer to form a signal reference for the backside rows, and phase shifted between adjacent line-arrays. The imposed phase shifts compensate for those arising from the different inter-element path lengths of the narrowband acoustic pulse incident on the line arrays. The resulting signals will be in phase and, when summed, will form a maximum acoustic interference pattern when receiving a wavefront arriving at a prescribed incidence angle. This maximum corresponds to the central axis of one of the main lobes of the formed beams. A second receive beam can be formed for incoming sound ray wavefronts traveling in the −X direction and at an angle $\Phi$ with the Z direction (at the predetermined incidence angle) by reversing the sign of the imposed phase shift on the four signals and summing the signals. Since the set of four signal phases repeats for additional sets of line-arrays, larger arrays can be implemented by summing the signals from all sets of line-arrays to further enhance the interference patterns at the predetermined incidence. When additional sets of line-array segments are utilized as described, the acoustic signal gain along the predetermined incidence angle directions is increased, or correspondingly, the beamwidth in that direction is reduced, as additional sets of arrays are added.

An equivalent beamforming method is to first sum all of the equal phase signals from different array sets, then apply the imposed phase shifts between the summed set of signals.

During the transmit mode, operation of the 2-axis array is similar to the above described receive mode except the flow of signals is reversed. A long tone burst carrier frequency is applied to a phase shift transmit beamformer, generating drive signals with different relative phases. These are applied to the parallel wired sets of Y columns from low impedance drivers. The imposed phase shifts will compensate for those arising from the different path lengths between line arrays, and a transmitted acoustic signal interference pattern at a predetermined incidence angle will be formed, corresponding to the center of one of the main beam lobes. Another transmitted beam can be formed at the negative of the predetermined incidence angle (relative to the Z vector). incidence angle by reversing the sign of the imposed phase shift as previously described.

Receive and transmit operation in the Y-axis is the same. When considering signals applied and received from the backside rows, the frontside columns are coupled through a low impedance to signal ground. The presence of the low transmit drive and receiver load impedance to ground on each side results in fully independent X and Y axis operation. From superposition of the X and Y axis signals, it can also be seen that both axes (i.e., rows and columns) can be in operation simultaneously.

The above described 2-axis beamforming technique using fixed phase delays in forming narrow transmit and receive beams and is referred to as a "two-dimensional phased array" transducer. It is suitable for use in narrowband applications which transmit a single frequency (narrowband) long tone burst.

Figure 31E:
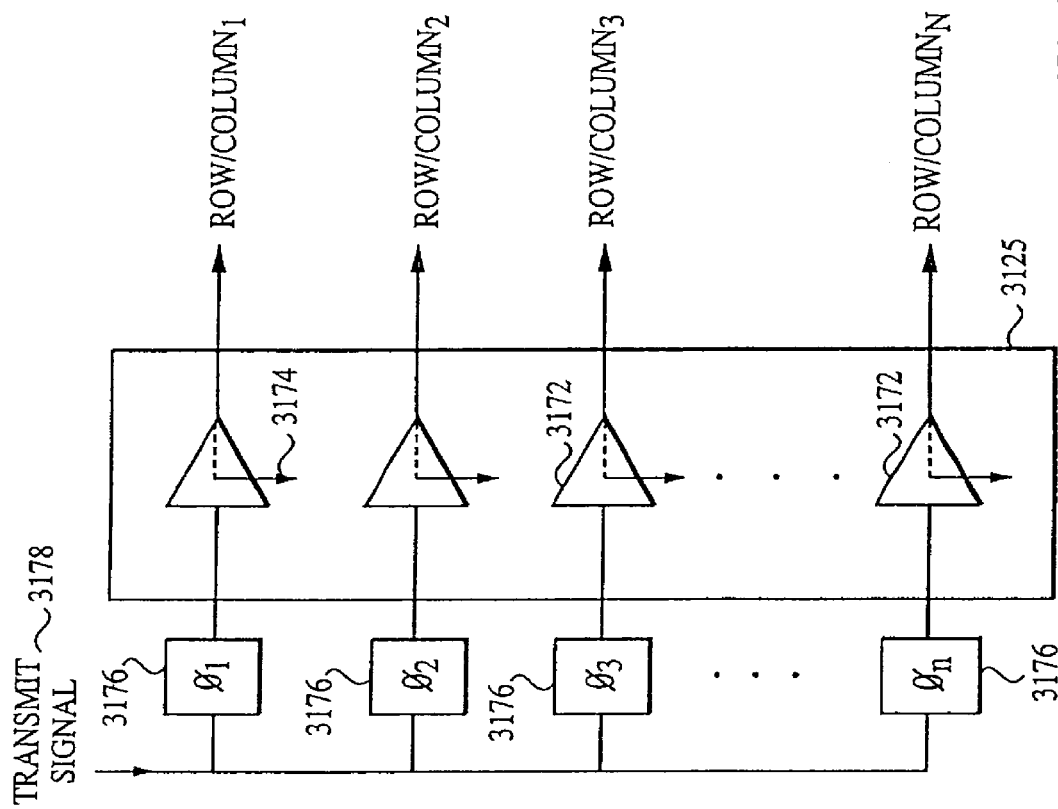
FIG. 31e is a partial schematic of an exemplary transmit/receive beamformer device of the circuit of FIG. 31d.
Figure 31F:
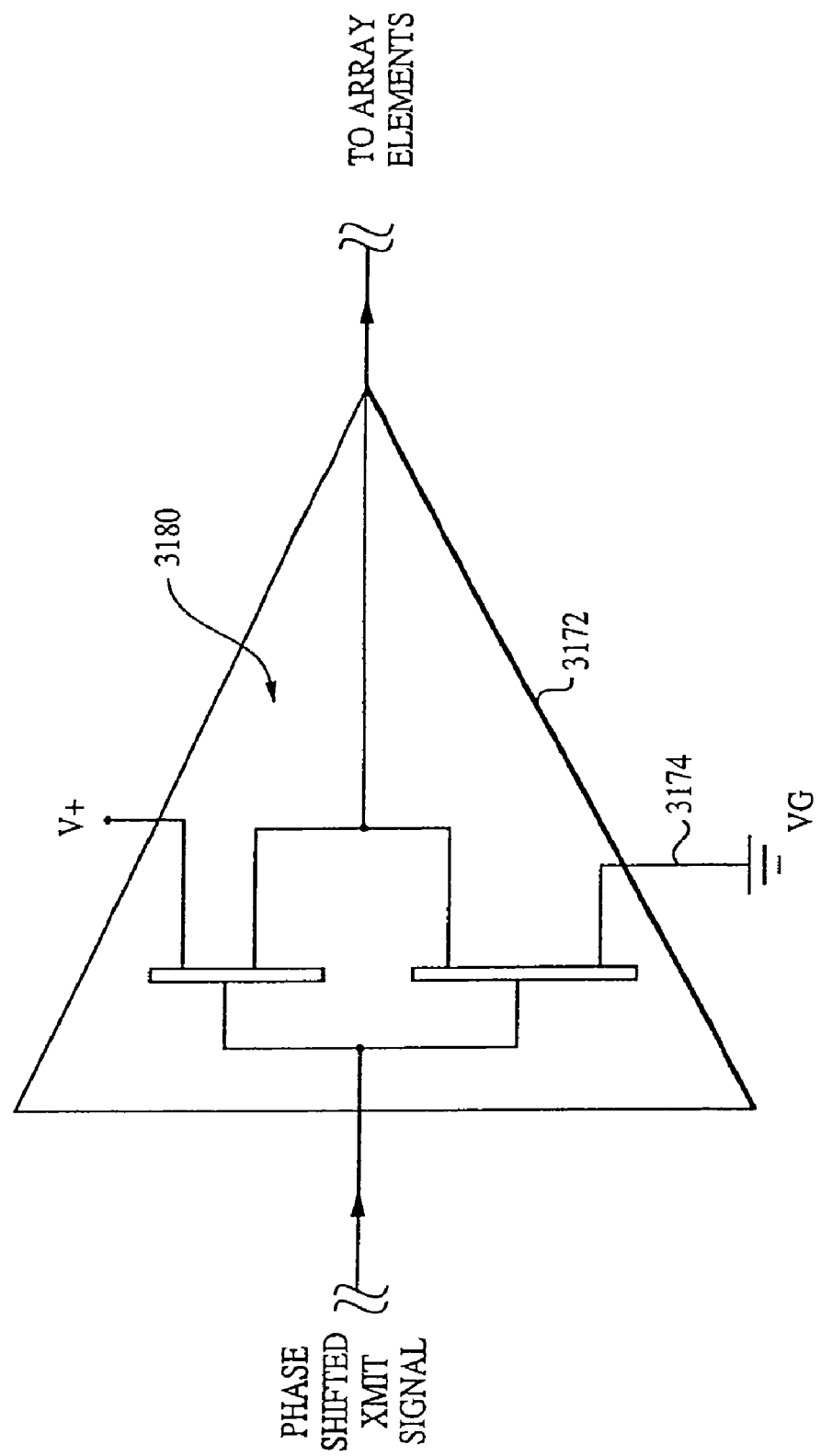
FIG. 31f is a schematic of one exemplary embodiment of the amplifier assembly of the beamformer circuit of FIG. 31e.
Figure 31G:
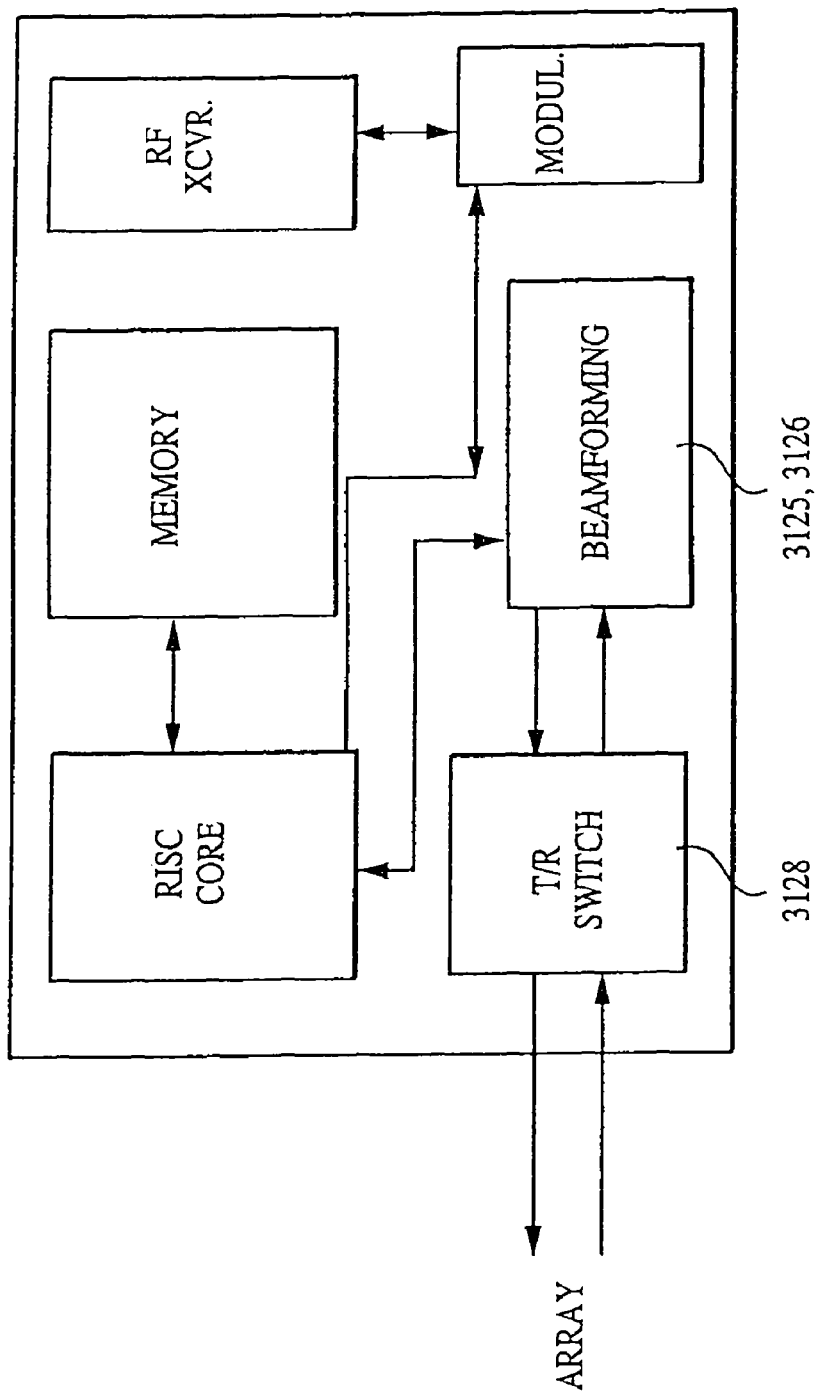
FIG. 31g is a functional block diagram illustrating the relationship of the electronic components of the probe of FIG. 31a, including processor core, memory, T/R switch, and RF transceiver/modulator.

One embodiment of the time-delay receive mode beamformer circuitry used in conjunction with the array 3102 of the present embodiment is described in greater detail in U.S. Pat. No. 5,808,967, previously incorporated herein. Such circuitry is also well known to those of ordinary skill in the acoustic hardware and signal processing arts, and hence other variants may be used consistent with the invention to provide equivalent results. As illustrated in FIG. 31*e*, the circuitry 3170 generally comprises the respective transmit/receive beamformer 3125, 3126 (transmit "Y" beamformer shown), which comprises a plurality of signal amplifiers 3172 and associated virtual grounds 3174, each amplifier 3172 supplying a signal to a respective row of transducer elements 3106 (e.g., "Y" axis elements). The amplifiers of the present embodiment are constructed using a push-pull field-effect transistor stage 3180, as shown in FIG. 31*f*, although other arrangements may be used. Respective phase shifters 3176 of the type well known in the electronic arts are disposed on the input of each amplifier which temporally (phase) shift the transmit signal 3178 for successive array rows/columns of array elements 3106 as previously described in order to form angularly disposed beams relative to the array face. Similarly, in the "X" dimension, the application of similar signals to the columns/rows on the opposite face of the transducer elements induces beam formation with respect to the X dimension of the array, such signals advantageously being applied simultaneously with the "Y" axis signals as previously described.

It is noted that due to the extreme space limitations of the probe of the present invention, two primary hardware environment approaches are used to implement the ultrasonic functionality described above: (i) the use of a highly integrated, "SoC" device with macro function blocks adapted for ultrasonic signal processing/beamforming (FIG. 31*g*); and/or (ii) substantial "off-probe" beamforming processing and signal processing of acquired ultrasonic data.

As is well known, significant signal processing capability is found within the conventional fixed point or floating point DSP or RISC processor. In order to economize on space within the probe otherwise consumed by comparatively bulky DSP packages, one embodiment of the invention incorporates an extensible RISC processor core as described with respect to FIG. 16 herein which has an instruction set and configuration optimized for beamforming and signal processing calculations (e.g., FFT) associated with ultrasonic devices such as those of FIGS. 31*a-g*. In this fashion, the processor core is made with reduced gate count, and accordingly the ASIC in which the core is disposed has reduced size and power requirements.

Alternatively, much of the signal processing associated with the ultrasonic system may be transmitted off-probe, either real time or in delayed fashion (such as, for example, through a data buffering system which allows for transmission across communications links having reduced bandwidth compared to the ultrasonic data being generated, or through storage of information in memory for download after excretion of the probe, as previously described). Real-time transmission may be accomplished, for example, via the inductive data transfer circuit previously described herein, or via the "Bluetooth" RF transceiver-equipped ASIC of FIG. 16. Accordingly, in one embodiment, after the "raw" unprocessed acoustic echo data is received by the probe transducer array 3102, it is buffered (for example in a RAM buffer memory as previously described) and subsequently transmitted over the wireless data interface to the MCD 804 or other remote device adapted to receive the data. A digital signal processor (DSP) resident in the remote device, along with attendant memory, software, and display devices well known in the electronic arts, subsequently perform the beamforming computations previously described, and further process the data to generate a video image (and/or audio representation) of the echoes received by the transducer array. The remote device, via reverse link communications to the probe, can also advantageously be used to "steer" the beams of the phased array to obtain imaging of particular solid angles within the field of ensonification of the array at that given time. Steering of the beams is accomplished based on the relative timing of drive signals applied to various transducer elements 3106 of the array 3102, as previously described.

Yet other configurations are possible, however. For example, the field-effect transistor(s) (FET) used in the beamformer and amplifier circuitry. 3172 previously referenced herein may be embodied in the "structural electronics" housing of FIG. 28, thereby obviating the use of either a discrete PCBA-mounted or integrated FET device.

It will also be recognized that while the present embodiment incorporates a unitary phased array transducer and associated beamforming and processing adapted to generate ultrasound images, other less sophisticated approaches may be used to accomplish less demanding objectives. For example, in order to accomplish simple ultrasonic echo-ranging within the intestine (such as to determine the range from the probe to an intestinal obstruction or artifact), a single non-phased transducer element could be used to radiate pulsed ultrasonic waves of the desired frequency and receive echoes resulting therefrom, the interval between transmission and echo return being correlated to the range of the obstruction/artifact based on wave propagation speed. Alternatively, such transducer could be used to generate ultrasonic waves and receive echoes which are processed for Doppler shift induced by movement of the intestine wall and/or probe (the latter due, for example, to the peristaltic action of the intestine).

Antigen Detection

Figure 32:
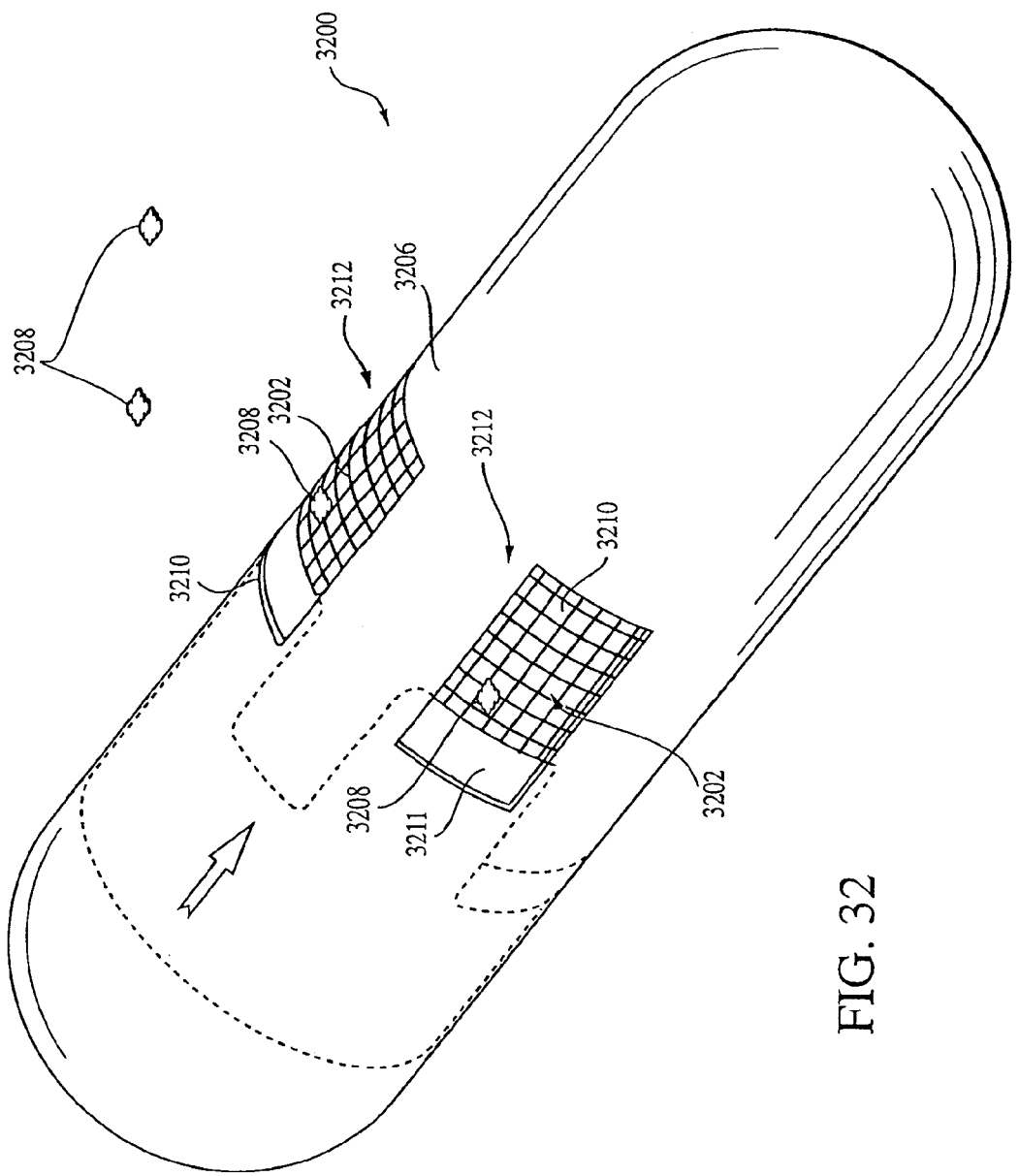
FIG. 32 is a perspective view of one exemplary embodiment of the smart probe of the invention having detection arrays adapted to detect the presence of one or more molecular species.

Referring now to FIG. 32, an improved apparatus and method for detecting the presence of certain substances or antigens is disclosed. As used herein, the term antigen generally refers to any substance or entity which promotes a response in vivo, and more specifically to substances (such as proteins, polysaccharides, or lipoids) which induce, whether directly or indirectly, the production of one or more antibodies or proteins as a response to the antigen.

In the embodiment of FIG. 32, the apparatus comprises an autonomous probe 3200 having one or more sensing arrays 3202 disposed at or near the surface 3206 of the probe (accessible to the intestinal epithelium and fluids present in the intestine). The sensing arrays 3202 are exposed to the tissue of the intestine wall during travel of the probe 3200, allowing each sensing array to detect the presence of antigen(s) 3208. In the variant of FIG. 32, the sensor arrays 3202 comprise a plurality of molecular receptor sites 3210 which are bonded to an organic or other suitable substrate adapted to retain a plurality of receptor molecules attached thereto. The attachment of receptor molecules to various substances is readily accomplished using any number of available methods known to those of ordinary skill, and accordingly is not described further herein. The receptor molecules 3210 are specially configured to receive only one target molecule (or class of molecules) corresponding to the desired antigen 3208. For example, Tumor necrosis factors (TNF) alpha and beta are examples of cytokines which act through TNF receptors to regulate numerous biological processes in the human body, including protection against infection and induction of inflammatory disease. The TNF molecules belong to the TNF-ligand family, and act together with their complementary receptors, the TNF-receptor family. Such TNF ligands include TNF-a, lymphotoxin-a (LT-a, also known as TNF-b), LT-b, FasL, CD40L, CD27L, CD30L, 4-1BBL, OX40L and nerve growth factor (NGF). TNF receptors includes the p55TNF receptor, p75TNF receptor, TNF receptor-related protein, FAS antigen or APO-1, CD40, CD27, CD30, 4-IBB, OX40, NGF-receptor, and low affinity p75. It will be readily appreciated, however, that myriad ligand/receptor families may be used with equal success consistent with the present invention.

Figure 32A:
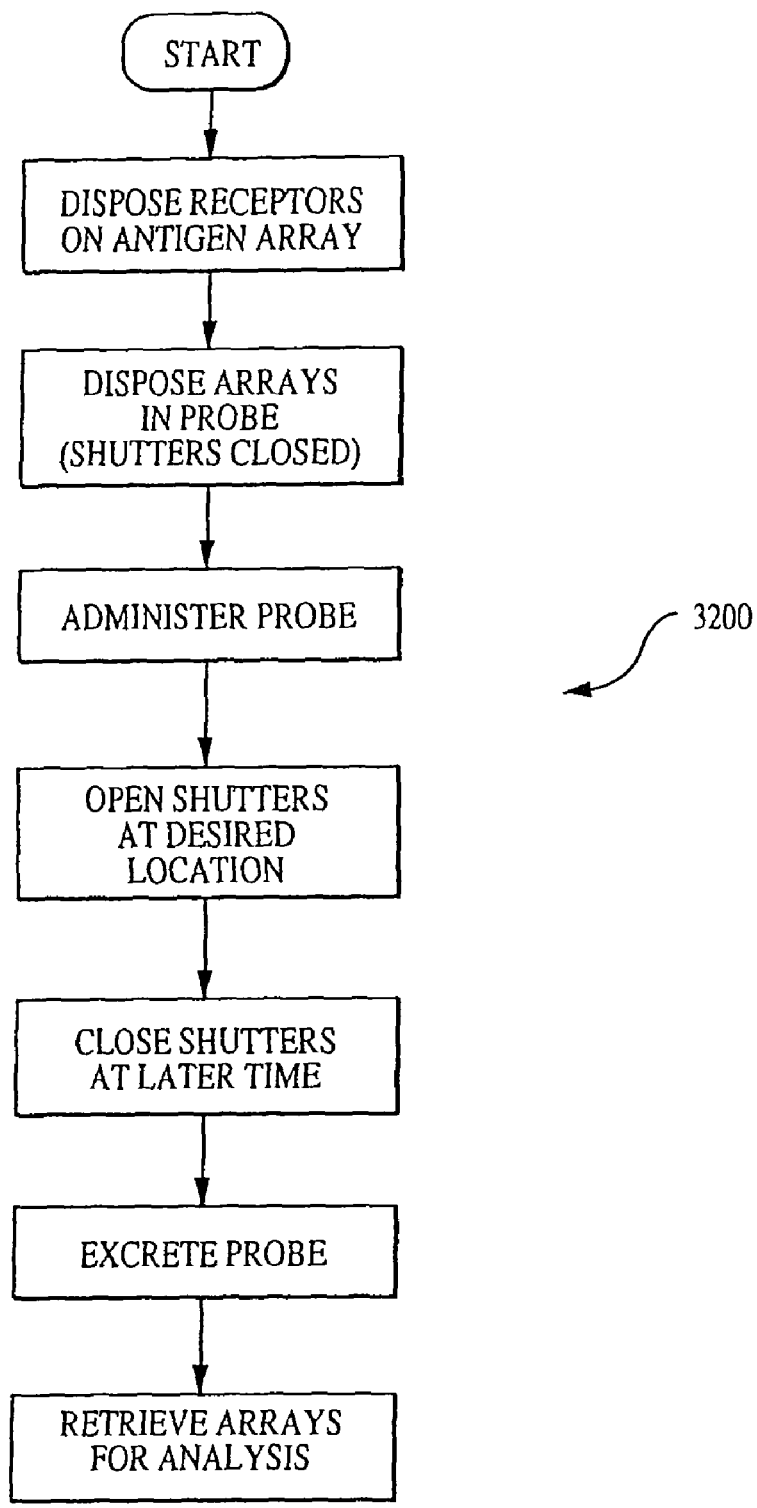
FIG. 32a is logical flow diagram illustrating one exemplary embodiment of the method of detecting molecular compound(s) utilizing the probe of FIG. 32.

The sensing arrays 3202 of the probe 3200 may selectively uncovered via a series of apertures 3212 using a shutter arrangement 3211 such as that described previously herein with generally respect to FIG. 18. Hence, the arrays 3202 are shielded or covered from direct exposure to the intestinal tract (including any gastric substances) until the shutters 3211 are opened. The shutter apertures are also optionally covered with a readily dissolvable non-toxic compound (such as the aforementioned "gel cap" material) which acts as a sealant for the apertures before shutter opening. Target molecules present in the intestinal wall or associated fluids (if any) are received at the receptor sites and captured on the arrays 3202 while the shutters 3211 are open. Subsequently, the shutters 3211 are shut via on-probe or externally generated signal (as previously described) so as to avoid further contamination of the arrays during the remaining length of the intestine, and the probe ultimately excreted from the subject's intestine. The probe 3200 is then retrieved and analyzed using well known laboratory techniques to determine the presence of the target molecules on the array(s). FIG. 32a graphically illustrates the foregoing methodology.

Liquid (such as water for example) may also be introduced if necessary either orally, or via the probe 3200 itself using apparatus such as previously described herein with respect to ligand or radionuclide delivery, at an appropriate time with respect to probe travel in the intestine so as to further facilitate mobility of the target molecules within the intestine and array(s).

In another embodiment, electrical conductivity (or alternatively resistivity) is measured across a membrane or other device disposed on an array proximate to the outer housing of the probe and such that it is exposed to the intestinal wall/fluids; the presence of target molecules (analytes) is reflected in changes in the conductivity due to, inter alia, ion diffusion. See U.S. Pat. No. 5,874,316 entitled "Receptor membranes and ionophore gating" issued Feb. 23, 1999, incorporated herein by reference in its entirety, which details a membrane, the conductivity of which is dependent on the presence or absence of an analyte. The membrane of the '316 patent comprises a closely packed array of self-assembling amphiphilic molecules and multiple ionophore components. A receptor molecule reactive with the analyte is provided on one of the ionophore components. The binding of the analyte to the receptor molecule causes a change in the relationship between the ionophore components such that the flow of ion across the membrane is prevented or allowed. One or more such membrane-based devices are used in this embodiment of the probe as detection arrays. Change in conductivity is readily measured across the membrane by monitoring the passage of electrical current through the membrane using, for example, any well known conductivity cell arrangement (e.g., Wheatstone bridge) which may be included within the probe, the electrical power supplied by the on-probe or off-probe power sources previously described.

In yet another embodiment, the detection of the target molecules is performed using a bio-electronic sensor comprising a thin, electrically conductive surfactant polymeric layer to which members (e.g., receptors) of specific binding pairs are bound. Specific binding of target molecules (or "competitor" molecules) to the bound specific binding pair receptor results in a change in the conductivity of the polymer. The resultant change in conductivity is related to the presence of the target molecule in the sample. See U.S. Pat. No. 5,491,097 entitled "Analyte detection with multilayered bioelectronic conductivity sensors" issued Feb. 13, 1996, also incorporated herein by reference in its entirety.

As yet another alternative, a plurality of "bridges" of receptor molecules disposed between pairs of inorganic conductive terminals 3301 are used to identify the presence of target molecules, as illustrated in FIG. 33. The receptor molecules 3330 are bound to the terminals 3301 using a thin conductive surfactant polymer layer such as previously described, or alternatively via direct bonding of the receptor complex to the inorganic metal atoms of the terminals as recently demonstrated at University of Texas at Dallas. When the bridge 3302 is completed via the reception of the target molecule(s) 3302 between the two receptor molecules 3330, the electrical conductivity increases (or conversely, the resistance decreases) due to outer shell electron transfer across the target molecule(s) and receptor(s). The conductivity increase (or resistance decrease) is detected by conductivity circuitry 3306 within the probe, which comprises a potential source 3307 applied across the terminals, current sensing circuit 3308 of the type well known in the electronic arts, and analog-to-digital converter (ADC) 3310, the latter both optimally disposed within the "front end" of the customized ASIC of FIG. 16. The ADC 3310 converts the analog voltage values generated by the current sensing circuit 3308 to binary digital format for subsequent processing by other components in the ASIC (e.g., processor core and associated embedded conductivity analysis algorithms). In the illustrated embodiment, a plurality of parallel bridge circuits 3321 are provided, and coincidence logic 3320 is used to help avoid detection of "false positives" due to any number of sources including inadvertent reception of non-target molecules on one or more bridges, etc. Specifically, the coincidence logic 3320 comprises a logic gate network 3324 having a two-out-of-three (⅔) coincidence as illustrated in FIG. 33a. The digitized conductivity values output from the ADC circuitry 3210 associated with each conductivity channel 3321 are compared using a comparator function within the ASIC, or alternatively using software algorithms running on the ASIC core, to a predetermined threshold level (or other criterion) to determine whether one or more target molecules have been received by the receptors 3304 for each channel. If the threshold and/or other criteria are met, a logic "high" is output by the comparator/core for that channel. Such information may then be stored in the probe along with a "time-stamp" generated by the processor, and/or streamed off the probe via one of the aforementioned communication channels (RF, etc.) As shown in the logic state table 3335 of FIG. 33a, ⅔ coincidence is effected for these comparator/core output signals. Other coincidence schemes and/or numbers of conductivity channels may also be substituted if desired. Furthermore, the coincidence logic described above may be applied to multiple channels of other types of detectors within the probe, including for example the (i) conductivity detecting membrane of the '316 patent; and/or (ii) bioelectronic sensor with electrically conductive surfactant polymeric layer of the '097 patent, both previously described herein.

In another embodiment, the conductivity values of the parallel bridge channels 3321 are digitized and multiplexed via a multiplexer (MUX) and analyzed by coincidence detection algorithms running on the ASIC core, the latter being adapted to perform such analysis. Many other approaches for utilizing on-probe assets for measuring conductivity are also possible. Furthermore, the "raw" conductivity data may also be transmitted off-probe via one of the aforementioned data communication paths, thereby facilitating analysis of the data off-probe in real time.

Secondary Probe Deployment

Apparatus and methods for utilizing "secondary" special function probes within a living subject are now described. The aforementioned smart probe ("primary" probe) is used to deploy one or more special function secondary probes within the subject's intestinal tract, the special function probes being adapted to perform a variety of therapeutic or analytical functions including, for example irradiation of tissue within the subject's intestine, biopsy, ultrasonic analysis, or timed release of ligands or other pharmaceuticals. The primary probe of the present embodiment advantageously may be used for, inter alia, various support functions including positioning and deployment of the secondary probe, power supply, communications/data streaming functions, thereby relieving the secondary probe of these functions, and allowing the latter to be less complex and/or smaller in profile. As described in greater detail below, the secondary special function probes may further be adapted to maintain a substantially constant location within the intestine of the subject for at least a period of time, thereby facilitating extended operations (e.g., irradiation or ablation) relating to specific tissue locations within the intestine. Other such specialized functions may also be performed using the secondary probes. While the following discussion is cast in terms of a separable secondary probe adapted for extended irradiation of a portion of the intestinal epithelium, it will be recognized that myriad other configurations and functions may be employed consistent with the invention, such functions including, without limitation, (i) positron irradiation in support of PET scanning, (ii) delayed or extended delivery of ligands or other agents, (iii) tissue biopsy, (iv) peristaltic pressure measurements, (v) ultrasonic imaging, (vi) antigen detection, (vii) temperature detection, (viii) magnetic field therapy, and (ix) laser or microwave ablation.

In one exemplary embodiment, the primary smart probe includes a secondary or "trailer" probe of the general type described previously herein with respect to FIG. 25. The secondary probe is selectively separable from the primary probe by the operator, or upon the occurrence of a predetermined condition or set of conditions, as has been previously described with respect to the variety of foregoing embodiments. This severance is accomplished by any number of means, including, as in the present embodiment, electrical energization of the solenoid assembly in the primary probe which causes release of the secondary probe through retraction of a retaining pin (not shown) holding the secondary probe to the umbilical between the primary and secondary probes. Alternatively, the use of other mechanical, chemical, or electrical means may be employed, as will readily be apparent to those of ordinary skill.

The trailer probe of the present embodiment is further equipped to subsequently expand and/or "wedge" itself within the intestine, such that it remains effectively stationary for a period of time while the primary probe continues down the intestinal tract via peristalsis. Probe expansion may be accomplished using the configuration previously described herein with respect to FIG. 25 (i.e., inflation), or alternatively through use of salient structures (e.g., scoops) projecting from the surface of the otherwise un-deformed probe housing.

The therapy agent (such as, for example, a radionuclide source) is disposed within the trailer, thereby allowing the extended application of the therapeutic action to the desired intestinal tissue. Upon command from the operator and/or the occurrence of a predetermined event, the trailer probe alters its shape/configuration (e.g., deflates, or retracts the salient structures), thereby allowing it to subsequently proceed down the intestinal tract via peristalsis. In one variant, the trailer probe comprises a microchip pharmaceutical delivery device of the type previously described herein which has been adapted for controlled release of pharmaceuticals or other agents to a localized region of the intestine for an extended period.

Microwave Ablation

Referring now to FIGS. 34a-34b, yet another embodiment of the multi-probe system 3400 of the invention is disclosed. As is well known in the radiotherapy arts, electromagnetic energy may be used to ablate tissue. Direct ablation (e.g., the application of electromagnetic energy directly to target tissue within the intestine from a source of electromagnetic energy disposed on-probe) has been previously discussed herein. However, in certain applications requiring more significant radiated power or thermal energy than that produced by the on-probe semiconductor laser diode previously described, off-probe sources of such energy are needed. Accordingly, the present invention contemplates the use of an external "pumping" source of microwave energy which interacts with a resonant cavity probe positioned in vivo to ablate tissue. In the illustrated embodiment, the secondary probe 3402 comprises a metallic target structure 3403 optimized to resonate, reflect, and/or absorb electromagnetic radiation (e.g., microwaves or millimeter waves) incident on the target under certain aspects.

As shown in FIG. 34, the resonant cavity 3406 of the target structure 3403 is generally constructed such that its dimensions and physical properties (e.g., material of construction, presence and positioning of dielectrics within the cavity, etc.) act to (i) resonate incident microwave energy having frequency on the order of 30 GHz nominal; or (ii) induce high dielectric losses within the probe, thereby causing significant heating thereof. The selected cavity is a transverse electric 1, 0, 2 mode ($TE_{102}$) cavity with interior dimensions of approximately 10.2 mm×22.8 mm×10.2 mm, with the latter 10.2 mm correlating to the "Z" dimension 3405 of the cavity based on 29.4 GHz nominal, although other dimensions may be used. This symmetry between the Y and Z dimensions of the cavity allows the cavity to perform effectively identically with respect to two axes. Energy is introduced into cavity 3406 via one or more apertures 3407 disposed at the side(s) of the cavity when the probe is properly oriented with respect to the magnetron (described below), and to some degree through direct transmission through the cavity walls. Losses due to Joule heating in the metallic cavity walls, radiant heating of the materials surrounding the cavity structure, energy absorption in high-loss dielectrics positioned within the cavity, or leakage of energy from apertures present in the walls of the cavity, transfer both heat and electromagnetic energy to the tissues surrounding the cavity 3406 and probe 3402 which are to be ablated. Heat energy transfer occurs by, inter alia, conduction between the cavity and the outer housing 3431 of the probe 3402, and emission of infrared radiation thereby. Additionally, leakage of the millimeter wave energy by the cavity (as well as direct incident and reflected millimeter wave energy) induces excitation and heating of surrounding tissue cells and their molecules.

The construction of microwave resonant cavities is well known in the arts. See, for example U.S. Pat. No. 5,712,605 entitled "Microwave resonator" issued Jan. 27, 1998, and U.S. Pat. No. 6,131,386 entitled "Single mode resonant cavity" issued Oct. 17, 2000, both incorporated herein by reference in their entirety, which describes the construction of various types of microwave resonators, the general principles of which are applicable to the resonator cavity 3406 of the present embodiment. As is well known in the art, Q factor is defined as the microwave frequency of the resonator times a ratio of the microwave energy stored in the resonator and the average microwave power loss in the resonator. As is also known, Q factor of traditional metallic cavities can be considerably affected by using dielectric materials properly placed within the cavity. Furthermore, through the use of high-loss dielectrics, the energy absorbed in the dielectrics may be adjusted. The Q factor (and relatedly the ratio of transmitted to reflected power for the cavity) in the present embodiment is selected so as to produce the desired degree of thermal heating of the cavity, as well as ablation of surrounding tissue due to reflected microwave energy. For example, in one embodiment, a fairly low Q factor resonator is used in conjunction with the aforementioned dielectric materials to induce minimal energy storage within the resonator under certain spatial orientations of the probe and incident microwave energy.

It will be readily appreciated that the physical dimensions and configuration of the cavity 3406 of the invention may be varied significantly in order to achieve the desired objectives. Accordingly, one embodiment of the invention utilizes a substantially rectangular structure (e.g., parallelpiped) for the cavity 3406 as previously described. For resonance in the rectangular (Cartesian) cavity, the following relationship must be satisfied: (18-129 of Reitz)

Where:
C=propagation speed
ω=angular frequency
$E_x$=Electric field vector component in x direction
The resonant frequencies of such cavity are given by:

$$k_x^2+k_y^2+k_z^2-\omega^2/c^2=0$$

Where $k_{x,y,z}$=magnitude of wave vector in x,y,z directions Other configurations may also be used. For example, in a second embodiment, a right circular resonant cavity is used. This configuration has the advantage of conforming substantially well with the outer housing 3431 of the probe 3402, thereby mitigating the creation of complex reflections within the probe structure. For a right circular resonant cavity, Bessel functions of the type well known in the mathematical arts are used to determine the physical dimensions configuration satisfying the required boundary conditions.

Furthermore, discontinuities between media of the probe 3402, including the interface of the cavity walls 3420 and the outer housing of the probe 3402 are also considered with respect to the complex dielectric constant (j) for determination of the transmission/reflection ratio of the probe. Accordingly, in yet another of the probe, a cylindrical cavity is utilized with a high-loss dielectric protective coating. In yet another embodiment, the cavity 3406 is filled with a high-loss dielectric fluid in order to affect Q.

The microwave energy incident on the probe 3402 is generated by a conventional magnetron device of the type well known in the electrical arts, and accordingly is not described further herein. However, in order to mitigate collateral ablation or EM radiation dose to healthy or otherwise non-targeted intervening and surrounding tissues, the +/−29.4 GHz microwave beam is collimated and focused using a conventional rectangular cross-section transverse electric 1, 0 mode ($TE_{10}$) waveguide having nominal dimensions of 10.2 mm and 22.8 mm, for a maximum wavelength of approximately 4.6 cm (approx. 6.5 GHz), although other dimensions may be substituted. As is well known, the path attenuation associated with the propagation of the microwave energy is proportional to both the square of the distance between the radiating device and receiver, and the frequency, as well as the character of any interposed media. Hence, the power radiated by the magnetron is selected so as to produce the desired transmitted and reflected power levels from the resonant cavity of the probe 3402 when disposed in vivo within the intestine, without significant dielectric losses in the surrounding tissues which otherwise would result in collateral tissue ablation. The present invention also contemplates the variation of such power level (e.g., through temporal pulsation, such as by generating a microwave pulse train of period t, and/or through control of the field strength applied to the magnetron), as well as the frequency of the radiation emitted by the magnetron, thereby allowing the user to "tune" the degree of resonance within/reflection by the cavity 3406 and target 3403, and accordingly the ablation energy reflected/radiated from the probe in vivo. The dielectrics (if any) used with the probe are also be selected so as to produce the desired losses within the probe.

The present invention further contemplates the use of a variable geometry resonance cavities in which one dimension (e.g., "Z") is variable with the probe in vivo. As the critical dimension of the cavity 3406 is varied, it's resonance properties (and Q factor) are varied, thereby allowing for fine-tuning of the cavity for the desired transmission/reflection coefficient and ultimately ablation of the surrounding tissue.

It will further be recognized that pulsed or CW electromagnetic radiation (e.g., millimeter waves, IR, or coherent light energy) or even ultrasonic energy may be used consistent with the nanostructures (e.g., fullerenes) and microparticles of the present invention for the enhancement of drug delivery in, inter alia, solid tumors. As previously described, the particles can be attached to molecules (e.g., antibodies) targeted for specific antigens present in tumor vasculature, thereby permitting selective delivery to the walls of the blood vessels of such tumors. See, for example, U.S. Pat. No. 6,165,440 entitled "Radiation and nanoparticles for enhancement of drug delivery in solid tumors" issued Dec. 26, 2000 and incorporated herein by reference in its entirety, which details perforation of tumor blood vessels, microconvection in the interstitium, and perforation of cancer cell membrane, via cavitation induced by the selective application of pulsed electromagnetic energy or ultrasonic waves.

Diagnostic Apparatus and Methods

Figure 35:
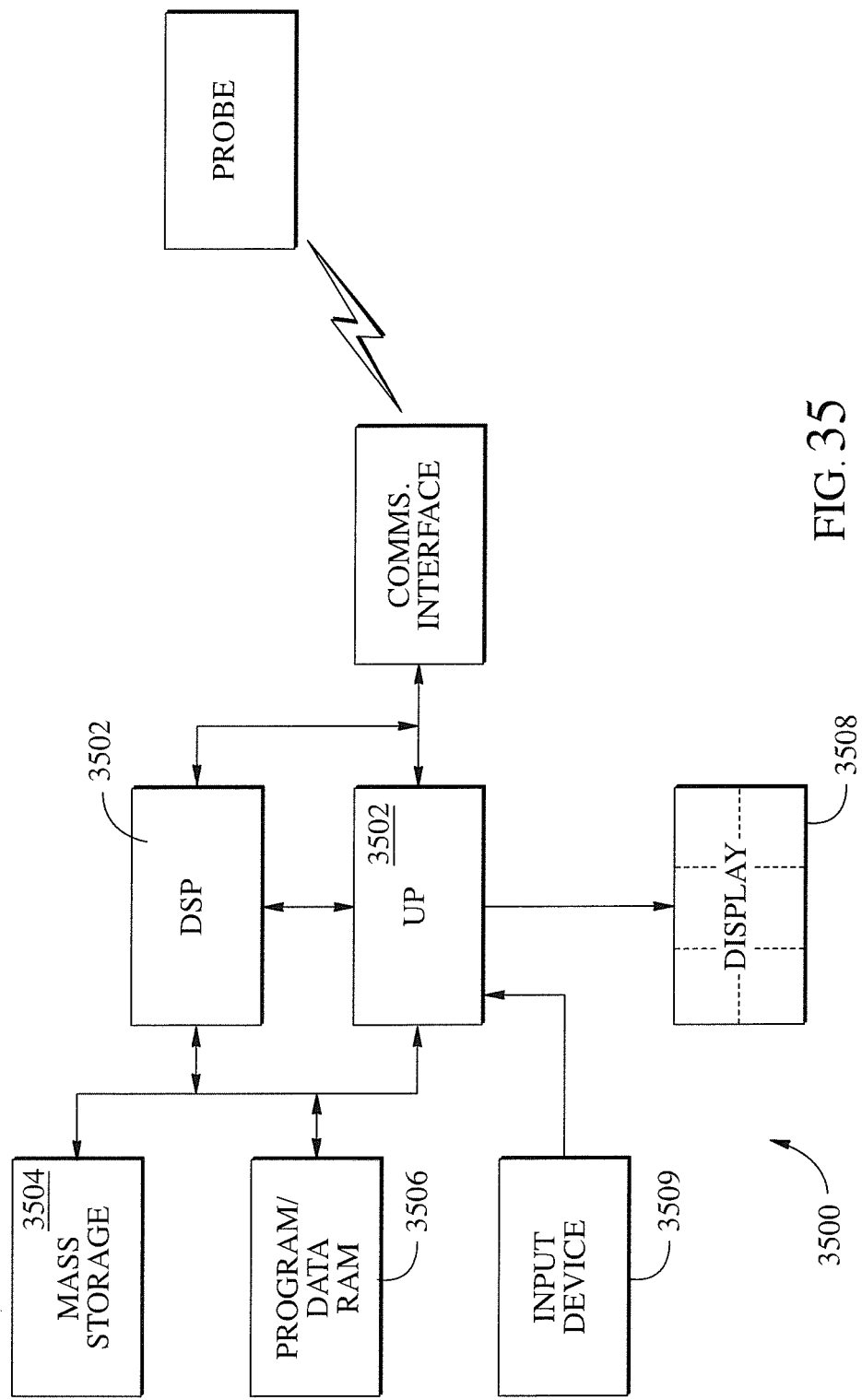
FIG. 35 is functional block diagram illustrating one exemplary embodiment of the data processing apparatus of the present invention.
Figure 36A:
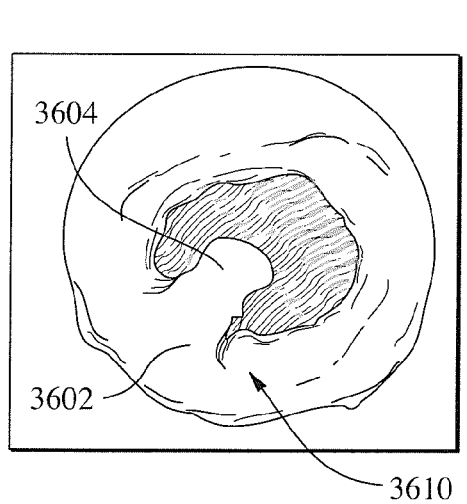
FIG. 36a is a graphical representation of typical endoscopic probe data indicating the presence of an intestinal polyp.
Figure 36B:
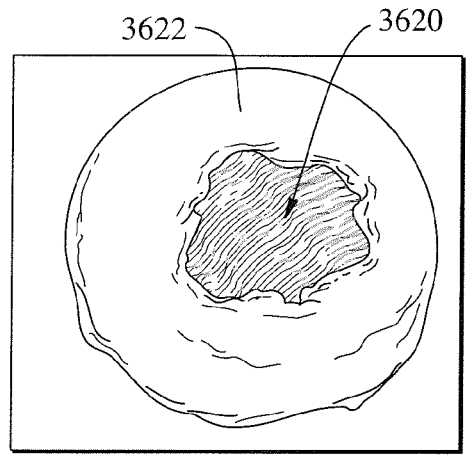
FIG. 36b is a graphical representation of typical endoscopic probe data indicating normal tissue.
Figure 36C:
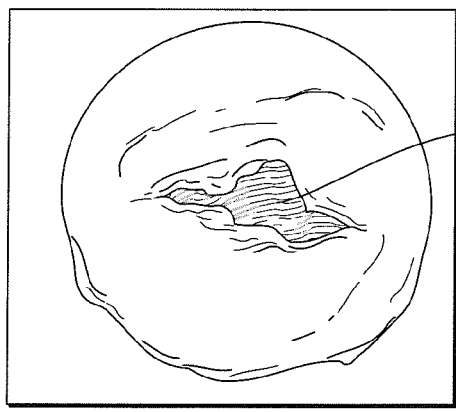
FIG. 36c is a graphical representation of typical endoscopic probe data indicating the presence of a partial occlusion or adhesion.
Figure 37:
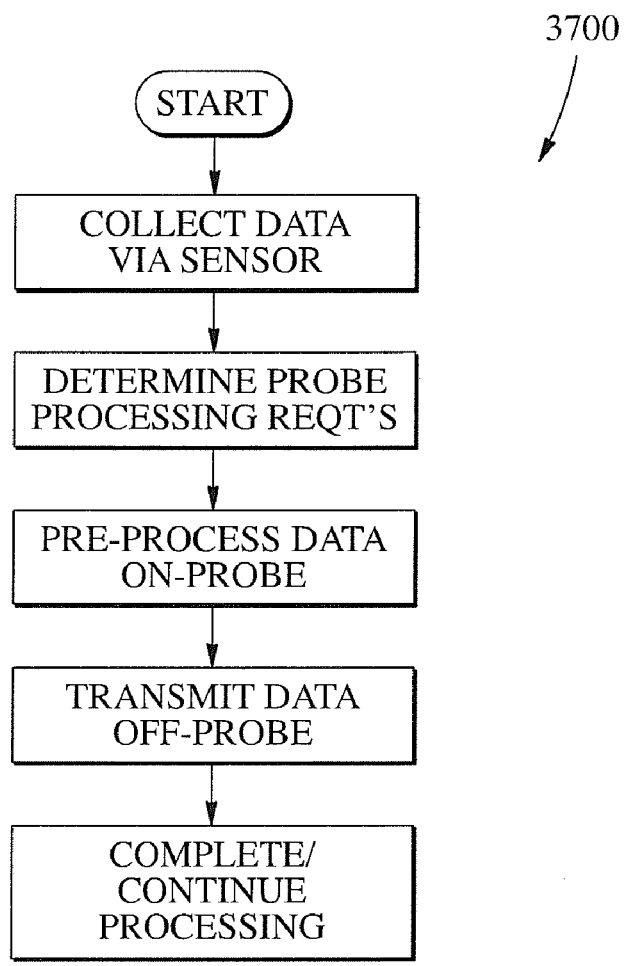
FIG. 37 is a logical flow diagram illustrating one exemplary embodiment of the generalized methodology for on-probe/off-probe data processing according to the invention.

Referring now to FIGS. 35-37, improved apparatus and methods for reviewing data generated by the aforementioned probes and diagnosing the subject based on this data are disclosed.

It will be recognized that the phrase "received from the probe" or similar is meant to include direct or indirect receipt of data from the probe, whether in real time or not, whether directly from the probe or one of its components or via other external or intermediary devices. Hence, such terms are merely expedients for describing any one of a myriad of different data flows from the probe.

Furthermore, as used herein, the terms "snapshot" and "frame" are meant to loosely refer to the concept of a collection of image data corresponding to an image formed by a sensor. For example, where an interlaced display is used, such frame may comprise a plurality of bytes of data, or a data packet of finite length. Hence, these terms are in no way limiting or specific to any particular technology, but rather generally applied to an aggregation of sensor data comprising all or portion of an image with some degree of temporal correlation.

As described below, various aspects of the present invention are embodied in the form of one or more computer programs (including "software" and "algorithms"). Such program(s) may be rendered in virtually any programming language/environment including for example C, C++, Java, Fortran, Basic, Visual Basic, Unix, Perl, CORBA, or any other medium capable of reasonably implementing such a functionality. For example, in one exemplary embodiment, the software comprises a "C" based computer program adapted to run on a conventional stand-alone Pentium-based microcomputer, the microcomputer having a direct link to the screen or display device. However, it will be recognized that other software and/or hardware environments may be utilized consistent with the invention and user's particular needs. For example, the software may comprise an object-oriented distributed program having client and server portions distributed on respective client and server devices, thereby facilitating transmission of data from one location to another, or alternatively analysis at one location, and viewing at another after transmission thereto. As used herein, the term "client device" includes, but is not limited to, large-screen displays, personal computers (PCs), whether desktop, laptop, or otherwise, personal digital assistants (PDAs) such as the Apple Newton®, "Palm®" family of devices, handheld computers such as the Hitachi "e-Plate", Motorola EVR-8401, J2ME equipped devices, cellular telephones, set-top boxes, or literally any other device capable of interchanging data with a network. Such devices may interface using wired or optical fiber mechanisms such as an IEEE Std. 802.3 Ethernet interface, Digital Subscriber Line (DSL), V.90 modem, DOCSIS modem, hybrid fiber-coax (HFC) cable, or alternatively via wireless mechanisms and protocols such as IS-95/CDMA-2000, Bluetooth™, IrDA interface, IEEE Std. 802.11(a) or (b), Wireless Application Protocol (WAP), GPRS, GSM, third-generation or "3G" systems, or any other of myriad data communication systems and protocols well known to those of skill in the communications arts. Creation of such computer programs and porting to the various hardware environments referenced above is readily accomplished by those of ordinary skill in the programming arts, and accordingly is not described further herein, except with regard to the specific attributes and aspects of the present invention.

In a first exemplary embodiment (FIG. 35), improved data processing and reviewing apparatus 3500 is disclosed which allows the physician or caregiver to efficiently analyze data obtained from a subject. The apparatus 3500 includes digital data processors 3502 (i.e., a microprocessor and DSP in data communication therewith), a mass storage device 3504 (e.g., Ultra-ATA or SCSI drive, CDROM, etc.), random access memory 3506, display device 3508, input device 3509 (e.g., joystick, mouse, keyboard, etc.), and specially adapted computer program (not shown, yet described below) for processing data obtained from the probe. In the present context, processing of video data (i.e., data visible to the human eye) is described; however, it will be appreciated that the invention and associated processing described herein may be adapted to autofluorescence data as previously described herein, as well as non-visible types of radiation such as IR and UV. Furthermore, some or all of the components of the apparatus 3500 may be incorporated into the MCD previously described herein, or similar devices.

Motorola MSC-8101/8102 "DSP farms" are chosen as the digital processors 3502 for the present embodiment due to their extremely high performance and use of parallel processor cores, although other devices such as for example the Texas Instruments TMS320C6x or Lucent DSP16000 series may be used for the signal processing functions.

Figure 35A:
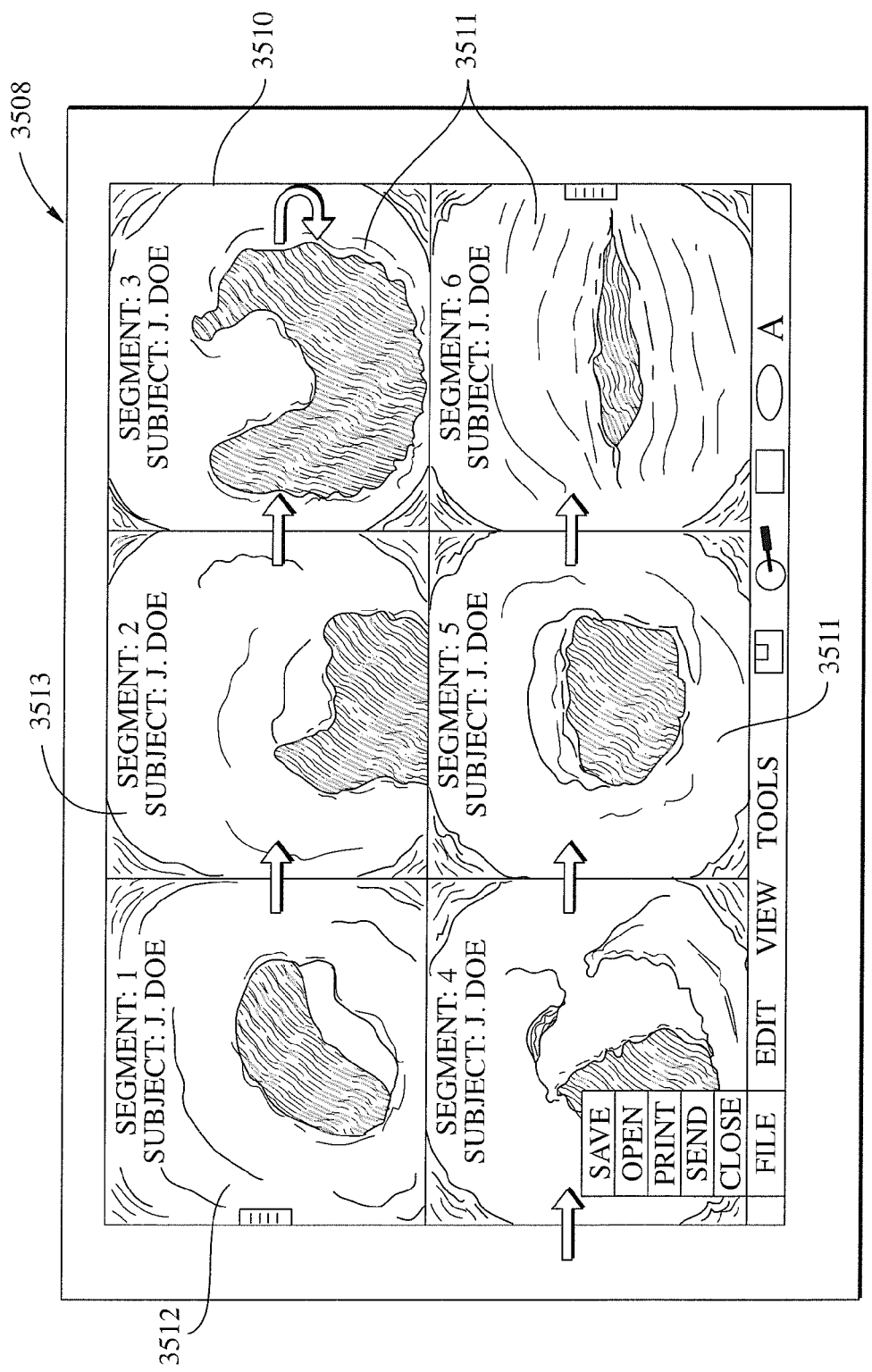
FIG. 35a is a graphical representation of an exemplary multi-portion screen display utilized by the apparatus of FIG. 35.

As shown in FIG. 35a, the display device 3508 includes a screen 3510 which in the present embodiment is enlarged relative to the normal computer display to permit easy viewing by the physician, although this is not a requirement. The screen 3510 is, through data processing and electronics well known in the electronics and television arts, divided into a plurality of contiguous display portions 3511 wherein different images can be viewed simultaneously in the different portions 3511 (i.e., "mosaic" display). This split or divided screen approach is similar to the well known "picture in a picture" or PIP television technology or minicomputer "windowing" in a Windows® environment, yet there is no overlap between the various portions 3511 in the present embodiment. It will be recognized that while a six-portion screen is shown, the screen (and data) may be divided into most any number (n) of portions, whether whole or fractional, and some degree of overlap may be used if desired.

The software associated with the apparatus 3500 processes the image data stream received from the probe via the communications protocol into a corresponding plurality (e.g., 1/n) of data streams for display onto the various portions 3511 of the screen 3510. Such processing can be accomplished after-the-fact by simply knowing the total run length L of the data, and dividing by n, or if the data is streamed in real time (or near-real time), by delaying the display of the data until an extrapolation of probe travel time is made (such as by measuring the progress of the probe over a given time interval t, and then extrapolating this value out to a total run length $L_e$, and then dividing the streamed data accordingly.)

As an example of the latter, consider the case where the probe is introduced into the intestine of the patient, and enters the duodenum at relative time t=0. The probe is then observed to propagate through the intestine at a rate of X cm/hr. Knowing total intestinal tract length (approximate) as Y, the system can then, based on these inputs from the operator, extrapolate the total duration of traversal by the probe as Y/X hours. Assume that two (n=2) portions 3511 are desired for the screen view. The system 3500 then knows that to run two parallel segments of roughly equal duration on the screen 3510, it must take the total duration Y/X and divide by n=2, to produce two segments of Y/2X duration. Hence, the system collects the streamed data until the system timer reaches t=Y/2X, at which point, the actual (real time) incoming data is allocated into one portion 3511 of the screen, while the stored data segment representing data obtained from t=0 through t=Y/2X is displayed on the second screen portion 3511. The user is presented with two parallel video streams, one from stored data and one in real time, which will co-terminate at approximately the same time. Hence, the user can advantageously view data of length Y/X hours in only approximately Y/2X actual time.

As will be recognized, the system 3500 of the present invention can also be configured to perform the foregoing calculations based on user input (i.e., number of portions desired, total patient intestinal tract length, etc.) and automatically provide the user with an indication when the viewing time will begin, so as to obviate wasted physician time. Such indication may be coupled to a warning mechanism (e.g., audible alarm, pager, cellular telephone, etc.) to alert the physician of the impending "start" time for monitoring. Alternatively, the system 3500 may be programmed to alert the viewer after all image processing (described below) has been completed.

Furthermore, more complex models of intestinal propagation can be used as the basis of the calculation, such as where a non-linear rate of propagation occurs in various regions of the intestine. As a simplistic example for illustration, consider the instance where small intestine propagation rate is double that of large intestine rate. Knowing the relative lengths of each part of the intestine, the aforementioned calculations can be adjusted to compensate for the "start" point of screen monitoring. Furthermore, heuristics, statistical data, or empirical data previously derived from the patient being monitored (or other single patients or groups of patients) may be used as the basis for the aforementioned calculations by the system algorithm.

In one exemplary variant, the software of the system 3500 divides a pre-existing data stream of finite length L into portions of data each having length L/n. Hence, for example, where a four-hour or 240-minute data stream (at real time speed) is recorded from the subject during capsule propagation through the intestine, the software of the present invention divides this four-hour stream into six forty-minute segments, each allocated to a different portion 3511 of the screen 3510. Division of the data stream may be according to a frame or packet index count, via queue or buffer mechanisms, or alternatively based on the physical addresses within memory where the streamed data is stored, or any number of other well known techniques. The allocation of data stream segments to screen portions 3511 may be according to any desired scheme, including for example (i) increasing row-column temporal (i.e., the first portion 3512 displays the earliest segment, while the next portion 3513 to the right in the same row, discloses the next temporal segment, and so forth); (ii) priority (i.e., those segments corresponding to what are identified by the physician or other means as the most likely regions of the intestine for disease are disposed in priority order on the screen, such that the reviewing physician can preferentially view one corner or region of the screen 3510 and periodically scan the others corresponding to the "lower risk" portions of the intestine); (iii) random (i.e., order selected according to output of seeded pseudo-random number generator, so as to avoid predisposition of physician or prior knowledge to affect diagnosis); or (iv) inversion (e.g., wherein a "central" point within the intestine, and hence the data stream, is used as the basis for n/2 segments displayed in forward motion in sequence, and the remaining n/2 segments displayed in reverse motion in sequence, such that the viewer is effectively presented with data mimicking two probes within the intestine converging on a central point, the second probe "virtually" propagating upwards through the intestine or against the peristaltic action of the intestine). Myriad other display schemes are possible, the foregoing being merely illustrative of the broader concepts of the invention.

The individual portions 3511 of the screen 3510 may also be supported by separate software processes, threads, or objects (depending on the software environment chosen), each individually controllable by the user. For example, in one exemplary embodiment, the software of the system 3500 is adapted to allow the user to select an individual portion 3511 of the screen during viewing, such as by using the attached computer mouse 3509 or other input device, and varying the properties of that portion. Specifically, by "right-clicking" on the mouse 3509 after the user has selected a given portion 3511, the user is then presented with a menu bar or window of the type well known in the software arts which includes a plurality of options for that portion. Such options may include, inter alia, common video viewing functions such as "fast forward", "pause", and "reverse", as well as other functions such as "zoom", zoom-pan, image enhancement, digital whiteboard (activating a light pen or similar means for annotating the display for later use or contemporaneous collaboration via a data network interface), save/print, and the like. Myriad types of well known user interfaces which provide the physician with control over the displayed images may be employed consistent with the invention.

The use of a larger sized screen 3510 of the illustrated embodiment also permits the physician to clearly visualize each of the individual images as if they were only viewing that image. Conventional CRT, flat-screen, HDTV, or similar technologies may be utilized as desired in providing and rendering the images. Hence, in the illustrated embodiment, a screen which is roughly six times the normal computer or monitor screen area is utilized to provide enhanced image viewing quality and resolution, and the ability for multiple physicians to collaborate without having to "crowd around" a smaller display. The images displayed may also be networked to other local or remote devices if desired, using for example conventional data networking techniques, to allow for multi-user visualization.

It will also be recognized that separate display devices, whether single or multi-portioned, can be used to evaluate data from one or more subjects contemporaneously.

The foregoing approach capitalizes on the innate human capability for substantially parallel or multiplexed image processing within the brain, especially where the subject matter of the multiple parallel/multiplexed images is substantially similar and the changes occurring in the images are not complex or rapid. Consider the limiting example of several (e.g., six) similar images of different blades of grass projected in corresponding portions of a display screen; an average human being can "scan" these six images using periodic eye movement to detect changes in the images (such as changes in coloration, movement, or shape/size), without having to intently focus on one image at a time, or by time-multiplexing the images to the brain. In this example, the rate of new information introduction into the eye (and brain) of the viewer is quite slow; hence, to watch each sequence sequentially (i.e., watch each blade of grass grow, followed by the next, and so forth) would dramatically underutilize the capabilities of the brain, and comprise a significant waste of time. Conversely, images of six fast-paced action movies projected contemporaneously on a screen would on average greatly overtax the abilities of the viewer's brain, thereby causing significant loss of information. The viewing of multiple images of an intestinal probe moving through the intestine of a human considered to be closer to the former (grass) paradigm than the latter, since the movement of the probe through the intestine via peristaltic action is comparatively slow, and the subject matter does not vary significantly (i.e., different portions of the intestine are generally somewhat similar).

Human peripheral vision (i.e., that outside the area of direct focus of the eye) is also advantageously adapted to detect movement and changes, which is used by the present invention to some degree to allow a physician to monitor a plurality of regions of the intestine in parallel for changes or physiologic features of interest (i.e., disease).

It will also be appreciated that the update of the display portions 3511 of the present invention may be made discrete as opposed to continuous in nature; i.e., the sequence of images may be non-continuous or comprise "snapshots" of data obtained from the probe. The sequence and/or timing of the images displayed in one portion 3511 may also be coordinated with those of one or more other portions of the screen 3510, so as to minimize the opportunity for lost or non-viewed data. For example, wherein a row-and-column display is used (e.g., two rows of three portions 3511 each), the display interval can be staggered such that an image will change or "flip" at a predetermined interval after the change in the prior portion 3511, thereby creating a ripple effect across the screen in row- and column order. Hence, the physician or other user can coordinate their eye movement to scan each portion just after it changes, thereby in effect creating a loop wherein the physician can jump portion-to-portion with their eyes to view the next changing frame.

In terms of data efficiency, consider the exemplary embodiment wherein a four-hour total length (L) data stream in real time is divided into six forty-minute segments as previously discussed. If each segment is sampled once every period t and updates its display portion at a predetermined rate, then the desired level of image compression can be achieved by adjusting the sampling and display rates accordingly. Hence, if the program samples data from each of the six segments at a rate of one "frame" every six seconds, and then displays each sampled frame in its respective portion 3511 on a staggered basis for one second before the next portion is updated, an overall display update rate of once per six seconds is established. Accordingly, the algorithm samples a give segment for a screen portion once every six seconds, and displays the sampled image for six seconds, until it is time to again sample the segment for that portion. The effect is to permit viewing of all six segments as previously described (i.e., 6:1 compression), yet with the user only viewing one portion 3511 at a time on a rotating basis as compared to simultaneously running segments in the prior embodiment.

If greater compression is desired, the display update rate and/or sampling rate can be adjusted. For example, if an update rate of once every ½ second is chosen, then each portion will be updated every three seconds. If the displayed data is sampled once every six seconds of segment data as before, yet displayed once every three seconds, then the algorithm(s) must "fast forward" each segment by three seconds during each interval in order to present a snapshot at three second intervals of data taken once every six seconds. Stated differently, the user is presented with a "snapshot" from each segment taken six seconds apart (in data space) every three seconds (in display space). Likewise, lower compression can be afforded by increasing the sampling rate above the display rate, thereby either lengthening the total runtime for each segment beyond that associated with real-time running of 6:1 compression (i.e., 40 minutes in the present example), or alternatively allowing the software to "drop" every other sampled frame. Myriad other permutations of data rate/sampling rate/compression ratio may be used consistent with the invention.

In another embodiment of the invention, the system 3500 may be coupled to a headset (not shown) worn by the physician which is adapted to scan the retina or other portion of the physician's eye(s) using incident or reflected energy to determine where the physician is looking as a function of time relative to the headset's coordinate system. As the physician moves their eye(s) to look at another portion 3511 of the screen 3510 (or alternatively fails to move their eyes for a prescribed period of time), the signal processing associated with the reflected energy determines the portion 3511 of the screen 3510 at which the physician is looking, and performs the desired function. Hence, where something in an image displayed in a given portion 3511 of the screen 3510 captures the physician's attention, the algorithm can detect this interest and perform one or more desired functions relating to the data displayed in that portion, such as zooming, fast-forwarding, slow-motion, tagging of data for later examination, updating (if the non-continuous embodiment of the invention is utilized), etc. The retinal device is also optionally used to trigger software generation of pull-down menus or pop-up windows on the screen 3501, allowing the user to coordinate selection via an input device 3509 (or via speech, described below) with their eye movement in order to effect selection from the menu.

Various embodiments of optical scan technology are known in the prior art, including for example the infrared (IR) that developed by CAE Electronics Ltd. of Montreal, Canada. The CAE eye-tracking device can record and analyze accurately up to 500 eye positions per second, and works by capturing and processing the reflections of a low-level beam of infrared light shone onto the eye. Multi-element arrays capture the image of the eye and digitize the information, which is then processed in real time by a fast, dedicated signal processing unit. The difference in position between the light reflected by the pupil reveals the instantaneous direction of user gaze. Yet other methods for determining the direction of a subject's gaze relative to a fixed point or region in space are well known in the art, and accordingly not described herein. See, e.g., U.S. Pat. No. 6,394,602 entitled "Eye tracking system" issued May 28, 2002, U.S. Pat. No. 6,154,321 entitled "Virtual retinal display with eye tracking" issued Nov. 28, 2000 and U.S. Pat. No. 5,712,684 entitled "Viewing apparatus with visual axis detector" issued Jan. 27, 1998, each of which are incorporated herein by reference in their entirety.

Alternatively, a prismatic "HUD" (Head-up display) of the type well known in the art may be substituted in the aforementioned headset for the retinal scan technology. Specifically, a miniature screen or prism disposed in front of one eye of the subject via the suspension mechanism (e.g., arm) of the headset receives optical signals for display to the user. Such devices are disclosed in, inter alia, U.S. Pat. Nos. 6,222,677 entitled "Compact optical system for use in virtual display applications" issued Apr. 24, 2001, and 5,943,171 entitled "Head mounted displays using reflection light valves" issued Aug. 24, 1999, both of which are assigned to IBM Corporation and incorporated herein by reference in their entirety. For example, in one variant, the head-mounted display is used to display option menus to the user, such as GUI pull-down menus from which the user may select using one or more input devices (including speech commands as described subsequently herein).

Furthermore, it will be recognized that speech recognition technology of the type well known in the art may be used consistent with the present invention. Software and audio apparatus (microphone, etc.) adapted to recognize the voice commands of a user and translate them into actions relating to the system 3500 is used in one embodiment to facilitate more efficient viewing. For example, a user voice command of "Zoom in 2x, Zone 3" would be interpreted by the system processor 3502 and accordingly cause the display of the segment contained in a particular portion 3511 of the display 3510 to be enlarged or increased in scale by a factor of 2. This functionality may also be coupled with the optical direction apparatus previously described, thereby simplifying the verbal command syntax by providing spatial context to the commands. Hence, using such apparatus, the user would state "Zoom in, 2x" while looking at Zone 3 on the display, the software being adapted to recognize that the verbal command was given in the context of the "viewed" zone at that point in time. Similarly, if multiple displays 3510 are being viewed simultaneously, the optical apparatus provides spatial context as between the multiple displays.

The speech recognition apparatus of the present invention includes a high quality, high SNR audio microphone, analog-to-digital converter (ADC), and linear predictive coding (LPC)-based spectral analysis algorithm run on the system digital signal processor. It will be recognized that other forms of spectral analysis, such as MFCC (Mel Frequency Cepstral Coefficients) or cochlea modeling, may be used. Phoneme/word recognition in the present embodiment is based on HMM (hidden Markov modeling), although other processes such as, without limitation, DTW (Dynamic Time Warping) or NNs (Neural Networks) may be used. Myriad speech recognition systems and algorithms are commercially available (such as for example those offered by IBM Corporation or Scansoft Inc.), all considered within the scope of the invention disclosed herein.

In yet another embodiment of the invention, the foregoing display 3510 is divided into a plurality of portions 3511 based not on the segments of the data stream of a single subject, but rather the data streams of two or more subjects. For example, the physician may desire to aggregate the data from six separate patients onto the aforementioned six-portion display 3510, such that instead of viewing the nominal four-hour data stream from a single patient as with the prior art, he/she can view data for six patients simultaneously during the same four hour period, thereby again providing 6:1 compression, and reducing the time spent per patient from four hours to forty minutes. This approach has the benefit of allowing viewing of generally comparable portions of the intestinal tract of the various patients simultaneously, thereby offering the physician with some level of comparative visual data by which to analyze a specific patient's data. Alternatively, data from a "normal" or control intestine may be inserted into one of the portions 3511 if desired for such purposes.

Where the various individual data sets are different in total length L, the algorithm is adapted to optionally expand or compress the data for each patient so as to make the various data coextensive in time. Hence, in effect, the system 3500 adjusts the viewing speed of each stream at start-up (or during operation) so as to have all segments start and stop at the same point in time, thereby maximizing physician efficiency. Such adjustments may also be dynamic during operation, such that if for example the physician pauses one data stream part-way through for closer examination, the speed of display of that stream after removing the pause condition is accelerated based on an extrapolation of remaining run time as compared to those for the other segments, such that (assuming no further pauses), the viewing of various streams will be completed at the same time.

Alternatively, the speed of display of the remaining (i.e., non-paused) segments may be slowed, such that approximately coincident completion is again achieved, yet with longer overall duration. This approach may be desirable where the paused segment shows disease or other problematic conditions warranting a closer, slower inspection. For example, if the physician pauses a segment associated with a given patient, and upon discovering signs of disease, releases the pauses in favor of a slow or reduced rate of display (i.e., slow motion forward), the data streams for the other patients may be proportionately adjusted by the algorithm to preserve the common termination time if desired. In this fashion, the physician can place the entire display (i.e., all n portions) in slow motion.

Furthermore, upper and/or lower "speed limits" may be placed on the system 3500 via the algorithm, such as by user entry of data via a start-up or configuration menu of the type well known in the art, or via pull-down menu or similar GUI. Such speed limits may act as artificial boundaries to the speeding up or slowing down of data at start-up or dynamically as previously described. Hence, for example, where the data segments for the various subjects are very different in length, the upper speed limit may act to control the degree of display rate increase for a segment undergoing temporal compression so as to avoid the physician "missing" data. If it is known that a given value for the display rate of the data is the maximum upper limit for reliable diagnosis, then any attempts by the system's algorithm to increase the display rate of a given segment above that maximum prescribed rate in order to compress the run-time of the segment will be frustrated by the upper speed limit. Accordingly, at that point, the system 3500 will offer the user (via, e.g., interactive menus or windows) the option of slowing down the other segments as necessary to provide coincident data termination, or alternatively just letting the other segments complete "earlier", thereby allowing the physician to focus more effort on the remaining (running) segments after such termination of the other segments.

In practical use, there is little real danger afforded by running a data stream's screen display rate too low; however, the low speed limit of the present invention can be used to, inter alia, prevent the user or physician from inadvertently extending the duration of one or more segments beyond that desired, or missing motion-related artifact (e.g., pulsations of tissue, severe jars to the patient, etc.) which can be best visually detected at a minimum display rate or greater.

Figure 35B:
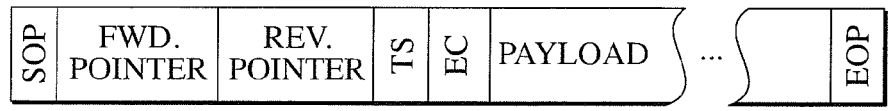
FIG. 35b is a graphical representation of an exemplary data packet protocol used with the system of FIG. 35.

In yet another embodiment, the apparatus 3500 of the invention is adapted to select and display only designated portions of the data stream generated by one or more probes. Specifically, in one variant, the system software is adapted to select frames of data at pre-selected intervals regularly spaced along the duration of the data stream, in effect forming a series of snapshots for the physician to view. Each of the selected frames are stored in a data buffer associated with the system; e.g., a FIFO buffer memory of the type well known in the data processing arts, or other types of storage scheme such as virtual memory on the system hard drive, etc. The frames are also stored with one or more data fields associated with each, the data fields being used in the present embodiment as absolute or relative pointers to other locations in the data stream. In one variant, the data stream protocol comprises a sequence of uniform data packets, a group of packets in the aggregate comprising a frame and being assigned a sequence number. Each of the frames selected by the system software for display to the user is stored in the data buffer along with its sequence number, the latter being used to index the frame with respect to other frames in the stream so as to permit the user to "grab" frames for subsequent closer inspection. Hence, in the instant embodiment, the user views a series of frames representing only discrete portions of the total data stream (e.g., every sixth frame or container of data), and is able via software commands to select individual ones of the displayed frames for subsequent evaluation. The selected frames are stored in the data buffer along with a sequence or index, thereby allowing the user to (i) identify the relative timing of multiple frames selected, and (ii) select portions of the data stream for complete viewing. FIG. 35*b* illustrates an exemplary packet protocol useful with the invention.

Specifically, the index number can be used to display to the user the relative timing or sequence of the multiple frames selected that they are viewing. Alternatively, a time stamp can be used for each selected frame to display the relative timing of frame with respect to the total duration of the data stream. For example, where six frames of data are selected, six different time stamps (or indexes) will be displayed to the user so as to indicate which frame came first, second, and so forth. This index or time stamp information is also used to sequentially order the selected frames in lineal order on the display screen 3510.

Furthermore, the index or time stamp can be used as the basis for retrieving selected portions of the data stream as specified by the user. For example, in one embodiment, the system software provides the user with menu or "right click" capability via the input device to select various options for expanded viewing of one or more frames. Where a selected frame displays data of possible interest, the user simply selects the appropriate pull-down menu or right-clicks the mouse, while selecting the screen portion 3511 or window of interest, and selects one of the options allowing for viewing of the data contiguous with the selected frame. The index/time stamp is accessed by the software based on the user's selection, and used as the seed for the calculations to identify stream data for retrieval. In one embodiment, the frames or aggregation of packets are a known temporal duration, as is the total length of the data stream, and hence the user selection of a given period of time for viewing with respect to the indexed/stamped frame of interest is used to determine the number of packets to be retrieved relative to the selected frame. The user is further able, via the aforementioned user interfaces, to select the relative temporal position of the selected frame to the retrieved data, such as for example by selecting "+5 min." on the menu. This command assigns the originally selected frame as the temporal or index starting point for data retrieval, with the equivalent of 5 min. of subsequent data retrieved from the stored stream and displayed to the user as a video "clip". Alternatively, the user may select the option "+/−5 min." from the menu, wherein the system software designates the selected frame as the center point of the data retrieval, and accordingly retrieves data equivalent to 5 min. before the reference frame, and 5 min. after, and displays the data again as one continuous clip. Alternatively, the user can select via menu to zoom in on the selected frame. As can be appreciated by those of ordinary skill, myriad other options for data manipulation, selection and display are possible consistent with the invention, the foregoing being merely exemplary of the broader concepts.

Other embodiments of the invention permit the selection of data frames based on criteria other than periodicity, including for example the following:

(i) User pre-selection—The selection of frames may be based on inputs obtained from the user before or at the time of viewing, such as the selection of points along a graphical or other depiction of a timeline representative of the entire length of the data stream (e.g., by dividing the data stream into n segments of the same or different length, and then sampling at the segment boundaries).

(ii) External inputs—The selection of frames may be based on one or more external inputs, such as data corresponding to one or more actual physical locations of the probe generating the data within the subject's intestine during passage. For example, where the probe is tracked during its progression through the intestine by ultrasound, RF energy, X-ray/CAT scan, MRI, or the like, data obtained from such tracking methods may be correlated to temporal coordinates in the data stream. This approach may be useful, for example, where the subject complains of pain or discomfort in one or more given locations of the intestine; the physician can decide to selectively view the portions of the data stream relating to the probe being disposed at or near these locations. Such correlation can be accomplished using any number of methods, such as artificially inserting a time stamp into the system 3500 via the GUIs/input device 3509 when the location of the probe is known to physically coincide with the location of the subject's discomfort, etc.

(iii) Autofluorescence data—Portions of the data stream may be selected by the user based on data relating to autofluorescence analysis (described above). Specifically, the probe may be configured and operated such that the autofluorescence analysis is conducted at periodic intervals during the traversal of the probe through the intestine, as specified by a sampling ratio R. For example, the autofluorescence diode and array may be activated once per minute of travel for a duration of t seconds (R=60/t) so as to obtain a series of periodic "snapshots" of the auto-fluorescent signature of the tissue in the intestine proximate the probe. This data is transmitted off-probe along with the visual data (such as via time-division multiplexing (TDM), FDM or sideband transmission, or other technique), such that the system 3500 has both sets of data available for viewing by the physician. Alternatively, the probe (or different probes) can be sent down the intestine multiple times to collect the various data. The autofluorescence data stream can then be previewed by the physician either manually, such as via a visual display of the data in sequential or mosaic form as previously described herein, or alternatively via another technique such as software processing of the data. Such software processing may comprise, for example, analyzing the "snapshot" frames of autofluorescence data for changes in the remitted energy spectrum as a function of time (e.g., versus prior data obtained for the same patient, whether in the current traversal or one or more prior thereto), or against empirical data derived from other patients, or even against an established criterion such as a threshold remittance intensity. For example, the integrated area under each remittance spectrum may be calculated in order to compare different spectra. Alternatively, the normalized magnitude of the remittance intensity peak may be computed for comparison. As yet another alternative, the spectral location (i.e., wavelength $\lambda$ or frequency f) of the peak in the remittance spectra may be compared in order to identify shifts or variations potentially relating to disease. Myriad techniques for analyzing spectra for shape, artifacts and/or changes may be used consistent with the present invention, such techniques being well known to those of ordinary skill in the mathematical and experimental arts.

When the physician has identified one or more regions of interest within the subject's intestine (corresponding to one or more of the periodic autofluorescence frames), they simply select the frames of interest via the system 3500, such as via GUI menu or input device. The system software of the instant embodiment is programmed to correlate the time stamp associated with each frame selected to the appropriate portion of the visual data stream, and select and buffer data from the visual stream within prescribed temporal coordinates of the selected frame(s). For example, where the physician selects two frames of autofluorescence data and requests (via the user interfaces previously described herein) the viewing of +/−5 minutes of data on either side of the frame, the system software obtains the time stamps of the selected autofluorescence frames, locates the corresponding point(s) within the visual data stream, and then selects +/−5 min. of data for each (for a total of 20 min. of visual data in the present example). Hence, rather than watch several hours of data in a contiguous stream, thereby potentially fatiguing the physician and detracting from the cost efficiency of the diagnosis, the present embodiment of the invention allows the viewer to preview the entire visual data stream based on a series of autofluorescence snapshots, and then focus in on the regions of interest within the visual data stream accordingly, thereby greatly enhancing the cost efficiency and quality of the diagnostic process.

(iv) Antigen/chemical detection—As previously discussed, one embodiment of the probe of the present invention is adapted to detect one or more antigens within the intestinal tract, and provide a signal (or data) to the system so as to alert the operator to the presence of the antigen(s). Accordingly, the system 3500 of FIG. 35 may be configured to time stamp such antigen detections, and use this time stamp information as the basis for expanded viewing by the physician. For example, the physician may preview the entire visual data stream for corresponding antigen or chemical detection events, and select portions of the visual data relating to these events for examination in much the same way the autofluorescence data time stamps were used as described above.

Hence, if the physician is screening the patient based on narrowly focused criteria, such as the presence ("go/no-go" test) of a particular condition or disease with no other ancillary screening, the physician can efficiently locate the potentially relevant portions of the visual data stream based on the presence of one or more "markers".

While specifically described herein with respect to antigen/chemical detection and autofluorescence data, it will be appreciated that this concept (i.e., the use of a narrowly focused screening criterion, such as a "go/no-go" test) may be applied more broadly to most any type of event occurring contemporaneously with the collection of visual data, and/or even those artifacts present in the visual data alone which are indicative of the potential for conditions warranting increased scrutiny.

(v) External prior data—Similarly, the system 3500 may be adapted to use prior existing data and/or inputs as a means of targeting the selected acquisition of data from the patient during probe traversal. For example, data relating to procedures or inspections such as prior endoscopic, CAT scan, or MRI analyses can be analyzed in order to generate windowing criteria used during probe traversal. Consider the simple yet exemplary case wherein a prior upper GI series of the subject yields information indicating that portions of the small intestine may be ulcerated or perforated. Knowing the rate of traversal of the probe through the subject's upper GI tract (which may be selected from a database of empirical data, or entered by the user via GUI or other input prior to probe introduction in the patient), the probe can be programmed to collect data only during prescribed "windows" specified by the system software and corresponding to the approximate locations of the disease, thereby, inter alia, minimizing the amount of potentially extraneous data obtained by the probe. It will also be recognized that such windowing or blanking need not necessarily be tied to any specific prior or contemporaneous event, but rather may alternatively be programmed into the system 3500 for any reason. For example, where the physician wishes to examine only a portion of the intestinal tract, such as to limit their potential malpractice liability for inspections of areas of the intestine not conducted, they may configure the probe and/or system 3500 as applicable (i.e., either by shutting the probe off, or simply dumping data streamed from the probe at the system 3500) to capture data only during the relevant potions, such as just for the small intestine, etc.

In this fashion, the system 3500 can also be controlled and made legally comparable to other prior art technologies (such as the fiber-optic endoscope) which have only limited reach into the intestinal tract. Stated differently, the diagnosing physician can avoid legal malpractice issues relating to non-diagnosis of or failure to identify conditions occurring in non-considered regions of the intestinal tract by in effect switching off the data corresponding to that non-diagnosed portion. As will be recognized by those of ordinary skill, the system 600 may further be equipped with verification and audit capability in this regard, such that a printed and/or electronic record of the data collection process and times (such as via data time-stamping) is preserved for future use. A digital watermark or signature of the type well known in the encryption and security arts may be employed to this end in order to authenticate data for later use, such as during legal proceedings. Additionally, a network interface may be used, wherein the system 3500 transmits one or more authentication data packets (e.g., containing the viewed portion of the data stream, and/or the temporal window specifications of the session) to a third party facility adapted to receive, store, and authenticate the data for later use, much as an electronic transfer of funds is conducted within the financial industry. Myriad other techniques for guaranteeing the authenticity of prior collected data are available and may be used with the present invention.

Similarly, the data rate of the system 3500 may be adjusted during one or more temporal windows so as to accelerate the viewing of data during periods corresponding to portions of the intestinal tract having a lower probability of disease. For example, where a given patient has recently undergone a colonoscopy with no identified disease or problems in that region, the probability of disease occurring in that region in the interim since the colonoscopy is very low. Hence, the physician may decide to "fast forward" that portion of the data stream corresponding to the colon. This fast-forwarding is accomplished in one exemplary embodiment through the system display software, which increases the data display rate on the display device 3510 according to a pre-selected compression ratio, thereby effectively compressing the time needed to complete that segment of the data stream.

Hence, if desired, the operation of the system 3500, and specifically its software and which data stream frames are displayed to the user, may advantageously be coupled to events occurring before, contemporaneously with, and/or after the collection of data via the probe. In this fashion, the comparatively large amount of data collected by the probe during a normal traversal of the intestine can be intelligently reduced and screened based on other data or information available to the physician. These events may be intra-probe (e.g., antigen detection, ultrasound detection, coupled to the in situ power-up of the probe or receipt of an external signal; etc.), or external to the probe (e.g., data derived from other tests or external analysis of data derived from the probe, based on the user's input, etc.) as will be appreciated by those of ordinary skill.

Image Recognition

In yet another embodiment of the invention, the software of the system 3500 is configured to perform analysis of the data obtained by the probe optical band sensor (e.g., CCD or CMOS array) so as to automatically identify one or more artifacts or features contained therein. Specifically, in one exemplary configuration, the software includes algorithms adapted for feature recognition based on pre-stored data contained within the system 3500. These algorithms have commonalities with two prior art technologies, namely 1) DSMAC (digital scene matching area correlation) as used on, inter alia, the Raytheon BGM-109 "Tomahawk" cruise missile; and 2) facial recognition software currently being used with respect to the identification of terrorists and other criminals, such as the FaceIt® ARGUS software offered by Identix Corporation.

As is well known, the DSMAC technology utilizes digitized images obtained from an optical, electro-optic (EO) or IR sensor disposed within the parent platform as the basis for comparison to pre-stored "images" of targets, the latter obtained from, for example, low-earth orbit optical or IR satellites. Since the missile may attack such targets from various attitudes, mathematical manipulations of data obtained via the input sensor are conducted in essentially real time in order to align the image or convert it to the desired perspective, and extract features which are then correlated to similar features within the pre-stored data. This feature may be used, for example, in the terminal guidance phase of the missile, in order to validate the target before activation and delivery of the missile's munitions. See, for example, the techniques described in U.S. Pat. Nos. 4,925,274 entitled "Correlation Techniques" issued May 15, 1990, 4,802,757 entitled "System for determining the attitude of a moving imaging sensor platform or the like" issued Feb. 7, 1989, 5,146,228 entitled "Coherent correlation addition for increasing match information in scene matching navigation systems" issued Sep. 8, 1992, and 5,173,949 entitled "Confirmed boundary pattern matching" issued Dec. 22, 1992, all of which are incorporated by reference herein in their entirety.

Facial recognition software such as ARGUS utilizes a generally analogous technique, of image digitization, wherein certain facial features are identified and evaluated for a plurality of individuals (such as the patrons of a football game) passing in proximity to the sensor(s), and then subsequently compared to pre-stored data in order to attempt to match the in situ data to one or more entries within the pre-stored data, thereby in effect identifying the individual. Images captured of the individual are first scanned to localize the region of interest, then these regions are analyzed (including, for example, alignment and normalization of the image) to measure a plurality of physical features associated with the face of the individual being evaluated. See, e.g., U.S. Pat. No. 6,108, 437 entitled "Face recognition apparatus, method, system and computer readable medium thereof" issued Aug. 22, 2000, also incorporated herein by reference in its entirety.

Both of the foregoing technologies are generally speaking quite computationally intensive, requiring significant MIPS for even routine correlation and identification tasks. With the advent of ultra-high speed digital processors (such as the aforementioned Motorola MSC8101/8102 series devices, or the Texas Instruments TMS320C6x or C80 DSPs), such processing can presently be conducted in real time or near real time. However, it is desirable to reduce the computation requirements of such analysis, thereby permitting yet faster evaluation.

With this backdrop, an exemplary embodiment of the present invention is now described with respect to FIGS. 36a-36f.

As previously discussed, the probe of the invention is adapted to generate a stream of data (either via real-time off probe transmission, or via delayed readback from a storage device) relating to visual images obtained within the subject's intestine. This data is processed by the software disposed on the monitoring system 3500 which, in the instant embodiment, is adapted to analyze the visual data stream for one or more artifacts or features. As used herein, the term "visual" refers to any portion of the electromagnetic spectrum which may be perceived by a sensor, including the IR and UV portions as well as the visual region.

As described above, packets or aggregations of data in the visual data stream are packaged into data frames of predetermined length in bytes or temporal duration, for additional processing. In the present context, such additional processing comprises analysis of the frames via algorithms running on the system processor(s) 3502 for specific features or artifacts relating to known diseases or conditions within the intestine. For example, the formation of intestinal polyps is well documented and readily observed through visual endoscopic analysis under the prior art. Such polyps generally have a characteristic shape; i.e., the formation of a protrusion or projection 3604 from the wall of the intestine 3602 as shown best in FIG. 36a. Hence, the visual-band image obtained via a sensor approaching a polyp within the intestine from the "upstream" side would generally contain (i) a curved and substantially consistent feature 3610 representing the wall of the intestine, and (ii) a projection 3604 punctuating the curved feature 3610, as shown in FIG. 36a.

Similarly, a normally shaped intestine when viewed by such sensor would appear as in FIG. 36b, with an aperture 3620 of appreciable size formed generally near the center of a "band" of lighter colored tissue 3622. In contrast, an occluded or distended intestine (FIG. 36c) would appear to have an irregularly-shaped aperture 3624 and/or a reduced area of the aperture (i.e., larger ratio of light-colored or reflective tissue area to aperture area).

Numerous other types of maladies or diseases associated with the intestinal tract can be similarly characterized by features or artifacts within their visual images, including without limitation various different types of polyps, diverticulitis, occlusions/adhesions, carcinomas, and ulcerations.

Accordingly, the present invention capitalizes on the foregoing ability to visually characterize conditions of the intestine coupled with the efficiency of digital data processing in order to provide the physician with a substantially automated process for screening data obtained from the probe for such features or artifacts. In the illustrated embodiment, each type of known feature or artifact associated with one or more diseases or conditions is to some degree unique (much as the human face or the target facility) and can be characterized in terms of a number of nodal points. Using the signal processing power of the aforementioned DSPs, the database of such diseases used with the present invention can advantageously be expanded to a large number of different "template" images, the latter being used as the basis for comparison and identification.

It will be recognized that while the following discussion is cast in terms of the aforementioned polyp in the context of visual band image data, the method is generally applicable to a broad range of artifacts and conditions occurring within the intestine, as well as to other ranges of electromagnetic radiation (e.g., IR) and even acoustic energy with sufficiently high frequency.

In the illustrated embodiment, eight (8) nodal points 3627 are assigned on the feature of interest, as best shown in FIG. 36d. Obviously, more or less and/or different nodal points may be used consistent with the invention. These nodal points are discrete locations on the image frame which the software assigns based on, inter alia, decomposition of the frame into a plurality of pixels or image segments, each having its own discrete properties, and subsequent mathematical analysis. Specifically, the instant embodiment (i) first identifies the feature boundaries through analysis of the intensity of pixels processed according to a pixel map; (ii) performs mathematical curve-fitting to the pixels identified as being part of the boundary as shown in FIG. 36e, and then (ii) selects the nodal points used to characterize the feature based on these mathematical functions. In the present embodiment, the entire field of view (FOV) of the frame is used as the basis for analysis since it is spatially small, and the features generally comprise a significant fraction of the FOV. However, the FOV may be reduced if desired, much as the aforementioned face recognition technology of the prior art first identifies the facial region of an image of a person as being the "region of interest" before performing the facial recognition computations. A multi-scale algorithm of the type well known in the facial recognition software arts may optionally be used for scanning image frames for features or artifacts which are not in the immediate focal region of the sensor, with any such identified features then being identified for further analysis as described below.

In the instant embodiment, image processing of each pixel in the FOV of interest is accomplished on the basis of pixel intensity (or "pixel grayscale value"), measured as an absolute value independent of image depth (or alternatively as a relative value with respect to other pixels in the image). Hence, the polyp boundary 3625 shown in FIG. 36d is first discerned via analysis of the pixel matrix based on intensity, specifically a multi-bit binary digital value representing the intensity of that pixel. Higher intensity indicates light-reflective tissue closer to the sensor, while lower intensity pixels are correlated to more distant tissue (or no tissue). Feature boundaries are determined from these intensity values according to well-known algorithms not described further herein.

As will be recognized by those of ordinary skill in the image processing arts, the image depth of the data (i.e., the number of bytes per pixel, roughly correlated to the "richness" of the image) obtained from the data stream may be adjusted in order to provide desired attributes for data filtering and analysis, whether on-probe or off. Furthermore, color images (e.g., wherein each pixel carries data relating to the respective R-G-B intensities, or a "fake" color index assigned by grayscale coding) may be used as the basis for feature analysis.

The instant embodiment of the present invention also capitalizes on the observation that there are only a limited number of possible orientations for features within the intestinal tract. Specifically, all features or artifacts of interest occurring within the intestine are oriented or in some way related to the interior surface of the intestine, modeled herein as a substantially cylindrical tube disposed substantially co-axially with the longitudinal axis of the sensor of the probe. Furthermore, at least portions of most features of interest will be disposed transverse within the intestine, since the substantially circular FOV of the probe sensor intersects the cylindrical intestine interior wall as a radial circle or band. These assumptions, coupled with the use of ratios versus absolute measurements, greatly simplify the image processing and recognition algorithms, since no determination of size (i.e., how large the feature is in absolute terms) or alignment (i.e., how the feature is aligned relative to the sensor) or image normalization is required, as is required in other software approaches.

As a simple example, the feature boundary 3625 of the foregoing polyp can be simply modeled in a template as a semi-circle of different radius intersecting with two linear functions. For comparison between the template and an actual in situ image, the system 3500 need not know the orientation of the template feature or the actual feature, but rather only their parameter ratios. The orientation is not needed since the polyp, regardless of orientation, will always have one portion contacting the inner intestinal wall (cylinder), and will always present a cross-sectional area to the FOV of the sensor. In many cases, the back side of the polyp looks similar to the front, and the side. Also, in the cylindrical coordinate system (r, Φ, Z) of the intestine/probe, information regarding the azimuthal disposition of a feature (i.e., where on the circumference of the intestine the feature is located) is generally not needed, since only the recognition of the shape is of significance, and not its relative angular displacement. Contrast the face in the face recognition system, wherein (i) the subject's head does not always present a "useable" cross-section (such as if the face is turned away or looking down), and (ii) the aspect or alignment of the face is critical, since the parameters being measured are unique to one aspect.

The algorithm of the system software next performs curve-fitting (either piece-wise or continuous, as appropriate) to assign a mathematical function to each portion of the feature boundary. Algorithms for mathematical curve fitting are well known in the software arts, and accordingly not described further herein. These functions are next used, in the context of a relative coordinate system assigned to the image data by the curve-fitting software, to characterize the feature (polyp) in terms of the eight aforementioned nodal points, as shown in FIG. 36e. Specifically, the feature maximum width 3627, height 3629, and base width 3631 are determined through analysis (such as local maxima/minima identification etc.) of the determined functions. In the illustrated example, the salient portions of the polyp feature 3604 can be modeled as two circular functions (form of $x^2+y^2=r^2$) of different radius, and two linear functions of the form y=mx+b, the former two intersecting the latter two. These functions are then analyzed for example based on (i) the diametric point of the first circular function (width 3627), (ii) the maximum distance between first and second circular functions (height 3629), and (iii) the distance between the points of intersection of the two linear functions and the second circular function (base width 3631).

It will further be recognized that the component functions generated during curve-fitting may be used as the basis for feature identification as well. Specifically, the functions comprising the feature boundary may themselves be descriptive of the feature. As a simple example, consider a cube which, regardless of aspect or attitude, will never have a curved feature boundary. More sophisticated analysis of the types, intersections, and curvatures associated with a given feature may also be employed. In the case of the exemplary polyp previously described, the relative positions and compositions of the various mathematical functions used to generate the boundary (i.e., two semi-circles of different radius intersecting two linear functions) are descriptive of feature. Hence, the software of the system 3500 may be configured to search the "feature database" based on feature constituent functions. Similarly, the feature templates may be constructed so as to include this information, along with or in place of the parametric ratios.

The parameters derived from the foregoing feature analysis are stored as a multi-byte feature descriptor packet 3670 (FIG. 36f) which uniquely identifies the feature in terms of the foregoing parameters, as well as the time stamp associated with the frame under analysis. This packet is stored in a designated storage location or held in buffer memory for later retrieval, such as for use in the previously described-"mosaic" display mode.

Relevant portions of the descriptor packet (i.e., the data corresponding to feature characteristics) may also be compared to pre-stored templates or models in order to assist in classification of the feature. Specifically, since the system has no a priori knowledge that the feature in question is a polyp, or what type of polyp, it can be configured to attempt to match the subject feature to one stored in the system database. For example, the system may store a plurality of paradigms or templates for polyps that have different maximal width, base width, and height ratios, dependent on the type of polyp (e.g., sessile, pendunculated, carcinoma neoplasm, etc.). In the present context, these are known as "thin" templates since they only include parametric ratio information (or constituent function information). The algorithm accordingly calculates the ratios for the subject feature (e.g., maximal width to height, height to base width, etc.) and compares these relative ratios to those stored previously within the system, and scores the subject feature against the stored templates using any number of well known data comparison and scoring techniques well known in the art, including for example least squares. A probability or "score" is then generated for use, inter alia, by the user. For example, a typical screen display would comprise a table having the feature time stamp, and the scores or probabilities for each type of pre-stored feature contained therein. Myriad other display formats may be used.

Additionally, templates may be generated based on images obtained, for example, from the probe itself (or another like it), an endoscopic device with camera or other imaging apparatus attached, or may even be artificially generated such as via a computer program. Such templates are considered "fat" in that they contain not only the processed parametric ratio data and or constituent feature information, but also the underlying image data from which the template was derived. A database or library of templates (thin and/or fat) may be made accessible via LAN, WAN, interne, or other resources (such as distributed CD-ROM), with corresponding feature definitions in much the same way that computer virus definitions are periodically updated by a user of a standard PC. In this fashion, the user of the present invention can make use of images gathered by other physicians corresponding to known conditions or diseases, either in direct visualization (i.e., by displaying the in situ feature contemporaneously with the template image), or by the parametric data, or both.

The templates may also be annotated with one or more bytes of information (text, notes, etc.) providing background or explanatory information associated with each template in order to assist others using the template in diagnosis of their patient. For example, it may be useful to know the age, sex, ethnicity, stage of progression of the disease, and brief treatment history for the subject from which the template (image) was obtained. Such information can be read by the system processor 3502 from the template description field(s) in the packet (not shown) and displayed on the display device 3510, printed out, or otherwise accessed by the user.

The use of ratios in the instant embodiment advantageously allows comparison of data on a relative footing, thereby obviating the need for any sort of absolute distance measurement, alignment analysis/correction, or calibration, which may be exceedingly difficult based on variations in the distance of the feature from the probe sensor when the data is taken. Standardized types and numbers of parameters can be assigned to various classes of features so as to allow complete characterization, yet make the matching process more efficient. For example, all sessile polyps may be characterized using the maximal width, height and base width criteria previously described.

The aforementioned cylindrical coordinate system can also be used as the basis for image recognition. Specifically, curves "fit" to the digitized features or nodes may be mathematically rotated around the longitudinal axis (Z) and iteratively matched to the template(s) in question (according to "point-to-point" methods described subsequently herein). The axis point, i.e., where the longitudinal axis intersects a plane disposed normally within the FOV, is for simplicity assumed to be the geometric center of the FOV, although more complex techniques for locating the axis of virtual rotation may be utilized consistent with the invention. However, through use of ratioed nodal values as previously described, such mathematical or virtual rotation may be obviated, since the orientation of the feature in question is not necessary to compare the feature to the stored templates. Specifically, by determining the characterizing dimensions of the feature, matches for the ratios formed by the various characterizing dimensions can be searched irrespective of orientation. In a simple analogy, a cube disposed in the intestinal tract would be recognized to have length equal to width equal to height, thereby forming ratios of 1:1 for all measurements. Accordingly, the database may then be searched for templates having features characterized by one or more 1:1 ratios. Aspect correction (such as that used in the prior art face recognition techniques) may also be optionally applied if needed for certain shapes or templates so as to increase the probability of accurate correlation (e.g., to rotate the aforementioned exemplary cube along one or more axes).

Alternatively (or in combination), the algorithm of the present embodiment may be configured to evaluate the feature characteristics according to one or more criterion (deterministic or otherwise) to aid in identification and classification, as compared to the previously described technique of template comparison. For example, if the height-to-base width ratio calculated for the feature is less than a prescribed threshold, it may be selectively ignored by the system for further processing on the basis that it is likely not a polyp. As yet another alternative, the software of the system 3500 may be coded to generate a constellation of close matches to the feature in question for presentation to the user. Such constellation may be multi-parametric or dimensional. For example, wherein the feature undergoing analysis has a height-to-maximal width ratio of 2:1, and a height-to-base ratio of 3:1, other features with height-to-maximal width ratios of less than or greater than 2:1 may form part of the constellation in the height-to-maximal width dimension, whereas those with height-to-base rations less or more that 3:1 may form part of the constellation in that latter dimension. The various dimensions may then be mathematically cross-correlated to identify those templates which are members of two or more constellations and have the smallest "distance" from the subject feature, with a weighting or other quality factor being assigned based thereon. Obviously, this type of analysis can be extended to more than two constellation dimensions, thereby increasing the accuracy of the template matching process.

In yet another variant of the invention, the system 3500 may be configured to generate templates based on data obtained from the same probe as under evaluation, such as from visual image data obtained from an earlier (upstream) portion of the intestinal tract. In this fashion, the system database can be updated "on the fly", and correlation analysis between features observed in later (downstream) portions of the intestine and those observed further upstream conducted. Such in situ template generation may also be used to mask out later features which are similar or identical. For example, where a first upstream image is analyzed and determined to be a normal feature (i.e., benign, or not correlated to any disease or malady), then one or more templates for that upstream feature can be generated and used as a basis for eliminating downstream features subsequently detected as also being benign or not correlated.

In more sophisticated variants of the present invention, the system software is adapted to perform digital image matching on a point-to-point basis, as opposed to the foregoing parametric ratio approach. Such point-to-point techniques may be more useful where no "standardized" shape or parameter ratios can be defined for a feature of interest. A "point-to-point" association in the present context means that for any point P in one image, the software can identify which point Q in the other (e.g., template) image represents the same detail, or is homologous to P. Hence, digital matching implies that given two digital views of an object, the software can find automatically all or a significant fraction of the pairs of homologous details. For example, in one exemplary variant, the so-called "best correction principle" is used as the basis for digital matching. Specifically, if $r_1(c,l)$, $r_2(c,l)$ are matrices representing the two digital images undergoing comparison, then two homologous details, assimilated to pixels $P_1=(c_1, l_1)$, $P_2=(c_2,l_2)$, should exist identically in both images (i.e., $r_1(P_1)=r_2(P_2)$. However, many non-homologous pairs $Q_1,Q_2$ may exist such that $r_1(Q_1)=r_2(Q_2)$. But, if two pixels $P_1=(c_1, l_1)$, $P_2=(c_2,l_2)$ are homologous, then their local regions must appear identical, or:

$$vP_1(c,l)=vP_2(c,l) \text{ for } -h \leq c \leq h, -k \leq l \leq k,$$

where:

$$vP_1(c,l)=r_1(c_1+c,l_1+l), \text{ and}$$

$$vP_2(c,l)=r_2(c_2+c,l_2+l), -h \leq c \leq h, -k \leq l \leq k,$$

define two local regions of points $P_1,P_2$. One measure of the likeness of the two local regions comprises the number I(vP1, vP2), defined either through a distance, for example $I(vP_1, vP_2)=d_1(vP_1,vP_2)=\Sigma c,l|vP_1(c,l)-vP_2(c,l)|$, or alternatively through a correlation index such as $I(vP_1,vP_2)=\Sigma c,l\ vP_1(c,l)\ vP_2(c,l)$. The greater the similarity of the images, the closer is the value $I(vP_1,vP_2)$ to an optimum obtained with two identical local regions.

As will be appreciated by those of ordinary skill in the software arts, the foregoing equations are coded into the system algorithm in order to perform the required image matching and comparison using the system digital processor 3502, or alternatively a dedicated signal processor such as the DSPs previously identified herein specifically tasked for such computationally intensive algorithms.

The foregoing process is then extended to other points and local regions of the image as needed in order to establish the requisite level of confidence in the match.

Hence, in an exemplary protocol, the image recognition software of the invention may be configured to screen or scan all or portions of the visual data stream obtained from a patient in advance of the physician's review, and flag or identify frames of potential interest for subsequent review by the physician. In this fashion, the physician may first preview the results of the algorithmic analysis to determine whether any of the "hits" generated by the algorithm are valid or warrant further evaluation, thereby saving time on subsequent evaluation. Furthermore, the algorithmic analysis can be performed while the physician is performing other tasks in parallel.

While not necessarily a substitute for direct physician observation using the methods previously described herein, the image recognition software of the invention is most useful in combination with the other techniques; i.e., when used in layered fashion. The software may alternatively be run on only selected portions of data after the physician has screened them (Or other temporally proximate segments), in effect acting as a confirmatory check. Or, as yet another alternative, the software may be run contemporaneously with the physician's review; e.g., to flag potential features of interest in one segment of the data stream while the physician reviews other segments in parallel.

It will be recognized that while the foregoing embodiments of the invention (described with respect to FIGS. 35 and 36 generally) are adapted for processing of the various data streams and signals off-probe (i.e., at the system 3500 or other processing location in data communication with the system 3500 and/or probe), the improvements of the probe portion of the invention advantageously allow some or even all of the processing to be conducted on-probe, as shown in the exemplary method 3700 of FIG. 37. Herein lies an illustration of the inherent benefit of one particular aspect of the invention, specifically the inclusion of digital data processing on-probe. With software (embedded or otherwise) disposed and running on-probe, pre-processing of data may be readily conducted in order to (i) reduce the amount of data required to be transmitted off-probe, thereby increasing the speed, efficiency, and robustness of any communications interfaces; (ii) reduce the computational loading and/or system requirements of off-probe processing devices, thereby allowing such devices to be "thinner" (i.e., have less capability by virtue of less hardware and/or software); and/or (iii) adjust the data collection and other functions performed by the probe in situ.

For example, portions of the foregoing algorithms described for blanking selected portions of the visual data stream may be incorporated into the software of the probe, such that the probe automatically or autonomously "dumps" data before transmission (or storage in the on-probe storage device), thereby reducing the required communications bandwidth for the system.

Similarly, the probe can be configured to run algorithms adapted to perform the aforementioned digital image comparison against templates stored in the probe's memory or another location, and selectively transmitting only data or portions of the visual/IR data stream relating to the features matched by such algorithm, again significantly reducing required on-probe data storage and/or communications bandwidth requirements.

As yet another exemplary alternative, the probe may be configured to run the foregoing algorithms useful for dividing the data stream into a plurality of segments, and separately transmitting the various segments across two or more separate communication channels, or across the same channel in actual or permuted order. For example, the data from a given data stream (or selected portions thereof) can be buffered into the on-probe memory and divided by the algorithm into segments based, for example on memory address, with the data corresponding to one segment; e.g., from two-byte memory address 00000ACF to 000010CD, being transmitted as a block of data distinct from that of the other segments.

It should be recognized that while the foregoing discussion of the various aspects of the invention has described specific sequences of steps necessary to perform the methods of the present invention, other sequences of steps may be used depending on the particular application. Specifically, additional steps may be added, and other steps deleted as being optional. Furthermore, the order of performance of certain steps may be permuted, and/or performed in parallel with other steps. Hence, the specific methods disclosed herein are merely exemplary of the broader methods of the invention.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The described embodiments are to be considered in all respects only illustrative and not restrictive. The scope of the invention is, therefore, indicated by the appended claims rather than the foregoing description. All changes that come within the meaning and range of equivalence of the claims are to be embraced within their scope.

What is claimed is:

1. A method of processing data derived from a sensor disposed on a substantially autonomous intestinal probe, said data having been generated while said probe moved substantially autonomously through the intestinal tract of a living being, and said processing facilitating rapid evaluation of said data, comprising:

receiving said data at a location distant from said probe via a network interface; and using a computerized device having at least one computer program configured to run thereon and in data communication with said network interface, processing at least a portion of said received data at said distant location, said processing at said distant location comprising:

processing said at least portion of said received data so as to divide said at least portion of data into a plurality of frames;

generating a display comprising a plurality of images, at least a portion of said plurality of images corresponding to one or more of said frames of said divided data;

receiving user input as to one or more of said frames being selected for review; and presenting pre-stored data for use in comparison to at least one of said selected frames, said comparison facilitating identification of one or more physiologic conditions within said subject;

wherein said display comprises a computer screen, said computer screen configured to display respective portions of said divided data simultaneously in different portions thereof, and said simultaneous display decreasing an overall time necessary for reviewing said obtained data.

2. The method of claim 1, wherein said comparison is performed substantially automatically by a computer program.

3. The method of claim 1, wherein said identification is performed substantially automatically by a computer program.

4. The method of claim 1, wherein said processing at least a portion of said received data at said distant location comprises processing said received data at a centralized location that is also configured to receive and process data associated with at least one other probe.

5. The method of claim 1, wherein said at least one other probe is disposed at a medical facility different than that of said substantially autonomous intestinal probe, and is administered by a caregiver other than a caregiver that administered said substantially autonomous intestinal probe.

6. The method of claim 1, wherein said (i) division of said at least portion of data into a plurality of frames, and said (ii) generating a display, comprises selecting frames of data from a data stream, and forming a series of snapshots for the user to view.

7. The method of claim 6, wherein said computer program further comprises a user interface configured to provide video viewing functions comprising: (i) "fast forward", (ii) "pause", and (iii) "reverse".

8. The method of claim 1, wherein said display further comprises a user interface having video viewing functions comprising an image enhancement function.

9. The method of claim 1, wherein said pre-stored data comprises:
an image and
one or more bytes of textual information providing at least one of background or explanatory information associated with said image.

10. The method of claim 1, further comprises receiving and utilizing data particularly and uniquely related to said living being.

11. The method of claim 10, wherein said data particularly and uniquely related to said living being comprises at least one of: (i) Social Security Number; (ii) name; or (iii) date of administration of said probe within said living subject.

12. The method of claim 10, wherein said data particularly and uniquely related to said living being comprises at least one of: (i) age; (ii) sex, or (iii) ethnicity of said living subject.

13. The method of claim 10, wherein said receiving and utilizing data particularly and uniquely related to said living being is performed substantially contemporaneously with said act of receiving at least a portion of said plurality of processed data.

14. The method of claim 1, wherein said at least one computer program comprises a program adapted to generate one or more windows on a display device using a window-based computer operating system.

15. The method of claim 1, wherein said pre-stored data comprises at least one image associated with the intestinal tract of a human being, said intestinal tract having a disease or other medical abnormality.

16. A non-transitory computer readable apparatus having a storage medium and being adapted to store at least one computer program thereon, said at least one computer program being configured to process at least first and second data derived from at least first and second sensors, respectively, said sensors disposed on substantially autonomous intestinal probes so as to facilitate rapid viewing thereof by a user, each of said at least first and second sensors being disposed within an intestinal tract of a different ones of living beings, the computer program which, when executed:

receives, at a location distant from said probe via a network interface, at least a portion of said at least first and second data obtained using said at least first and second sensors, said at least first and second data generated while said probes moved substantially autonomously through the intestinal tract of said living beings; and using a computerized device having at least one computer program configured to run thereon and in data communication with said network interface, processes at least a portion of said received at least first and second data at said distant location, said processing at said distant location comprising:

processing said at least portion of said received at least first and second data so as to segregate said at least first and second data into a plurality of frames corresponding to individual ones of said living beings;

generation of a display having at least two portions, said portions simultaneously displaying data corresponding to said at least first and second sensors, said display comprising a plurality of images, at least a portion of said plurality of images corresponding to one or more of said frames of said divided data;

receipt of user input as to one or more of said frames being selected for review; and presentation of pre-stored data for use in comparison to at least one of said selected frames, said comparison facilitating identification of one or more physiologic conditions within said being.

17. A method of processing data derived from a sensor disposed on a substantially autonomous intestinal probe, said data having been generated while said probe moved substantially autonomously through the intestinal tract of a living being, and said processing facilitating expedient evaluation of said data, said method comprising:

receiving said data at a different location via a network interface; and using a computerized device having at least one computer program configured to run thereon and in data communication with said network interface, processing at least a portion of said received data at said different location, said processing at said different location comprising:

processing said at least portion of said received data so as to divide said at least portion of data into at least a first plurality of frames and second plurality of frames;

generating on a display information comprising at least first and second images, said at least first and second images corresponding to respective ones of said at least first plurality of frames and said second plurality of frames;

receiving user input as to one or more of said images being selected for review; and presenting pre-stored data for use in comparison to at least one of said selected images, said comparison facilitating identification of one or more physiologic conditions within said subject;

wherein said display comprises a computer screen, said computer screen configured to display said first and second images simultaneously in different portions thereof, said simultaneous display decreasing an overall time necessary for reviewing said obtained data.

18. The method of claim 17, wherein said comparison is performed substantially automatically by a computer program.

19. The method of claim 17, wherein said identification is performed substantially automatically by a computer program.

20. The method of claim 17, wherein said processing at least a portion of said received data at said different location comprises processing said received data at a centralized location that is also configured to receive and process data associated with at least one other probe.

21. The method of claim 20, wherein said at least one other probe is disposed at a medical facility different than that of said substantially autonomous intestinal probe, and is administered by a caregiver other than a caregiver that administered said substantially autonomous intestinal probe.

22. The method of claim 17, wherein said division of said at least portion of data into at least said first and second pluralities of frames comprises dividing said at least portion into substantially equal temporal segments.

23. The method of claim 22, wherein said computer program further comprises a user interface configured to provide video viewing functions comprising: (i) "fast forward", (ii) "pause", and (iii) "reverse".

24. The method of claim 17, wherein said display further comprises a user interface having video viewing functions comprising an image enhancement function.

25. The method of claim 17, wherein said pre-stored data comprises:

one or more images; and one or more bytes of textual information providing at least one of background or explanatory information associated with said one or more images.

26. The method of claim 17, further comprises receiving and utilizing data particularly and uniquely related to said living being.

27. The method of claim 26, wherein said data particularly and uniquely related to said living being comprises at least one of: (i) Social Security Number; (ii) name; or (iii) date of administration of said probe within said living subject.

28. The method of claim 26, wherein said data particularly and uniquely related to said living being comprises at least one of: (i) age; (ii) sex, or (iii) ethnicity of said living subject.

29. The method of claim 26, wherein said receiving and utilizing data particularly and uniquely related to said living being is performed substantially contemporaneously with said act of receiving at least a portion of said plurality of processed data.

30. The method of claim 17, wherein said at least one computer program comprises a program adapted to generate one or more windows on a display device using a window-based computer operating system.

31. The method of claim 30, wherein said pre-stored data comprises at least one image associated with the intestinal tract of a human being, said intestinal tract having a disease or other medical abnormality.

32. A method of processing data derived from a sensor disposed on a substantially autonomous intestinal probe, said data having been generated while said probe moved substantially autonomously through the intestinal tract of a living being, and said processing facilitating expedient evaluation of said data, said method comprising:
receiving said data at a different location via a network interface means; and
using a computerized means having at least one computer program configured to run thereon and in data communication with said network interface means, processing at least a portion of said received data at said different location, said processing at said different location comprising:
processing said at least portion of said received data so as to divide said at least portion of data into at least a first plurality of frames and second plurality of frames;
generating a display comprising at least first and second images, said at least first and second images corresponding to respective ones of said at least first plurality of frames and said second plurality of frames;
receiving user input as to one or more of said images being selected for review; and
presenting pre-stored data for use in comparison to at least one of said selected images, said comparison facilitating identification of one or more physiologic conditions within said subject;
wherein said generating a display comprises generating said first and second images on a a computer display means, said computer display means configured to display said first and second images simultaneously in different portions thereof, said simultaneous display decreasing an overall time necessary for reviewing said obtained data.

33. Apparatus for processing data derived from a sensor disposed on a substantially autonomous intestinal probe, said data having been generated while said probe moved substantially autonomously through the intestinal tract of a living being, and said processing facilitating expedient evaluation of said data, said apparatus comprising:
a network interface configured to enable receipt of said data at a different location from that of said probe; and
a computerized device having a display device and at least one computer program configured to run thereon and in data communication with said network interface, said computerized device being configured to process at least a portion of said received data by at least:
processing said at least portion of said received data so as to divide said at least portion of data into at least a first plurality of frames and second plurality of frames;
generating on said display device information comprising at least first and second images, said at least first and second images corresponding to respective ones of said at least first plurality of frames and said second plurality of frames;
receiving user input as to one or more of said images being selected for review; and
presenting pre-stored data for use in comparison to at least one of said selected images, said comparison facilitating identification of one or more physiologic conditions within said subject;
wherein said computer screen displays said first and second images simultaneously in different portions thereof, said simultaneous display decreasing an overall time necessary for reviewing said obtained data.

34. The apparatus of claim 33, wherein said comparison is performed substantially automatically by said at least one computer program.

35. The apparatus of claim 33, wherein said identification is performed substantially automatically by said at least one computer program.

36. The apparatus of claim 33, wherein said apparatus is disposed at a centralized location that is also configured to receive and process data associated with at least one other probe.

37. The apparatus of claim 33, wherein said division of said at least portion of data into at least said first and second pluralities of frames comprises dividing said at least portion into substantially equal temporal segments.

38. The apparatus of claim 37, wherein said computer program further comprises a user interface configured to provide video viewing functions comprising: (i) "fast forward", (ii) "pause", and (iii) "reverse".

39. The apparatus of claim 33, wherein said pre-stored data comprises:
one or more images; and
one or more bytes of textual information providing at least one of background or explanatory information associated with said one or more images.

40. The apparatus of claim 33, further comprises receiving and utilizing data particularly and uniquely related to said living being, said data comprising at least one of: (i) Social Security Number; or (ii) date of administration of said probe within said living subject.

41. The apparatus of claim 40, wherein said receiving and utilizing data particularly and uniquely related to said living being is performed substantially contemporaneously with said act of receiving at least a portion of said plurality of processed data.

42. The apparatus of claim 33, wherein: said at least one computer program comprises a program adapted to generate one or more windows on a display device using a window-based computer operating system; and
said pre-stored data comprises at least one image associated with the intestinal tract of a human being, said intestinal tract having a disease or other medical abnormality.

* * * * *

UNITED STATES PATENT AND TRADEMARK OFFICE
CERTIFICATE OF CORRECTION

| | | |
|---|---|---|
| PATENT NO. | : 8,068,897 B1 | Page 1 of 1 |
| APPLICATION NO. | : 12/381513 | |
| DATED | : November 29, 2011 | |
| INVENTOR(S) | : Robert F. Gazdzinski | |

It is certified that error appears in the above-identified patent and that said Letters Patent is hereby corrected as shown below:

CURRENTLY READS:
Title Page - Column 1 (63)

"Continuation-in-part of application No. 09/817,842, filed on Mar. 26, 2001, which is a continuation-in-part of application No. 09/259,194, filed on Mar. 1, 1999, now abandoned."

SHOULD READ:
Title Page - Column 1 (63)

-- Divisional of application No. 10/268,392, filed October 9, 2002, which is a continuation-in-part of application No. 09/817,842, filed on Mar. 26, 2001, which is a continuation-in-part of application No. 09/259,194, filed on Mar. 1, 1999, now abandoned. --

CURRENTLY READS:
CLAIMS, COLUMN 100, LINE 28

"5. The method of claim 1, wherein said at least one other"

SHOULD READ:
COLUMN 100, LINE 28

-- 5. The method of claim 4, wherein said at least one other --

Signed and Sealed this
Fourteenth Day of May, 2013

Teresa Stanek Rea
*Acting Director of the United States Patent and Trademark Office*